(12) United States Patent
Werner et al.

(10) Patent No.: US 9,055,743 B2
(45) Date of Patent: Jun. 16, 2015

(54) ALPHA, BETA-UNSATURATED IMINES

(75) Inventors: Stefan Werner, Berlin (DE); Ulrich Ebbinghaus-Kintscher, Dortmund (DE); Sebastian Horstmann, Leverkusen (DE); Michael Maue, Langenfeld (DE); Hans-Georg Schwarz, Dorsten (DE); Robert Velten, Langenfeld (DE); Arnd Voerste, Köln (DE); Ulrich Görgens, Ratingen (DE); Andreas Turberg, Haan (DE)

(73) Assignee: BAYER INTELLECTUAL PROPERTY GMBH, Monheim (DE)

(*) Notice: Subject to any disclaimer, the term of this patent is extended or adjusted under 35 U.S.C. 154(b) by 0 days.

(21) Appl. No.: 13/988,328

(22) PCT Filed: Nov. 24, 2011

(86) PCT No.: PCT/EP2011/070943
§ 371 (c)(1),
(2), (4) Date: Aug. 9, 2013

(87) PCT Pub. No.: WO2012/072489
PCT Pub. Date: Jun. 7, 2012

(65) Prior Publication Data
US 2013/0310254 A1  Nov. 21, 2013

Related U.S. Application Data

(60) Provisional application No. 61/417,664, filed on Nov. 29, 2010.

(30) Foreign Application Priority Data

Nov. 29, 2010 (EP) .................... 10192987
Mar. 14, 2011 (EP) .................... 11158085

(51) Int. Cl.
| | | |
|---|---|---|
| C07C 211/19 | (2006.01) |
| C07D 215/38 | (2006.01) |
| C07D 217/22 | (2006.01) |
| C07D 311/20 | (2006.01) |
| C07D 335/06 | (2006.01) |
| A01N 35/10 | (2006.01) |
| A01N 43/12 | (2006.01) |
| A01N 43/16 | (2006.01) |
| A01N 43/18 | (2006.01) |
| A01N 43/38 | (2006.01) |
| A01N 43/40 | (2006.01) |
| A01N 43/80 | (2006.01) |
| C07C 317/28 | (2006.01) |
| C07C 323/45 | (2006.01) |
| C07D 211/84 | (2006.01) |
| C07D 261/20 | (2006.01) |
| C07D 307/79 | (2006.01) |
| C07D 311/68 | (2006.01) |
| C07D 335/02 | (2006.01) |
| A01N 43/42 | (2006.01) |
| C07C 251/20 | (2006.01) |
| C07D 211/72 | (2006.01) |
| C07D 333/54 | (2006.01) |

(52) U.S. Cl.
CPC ............... *A01N 35/10* (2013.01); *A01N 43/12* (2013.01); *A01N 43/16* (2013.01); *A01N 43/18* (2013.01); *A01N 43/38* (2013.01); *A01N 43/40* (2013.01); *A01N 43/80* (2013.01); *C07C 317/28* (2013.01); *C07C 323/45* (2013.01); *C07C 2101/08* (2013.01); *C07C 2101/14* (2013.01); *C07C 2101/16* (2013.01); *C07C 2101/18* (2013.01); *C07C 2102/08* (2013.01); *C07C 2102/10* (2013.01); *C07C 2102/42* (2013.01); *C07C 2103/26* (2013.01); *C07D 211/84* (2013.01); *C07D 215/38* (2013.01); *C07D 261/20* (2013.01); *C07D 307/79* (2013.01); *C07D 311/68* (2013.01); *C07D 335/02* (2013.01); *A01N 43/42* (2013.01); *C07C 251/20* (2013.01); *C07D 211/72* (2013.01); *C07D 333/54* (2013.01); *C07D 335/06* (2013.01)

(58) Field of Classification Search
CPC .. C07C 211/19; C07D 311/20; C07D 335/06; C07D 217/22; C07D 215/38
USPC .............. 564/308; 549/28, 404; 546/143, 159
See application file for complete search history.

(56) References Cited

U.S. PATENT DOCUMENTS 4,245,432 A  1/1981  Dannelly
4,272,417 A  6/1981  Barke
(Continued)

FOREIGN PATENT DOCUMENTS

CN  102596931 A  7/2012
EP  0539588      5/1993
(Continued)

OTHER PUBLICATIONS

International Search Report for PCT/EP2011/070943 Mailed Jan. 23, 2012.
"A Method fo the Asymmetric Hydrosilylation of N-Aryl Imines", Organic Letters, 2000, vol. 2, No. 5, (Feb. 9, 2000), 713-715.
"A Stereocontrolled Cyclopentenone Synthesis via Cycloaddition", J. Am. Chem. Soc. 1989, 111, 7487-7500.
"An Efficient Synthesis of Highly Functionalized [5,6] Aromatic Spiroketals by Hetero-Diels-Alder Reaction", Organic Letters, 2008, vol. 10, No. 5, 721-724.
(Continued)

*Primary Examiner* — Shawquia Jackson
(74) *Attorney, Agent, or Firm* — Miles & Stockbridge, P.C.

(57) ABSTRACT

The present application relates to novel alpha, beta-unsaturated imines, to processes for their preparation, to their use for controlling animal pests including arthropods and in particular insects and to their use in the control of vectors.

7 Claims, No Drawings

(56) References Cited

U.S. PATENT DOCUMENTS

| | | | |
|---|---|---|---|
| 4,808,430 | A | 2/1989 | Kouno |
| 5,876,739 | A | 3/1999 | Turnblad |
| 6,468,747 | B1 | 10/2002 | De Beuckeleer |
| 2001/0029014 | A1 | 10/2001 | Beuckeleer |
| 2002/0102582 | A1 | 8/2002 | Levine |
| 2002/0120964 | A1 | 8/2002 | Rangwala |
| 2003/0097687 | A1 | 5/2003 | Trolinder |
| 2003/0126634 | A1 | 7/2003 | Spencer |
| 2003/0176428 | A1 | 9/2003 | Schneidersmann |
| 2003/0188347 | A1 | 10/2003 | Both |
| 2004/0116744 | A1 | 6/2004 | Furuya |
| 2004/0172669 | A1 | 9/2004 | Kraus |
| 2004/0250317 | A1 | 12/2004 | Huber |
| 2005/0039226 | A1 | 2/2005 | Barbour |
| 2005/0086719 | A1 | 4/2005 | Spencer |
| 2005/0188434 | A1 | 8/2005 | Spencer |
| 2005/0216969 | A1 | 9/2005 | Song |
| 2006/0059581 | A1 | 3/2006 | Spencer |
| 2006/0059590 | A1 | 3/2006 | Cerny |
| 2006/0070139 | A1 | 3/2006 | Bing |
| 2006/0095986 | A1 | 5/2006 | Cavato |
| 2006/0130175 | A1 | 6/2006 | Ellis |
| 2006/0162007 | A1 | 7/2006 | Guo |
| 2006/0230473 | A1 | 10/2006 | Johnson |
| 2006/0282915 | A1 | 12/2006 | Malven |
| 2007/0028322 | A1 | 2/2007 | Dizigan et al. |
| 2007/0049635 | A1 | 3/2007 | Ebihara |
| 2007/0066617 | A1 | 3/2007 | Mita |
| 2007/0067868 | A1 | 3/2007 | Negrotto |
| 2007/0129407 | A1 | 6/2007 | Koyanagi |
| 2007/0143876 | A1 | 6/2007 | Song |
| 2007/0292854 | A1 | 12/2007 | Behr |
| 2008/0004323 | A1 | 1/2008 | Itoh et al. |
| 2008/0028482 | A1 | 1/2008 | Beazley |
| 2008/0064032 | A1 | 3/2008 | Townshend |
| 2008/0070260 | A1 | 3/2008 | Krieb |
| 2008/0167456 | A1 | 7/2008 | Steiner |
| 2008/0196127 | A1 | 8/2008 | De Beuckeleer |
| 2008/0260932 | A1 | 10/2008 | Anderson |
| 2008/0275242 | A1 | 11/2008 | Ito |
| 2008/0305955 | A1 | 12/2008 | Bretschneider |
| 2008/0312082 | A1 | 12/2008 | Kinney |
| 2008/0320616 | A1 | 12/2008 | De Beuckeleer |
| 2009/0076282 | A1 | 3/2009 | Toriyabe |
| 2009/0111847 | A1 | 4/2009 | Li |
| 2009/0130071 | A1 | 5/2009 | Gao |
| 2009/0137395 | A1 | 5/2009 | Chicoine |
| 2009/0210970 | A1 | 8/2009 | Hondred |
| 2009/0217423 | A1 | 8/2009 | Cayley |
| 2009/0247551 | A1 | 10/2009 | Jeschke |
| 2009/0253749 | A1 | 10/2009 | Jeschke |
| 2009/0259046 | A1 | 10/2009 | Hamamoto |
| 2009/0265817 | A1 | 10/2009 | Weyens |
| 2009/0300784 | A1 | 12/2009 | Long |
| 2010/0024077 | A1 | 1/2010 | Cayley |
| 2010/0048646 | A1 | 2/2010 | Jeschke |
| 2010/0050282 | A1 | 2/2010 | Trolinder |
| 2010/0077501 | A1 | 3/2010 | Trolinder |
| 2010/0080887 | A1 | 4/2010 | Wagner |
| 2010/0184079 | A1 | 7/2010 | Cressman |
| 2010/0240705 | A1 | 9/2010 | Jeschke |
| 2010/0240729 | A1 | 9/2010 | Itoh |
| 2010/0256195 | A1 | 10/2010 | Fischer |
| 2011/0067141 | A1 | 3/2011 | Froman |
| 2011/0138504 | A1 | 6/2011 | Beazley |
| 2011/0195998 | A1 | 8/2011 | Goto |
| 2011/0212949 | A1 | 9/2011 | Bretschneider |
| 2011/0251388 | A1 | 10/2011 | Kutose |
| 2011/0306499 | A1 | 12/2011 | Bretschneider |
| 2012/0225895 | A1 | 9/2012 | Takahashi |
| 2013/0125253 | A1 | 5/2013 | Trolinder |

FOREIGN PATENT DOCUMENTS

| | | |
|---|---|---|
| JP | 2008297223 A | 12/2008 |
| JP | 2008297224 A | 12/2008 |
| JP | 2009108051 | 5/2009 |
| JP | 2009227655 | 10/2009 |
| JP | 2009227655 A | 10/2009 |
| JP | 2010018586 | 1/2010 |
| JP | 2010077075 A | 4/2010 |
| JP | 2010132583 A | 6/2010 |
| JP | 2010168328 A | 8/2010 |
| WO | WO9844140 | 10/1998 |
| WO | WO0026345 | 5/2000 |
| WO | WO0026356 | 5/2000 |
| WO | WO0131042 | 5/2001 |
| WO | WO0141558 | 6/2001 |
| WO | WO0151654 | 7/2001 |
| WO | WO0212172 | 2/2002 |
| WO | WO0228186 | 4/2002 |
| WO | WO0234946 | 5/2002 |
| WO | WO0236831 | 5/2002 |
| WO | WO0244407 | 6/2002 |
| WO | WO02096882 | 12/2002 |
| WO | WO-02096882 | 12/2002 |
| WO | WO-02100163 | 12/2002 |
| WO | WO03013224 | 2/2003 |
| WO | WO03052073 | 6/2003 |
| WO | WO03106457 | 12/2003 |
| WO | WO2004011601 | 2/2004 |
| WO | WO2002080675 | 5/2004 |
| WO | WO2004039986 | 5/2004 |
| WO | WO2004053062 | 6/2004 |
| WO | WO2004058723 | 7/2004 |
| WO | WO-2004072235 | 8/2004 |
| WO | WO2004074492 | 9/2004 |
| WO | WO-2004074492 | 9/2004 |
| WO | WO2004099160 | 11/2004 |
| WO | WO2004099447 | 11/2004 |
| WO | WO2004072235 | 3/2005 |
| WO | WO2005035486 | 4/2005 |
| WO | WO-2005042474 | 5/2005 |
| WO | WO2005042474 | 5/2005 |
| WO | WO2005054479 | 6/2005 |
| WO | WO2005054480 | 6/2005 |
| WO | WO2005059103 | 6/2005 |
| WO | WO2005061720 | 7/2005 |
| WO | WO2005063094 | 7/2005 |
| WO | WO2005070917 | 8/2005 |
| WO | WO-2005070917 | 8/2005 |
| WO | WO-2005077934 | 8/2005 |
| WO | WO2005077934 | 8/2005 |
| WO | WO-2005085216 | 9/2005 |
| WO | WO2005085216 | 9/2005 |
| WO | WO2005103266 | 11/2005 |
| WO | WO2005103301 | 11/2005 |
| WO | WO-2006043635 | 4/2006 |
| WO | WO2006043635 | 4/2006 |
| WO | WO2006056433 | 6/2006 |
| WO | WO2006089633 | 8/2006 |
| WO | WO2006098952 | 9/2006 |
| WO | WO2006100288 | 9/2006 |
| WO | WO2006108674 | 10/2006 |
| WO | WO2006108675 | 10/2006 |
| WO | WO2006128568 | 12/2006 |
| WO | WO2006128569 | 12/2006 |
| WO | WO2006128570 | 12/2006 |
| WO | WO2006128571 | 12/2006 |
| WO | WO2006128572 | 12/2006 |
| WO | WO2006128573 | 12/2006 |
| WO | WO2006130436 | 12/2006 |
| WO | WO2007017186 | 2/2007 |
| WO | WO-2007040280 | 4/2007 |
| WO | WO2007040280 | 4/2007 |
| WO | WO2007057407 | 5/2007 |
| WO | 2007063702 A2 | 6/2007 |
| WO | WO-2007063702 | 6/2007 |
| WO | WO2007075459 | 7/2007 |
| WO | WO2007091277 | 8/2007 |
| WO | WO-2007101369 | 9/2007 |

(56) References Cited

FOREIGN PATENT DOCUMENTS

| | | |
|---|---|---|
| WO | WO2007101369 | 9/2007 |
| WO | WO2007115643 | 10/2007 |
| WO | WO-2007115643 | 10/2007 |
| WO | WO-2007115644 | 10/2007 |
| WO | WO2007115644 | 10/2007 |
| WO | WO-2007115646 | 10/2007 |
| WO | WO2007115646 | 10/2007 |
| WO | WO2007140256 | 12/2007 |
| WO | WO2007142840 | 12/2007 |
| WO | WO2007149134 | 12/2007 |
| WO | WO2008002872 | 1/2008 |
| WO | WO-2008009360 | 1/2008 |
| WO | WO2008009360 | 1/2008 |
| WO | WO2008054747 | 5/2008 |
| WO | WO2008066153 | 6/2008 |
| WO | WO-2008066153 | 6/2008 |
| WO | WO2008067911 | 6/2008 |
| WO | WO2008104503 | 9/2008 |
| WO | WO2008112019 | 9/2008 |
| WO | WO2008114282 | 9/2008 |
| WO | WO2008122406 | 10/2008 |
| WO | 2008149962 A1 | 12/2008 |
| WO | WO2008151780 | 12/2008 |
| WO | 2009014267 A2 | 1/2009 |
| WO | 2009048152 A2 | 4/2009 |
| WO | WO-2009048152 | 4/2009 |
| WO | WO2009049851 | 4/2009 |
| WO | 2009064031 A1 | 5/2009 |
| WO | WO2009064652 | 5/2009 |
| WO | WO2009094442 | 7/2009 |
| WO | WO2009100188 | 8/2009 |
| WO | WO2009102873 | 8/2009 |
| WO | WO2009103049 | 8/2009 |
| WO | WO-2009111263 | 9/2009 |
| WO | WO2009111263 | 1/2010 |
| WO | WO2010005692 | 1/2010 |
| WO | WO2010006713 | 1/2010 |
| WO | WO2010024976 | 3/2010 |
| WO | WO2010037016 | 4/2010 |
| WO | 2010070910 A1 | 6/2010 |
| WO | WO2010069502 | 6/2010 |
| WO | WO-2010070910 | 6/2010 |
| WO | WO2010074747 | 7/2010 |
| WO | WO2010074751 | 7/2010 |
| WO | WO-2010076212 | 7/2010 |
| WO | WO2010077816 | 7/2010 |
| WO | WO2010080829 | 7/2010 |
| WO | WO2010076212 | 9/2010 |
| WO | WO2010011737 | 10/2010 |
| WO | WO2010117735 | 10/2010 |
| WO | WO2011022469 | 2/2011 |
| WO | WO2011034704 | 3/2011 |
| WO | WO2011049233 | 4/2011 |
| WO | 2011058963 A1 | 5/2011 |
| WO | WO-2011058963 | 5/2011 |
| WO | WO2011062904 | 5/2011 |
| WO | WO2011066360 | 6/2011 |
| WO | WO2011066384 | 6/2011 |
| WO | WO2011075593 | 6/2011 |
| WO | WO2011075595 | 6/2011 |
| WO | WO2011084621 | 7/2011 |
| WO | WO2011084632 | 7/2011 |

OTHER PUBLICATIONS

"Design, Synthesis, and X-ray Crystal Structure of a Potent Dual Inhibitor of Thymidylate Synthase and Dihydrofolate Reductase as an Antitumor Agent", J. Med. Chem. 2000, 43, 3837-3851.

Langer et al. "Efficient and Steroselective Syntheses of (3-Imino-2,3-dihydro-1H-indol-2-ylidene)acetonitriles and -sulfones", Synlett Letters, Apr. 1998, 396-398.

"Generation of Azomethine Ylides via the Desilylation Reaction of Immonium Salts", J. Org. Chem. 1984, 49, 3314-3322.

"International Search Report and Written Opinion (German) for International Application No. PCT/EP2011/070943, dated Jan. 23, 2012", 1-12.

Kiang et al., "The Structure of Linderone and Methyl-linderone", Journal of the Chemical Society, 1962, 4338-4345.

"Selective 0-Methyloxime Formation from 6-Methoxy-2-[(1'-methyl-2',5'-dioxocyclopentyl)- methyl]-3,4-dihydronaphthalen-1(2H)-one", Aust. J. Chem., 1994, 47, 649-661.

Campbell et al., "Spiroheterocycles Derived From Tetralone", Tetrahedron vol. 41, No. 23, 1985, 5637-5644.

"Stereoselective Synthesis of 2-Alkylidene-3-iminoindoles by Reaction of 1,1Dianions with Oxalic Acid Bis(imidoyl) Chlorides", J. Org. Chem. 2000, 65, (May 17, 2000), 3603-3611.

Zaleska et al., "Zwitterionic Compounds in the Synthesis of Water-Soluble 1,3-Oxathiolane Derivatives", Synthesis 2005, No. 17, (Dec. 8, 2005), 2946-2950.

Pesticide Manual, "The Pesticide Manual", 14*th* Ed., British Crop Protection Council 2006; see p. 102 of Specification for U.S. Appl. No. 13/988,328.

Wegler, R., "Chemie der Pflanzenschutz- und Schadlingsbekampfungsmittel", Chemistry of Plant Protection and Pest Control Agents, vol. 2, Springer Verlag, 1970, pp. 401-412. See p. 84 of Specification for U.S. Appl. No. 13/988,328.

ALPHA, BETA-UNSATURATED IMINES

CROSS REFERENCE TO RELATED APPLICATIONS

This application is a §371 National Stage Application of PCT/EP2011/070943, filed Nov. 24, 2011, which claims priority to European Application No. 10192987.5, filed Nov. 29, 2010, U.S. Provisional Application No. 61/417,664, filed Nov. 29, 2010, and European Application No. 11158085.8, filed Mar. 14, 2011.

BACKGROUND OF THE INVENTION

1. Field of the Invention

The present application relates to novel alpha, beta-unsaturated imines, to processes for their preparation and to their use as insecticides, acaricides and/or parasiticides.

2. Description of Related Art

Insecticidal alpha, beta-unsaturated imines are known from WO 2007/063702, US 2008/004323, JP 2008/297223, JP 2008/297224, WO 2008/297224, WO 2008/149962, WO 2009/064031, WO 2009/014267, JP 2009/227655, JP 2009/1108051, WO 2009/048152, WO 2010/070910, JP 2010/132583, JP 2010/168328, JP 2010/077075 and WO 2011/058963.

SUMMARY

The present invention provides novel insecticidally, acaricidally and/or parasiticidally active compounds of the formula (I)

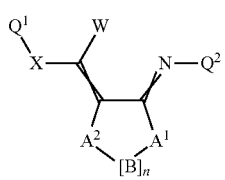

(I)

in which $Q^1$ represents in each case optionally substituted alkyl, alkenyl, alkynyl or a cyclic group;

X represents —O—, —S—, —S(O)—, or —S(O)$_2$—;

W represents H or optionally substituted alkyl;

$Q^2$ represents an optionally substituted cyclic group;

$A^1$ represents —C(R$^2$,R$^3$)—, —Y— or —N(R$^1$)—, with the proviso that, if $A^1$ represents —O— or —S— and -$A^2$-[B]$_n$— represents —(C(R$^2$,R$^3$))$_{n+1}$—, at least in one of these —C(R$^2$,R$^3$)— groups an R$^2$ and an R$^3$ of the same —C(R$^2$,R$^3$)— group together form V;

Y represents —O—, —S—, —S(O)—, or —S(O)$_2$—,

B in each case independently of the others represents Y, —N(R$^1$)— or —C(R$^2$,R$^3$)—;

n represents 0, 1, 2 or 3;

$A^2$ represents Y, —N(R$^1$)— or —C(R$^2$,R$^3$)—;

$R^1$ in each case independently of the others represents H or in each case independently of the others represents optionally substituted alkyl, alkenyl, alkynyl, haloalkyl, haloalkenyl, haloalkynyl, cyclic group, M$^2$-O—, M$^2$-C(O)—, M$^2$-O—C(O)—, M$^2$-C(O)—O—, M$^2$-S—, M$^2$-S(O)—, M$^2$-S(O)$_2$—, M$^2$M$^3$N—C(O)—, M$^2$-C(O)—NM$^3$-, M$^2$M$^3$N—, M$^2$-C(S)—, M$^2$-O—C(S)—, M$^2$-C(S)—O—, M$^2$M$^3$N—C(S)—, M$^2$-C(S)—NM$^3$- or M$^2$-C(=N—O-M$^3$)-; or $R^1$ of a first —N(R$^1$)— group together with a further $R^1$ of an adjacent —N(R$^1$)— group and together with the bond of the two nitrogen atoms of these adjacent groups forms a double bond between these two adjacent groups; or $R^1$ of a first —N(R$^1$)— group together with a further $R^1$ of an adjacent —N(R$^1$)— group and together with the two nitrogen atoms of the adjacent groups forms an optionally substituted heterocyclic system, i.e. the $R^1$ of a first —N(R$^1$)— group forms, together with a further $R^1$ of an adjacent —N(R$^1$)— group, an optionally substituted bridge U; or $R^1$ of a first —N(R$^1$)— group together with an $R^1$ of a non-adjacent —N(R$^1$)— group, the two nitrogen atoms of these two non-adjacent groups and the 1, 2 or 3 B located between these two non-adjacent groups forms an optionally substituted heterocyclic system, i.e. the $R^1$ of a first —N(R$^1$)— group forms, together with a further $R^1$ of a non-adjacent —N(R$^1$)— group, an optionally substituted bridge U;

$R^2$ in each case independently of the others represents H, halogen, formyl, cyano, nitro, hydroxyl or in each case independently of the others represents optionally substituted alkyl, alkenyl, alkynyl, haloalkyl, haloalkenyl, haloalkynyl, cyclic group, M$^2$-O—, M$^2$-C(O)—, M$^2$-O—C(O)—, M$^2$-C(O)—O—, M$^2$-S—, M$^2$-S(O)—, M$^2$-S(O)$_2$—, M$^2$M$^3$N—C(O)—, M$^2$-C(O)—NM$^3$-, M$^2$M$^3$N—, M$^2$-C(S)—, M$^2$-O—C(S)—, M$^2$-C(S)—O—, M$^2$M$^3$N—C(S)—, M$^2$-C(S)—NM$^3$- or M$^2$-C(=N—O-M$^3$)-; or $R^2$ of a first —C(R$^2$,R$^3$)— group together with a further $R^2$ of an adjacent —C(R$^2$,R$^3$)— group and together with the two carbon atoms of these adjacent groups forms an in each case optionally substituted cyclic system, i.e. the $R^2$ of a first —C(R$^2$,R$^3$)— group forms, together with a further $R^2$ of an adjacent —C(R$^2$,R$^3$)— group, an optionally substituted bridge U; or $R^2$ of a first —C(R$^2$,R$^3$)— group together with an $R^2$ of a non-adjacent —C(R$^2$,R$^3$)— group, with the two carbon atoms of these two non-adjacent —C(R$^2$,R$^3$)— groups and with the 1, 2 or 3 B located between these two non-adjacent groups forms an in each case optionally substituted cyclic system, i.e. the $R^2$ of a first —C(R$^2$,R$^3$)— group forms, together with a further $R^2$ of a non-adjacent —C(R$^2$,R$^3$)— group, an optionally substituted bridge U; or $R^2$ of a —C(R$^2$,R$^3$)— group together with an $R^1$ of an adjacent —N(R$^1$)— group and together with the carbon atom and the nitrogen atom of these two adjacent groups forms an optionally substituted heterocyclic system, i.e. the $R^2$ of a —C(R$^2$,R$^3$)— group forms, together with an $R^1$ of an adjacent —N(R$^1$)— group, an optionally substituted bridge U; or $R^2$ of a —C(R$^2$,R$^3$)— group together with an $R^1$ of a non-adjacent —N(R$^1$)— group, with the carbon atom and the nitrogen atom of these two non-adjacent groups and with the 1, 2 or 3 B located between these two non-adjacent groups forms an optionally substituted heterocyclic system, i.e. the $R^2$ of a —C(R$^2$,R$^3$)— group forms, together with an $R^1$ of a non-adjacent —N(R$^1$)— group, an optionally substituted bridge U;

$R^3$ in each case independently of the others represents H, halogen, formyl, cyano, nitro, hydroxyl or in each case independently of the others represents optionally substituted alkyl, alkenyl, alkynyl, haloalkyl, haloalkenyl, haloalkynyl, cyclic group, M$^2$-O—, M$^2$-C(O)—, M$^2$-O—C(O)—, M$^2$-C(O)—O—, M$^2$-S—, M$^2$-S(O)—, M$^2$-S(O)$_2$—, M$^2$M$^3$N—C(O)—, M$^2$-C(O)—NM$^3$-, M$^2$M$^3$N—, M$^2$-C(S)—, M$^2$-O—C(S)—, M$^2$-C(S)—O—, M$^2$M$^3$N—C(S)—, M$^2$-C(S)—NM$^3$- or M$^2$-C(=N—O-M$^3$)-; or R³ together with a further R³ of an adjacent —C(R²,R³)— group and together with the bond of the two carbon atoms of these adjacent groups forms a double bond between these two adjacent groups; or R³ together with an R¹ of an adjacent N(R¹) group and together with the bond of the carbon and the nitrogen atoms of these adjacent groups forms a double bond between these two adjacent groups; or R³ of a first —C(R²,R³)— group together with a further R³ of an adjacent —C(R²,R³)— group and together with the two carbon atoms of these adjacent groups forms an in each case optionally substituted cyclic system, i.e. the R³ of a first —C(R²,R³)— group forms, together with a further R³ of an adjacent —C(R²,R³)— group, an optionally substituted bridge U; or R³ of a first —C(R²,R³)— group together with an R³ of a non-adjacent —C(R²,R³)— group, the two carbon atoms of these two non-adjacent —C(R²,R³)— groups and the 1, 2 or 3 B located between these two non-adjacent groups forms an in each case optionally substituted cyclic system, i.e. the R³ of a first —C(R²,R³)— group forms, together with a further R³ of a non-adjacent —C(R²,R³)— group, an optionally substituted bridge U; or R² and R³ of the same —C(R²,R³)— group represent V or an in each case optionally substituted spiro-linked cyclic system, i.e. the R² and R³ form an optionally substituted bridge U;

V in each case independently of the others represents doubly attached oxygen (ketone; =O), doubly attached sulphur (thion; =S), a doubly attached N(R⁴) group (imine, oxime, etc.), or a doubly attached carbon group (=C(M¹)₂, or =C(H,M¹), or =C(H)₂);

R⁴ in each case independently of the others represents H, halogen, formyl, cyano, nitro, hydroxyl or in each case independently of the others represents optionally substituted alkyl, alkenyl, alkynyl, haloalkyl, haloalkenyl, haloalkynyl, cyclic group, M²-O—, M²-C(O)—, M²-O—C(O)—, M²-C(O)—O—, M²-S—, M²-S(O)—, M²-S(O)₂—, M²M³N—C(O)—, M²-C(O)—NM³-, M²M³N—, M²-C(S)—, M²-O—C(S)—, M²-C(S)—O—, M²M³N—C(S)— or M²-C(S)—NM³-;

M¹ in each case independently of the others represents halogen, formyl, cyano, nitro, hydroxyl, or in each case optionally independently represents, substituted by one or more M⁴, alkyl, alkenyl, alkynyl, haloalkyl, haloalkenyl, haloalkynyl, cyclic group, M⁵-O—, M⁵-S—, M⁵-S(O)—, M⁵-S(O)₂—, M⁵-C(O)—, M⁵-O—C(O)—, M⁵-C(O)—O—, M⁵M⁶N—C(O)—, M⁵-C(O)—NM⁶-, M⁵M⁶N—, M⁵-C(S)—, M⁵-O—C(S)—, M⁵-C(S)—O—, M⁵M⁶N—C(S)—, M⁵-C(S)—NM⁶- or M⁵-C(=N—O-M⁶)-;

M², M³ in each case independently of one another represent H, alkyl, alkenyl, alkynyl, haloalkyl, haloalkenyl, haloalkynyl, cyclic group, cyclic group alkyl;

M⁴ independently of the others represents halogen, formyl, cyano, nitro, hydroxyl, alkyl, alkenyl, alkynyl, haloalkyl, haloalkenyl, haloalkynyl, M²-O—, M²-S—, M²-S(O)—, M²-S(O)₂—, M²-C(O)—, M²-O—C(O)—, M²-C(O)—O—, M²M³N—C(O)—, M²-C(O)—NM³-, M²M³N—, M2⁵-C(S)—, M²-O—C(S)—, M²-C(S)—O—, M²M³N—C(S)— or M²-C(S)—NM³-, a cyclic group which is optionally substituted by one or more halogen, cyano, nitro, alkyl, alkoxy, alkylthio, haloalkyl, haloalkoxy and/or haloalkylthio;

M⁵, M⁶ in each case independently of one another represent H or in each case independently of one another represent optionally cyano- or nitro-substituted alkyl, alkenyl, alkynyl, haloalkyl, haloalkenyl, haloalkynyl or in each case independently of one another represent an optionally formyl-, halogen-, cyano-, nitro-, alkyl-, haloalkyl-, alkoxy-, haloalkoxy-, alkylthio- or haloalkylthio-substituted cyclic group or cyclic group alkyl;

U independently represents an optionally substituted chain of 1 to 13 —(C(H)₂)— units, where in each case two hydrogen atoms of two adjacent —(C(H)₂)— units may be replaced by a double bond and where the respective terminal positions of the chain are linked by a bridging position; or represents an optionally substituted 1- to 13-membered chain comprising at least one heteroatom and otherwise optionally —(C(H)₂)— units, where in each case two hydrogen atoms of two adjacent —(C(H)₂)— units or one hydrogen of one —(C(H)₂)— unit and one hydrogen attached to an adjacent heteroatom or two hydrogen atoms attached to adjacent heteroatoms may be replaced by a double bond, where the respective terminal positions of the chain are linked by a bridging position; or represents an optionally substituted mono- or bicycle which, with two of its positions, in each case forms a bond to a bridging position;

and also salts, N-oxides and tautomeric forms of the compounds of the formula (I);

with the proviso that compounds of the formula (I) do not represent

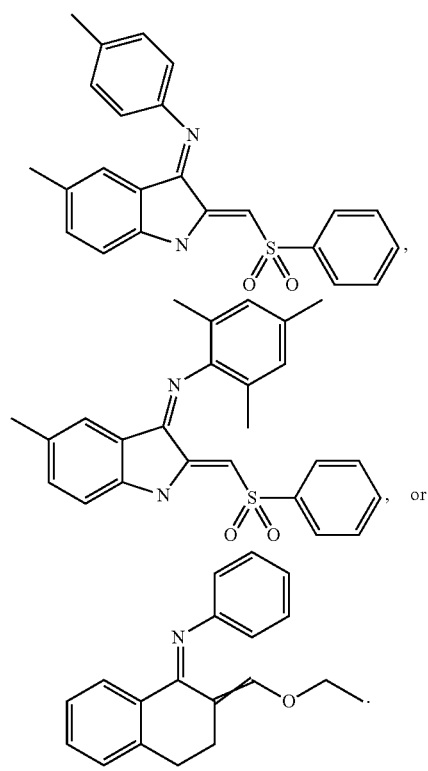

Depending on the nature of the substituents, the compounds of the formula (I) may, if appropriate, be present as geometrically and/or as optically active isomers or corresponding isomer mixtures of varying compositions. The invention relates both to the pure isomers and to the isomer mixtures.

DETAILED DESCRIPTION OF A PREFERRED EMBODIMENT

The compounds according to the invention can also be present as metal complexes.

DEFINITIONS

The person skilled in the art is aware that the terms "a" or "an", as used in the present application, may, depending on the situation, mean "one (1)" "one (1) or more" or "at least one (1)".

For all the structures described above such as cyclic systems and groups, adjacent atoms must not be —O—O— or —O—S—.

The term "optionally substituted" means, if no specific substituents are indicated, that the group in question may be mono- or polysubstituted by $M^1$, where in the case of polysubstitution the substituents $M^1$ may be identical or different.

In the present application structures having a variable number of possible carbon atoms may be referred to as $C_{lower\ limit\ carbon\ atoms}$-$C_{upper\ limit\ carbon\ atom}$-structures (($C_{ll}$-$C_{ul}$)-structures) in order to be defined more precisely. Example: an alkyl group may have 3 to 10 carbon atoms, in which case it corresponds to $(C_3-C_{10})$-alkyl. Ring structures of carbon atoms and heteroatoms may be referred to as "ll- to ul-membered" structures. One example of a 6-membered ring structure is toluene (a 6-membered ring structure which is substituted by a methyl group).

If a collective term for a substituent, for example $(C_{ll}-C_{ul})$-alkyl, is located at the end of a composite substituent, such as, for example, in the case of $(C_{ll}-C_{ul})$-cycloalkyl-$(C_{ll}-C_{ul})$-alkyl, the component at the beginning of the composite substituent, for example the $(C_{ll}-C_{ul})$-cycloalkyl, may be mono- or polysubstituted independently by identical or different substituents belonging to the latter group, for example $(C_{ll}-C_{ul})$-alkyl. All of the collective terms used in this application for chemical groups, cyclic systems and cyclic groups may be defined more precisely by adding "$(C_{ll}-C_{ul})$" or "ll- to ul-membered".

Unless defined otherwise, the definition for collective terms also applies to these collective terms in composite substituents. Example: the definition of $(C_{ll}-C_{ul})$-alkyl also applies to $(C_{ll}-C_{ul})$-alkyl as a component of a composite substituent such as, for example, $(C_{ll}-C_{ul})$-cycloalkyl-$(C_{ll}-C_{ul})$-alkyl.

To the person skilled in the art, it is clear that examples given in the present application are not to be considered as limiting but only illustrate some embodiments in more detail.

In the definitions of the symbols given in the formulae above, collective terms were used which are generally representative of the following substituents:

Collective Terms

Halogen, unless defined otherwise: elements of the 7$^{th}$ main group, preferably fluorine, chlorine, bromine and iodine, more preferably fluorine, chlorine and bromine and even more preferably fluorine and chlorine.

Alkyl, unless defined otherwise elsewhere: saturated straight-chain or branched hydrocarbon radicals having preferably $(C_1-C_{10})$-, $(C_1-C_6)$- or $(C_1-C_4)$-carbon atoms. Examples: methyl, ethyl, propyl, 1-methylethyl, butyl, etc.

Alkenyl, unless defined otherwise elsewhere: unsaturated straight-chain or branched hydrocarbon radicals having a double bond. Alkenyl is preferably $(C_2-C_{10})$-, $(C_2-C_6)$- or $(C_2-C_4)$-alkenyl. Examples: ethenyl, 1-propenyl, 3-butenyl, etc.

Alkynyl, unless defined otherwise elsewhere: unsaturated straight-chain or branched hydrocarbon radicals having a triple bond. Alkynyl is preferably $(C_2-C_{10})$-, $(C_2-C_6)$- or $(C_2-C_4)$-alkynyl. Examples: ethynyl, 1-propynyl, etc.

Alkoxy (alkyl radical —O—), unless defined otherwise elsewhere: an alkyl radical which is attached via an oxygen atom (—O—) to the basic structure. Alkoxy is preferably $(C_1-C_{10})$-, $(C_1-C_6)$- or $(C_1-C_4)$-alkoxy. Examples: methoxy, ethoxy, propoxy, 1-methylethoxy, etc.

Analogously, alkenoxy and alkynoxy, unless defined otherwise elsewhere, are alkenyl radicals and alkynyl radicals, respectively, which are attached via —O— to the basic structure. Alkenoxy is preferably $(C_2-C_{10})$-, $(C_2-C_6)$- or $(C_2-C_4)$-alkenoxy. Alkynoxy is preferably $(C_3-C_{10})$-, $(C_3-C_6)$- or $(C_3-C_4)$-alkynoxy.

Alkylcarbonyl (alkyl radical —C(=O)—), unless defined otherwise: alkylcarbonyl is preferably $(C_1-C_{10})$-, $(C_1-C_6)$- or $(C_1-C_4)$-alkylcarbonyl. Here, the number of carbon atoms refers to the alkyl radical in the alkylcarbonyl group.

Analogously, alkenylcarbonyl and alkynylcarbonyl, are, unless defined otherwise elsewhere: alkenyl radicals and alkynyl radicals, respectively, which are attached via —C(=O)— to the basic structure. Alkenylcarbonyl is preferably $(C_2-C_{10})$-, $(C_2-C_6)$- or $(C_2-C_4)$-alkenylcarbonyl. Alkynylcarbonyl is preferably $(C_2-C_{10})$-, $(C_2-C_6)$- or $(C_2-C_4)$-alkynylcarbonyl.

Alkoxycarbonyl (alkyl radical —O—C(=O)—), unless defined otherwise elsewhere: alkoxycarbonyl is preferably $(C_1-C_{10})$-, $(C_1-C_6)$- or $(C_1-C_4)$-alkoxycarbonyl. Here, the number of carbon atoms refers to the alkyl radical in the alkoxycarbonyl group.

Analogously, alkenoxycarbonyl and alkynoxycarbonyl, unless defined otherwise elsewhere, are: alkenyl radicals and alkynyl radicals, respectively, which are attached via —O—C(=O)— to the basic structure. Alkenoxycarbonyl is preferably $(C_2-C_{10})$-, $(C_2-C_6)$- or $(C_2-C_4)$-alkenoxycarbonyl. Alkynoxycarbonyl is preferably $(C_3-C_{10})$-, $(C_3-C_6)$- or $(C_3-C_4)$-alkynoxycarbonyl.

Alkylcarbonyloxy (alkyl radical —C(=O)—O—), unless defined otherwise elsewhere: an alkyl radical which is attached via a carbonyloxy group (—C(=O)—O—) by the oxygen to the basic structure. Alkylcarbonyloxy is preferably $(C_1-C_{10})$-, $(C_1-C_6)$- or $(C_1-C_4)$-alkylcarbonyloxy.

Analogously, alkenylcarbonyloxy and alkynylcarbonyloxy, unless defined otherwise elsewhere, are: alkenyl radicals and alkynyl radicals, respectively, which are attached via (—C(=O)—O—) to the basic structure. Alkenylcarbonyloxy is preferably $(C_2-C_{10})$-, $(C_2-C_6)$- or $(C_2-C_4)$-alkenylcarbonyloxy. Alkynylcarbonyloxy is preferably $(C_2-C_{10})$-, $(C_2-C_6)$- or $(C_2-C_4)$-alkynylcarbonyloxy.

Alkylthio, unless defined otherwise elsewhere: an alkyl radical which is attached via —S— to the basic structure. Alkylthio is preferably $(C_1-C_{10})$-, $(C_1-C_6)$- or $(C_1-C_4)$-alkylthio.

Analogously, alkenylthio and alkynylthio, unless defined otherwise elsewhere, are: alkenyl radicals and alkynyl radicals, respectively, which are attached via —S— to the basic structure.

Alkenylthio is preferably $(C_2-C_{10})$-, $(C_2-C_6)$- or $(C_2-C_4)$-alkenylthio. Alkynylthio is preferably $(C_3-C_{10})$-, $(C_3-C_6)$- or $(C_3-C_4)$-alkynylthio.

Alkylsulfinyl, unless defined otherwise elsewhere: an alkyl radical which is attached via —S(=O)— to the basic structure. Alkysulfinyl is preferably $(C_1-C_{10})$-, $(C_1-C_6)$- or $(C_1-C_4)$-alkylsulfinyl.

Analogously, alkenylsulfinyl and alkynylsulfinyl, unless defined otherwise elsewhere, are: alkenyl radicals and alkynyl radicals, respectively, which are attached via —S(=O)— to the basic structure. Alkenylsulfinyl is preferably ($C_2$-$C_{10}$)-, ($C_2$-$C_6$)- or ($C_2$-$C_4$)-alkenylsulfinyl. Alkynylsulfinyl is preferably ($C_3$-$C_{10}$)-, ($C_3$-$C_6$)- or ($C_3$-$C_4$)-alkynylsulfinyl.

Alkylsulfonyl, unless defined otherwise elsewhere: an alkyl radical which is attached via —S(=O)$_2$— to the basic structure. Alkylsulfonyl is preferably ($C_1$-$C_{10}$)-, ($C_1$-$C_6$)- or ($C_1$-$C_4$)-alkylsulfonyl.

Analogously, alkenylsulfonyl and alkynylsulfonyl, unless defined otherwise elsewhere, are: alkenyl radicals and alkynyl radicals, respectively, which are attached via —S(=O)$_2$— to the basic structure. Alkenylsulfonyl is preferably ($C_2$-$C_{10}$)-, ($C_2$-$C_6$)- or ($C_2$-$C_4$)-alkenylsulfonyl. Alkynylsulfonyl is preferably ($C_3$-$C_{10}$)-, ($C_3$-$C_6$)- or ($C_3$-$C_4$)-alkynylsulfonyl.

Haloalkyl, haloalkenyl, haloalkynyl, haloalkoxy, haloalkenoxy, haloalkynoxy, haloalkylcarbonyl, haloalkenylcarbonyl, haloalkynylcarbonyl, haloalkoxycarbonyl, haloalkenoxycarbonyl, haloalkynoxycarbonyl, haloalkylcarbonyloxy, haloalkenylcarbonyloxy, haloalkynylcarbonyloxy, haloalkylthio, haloalkenylthio, haloalkynylthio, haloalkylsulphinyl, haloalkenylsulphinyl, haloalkynylsulphinyl, haloalkylsulphonyl, haloalkenylsulphonyl, haloalkynylsulphonyl are in each case, unless defined otherwise, analogous to alkyl, alkenyl, alkynyl, alkoxy, alkenoxy, alkynoxy, alkylcarbonyl, alkenylcarbonyl, alkynylcarbonyl, alkoxycarbonyl, alkenoxycarbonyl, alkynoxycarbonyl, alkylcarbonyloxy, alkenylcarbonyloxy, alkynylcarbonyloxy, alkylthio, alkenylthio, alkynylthio, alkylsulphinyl, alkenylsulphinyl, alkynylsulphinyl, alkylsulphonyl, alkenylsulphonyl, alkynylsulphonyl, where at least one hydrogen atom is replaced by a halogen atom as mentioned above. In one embodiment, all hydrogen atoms are replaced by halogen. Examples of halogenated structures are, for example, chloromethyl, bromomethoxy, dichloromethylthio, trichloromethyl, fluoromethyl, chlorofluoromethyl, dichlorofluoromethyl, trifluoromethyl, 2,2-difluoroethyl, difluoromethyl, trifluoromethoxy, difluoromethoxy.

Cyclic Groups

Cyclic group, unless defined otherwise elsewhere: a carbocyclic group, a heterocyclic group, a halogenated carbocyclic group, a halogenated heterocyclic group. Cyclic groups are attached by one (1) bond to $A^1$, a B or $A^2$, where the bond may be a single bond or a double bond. However, they have no further bond to any $A^1$, B or $A^2$. In other words, substituents which are attached to the central C(=C(W,X-$Q^1$))—C(=N-$Q^2$)-$A^1$-[B]$_n$-$A^2$ ring only via a single or double bond are referred to as cyclic groups. Substituents which are attached to the central C(=C(W,X-$Q^1$))—C(=N-$Q^2$)-$A^1$-[B]$_n$-$A^2$ ring via at least two single bonds, a single and a double bond or two double bonds are referred to as cyclic systems hereinbelow. In general, cyclic groups are 3- to 14-membered cyclic groups.

Carbocyclic group, unless defined otherwise elsewhere: cycloalkyl, cycloalkenyl, aryl, halogenated cycloalkyl, halogenated cycloalkenyl, halogenated aryl.

Cycloalkyl, unless defined otherwise elsewhere: mono-, bi- or tricyclic saturated hydrocarbon groups, preferably with ($C_3$-$C_{14}$)—, ($C_3$-$C_8$)- or ($C_3$-$C_6$)-ring atoms. Examples: cyclopropyl, -butyl, -pentyl, -hexyl, -heptyl, bicyclo[2.2.1]heptyl or adamantyl. "Cycloalkyl" preferably represents monocyclic groups of 3, 4, 5, 6 or 7 ring atoms.

Analogously, cycloalkenyl, unless defined otherwise elsewhere, is: a mono-, bi- or tricyclic, but partially unsaturated hydrocarbon group having at least one double bond, preferably with ($C_3$-$C_{14}$)—, ($C_3$-$C_8$)- or ($C_3$-$C_6$)-ring atoms. Examples: cyclopropenyl, cyclobutenyl, cyclopentenyl and cyclohexenyl.

Aryl, unless defined otherwise elsewhere: a mono-, bi- or tricyclic ring system group where at least one cycle is aromatic, preferably with ($C_6$-$C_{14}$)—, ($C_6$-$C_8$)- or ($C_6$)-ring atoms. Aryl is preferably an aromatic $C_6$-monocyclic ring system group; a bicyclic ($C_8$-$C_{14}$)-ring system group; or a tricyclic ($C_{10}$-$C_{14}$)-ring system group. Examples: phenyl, naphthyl, anthryl, phenanthryl, tetrahydronaphthyl, indenyl, indanyl, fluoroenyl.

A halogenated carbocyclic group, halogenated cycloalkyl, halogenated cycloalkenyl, halogenated aryl are, unless defined otherwise, defined analogously to a carbocyclic group, cycloalkyl, cycloalkenyl, aryl, where at least one hydrogen atom is replaced by a halogen atom as mentioned above.

In one embodiment, all hydrogen atoms are replaced by halogen. Examples of halogenated structures are 3-chlorophenyl, 2-bromocyclopentyl.

Cyclic Systems

Cyclic system, unless defined otherwise elsewhere: substituents which are attached to the central C(=C(W,X-$Q^1$))—C(=N-$Q^2$)-$A^1$-[B]$_n$-$A^2$ ring via at least two single bonds, a single and a double bond or two double bonds are referred to as cyclic systems hereinbelow since, in addition to the central C(=C(W,X-$Q^1$))—C(=N-$Q^2$)-$A^1$-[B]$_n$-$A^2$ ring, they form a further ring system consisting of one or two bridging positions, positions B which are optionally located between the bridging positions, and a bridge U. In all cyclic systems, one, two or more positions selected from the group consisting of $A^1$, B and $A^2$, which are already part of the C(=C(W,X-$Q^1$))—C(=N-$Q^2$)-$A^1$-[B]$_n$-$A^2$-ring of the basic structure of the formula (I), are additionally part of this cyclic system. This means that one or two positions (bridging positions) selected from $A^1$, B and $A^2$ of the C(=C(W,X-$Q^1$))—C(=N-$Q^2$)-$A^1$-[B]$_n$-$A^2$ ring is/are additionally attached to one another by at least one further atom or an atom group (for simplicity referred to as bridge U hereinbelow), where this bridge U is not identical to positions of the C(=C(W,X-$Q^1$))—C(=N-$Q^2$)-$A^1$-[B]$_n$-$A^2$ ring of the basic structure of the formula (I) and where the bridge U is always at least attached either through one of its atoms to two bridging positions or through two of its different atoms to one or two bridging positions. Bridging positions consist either of an N($R^1$)— or of a —C($R^2$,$R^3$)— group, where the bridge U is formed by the two $R^2$; or the two $R^3$; or the two $R^1$; or $R^1$ and $R^2$; or $R^1$ and $R^3$ of the respective bridging positions or $R^2$ and $R^3$ of the single bridging position (in the case of spiro compounds). In general, cyclic systems are 3- to 14-membered cyclic systems, preferably 3-, 4-, 5-, 6- or 7-membered cyclic systems.

Accordingly, for the purpose of the present invention, a cyclic system consists of:
a position selected from $A^1$, B and $A^2$ which is already part of the C(=C(W,X-$Q^1$))—C(=N-$Q^2$)-$A^1$-[B]$_n$-$A^2$ ring of the basic structure of the formula (I) (in the case of spiro compounds); and
a bridge U;
or
two or more positions selected from $A^1$, B and $A^2$ which are already part of the C(=C(W,X-$Q^1$))-C(=N-$Q^2$)-$A^1$-[B]$_n$-$A^2$ ring of the basic structure of the formula (I) and which in addition to their ring bonds are also attached to one another via a bridge U which is not identical to positions of the C(=C(W,X-Q$^1$)-C(=N-Q$^2$)-A$^1$-[B]$_n$-A$^2$ ring of the basic structure of the formula (I) (bridging positions);

a bridge U, and if present, of B positions located between the two bridging positions (non-fused systems).

The number of atoms which, as bridge U together with the bridging position(s) and the positions B optionally located between the bridging positions, form a cyclic system can easily be calculated by the person skilled in the art if the total number of atoms forming a cyclic system is known. For example, a 3- to 14-membered cyclic system consists, in the case of a spiro compound, of a bridging position A$^1$, B or A$^2$ and the bridge U, where the number of atoms which, together with the bridging position, form the cyclic system has to be between 2 and 13; in the case of a fused 3- to 14-membered cyclic system, independently of the variable n in formula (I), the number of atoms in the bridge U is between 1 and 12; in the case of a 3- to 14-membered cyclic system with A$^1$ and A$^2$ as bridging positions, the number of atoms in the bridge U which together with the bridging positions and the positions B located inbetween (n=1, 2 or 3) form the cyclic system, is calculated to be from 1 to 11 (n=1), from 1 to 10 (n=2) or from 1 to 9 (n=3). Analogously, the person skilled in the art may also determine the number of atoms in the bridge U if the cyclic systems have other lower and upper limits of ring members or a fixed number of ring members, such as, for example, a fused C$_6$-aromatic system which, by definition, consists of two adjacent bridging positions (each representing a —C(R$^2$,R$^3$)— group) and a bridge U comprising 4 carbon atoms, which together with the bridging positions form an aromatic system. A bridge U is generally an optionally substituted chain of 1, 2, 3, 4, 5, 6, 7, 8, 9, 10, 11, 12 or 13 —(C(H)$_2$)— units, where at least one —(C(H)$_2$)— unit may be replaced by a heteroatom, where in each case two hydrogen atoms of two adjacent —(C(H)$_2$)— units or one hydrogen of a —(C(H)$_2$)— unit and one hydrogen attached to an adjacent heteroatom (for example —N(H)—) may be replaced by a double bond and where the respective terminal positions of the chain are attached to a bridging position; or a bridge U is a mono- or bicycle which, with two of its positions, in each case forms a bond to a bridging position and thus together with the bridging positions and the positions B optionally located between the bridging positions forms a bicyclic, tricyclic system. It is obvious to the person skilled in the art that a bridge U together with the bridging positions and any B positions located between the bridging positions may form a conjugated/aromatic system. Preferably, a bridge U is:

an optionally substituted chain of 1, 2, 3, 4, 5, 6, 7, 8, 9, 10, 11, 12 or 13 —(C(H)$_2$)— units, particularly preferably a chain of 1 or 4 —(C(H)$_2$)— units, where in each case two hydrogen atoms of two adjacent —(C(H)$_2$)— units may be replaced by a double bond, such as, for example, an optionally substituted —C(H)$_2$— chain or optionally substituted —CH=CH—CH=CH— chain or =CH—CH=CH—CH— chain, where the respective terminal positions of the chain are attached to a bridging position;

an optionally substituted 1-, 2-, 3-, 4-, 5-, 6-, 7-, 8-, 9-, 10-, 11-, 12- or 13-, 1- to 4- or 1- to 3-membered chain comprising at least one heteroatom and otherwise optionally —(C(H)$_2$)— units, where in each case two hydrogen atoms of two adjacent —(C(H)$_2$)— units or one hydrogen of a —(C(H)$_2$)— unit and one hydrogen attached to an adjacent heteroatom or 2 hydrogen atoms attached to adjacent heteroatoms may be replaced by a double bond, particularly preferred 1- to 13-membered chains are —O—, —S— or an optionally substituted chain selected from the group consisting of —N(H)—, —C(H)$_2$—N(H)—, —CH=NH—, —C(H)$_2$—C(H)$_2$—S—, —C(H)$_2$—C(H)$_2$—O—, —CH=CH—S—, —CH=CH—O—, —CH=N—O—, —C(H)$_2$—C(H)$_2$—N(H)—, —C(H)$_2$—N(H)—C(H)$_2$—, —C(H)$_2$—C(H)$_2$—O—, —C(H)$_2$—O—C(H)$_2$—, —C(H)$_2$—C(H)$_2$—S—, —C(H)$_2$—S—C(H)$_2$—, —C(H)$_2$—C(H)$_2$—C(H)$_2$—NH—, —C(H)$_2$—C(H)$_2$—NH—C(H)$_2$—, —C(H)$_2$—C(H)$_2$—C(H)$_2$—O—, —C(H)$_2$—C(H)$_2$—O—C(H)$_2$—, —C(H)$_2$—C(H)$_2$—C(H)$_2$—S—, —C(H)$_2$—C(H)$_2$—S—C(H)$_2$—, —CH=CH—CH=N— and —CH=CH—N=CH—, very particularly preferably —CH=CH—S, —CH=CH—O—, —CH=N—O—, —CH=CH—CH=N— or —CH=CH—N=CH—, where the respective terminal positions of the chain are attached to a bridging position;

an optionally substituted mono- or bicycle, such as a carbocyclic mono- or bicycle, such as, for example,

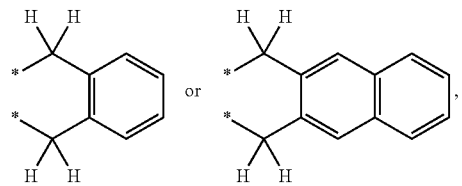 [SMILES: *Cc1ccccc1C* ; *Cc1cc2ccccc2cc1C*]

where * in each case denotes a bridging position.

Examples of such cyclic systems are disclosed, for example, by compounds of the formulae (I-0) to (I-9). In contrast, cyclic groups as defined above are attached through one (1) individual single bond or one (1) individual double bond to one of the ring positions A$^1$, B or A$^2$, but they have no further bond to any position of the C(=C(W,X-Q$^1$)-C(=N-Q$^2$)-A$^1$-[B]$_n$-A$^2$ ring.

Preference is given to an optionally substituted C(=C(W, X-Q$^1$)—C(=N-Q$^2$)-A$^1$-[B]$_n$-A$^2$ ring in which A$^1$ is a C(R$^2$, R$^3$) group selected from the group consisting of:

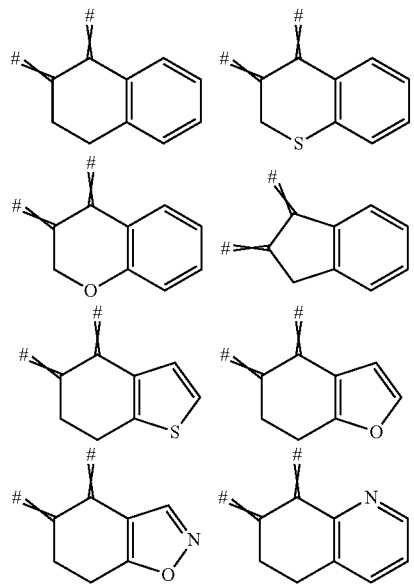

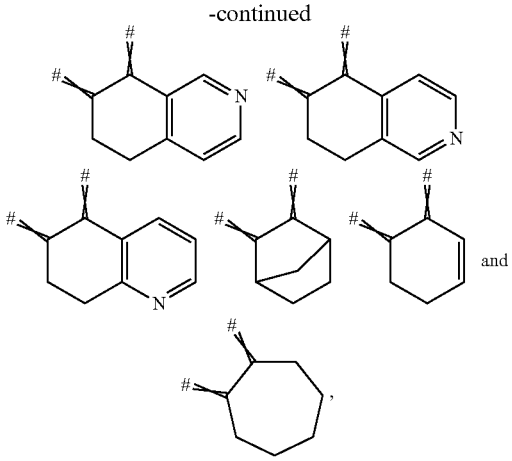

particularly preferably, this optionally substituted C(=C(W, X-Q$^1$)—C(=N-Q$^2$)-A$^1$-[B]$_n$-A$^2$ ring in which A$^1$ is a C(R$^2$, R$^3$) group comprises an optionally substituted cyclic system which corresponds to the formulae

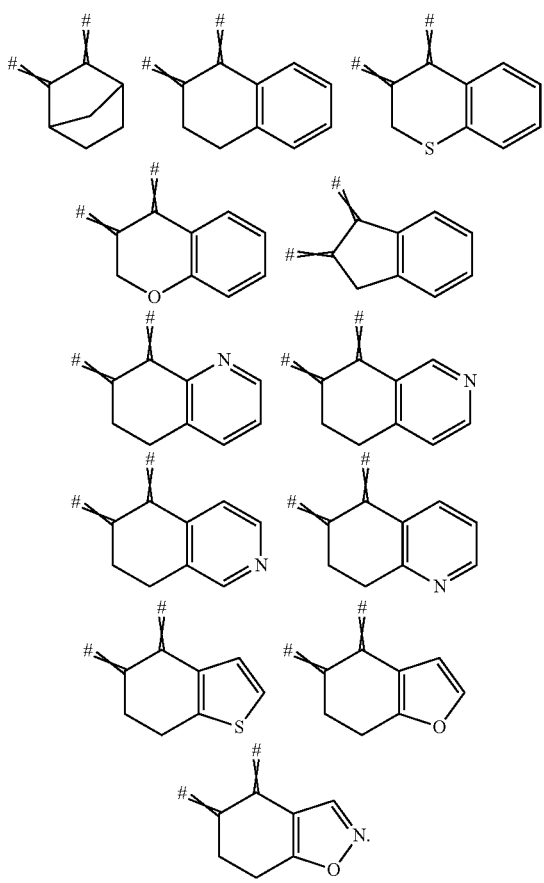

If it is a non-fused carbocyclic system having C$_6$-C$_{14}$ ring atoms, the person skilled in the art can easily calculate the number of atoms in the bridge U by subtracting the two bridging positions and the B positions located between the two bridging positions from the total number of carbon atoms. For example: if the two bridging positions are A$^1$ and A$^2$ and in a compound of the formula (I) n=3, the number of carbon atoms in the bridge U is between 1 and 9.

In a preferred embodiment, only two positions of the C(=C(W,X-Q$^1$)-C(=N-Q$^2$)-A$^1$-[B]$_n$-A$^2$ ring are part of a cyclic system, i.e. the cyclic system is a fused cyclic system and the two bridging positions selected from A$^1$, B and A$^2$ are adjacent positions which, together with the bridge U, form the cyclic system. If, for example, two adjacent C(R$^2$,R$^3$)-groups are involved in the formation of a fused cyclic (C$_3$-C$_{14}$)-system, the two R$^2$ of the adjacent C(R$^2$,R$^3$)-groups may form the (C$_1$-C$_{12}$)-radical (bridge U) of the cyclic systems. A fused cyclic system may consist of A$^1$ and an adjacent B, or of A$^1$ and an adjacent A$^2$, or of B and an adjacent B, of B and an adjacent A$^2$ and in each case a cyclic radical (bridge U) which is in each case correspondingly attached to A$^1$ and B, or A$^1$ and A$^2$, or B and B, or B and A$^2$. In a further case, a cyclic system may be a bridged system, i.e. the bridging groups are non-adjacent and separated by 1, 2 or 3 B. In such cases, a bridged cyclic system may comprise, for example, 4 positions of the C(=C(W,X-Q$^1$)-C(=N-Q$^2$)-A$^1$-[B]$_n$-A$^2$-ring (for example A$^1$, B, B and A$^2$) of the basic structure of the formula (I) and a radical (bridge U) which attaches the two bridging groups. One such example would be a bridged cyclic system of A$^1$ and a non-adjacent B as bridging groups, two B between the non-adjacent bridging groups and a radical (bridge U) which is attached to the two bridging groups A$^1$ and the non-adjacent B. A cyclic system may be a carbocyclic system, a heterocyclic system, a halogenated carbocyclic system or a halogenated heterocyclic system. In one embodiment, a cyclic system is a carbocyclic system, in particular a cycloalkane system or an aromatic system. A cyclic system may be substituted by one or more substituents M$^1$, as defined herein.

Pure Carbon Systems

Carbocyclic system, unless defined otherwise elsewhere: a cycloalkane system, a cycloalkene system, an aromatic system, a halogenated cycloalkane system, a halogenated cycloalkene system or a halogenated aromatic system. In all carbocyclic systems, two or more groups selected from the group consisting of A$^1$, B and A$^2$ are part of the carbocyclic system, where the A$^1$-, B- or A$^2$-positions which are part of the carbocyclic system each represent C(R$^2$,R$^3$). In a preferred embodiment, only two positions are part of the carbocyclic system (fused carbocyclic system). If, for example, two C(R$^2$,R$^3$) groups are involved in the formation of a fused 3- to 14-membered carbocyclic system, the two R$^2$ of the adjacent C(R$^2$,R$^3$) groups may form the (C$_1$-C$_{12}$) bridge U. In a fused C$_6$-carbomonocyclic system (such as a cycloalkane system or an aromatic system), the number of carbon atoms in the bridge U is four; in a non-fused C$_6$-carbocyclic system, the number of carbon atoms in the bridge is, depending on the number of B positions between the two bridging positions, between one (for example n is three and A$^1$ and A$^2$ are bridging positions) and three (for example n is 2 and A$^1$ is a bridging position and the B adjacent to A$^2$ is a bridging position or n is one and A$^1$ and A$^2$ are bridging positions). A carbocyclic system is preferably a C$_6$- or C$_5$-carbocyclic system.

Cycloalkane system, unless defined otherwise elsewhere: a mono-, bi- or tricyclic saturated ring system, preferably with (C$_3$-C$_{14}$)—, (C$_3$-C$_8$)- or (C$_3$-C$_6$)-ring atoms. A cycloalkane system may also be a spirocyclic system.

Cycloalkene system, unless defined otherwise elsewhere: a mono-, bi- or tricyclic partially unsaturated ring system, preferably with (C$_3$-C$_{14}$)-, (C$_3$-C$_8$)- or (C$_3$-C$_6$)-ring atoms. A cycloalkene system may also be a spirocyclic system.

Carbospiro compounds (for example spiro-linked 3- to 14-membered carbocyclic system such as spirocycloalkane, spirocycloalkene): unless defined otherwise elsewhere, a spiro-linked carbocyclic system is in each case attached through two of its atoms to a position selected from $A^1$, $A^2$ and B of the central $C(=C(W,X-Q^1)-C(=N-Q^2)-A^1-[B]_n-A^2$ ring of the basic structure of the formula (I).

Aromatic system, unless defined otherwise elsewhere: a mono-, bi- or tricyclic carbocyclic ring system where at least one cycle is aromatic, preferably with ($C_6$-$C_{14}$)-ring atoms, i.e. the ring system is formed by 6 to 14 carbon atoms. Preferably, the system is a monocyclic ring system with $C_6$-ring atoms; a bicyclic ($C_8$-$C_{14}$)-ring system; or a tricyclic ($C_{10}$-$C_{14}$)-ring system. In the case of a fused aromatic monocyclic $C_6$-, bicyclic ($C_8$-$C_{14}$)- or tricyclic ($C_{10}$-$C_{14}$)-ring system, the number of carbon atoms in a bridge U which, together with the bridging positions selected from $A^1$, B and $A^2$ and any positions B located between the bridging positions forms the cyclic system, is $C_4$ (monocyclic $C_6$-ring system), $C_6$-$C_{12}$ (bicyclic ($C_8$-$C_{14}$)-ring system) or $C_8$-$C_{12}$ carbon atoms (tricyclic ($C_{10}$-$C_{14}$)-ring system).

A halogenated carbocyclic system, a halogenated cycloalkane system, a halogenated cycloalkene system and a halogenated aromatic system are in each case, unless defined otherwise, defined analogously to a carbocyclic system, a cycloalkane system, a cycloalkene system, an aromatic system, where at least one hydrogen atom is replaced by a halogen atom as mentioned above. In one embodiment, all hydrogen atoms are replaced by halogen. Example of halogenated structures: 2-chlorocyclohexane.

Heteroatom: for example N, O, S, P, B, Si.

Heterocyclic Groups

A heterocyclic group, unless defined otherwise elsewhere: a heterocyclyl group or a heteroaryl group, a halogenated heterocyclyl group or a halogenated heteroaryl group.

Heterocyclyl, unless defined otherwise elsewhere: a saturated or partially unsaturated mono-, bi- or tricyclic ring system group of carbon atoms and at least one heteroatom preferably selected from the group consisting of N, O and S. Preferably, the ring system is a 3- to 9- or a 3- to 6-membered ring system. Preferably, the ring system contains 1, 2, 3 or 4 heteroatoms, particularly preferably 1 or 2 heteroatoms. Preference is also given to a monocyclic ring system. In a further preferred embodiment a monocyclic ring system is a partially unsaturated monocyclic ring system having a double bond. This definition also applies to heterocyclyl as component of a composite substituent such as, for example, heterocyclyl-alkyl, unless defined elsewhere.

Heteroaryl, unless defined otherwise elsewhere: a mono-, bi- or tricyclic heterocyclic group of carbon atoms and at least one heteroatom, where at least one cycle is aromatic, preferably selected from the group consisting of N, O and S. Preferably, the ring system is a 5- to 10- or a 5- to 6-membered ring system. In one embodiment, heteroaryl is an aromatic monocyclic ring system of 5 or 6 ring atoms. Preferably, heteroaryl is an aromatic monocyclic ring system which contains 1 to 4 heteroatoms from the group consisting of O, N and S. Heteroaryl may furthermore represent a bicyclic ring system which consists of 8 to 14 ring atoms or a tricyclic ring system which consists of 13 to 14 ring atoms. Examples: furyl, thienyl, pyrazolyl, imidazolyl, triazolyl, thiazolyl, indolyl, benzimidazolyl, indazolyl, benzofuranyl, benzothiophenyl, benzothiazolyl, benzoxazolyl, quinolinyl, isoquinolinyl. This definition also applies to heteroaryl as component of a composite substituent such as, for example, heteroaryl-alkyl, unless defined otherwise elsewhere. 5- and 6-membered heteroaryl groups are described in more detail below:

5-membered heteroaryl, unless defined otherwise elsewhere: a heteroaryl group which contains one to three or one to four nitrogen, oxygen and/or sulphur atoms as ring atoms. Examples: furanyl, thienyl, oxazolyl, thiazolyl. In one embodiment, a 5-membered heteroaryl group contains, in addition to carbon atoms, one to four nitrogen atoms or one to three nitrogen atoms as ring members. Examples: pyrrolyl, pyrazolyl, triazolyl, imidazolyl. In a further embodiment, a 5-membered heteroaryl contains one to three nitrogen atoms or one nitrogen atom and one oxygen or sulphur atom. Examples: thiazolyl, oxazolyl, oxadiazolyl.

6-membered heteroaryl, unless defined otherwise elsewhere: a heteroaryl group which contains one to three or one to four nitrogen atoms as ring atoms. In one embodiment, a 6-membered heteroaryl group contains one to three nitrogen atoms. Examples: pyridyl, pyridazinyl, pyrimidinyl, pyrazinyl, triazinyl, tetrazinyl.

A halogenated heterocyclyl group or a halogenated heteroaryl group is in each case, unless defined otherwise, defined analogous to a heterocyclyl group or a heteroaryl group, where at least one hydrogen atom is replaced by a halogen atom as mentioned above. In one embodiment, all hydrogen atoms are replaced by halogen. Example of halogenated heterocyclic structures: 3-chlorotetrahydrothiopyran-2-yl, 4-chloropyridin-2-yl.

Heterocyclic Systems

A heterocyclic system, unless defined otherwise elsewhere: a heterocycloalkane system, a heterocycloalkene system, a heteroaromatic system, a halogenated heterocycloalkane system, a halogenated heterocycloalkene system, a halogenated heteroaromatic system or heterospiro compounds.

In heterocyclic systems, two positions selected from the group consisting of $A^1$, B and $A^2$ are bridging positions. In one case, these $A^1$-, B- or $A^2$-bridging positions are each $C(R^2,R^3)$ groups. In a preferred embodiment, the two groups selected from the group consisting of $A^1$, B and $A^2$ are adjacent groups (fused heterocyclic system). If two $C(R^2,R^3)$ groups participate as bridging groups in forming a fused heterocyclic system, the two $R^2$ of the adjacent $C(R^2,R^3)$ groups form the heterocyclic radical of the heterocyclic system. Furthermore, in the case of heterocyclic systems one or both groups selected from the group consisting of $A^1$, B and $A^2$ may be an $N(R^1)$ group which is part of the heterocyclic system. In these case, one $R^1$ together with a further $R^1$ of the adjacent group or with an $R^2$ of the adjacent $C(R^2,R^3)$ group forms the radical of the heterocyclic system, the radical containing at least one heteroatom. A heterocyclic system may also be a bridged heterocyclic system. The person skilled in the art can determine the number of carbon atoms and/or heteroatoms in the bridge U analogously to the procedure for carbocyclic systems. It is obvious to the person skilled in the art that at least one position of the ring system is occupied by a heteroatom.

A heterocycloalkane system: unless defined otherwise elsewhere, a, preferably a ($C_3$-$C_{14}$)-, ($C_3$-$C_9$)- or ($C_3$-$C_6$)-membered, saturated mono-, bi- or tricyclic ring system in which at least one atom of the ring system is a heteroatom, preferably N, O or S. Preferably, the ring system contains 1, 2, 3 or 4 heteroatoms, particularly preferably 1 or 2 heteroatoms. Preference is also given to a monocyclic ring system; particularly preferably, the monocyclic ring system contains 1 or 2 heteroatoms, very particularly preferably selected from the group consisting of N, O and S. It is furthermore preferred for the monocyclic ring system to consist of 5 or 6 ring atoms. A heterocycloalkane system may be a spirocyclic system.

A heterocycloalkene system: corresponds to a heterocycloalkane system, unless defined otherwise elsewhere, but is partially unsaturated, i.e. it contains at least one double bond, but without forming an aromatic system. In a preferred embodiment, the system contains exactly one double bond.

A heteroaromatic system, unless defined otherwise elsewhere: an aromatic mono-, bi- or tricyclic ring system of carbon atoms and at least one heteroatom, where at least one cycle is aromatic. In one embodiment, a heteroaromatic system is an aromatic monocyclic ring system of 5 or 6 ring atoms. A heteroaromatic system is preferably a heteroaromatic monocyclic ring system which contains 1 to 4 heteroatoms from the group consisting of O, N and S. A heteroaromatic system may furthermore represent a bicyclic heteroaromatic ring system which consists of 8 to 14 ring atoms or a heteroaromatic tricyclic ring system which consists of 10 to 14 ring atoms.

A halogenated heterocycloalkane system, a halogenated heterocycloalkene system or a halogenated heteroaromatic system are defined analogously to a heterocycloalkane system, a heterocycloalkene system and a heteroaromatic system, where at least one hydrogen atom is replaced by a halogen atom as mentioned above. In one embodiment, all hydrogen atoms are replaced by halogen. Examples of halogenated structures: 3-fluoro-1,4-dioxane.

Heterospiro compounds (for example spiro-linked 3- to 14-membered heterocyclic system): unless defined otherwise elsewhere, a spiro-linked heterocyclic system is in each case attached through two of its ring atoms to a position selected from $A^1$, $A^2$ and B of the central $C(=C(W,X-Q^1)-C(N-Q^2)-A^1-[B]_n-A^2$ ring of the basic structure of the formula (I).

FURTHER DEFINITIONS

Adjacent groups/positions: a second position selected from the group of B and $A^2$ adjacent to a first position selected from the group consisting of $A^1$, B and $A^2$, where each of these positions for its part may represent a —$C(R^2,R^3)$— or —$N(R^1)$— group, where each of these second positions for its part may represent a —$C(R^2,R^3)$— or —$N(R^1)$— group, is linked by a direct bond of the carbon and/or nitrogen atoms of the —$C(R^2,R^3)$— and/or —$N(R^1)$— group(s) to the first position. Directly adjacent positions can be $A^1$ and B (n represents 1, 2, 3), $A^1$ and $A^2$ (n represents 0), B and B (n represents 2, 3) or B and $A^2$ (n represents 1, 2, 3).

Non-adjacent group/position: two positions selected from the group consisting of $A^1$, B and $A^2$, where each of these positions independently of the others may for its part represent a —$C(R^2,R^3)$— or —$N(R^1)$— group, which are not linked to each other via a direct bond between the carbon and/or nitrogen atoms of the —$C(R^2,R^3)$— or —$N(R^1)$— group(s), but separated by 1, 2 or 3 B, i.e. 1, 2 or 3 B are located between the two non-adjacent groups.

Bridging group/bridging position: a bridging group is a —$C(R^2,R^3)$— or —$N(R^1)$— group which is located at a position selected from the group consisting of $A^1$, B and $A^2$ (bridging positions), which links a cyclic system to the $C(=C(W,X-Q^1)-C(=N-Q^2)-A^1-[B]_n-A^2$-ring of the basic structure of the formula (I). In the case of non-adjacent bridging positions, the cyclic system (defined more precisely: an ll- to ul-membered cyclic system) also comprises the B positions located between the two non-adjacent bridging positions.

Not included are combinations which are against natural laws and which the person skilled in the art would therefore exclude based on his/her expert knowledge. Ring structures having three or more adjacent oxygen atoms, for example, are excluded.

EMBODIMENTS OF THE COMPOUNDS ACCORDING TO THE INVENTION

It is obvious to the person skilled in the art that all embodiments can be present alone or in combination.

Depending on the nature of the substituents, the compounds of the formula (I), the formula (II) and the formula (A) may, if appropriate, be present as salts, tautomers, geometrical and/or optically active isomers or corresponding isomer mixtures of varying compositions.

If appropriate, the compounds according to the invention can be present in various polymorphic forms or as mixture of various polymorphic forms. The invention provides both the pure polymorphs and the polymorph mixtures, and both can be used in accordance with the invention.

Embodiments of the compounds of the formula (I) are described in more detail below:

Compounds of the formula (I)

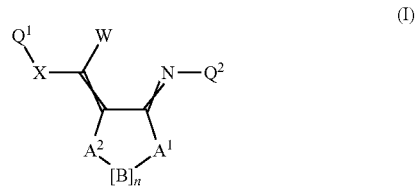

(I)

in which $Q^1$ represents in each case optionally substituted $(C_1-C_{10})$-alkyl, $(C_2-C_{10})$-alkenyl, $(C_2-C_{10})$-alkynyl or an ll- to ul-membered cyclic group;

X represents —O—, —S—, —S(O)—, or —S(O)$_2$—;

W represents H or optionally substituted $(C_1-C_{10})$-alkyl;

$Q^2$ represents an optionally substituted ll- to ul-membered cyclic group;

$A^1$ represents —$C(R^2,R^3)$—, —Y— or —$N(R^1)$—,
with the proviso that, if $A^1$ represents —O— or —S— and -$A^2$-[B]$_n$— represents —$(C(R^2,R^3))_{n+1}$—, at least in one of these —$C(R^2,R^3)$— groups an $R^2$ and an $R^3$ of the same —$C(R^2,R^3)$— group together form V;

Y represents —O—, —S—, —S(O)—, or —S(O)$_2$—,

B in each case independently of the others represents Y, —$N(R^1)$— or —$C(R^2,R^3)$—;

n represents 0, 1, 2 or 3;

$A^2$ represents Y, —$N(R^1)$— or —$C(R^2,R^3)$—;

$R^1$ in each case independently of the others represents H or in each case independently of the others represents optionally substituted alkyl, alkenyl, alkynyl, haloalkyl, haloalkenyl, haloalkynyl, cyclic group, $M^2$-O—, $M^2$-C(O)—, $M^2$-O—C(O)—, $M^2$-C(O)—O—, $M^2$-S—, $M^2$-S(O)—, $M^2$-S(O)$_2$—, $M^2M^3N$—C(O)—, $M^2$-C(O)—$NM^3$-, $M^2M^3N$—, $M^2$-C(S)—, $M^2$-O—C(S)—, $M^2$-C(S)—O—, $M^2M^3N$—C(S)—, $M^2$-C(S)—$NM^3$- or $M^2$-C(=N—O-$M^3$)-; or $R^1$ of a first —$N(R^1)$— group together with a further $R^1$ of an adjacent —$N(R^1)$— group and together with the bond of the two nitrogen atoms of these adjacent groups forms a double bond between these two adjacent groups; or $R^1$ of a first —$N(R^1)$— group together with a further $R^1$ of an adjacent —$N(R^1)$— group and together with the two nitrogen atoms of the adjacent groups forms an optionally substituted heterocyclic system, i.e. the $R^1$ of a first —$N(R^1)$— group forms, together with a further $R^1$ of an adjacent —$N(R^1)$— group, an optionally substituted bridge U; or $R^1$ of a first —$N(R^1)$— group together with an $R^1$ of a non-adjacent —$N(R^1)$— group, the two nitrogen atoms of these two non-adjacent groups and the 1, 2 or 3 B located between these two non-adjacent groups forms an optionally substituted heterocyclic system, i.e. the $R^1$ of a first —N($R^1$)— group forms, together with a further $R^1$ of a non-adjacent —N($R^1$)— group, an optionally substituted bridge U;

$R^2$ in each case independently of the others represents H, halogen, formyl, cyano, nitro, hydroxyl or in each case independently of the others represents optionally substituted alkyl, alkenyl, alkynyl, haloalkyl, haloalkenyl, haloalkynyl, cyclic group, $M^2$-O—, $M^2$-C(O)—, $M^2$-O—C(O)—, $M^2$-C(O)—O—, $M^2$-S—, $M^2$-S(O)—, $M^2$-S(O)$_2$—, $M^2M^3$N—C(O)—, $M^2$-C(O)—$NM^3$-, $M^2M^3$N—, $M^2$-C(S)—, $M^2$-O—C(S)—, $M^2$-C(S)—O—, $M^2M^3$N—C(S)—, $M^2$-C(S)—$NM^3$- or $M^2$-C(=N—O-$M^3$)-; or $R^2$ of a first —C($R^2$,$R^3$)— group together with a further $R^2$ of an adjacent —C($R^2$,$R^3$)— group and together with the two carbon atoms of these adjacent groups forms an in each case optionally substituted cyclic system, i.e. the $R^2$ of a first —C($R^2R^3$)— group forms, together with a further $R^2$ of an adjacent —C($R^2$,$R^3$)— group, an optionally substituted bridge U; or $R^2$ of a first —C($R^2$,$R^3$)— group together with an $R^2$ of a non-adjacent —C($R^2$,$R^3$)— group, with the two carbon atoms of these two non-adjacent —C($R^2$,$R^3$)— groups and with the 1, 2 or 3 B located between these two non-adjacent groups forms an in each case optionally substituted cyclic system, i.e. the $R^2$ of a first —C($R^2$,$R^3$)— group forms, together with a further $R^2$ of a non-adjacent —C($R^2$,$R^3$)— group, an optionally substituted bridge U; or $R^2$ of a —C($R^2$,$R^3$)— group together with an $R^1$ of an adjacent —N($R^1$)— group and together with the carbon atom and the nitrogen atom of these two adjacent groups forms an optionally substituted heterocyclic system, i.e. the $R^2$ of a —C($R^2$,$R^3$)— group forms, together with an $R^1$ of an adjacent —N($R^1$)— group, an optionally substituted bridge U; or $R^2$ of a —C($R^2$,$R^3$)— group together with an $R^1$ of a non-adjacent —N($R^1$)— group, with the carbon atom and the nitrogen atom of these two non-adjacent groups and with the 1, 2 or 3 B located between these two non-adjacent groups forms an optionally substituted heterocyclic system, i.e. the $R^2$ of a —C($R^2$,$R^3$)— group forms, together with an $R^1$ of a non-adjacent —N($R^1$)— group, an optionally substituted bridge U;

$R^3$ in each case independently of the others represents H, halogen, formyl, cyano, nitro, hydroxyl or in each case independently of the others represents optionally substituted alkyl, alkenyl, alkynyl, haloalkyl, haloalkenyl, haloalkynyl, cyclic group, $M^2$-O—, $M^2$-C(O)—, $M^2$-O—C(O)—, $M^2$-C(O)—O—, $M^2$-S—, $M^2$-S(O)—, $M^2$-S(O)$_2$—, $M^2M^3$N—C(O)—, $M^2$-C(O)—$NM^3$-, $M^2M^3$N—, $M^2$-C(S)—, $M^2$-O—C(S)—, $M^2$-C(S)—O—, $M^2M^3$N—C(S)—, $M^2$-C(S)—$NM^3$- or $M^2$-C(=N—O-$M^3$)-; or $R^3$ together with a further $R^3$ of an adjacent —C($R^2$,$R^3$)— group and together with the bond of the two carbon atoms of these adjacent groups forms a double bond between these two adjacent groups; or $R^3$ together with an $R^1$ of an adjacent N($R^1$) group and together with the bond of the carbon and the nitrogen atoms of these adjacent groups forms a double bond between these two adjacent groups; or $R^3$ of a first —C($R^2$,$R^3$)— group together with a further $R^3$ of an adjacent —C($R^2$,$R^3$)— group and together with the two carbon atoms of these adjacent groups forms an in each case optionally substituted cyclic system, i.e. the $R^3$ of a first —C($R^2$,$R^3$)— group forms, together with a further $R^3$ of an adjacent —C($R^2$,$R^3$)— group, an optionally substituted bridge U; or $R^3$ of a first —C($R^2$,$R^3$)— group together with an $R^3$ of a non-adjacent —C($R^2$,$R^3$)— group, the two carbon atoms of these two non-adjacent —C($R^2$,$R^3$)— groups and the 1, 2 or 3 B located between these two non-adjacent groups forms an in each case optionally substituted cyclic system, i.e. the $R^3$ of a first —C($R^2$,$R^3$)— group forms, together with a further $R^3$ of a non-adjacent —C($R^2$,$R^3$)— group, an optionally substituted bridge U; or $R^2$ and $R^3$ of the same —C($R^2$,$R^3$)— group may represent V or an in each case optionally substituted spiro-linked cyclic system, i.e. the $R^2$ and $R^3$ form an optionally substituted bridge U;

V in each case independently of the others represents doubly attached oxygen (ketone; =O), doubly attached sulphur (thion; =S), a doubly attached N($R^4$) group (imine, oxime, etc.), or a doubly attached carbon group (=C($M^1$)$_2$, or =C(H,$M^1$), or =C(H)$_2$);

$R^4$ in each case independently of the others represents H, halogen, formyl, cyano, nitro, hydroxyl or in each case independently of the others represents optionally substituted alkyl, alkenyl, alkynyl, haloalkyl, haloalkenyl, haloalkynyl, cyclic group, $M^2$-O—, $M^2$-C(O)—, $M^2$-O—C(O)—, $M^2$-C(O)—O—, $M^2$-S—, $M^2$-S(O)—, $M^2$-S(O)$_2$—, $M^2M^3$N—C(O)—, $M^2$-C(O)—$NM^3$-, $M^2M^3$N—, $M^2$-C(S)—, $M^2$-O—C(S)—, $M^2$-C(S)—O—, $M^2M^3$N—C(S)— or $M^2$-C(S)—$NM^3$-;

$M^1$ in each case independently of the others represents halogen, formyl, cyano, nitro, hydroxyl or in each case independently of the others represents optionally mono- or poly-$M^4$-substituted alkyl, alkenyl, alkynyl, haloalkyl, haloalkenyl, haloalkynyl, cyclic group, $M^5$-O—, $M^5$-S—, $M^5$-S(O)—, $M^5$-S(O)$_2$—, $M^5$-C(O)—, $M^5$-O—C(O)—, $M^5$-C(O)—O—, $M^5M^6$N—C(O)—, $M^5$-C(O)—$NM^6$-, $M^5M^6$N—, $M^5$-C(S)—, $M^5$-O—C(S)—, $M^5$-C(S)—O—, $M^5M^6$N—C(S)—, $M^5$-C(S)—$NM^6$- or $M^5$-C(=N—O-$M^6$)-;

$M^2$, $M^3$ in each case independently of one another represent H, alkyl, alkenyl, alkynyl, haloalkyl, haloalkenyl, haloalkynyl, cyclic group, cyclic group alkyl;

$M^4$ independently of the others represents halogen, formyl, cyano, nitro, hydroxyl, alkyl, alkenyl, alkynyl, haloalkyl, haloalkenyl, haloalkynyl, $M^2$-O—, $M^2$-S—, $M^2$-S(O)—, $M^2$-S(O)$_2$—, $M^2$-C(O)—, $M^2$-O—C(O)—, $M^2$-C(O)—O—, $M^2M^3$N—C(O)—, $M^2$-C(O)—$NM^3$-, $M^2M^3$N—, $M2^5$-C(S)—, $M^2$-O—C(S)—, $M^2$-C(S)—O—, $M^2M^3$N—C(S)— or $M^2$-C(S)—$NM^3$-, a cyclic group which is optionally substituted by one or more halogen, cyano, nitro, alkyl, alkoxy, alkylthio, haloalkyl, haloalkoxy and/or haloalkylthio;

$M^5$, $M^6$ in each case independently of one another represent H or in each case independently of one another represent optionally cyano- or nitro-substituted alkyl, alkenyl, alkynyl, haloalkyl, haloalkenyl, haloalkynyl or in each case independently of one another represent an optionally formyl-, halogen-, cyano-, nitro-, alkyl-, haloalkyl-, alkoxy-, haloalkoxy-, alkylthio- or haloalkylthio-substituted cyclic group or cyclic group-alkyl;

and also salts, N-oxides, metal complexes and tautomeric forms of the compounds of the formula (I);

with the proviso that compounds of the formula (I) do not represent

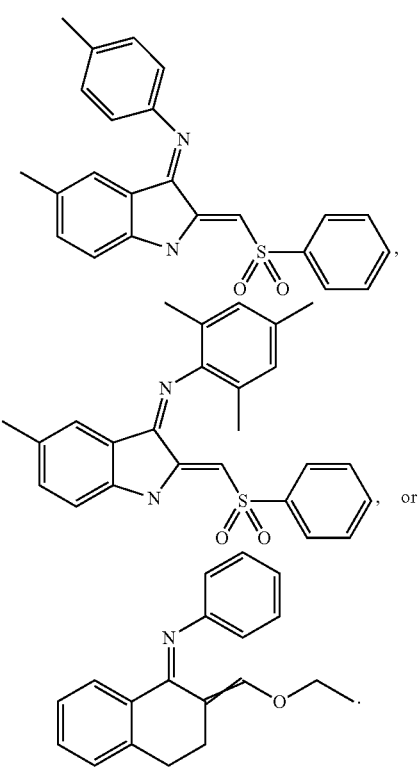

Substituents

In one embodiment, $Q^1$ represents an optionally substituted cyclic group, preferably optionally substituted aryl or heteroaryl, particularly preferably optionally substituted 6-membered aryl or optionally substituted 5- or 6-membered heteroaryl.

In one embodiment, $Q^1$ in each case represents optionally substituted methyl, propyl, butyl, pentyl, hexyl, heptyl, octyl, nonyl, decyl, alkenyl, alkynyl, a cyclic group or substituted ethyl.

In one embodiment, $Q^1$ represents an optionally substituted phenyl radical, an optionally substituted 5- or 6-membered carbocyclic group such as cyclopentyl or cyclohexyl or represents an optionally substituted 5- or 6-membered heteroaryl group such as pyridyl, indolyl.

In a further embodiment, X represents —S— or —O—, preferably —S—.

In a further embodiment, W represents H.

In a further embodiment, $Q^2$ represents optionally substituted aryl, preferably optionally substituted phenyl or optionally substituted naphthyl.

In one embodiment, $Q^2$ represents optionally substituted phenyl or optionally substituted naphthyl, where the substituents independently of one another are selected from the group consisting of halogen, cyano, $C_1$-$C_{10}$-alkyl (for example methyl or ethyl), $C_1$-$C_{10}$-alkoxy (for example methoxy or ethoxy), $C_1$-$C_{10}$-haloalkyl (for example halomethyl or haloethyl such as mono-, di- or trifluoromethyl, mono-, di- or trichloromethyl, mono-, di-, tri-, tetra- or pentafluoroethyl, mono-, di-, tri-, tetra- or pentachloroethyl).

In one embodiment $Q^2$ is a substituted phenyl, where the substituents independently of one another are selected from the group consisting of halogen, cyano, $C_1$-$C_{10}$-alkyl (for example methyl or ethyl), $C_1$-$C_{10}$-alkoxy (for example methoxy or ethoxy), $C_1$-$C_{10}$-haloalkyl (for example halomethyl or haloethyl such as mono-, di- or trifluoromethyl, mono-, di- or trichloromethyl, mono-, di-, tri-, tetra- or pentafluoroethyl, mono-, di-, tri-, tetra- or pentachloroethyl) and are located in the para- and/or meta-position to the position of the phenyl ring through which $Q^2$ is attached to the basic structure of the compounds of the formula (I) (see, for example, compounds of Table 1).

In one embodiment, $A^1$ represents —C($R^2,R^3$)—.

In one embodiment, $A^1$ represents a —C($R^2,R^3$)— group, where this group forms a double bond to the adjacent B position ($R^2$ or $R^3$ of the $A^1$-C($R^2,R^3$)— group forms a double bond with an $R^1$, an $R^2$ or an $R^3$ of the adjacent B position), or where this group is a bridging group which, together with a further bridging group and any B groups located between these bridging groups of the C(=C(W,X-$Q^1$)—C(=N-$Q^2$)-$A^1$-[B]$_n$-$A^2$ ring and a corresponding bridge U forms a cyclic system (for example a system selected from an unsubstituted or substituted cycloalkane system (for example a $C_4$-$C_{10}$- or $C_5$-$C_7$- or a $C_5$-cycloalkane system), an unsubstituted or substituted aromatic system (for example a 6-membered aromatic system (compound of the formula (I-6) or like a 10-membered aromatic system (for example naphthalene)) and a substituted or unsubstituted 5- or 6-membered heteroaromatic system (for example furan, thiophene, oxazole, isoxazole or pyridine)), or where this group carries a substituent V ($R^2$ and $R^3$ of the $A^1$-C($R^2,R^3$)— group together form a substituent V which is attached via a double bond to the carbon atom of the $A^1$ position.

In a further embodiment, $A^1$ is a bridging position and part of a cyclic system.

In a further embodiment, $A^1$ is a bridging position and part of a 5- or 6-membered carbocyclic or heterocyclic system.

In a further embodiment, $A^1$ is a bridging position and part of a fused 5- or 6-membered cyclic system.

In a further embodiment, $A^1$ is a bridging position and part of a 5- or 6-membered fused cyclic system selected from a group consisting of a 6-membered aromatic system, a cycloalkane system and a 5- or 6-membered heteroaromatic system.

In a further embodiment, $A^1$ is part of a fused aromatic or heteroaromatic system, preferably a 6-membered aromatic or heteroaromatic system or a 5-membered heteroaromatic system.

In one embodiment, $A^1$ and the position B, too, directly linked to $A^1$ through a bond (adjacent position B) are the bridging positions of a cyclic system, and both positions represent a —C($R^2, R^3$)— group.

In one embodiment, $A^1$, $A^2$ and all B represent —C($R^2, R^3$)—.

In one embodiment, $A^1$ and $A^2$ represent —C($R^2,R^3$)— and at least one B represents O or S.

In one embodiment, $R^2$ from a —C($R^2,R^3$)— group of at least one position B represents a substituent selected from the group consisting of halogen, $C_1$-$C_{10}$-alkyl (for example methyl or ethyl); $M^2$-O— (for example $C_1$-$C_{10}$-alkyl-O— or $C_1$-$C_{10}$-alkyl-S—, $C_1$-$C_{10}$-haloalkyl-O— or $C_1$-$C_{10}$-haloalkyl-S—); and an optionally substituted 3- to 14-membered cyclic group (for example phenyl, optionally substituted by halogen, $C_1$-$C_{10}$-haloalkyl or $C_1$-$C_{10}$-alkyl).

In one embodiment, $R^3$ of at least one position B represents a substituent selected from the group consisting of halogen, $C_1$-$C_{10}$-alkyl (for example methyl or ethyl); $M^2$-O— (for example $C_1$-$C_{10}$-alkyl-O— or $C_1$-$C_{10}$-alkyl-S—, $C_1$-$C_{10}$-haloalkyl-O— or $C_1$-$C_{10}$-haloalkyl-S—); and an optionally substituted 3- to 14-membered cyclic group (for example phenyl, optionally substituted by halogen, $C_1$-$C_{10}$-haloalkyl or $C_1$-$C_{10}$-alkyl).

In one embodiment, a compound of the formula (I) is a compound of the formula (I-5) and at least one $T^1$, $T^2$, $T^3$ or $T^4$ represents $CM^1$, where $M^1$ is selected from the group consisting of halogen (for example F or Cl), cyano, $C_1$-$C_{10}$-haloalkyl (for example $C_1$-, $C_2$-, $C_3$-, $C_4$-, $C_5$- or $C_6$-haloalkyl), $C_1$-$C_{10}$-alkyl (for example methyl, ethyl, propyl, butyl, pentyl), $C_1$-$C_{10}$-alkyl-O— (for example MeO-, EtO-) and a 3- to 14-membered group (for example optionally halogen-, $C_1$-$C_{10}$-haloalkyl- or $C_1$-$C_{10}$-alkyl-substituted phenyl or pyridyl).

In one embodiment, n=2.

In one embodiment, $A^2$ represents a —$C(R^2,R^3)$— group, where, preferably, $R^2$ and $R^3$ of this —$C(R^2,R^3)$— group in each case independently of one another represent H, $C_1$-$C_{10}$-alkyl, or a 3- to 14-membered cyclic group (for example phenyl, optionally substituted by halogen, $C_1$-$C_{10}$-haloalkyl or $C_1$-$C_{10}$-alkyl) or part of a cyclic system selected from a heteroalkane system or cycloalkane system—consisting of position $A^2$, position $A^1$ and, if present, B positions.

In a further embodiment, the two $R^2$ and the two $R^3$ of two adjacent $C(R^2,R^3)$ groups represent an optionally substituted aromatic system. Preferably, the optionally substituted aromatic system is an optionally substituted fused aromatic system. Also preferably, this system is fused to $A^1$ and to the B adjacent to $A^1$.

In a further embodiment, an $(R^2,R^3)$ pair of a $C(R^2,R^3)$ group at a position B or $A^2$ is V, preferably =O or =S.

In a further embodiment, $R^2$ represents a $C(R^2,R^3)$ group, preferably at a position B for —O-$M^2$ or —S-$M^2$.

In a further embodiment, a cyclic system or a bridge U in this cyclic system is mono- or disubstituted by a substituent $M^1$, preferably, $M^1$ is selected from a group consisting of halogen such as F or Cl, —O-$M^5$ or —S-$M^5$, optionally independently of one another with mono- or poly-$M^4$-substituted alkyl, haloalkyl or —N($M^6$)—C(O)-$M^5$.

In a further embodiment, $M^5$ is H or alkyl.

Position of the Double Bond X/$A^2$

Preference is given to compounds of the formula (I) in which X and $A^2$ are in the cis-position to one another.

Double Bonds Between $A^1$, B and $A^2$

In one embodiment, two adjacent positions selected from the group consisting of $A^1$, B and $A^2$ are linked by a double bond. Here, adjacent $A^1$, B, or $A^2$ positions represent —N($R^1$)— or —$C(R^2,R^3)$—. Alternatively, the $R^1$ of a first —N($R^1$)— group together with a further $R^1$ of an adjacent —N($R^1$)— group and together with the bond of the two nitrogen atoms of these adjacent groups forms a double bond between these two adjacent groups; or $R^3$ of a first —$C(R^2,R^3)$— group together with a further $R^3$ of an adjacent —$C(R^2,R^3)$— group and together with the bond of the two carbon atoms of these two adjacent groups forms a double bond between these two adjacent groups; or the $R^3$ of a —$C(R^2,R^3)$— group together with an $R^1$ of an adjacent —N($R^1$)— group and together with the bond of the carbon and nitrogen atoms of these adjacent groups forms a double bond between these two adjacent groups.

In one embodiment, there is a double bond between $A^1$ and an adjacent B (n is 1, 2, 3) or an adjacent $A^2$ (n is 0); here, $A^1$ preferably represents a —$C(R^2,R^3)$— group. More preferably, the double bond is part of a fused aromatic cyclic system comprising $A^1$ and an adjacent B or an adjacent $A^2$. In a preferred embodiment, the optionally substituted cyclic system is an aromatic system such as, for example, benzene or naphthalene.

In one embodiment, the $C(=C(W,X-Q^1)$-$C(=N-Q^2)$-$A^1$-$[B]_n$-$A^2$ ring of the basic structure of formula (I) contains two double bonds, for example, n may be 2 and the double bonds may be located between $A^1$ and the B adjacent to the $A^1$ and between $A^2$ and the B adjacent to the $A^2$.

In further embodiments, there is a double bond between two adjacent B or $A^2$ and an adjacent B.

Carbocyclic/Heterocyclic Systems and their Position

In addition to the $C(=C(W,X-Q^1)$-$C(=N-Q^2)$-$A^1$-$[B]_n$-$A^2$ ring of the basic structure of formula (I), two adjacent positions selected from the group consisting of $A^1$, B and $A^2$ may additionally be part of an optionally substituted cyclic system, preferably an optionally substituted $C_3$-$C_{14}$-membered carbocyclic or optionally substituted 3 to 14-membered heterocyclic system, i.e. these two adjacent positions selected from the group consisting of $A^1$, B and $A^2$ are bridging positions (fused system).

Here, adjacent $A^1$, B and $A^2$ firstly each represent —$C(R^2,R^3)$— and an $R^2$ of a first —$C(R^2,R^3)$— group together with a further $R^2$ of an adjacent —$C(R^2,R^3)$— group and together with the two carbon atoms of these adjacent groups forms an in each case optionally substituted carbocyclic or heterocyclic system; or an $R^3$ of first —$C(R^2,R^3)$— group together with a further $R^3$ of an adjacent —$C(R^2,R^3)$— group and together with the two carbon atoms of these adjacent groups forms an in each case optionally substituted carbocyclic or heterocyclic system. In one embodiment, only one $R^2$ pair at adjacent groups forms an optionally substituted cyclic system. In a further embodiment, both an $R^2$ pair and an $R^3$ pair of two adjacent groups forms an optionally substituted cyclic system.

Secondly, adjacent $A^1$, B and $A^2$ may each represent —N($R^1$)— and the $R^1$ of a first —N($R^1$)— group together with a further $R^1$ of an adjacent —N($R^1$)— group and together with the two nitrogen atoms of the adjacent groups forms an optionally substituted heterocyclic system.

Furthermore, a first adjacent $A^1$, B and $A^2$ may represent —N($R^1$)—, whereas a corresponding second adjacent $A^1$, B and $A^2$ represents —$C(R^2,R^3)$— and the $R^2$ of a —$C(R^2,R^3)$— group together with an $R^1$ of an adjacent —N($R^1$)— group and together with the carbon atom and the nitrogen atom of these two adjacent groups forms an optionally substituted heterocyclic system.

In a preferred embodiment, an optionally substituted fused system at $A^1$ and an adjacent B (n is 1, 2 or 3) or an adjacent $A^2$ (n is 0) is present. In further embodiments, such an optionally substituted fused system is present at two adjacent B or $A^2$ and one adjacent B. In a further embodiment, more than one optionally substituted fused system is present in a compound of the formula (I).

In a further preferred embodiment, $A^1$ is a —$C(R^2,R^3)$— group and part of an optionally substituted fused cyclic system.

In a further preferred embodiment, $A^1$ is a —$C(R^2,R^3)$— group and part of an optionally substituted fused aromatic system, preferably an optionally substituted fused monocyclic aromatic system.

In a further embodiment, non-adjacent $A^1$, B and $A^2$ may, in addition to the $C(=C(W,X-Q^1)$-$C(=N-Q^2)$-$A^1$-$[B]_n$-$A^2$ ring of the basic structure of the formula (I), form a further optionally substituted cyclic system, preferably an optionally substituted $C_4$-$C_{14}$-membered carbocyclic or optionally substituted 4 to 14-membered heterocyclic system (bridged system).

Here, non-adjacent $A^1$, B and $A^2$ firstly each represent —N($R^1$)— and an $R^1$ of a first of these —N($R^1$)— groups together with an $R^1$ of a non-adjacent —N($R^1$)— group, the two nitrogen atoms of these two non-adjacent groups and the 1, 2 or 3 B located between these two non-adjacent groups forms an optionally substituted heterocyclic system.

Alternatively, a non-adjacent $A^1$, B and $A^2$ which is part of an optionally substituted bridged system may represent a —$C(R^2,R^3)$— group and a second non-adjacent $A^1$, B and $A^2$ which is part of this optionally substituted bridged system may represent a —$N(R^1)$— group and an $R^2$ of a —$C(R^2,R^3)$— group together with an $R^1$ of a non-adjacent —$N(R^1)$— group, with the carbon atom and the nitrogen atom of these two non-adjacent groups and with the 1, 2 or 3 B located between these two non-adjacent groups forms an optionally substituted heterocyclic system.

Finally, non-adjacent $A^1$, B and $A^2$ may each represent a —$C(R^2,R^3)$— group, and an $R^2$ of a first —$C(R^2,R^3)$— group together with an $R^2$ of a second non-adjacent —$C(R^2,R^3)$— group, with the two carbon atoms of these two non-adjacent —$C(R^2,R^3)$— groups and with the 1, 2 or 3 B located between these two non-adjacent groups forms an in each case optionally substituted carbocyclic or heterocyclic system.

In a preferred embodiment, a bridged system is present at $A^1$ and a non-adjacent B (n is 2 or 3) or a non-adjacent $A^2$ (n is 1, 2, or 3). In further embodiments, such a bridged system is present at two non-adjacent B or $A^2$ and a non-adjacent B. In a preferred embodiment, a compound of the formula (I) contains only one bridged system.

In a further preferred embodiment, compounds of the formula (I) are compounds of the formula (I-0) in which $A^1$, $A^2$, $Q^1$, X, W, B, n and $Q^2$ are as defined above. The cyclic system is a cyclic system defined by one or two bridging positions, optionally positions B located between the bridging positions, and a bridge U. Thus, a compound of the formula (I-0) can also be depicted as a compound of the formula (I-0'). It is obvious to the person skilled in the art that the bridge U is part of the cyclic system of the compounds of the formula (I-0). The cyclic system may be an optionally substituted fused or bridging (non-fused) cyclic system or a spiro system.

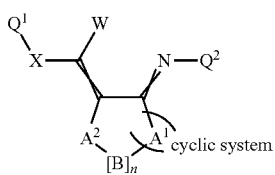

(I-0)

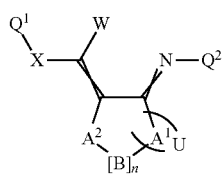

(I-0')

In one embodiment, $A^1$ in a compound of the formula (I-0) is a —$C(R^2,R^3)$— group. In a further embodiment, $A^1$ in a compound of the formula (I-0) is a bridging position, i.e. $A^1$ is part of the cyclic system and a —$C(R^2,R^3)$— group. In a further embodiment, the cyclic system of a compound of the formula (I-0) is a fused cyclic system formed by $A^1$, the group adjacent to $A^1$ ($A^2$ if n=0 or the B adjacent to $A^1$ if n=1, 2 or 3) and a bridge U.

In one embodiment, compounds of the formula (I) are compounds of the formula (I-1)

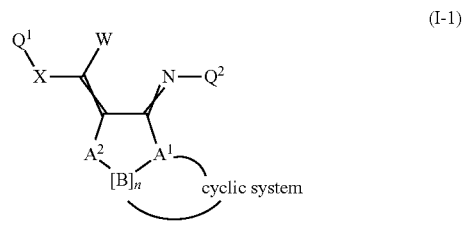

(I-1)

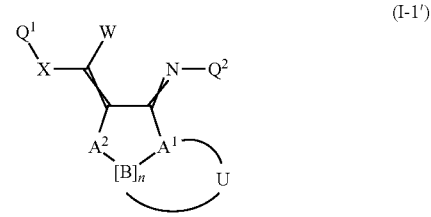

(I-1')

in which the cyclic system consists of the bridging position $A^1$, a bridging position B, any B positions located between the bridging positions, and a bridge U (see FIG. (I-1')). It is obvious to the person skilled in the art, that the term "cyclic system" used in the FIG. (I-1), as well as in all the other figures shown here, comprises the bridge U which is attached to the bridging positions (this is shown in FIG. (I-1')), and in which $A^2$, $Q^1$, X, W and $Q^2$ are as defined above and n is 1;
$A^1$ is —$C(R^2,R^3)$— or —$N(R^1)$—, preferably —$C(R^2,R^3)$—;
B is —$C(R^2,R^3)$— or —$N(R^1)$—, preferably —$C(R^2,R^3)$—; and
$A^1$ and the adjacent B are part of an optionally substituted cyclic system, preferably an optionally substituted 3- to 6-membered monocyclic system; or
n is 2 or 3;
$A^1$ is —$C(R^2,R^3)$— or —$N(R^1)$—, preferably —$C(R^2,R^3)$—;
B adjacent to $A^1$ is —$C(R^2,R^3)$— or —$N(R^1)$—, preferably —$C(R^2,R^3)$—;
B is otherwise Y, —$C(R^2,R^3)$— or —$N(R^1)$—; and
$A^1$ and the adjacent B are part of an optionally substituted cyclic system, preferably an optionally substituted 3- to 6-membered monocyclic system; or
n is 2;
$A^1$ and $A^2$ in each case independently of one another are —$C(R^2,R^3)$— or —$N(R^1)$—, preferably —$C(R^2,R^3)$—;
the B adjacent to $A^1$ may be —$C(R^2,R^3)$— or —$N(R^1)$—, preferably —$C(R^2,R^3)$—; and
the B adjacent to $A^2$ may be Y, —$C(R^2,R^3)$— or —$N(R^1)$—; and
$A^1$ and the adjacent B are, as bridging positions, part of an optionally substituted fused cyclic system, preferably an optionally substituted 5- to 6-membered monocyclic system; or
n is 2 or 3;
$A^1$ is —$C(R^2,R^3)$— or —$N(R^1)$—, preferably —$C(R^2,R^3)$—; and
B non-adjacent to $A^1$ and non-adjacent to $A^2$ (for n equals 3) or non-adjacent to $A^1$ and adjacent to
$A^2$ (for n equals 2, 3) is —$C(R^2,R^3)$— or —$N(R^1)$—, preferably —$C(R^2,R^3)$—;
B is otherwise Y, —$C(R^2,R^3)$— or —$N(R^1)$—; and
$A^1$ and this non-adjacent B and the 1 (for n equals 2, 3) or 2 B (for n equals 3) between $A^1$ and the non-adjacent B are part of an optionally substituted cyclic system, preferably an optionally substituted 4- to 6-membered monocyclic system.

In a further embodiment, compounds of the formula (I) are compounds of the formula (I-2)

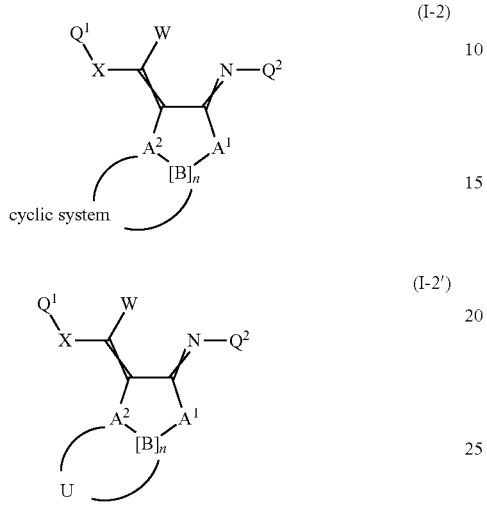

(I-2)

(I-2')

in which the cyclic system (FIG. (I-2)) consists of the bridging position $A^2$, a bridging position B, any B positions located between the bridging positions and a bridge U (see FIG. (I-2')) and in which $A^1$, $Q^1$, X, W and $Q^2$ are as defined above and n is 1;

$A^2$ is —C($R^2$,$R^3$)— or —N($R^1$)—, preferably —C($R^2$,$R^3$)—; and

B is —C($R^2$,$R^3$)— or —N($R^1$)—, preferably —C($R^2$,$R^3$)—; and $A^2$ and the adjacent B are part of an optionally substituted cyclic system, preferably an optionally substituted 3- to 6-membered monocyclic system; or n is 2 or 3;

$A^2$ is —C($R^2$,$R^3$)— or —N($R^1$)—, preferably —C($R^2$,$R^3$)—;

B adjacent to $A^2$ is —C($R^2$,$R^3$)— or —N($R^1$)—, preferably —C($R^2$,$R^3$)—;

B is otherwise Y, —C($R^2$,$R^3$)— or —N($R^1$)—; and $A^2$ and the adjacent B are part of an optionally substituted cyclic system, preferably an optionally substituted 3- to 6-membered monocyclic system; or n is 2 or 3;

$A^2$ is —C($R^2$,$R^3$)— or —N($R^1$)—, preferably —C($R^2$,$R^3$)—;

B non-adjacent to $A^1$ and non-adjacent to $A^2$ (for n equals 3) or non-adjacent to $A^1$ and adjacent to $A^2$ (for n equals 2, 3) is, —C($R^2$,$R^3$)— or —N($R^1$)—, preferably —C($R^2$,$R^3$)—;

B is otherwise Y, —C($R^2$,$R^3$)— or —N($R^1$)—; and $A^1$ and this non-adjacent B and the 1 (for n equals 2, 3) or 2 B (for n equals 3) between $A^1$ and the non-adjacent B are part of an optionally substituted cyclic system, preferably an optionally substituted 4- to 6-membered monocyclic system.

In a further embodiment, compounds of the formula (I) are compounds of the formula (I-3)

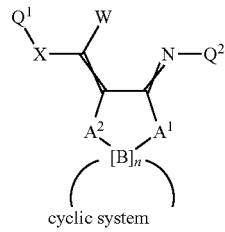

(I-3)

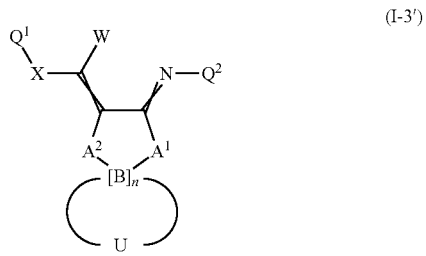

(I-3')

in which the cyclic system (FIG. (I-3)) consists of one or two bridging position(s) B, any B position located between the bridging positions, and a bridge U (see FIG. (I-3')) and in which $A^1$, $A^2$, $Q^1$, X, W and $Q^2$ are as defined above and n is 2;

B are each independently of one another —C($R^2$,$R^3$)— or —N($R^1$)—, preferably —C($R^2$,$R^3$)—, and the two B are part of a cyclic system, preferably an optionally substituted 3- to 6-membered monocyclic system; or n is 3;

two adjacent B are —C($R^2$,$R^3$)— or —N($R^1$)—, preferably —C($R^2$,$R^3$)—;

B is otherwise Y, —C($R^2$,$R^3$)— or —N($R^1$)—; and the two adjacent B are part of an optionally substituted cyclic system, preferably an optionally substituted 3- to 6-membered monocyclic system; or n is 3;

two non-adjacent B are —C($R^2$,$R^3$)— or —N($R^1$)—, preferably —C($R^2$,$R^3$)—;

a B between the two non-adjacent B is Y, —C($R^2$,$R^3$)— or —N($R^1$)—; and the two non-adjacent B and the one B are part of an optionally substituted cyclic system, preferably an optionally substituted 4- to 6-membered monocyclic system.

In a further embodiment, compounds of the formula (I) are compounds of the formula (I-4)

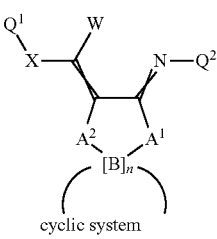

(I-4)

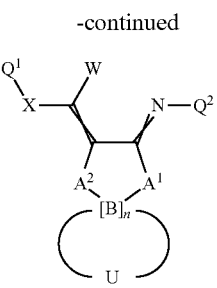

(I-4')

in which the cyclic system (FIG. (I-4)) consists of the bridging position $A^1$, a bridging position $A^2$, any B positions located between the bridging positions, and a bridge U (see FIG. (I-4')) and in which $Q^1$, X, W and $Q^2$ and B are as defined above and n is 0;

$A^1$ and $A^2$ are each independently of one another —C($R^2$, $R^3$)— or —N($R^1$)—, preferably —C($R^2$,$R^3$)—, and $A^1$ and $A^2$ are part of an optionally substituted cyclic system, preferably an optionally substituted 3- to 6-membered monocyclic system; or n is 1;

$A^1$ and $A^2$ are each independently of one another —C($R^2$, $R^3$)— or —N($R^1$)—, preferably —C($R^2$,$R^3$)—;

B is Y, —C($R^2$,$R^3$)— or —N($R^1$)—; and $A^1$ and $A^2$ together with B are part of an optionally substituted cyclic system, preferably an optionally substituted 4- to 6-membered monocyclic system; or n is 2;

$A^1$ and $A^2$ are each independently of one another —C($R^2$, $R^3$)— or —N($R^1$)—, preferably —C($R^2$,$R^3$)—;

B independently of the other are Y, —C($R^2$,$R^3$)— or —N($R^1$)—; and $A^1$ and $A^2$ together with the two B are part of an optionally substituted cyclic system, preferably an optionally substituted 5- to 6-membered monocyclic system; or n is 3;

$A^1$ and $A^2$ are each independently of one another —C($R^2$, $R^3$)— or —N($R^1$)—, preferably —C($R^2$,$R^3$)—; B independently of the others is Y, —C($R^2$,$R^3$)— or —N($R^1$)—; and $A^1$ and $A^2$ together with the three B are part of an optionally substituted cyclic system, preferably an optionally substituted 5-6-membered monocyclic system.

If $A^1$ together with a preferably adjacent B (formula (I-1)) or a preferably adjacent (n is 0) $A^2$ (formula (I-4)), or a B with a further preferably adjacent B (formula (I-3)) or preferably adjacent $A^2$ (formula (I-2)) forms an in each case optionally substituted cyclic system, preferably an optionally substituted carbocyclic system or an optionally substituted heterocyclic system, it is obvious to the person skilled in the art that $A^1$, B and/or $A^2$ in the first case each represent C($R^2$,$R^3$) and in the second case may represent either N($R^1$) and/or C($R^2$, $R^3$).

In a preferred embodiment of the compounds of the formula (I-1), the optionally substituted cyclic system is a fused system, i.e. $A^1$ and the adjacent B are part of the optionally substituted cyclic system, preferably an optionally substituted 3- to 6-membered monocyclic system.

In a further embodiment of the compounds of the formula (I-1), the optionally substituted fused cyclic system is a ($C_{ll}$-$C_{ul}$)-carbocyclic system, preferably a 6-membered monocyclic aromatic system.

In a further embodiment of the compounds of the formula (I-1), the fused optionally substituted cyclic system is a ($C_5$-$C_6$)-heteroaromatic system.

If two C($R^2$,$R^3$) groups are involved in the formation of a fused carbocyclic or heterocyclic system, the two $R^2$ of the adjacent C($R^2$,$R^3$) groups form the ($C_{ll-2}$-$C_{ul-2}$)-radical of an ll- to ul-membered carbocyclic or heterocyclic system. The carbocyclic system may be an optionally substituted cycloalkane system or an optionally substituted cycloalkene system. Furthermore, the two $R^3$ may optionally together with the C($R^2$,$R^3$)—C($R^2$,$R^3$) bond form a C($R^2$)=C($R^2$) double bond. Thus, here, the carbocyclic system may represent a cycloalkene system or an aromatic system.

In a further embodiment, $A^1$ is a C($R^2$,$R^3$) group and $R^3$ with an $R^3$ if an adjacent C($R^2$,$R^3$) group ($A^2$ if n equals 0 or B if n equals 1, 2, 3) together with the bond between the two adjacent groups forms a double bond. Preferably, the two $R^3$ of the two adjacent groups form an in each case optionally substituted carbocyclic system or heterocyclic system. More preferably, the optionally substituted carbocyclic system is an optionally substituted aromatic system or the optionally substituted heterocyclic system is an optionally substituted heteroaromatic system. Particularly preferably, the optionally substituted aromatic system is a 6-membered monocyclic system or the optionally substituted heteroaromatic system is a 5- or 6-membered monocyclic system.

One embodiment of the compounds of the formula I-1 are compounds of the formula (I-5)

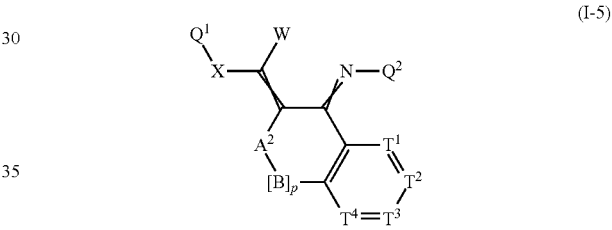

(I-5)

in which $Q^1$, $Q^2$W, X, $A^2$, B and $M^1$ have the meaning described above, p represents 0, 1 or 2, preferably 1, and $T^1$, $T^2$, $T^3$ and $T^4$ independently of one another represent CH or $CM^1$ or N, where at most 2 T selected from the group consisting of $T^1$, $T^2$, $T^3$ and $T^4$ represent N and preferably 0, 1 or 2 T selected from the group consisting of $T^1$, $T^2$, $T^3$ and $T^4$ represent $CM^1$; particularly preferably, 0 or 1 T represents $CM^1$.

In one embodiment, compounds of the formula (I-5) are compounds of the formula (I-6)

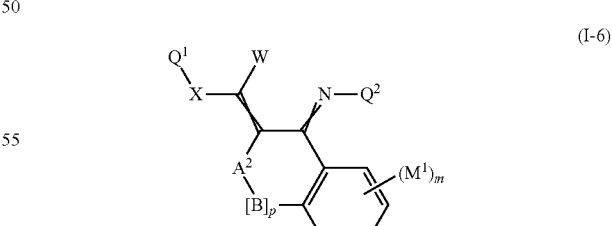

(I-6)

where $Q^1$, $Q^2$W, X, $A^2$, B and $M^1$ have the meaning described above, p represents 0, 1 or 2 and m represents 0, 1, 2, 3 or 4, preferably 0, 1 or 2 and more preferably 0 or 1.

In one embodiment, $A^2$ in a compound of the formula (I-6) is —C($R^2$,$R^3$)—.

In one embodiment, n in a compound of the formula (I-6) equals 0.

In a further embodiment, n in a compound of the formula (I-6) equals 1.

In a further embodiment, n in a compound of the formula (I-6) equals 1 and B is —C(R², R³)—.

In one embodiment, n in a compound of the formula (I-6) equals 1 and B is O or S.

In one embodiment, compounds of the formula (I-5) are compounds of the formula (I-7)

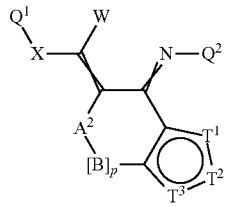

(I-7)

where $Q^1$, $Q^2W$, X, $A^2$, B and $M^1$ have the meaning described above, p represents 0, 1 or 2 and $T^1$, $T^2$ and $T^3$ represents CH or $CM^1$, O, S or N or NH or $NM^1$, with the proviso that $M^1$ is not halogen if it is attached to N, where at most one $T^1$, $T^2$ or $T^3$ represents O or S and at most 2 T selected from the group consisting of $T^1$, $T^2$ and $T^3$ represents CH or $CM^1$; preferably, 0 or 1 T represents CH or $CM^1$.

In one embodiment, in compounds of the formula (I-7) $T^1$ and $T^2$ represent CH or $CM^1$ and $T^3$ represents O or S.

In one embodiment, in compounds of the formula (I-7) $T^1$, $T^2$ and $T^3$ represent CH or $CM^1$.

In one embodiment, in compounds of the formula (I-7) n represents 1.

A further embodiment are compounds of the formula (I-8)

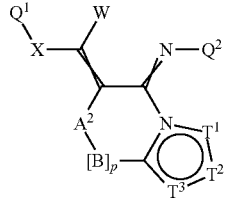

(I-8)

where $Q^1$, $Q^2W$, X, $A^2$, B and $M^1$ have the meaning described above, p represents 0, 1 or 2 and $T^1$, $T^2$ and $T^3$ represent CH or $CM^1$ or N or NH or $NM^1$, with the proviso that $M^1$ is not halogen if it is attached to N, where at most two T selected from the group consisting of $T^1$, $T^2$ and $T^3$ represent $NM^1$ or NH; preferably 0 or 1 T represents $NM^1$ or NH.

A further embodiment are compounds of the formula (I-9)

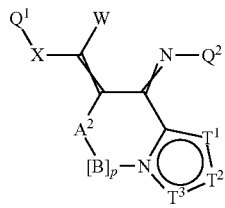

(I-9)

where $Q^1$, $Q^2W$, X, $A^2$, B and $M^1$ have the meaning described above, p represents 0, 1 or 2 and $T^1$, $T^2$ and $T^3$ represent CH or $CM^1$ or N or NH or $NM^1$, with the proviso that $M^1$ is not halogen if it is attached to N, where at most two T selected from the group consisting of $T^1$, $T^2$ and $T^3$ represent $NM^1$ or NH; preferably, 0 or 1 T represents $NM^1$ or NH.

Further embodiments describe compounds of the formula (I) according to the invention

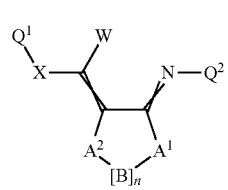

(I)

in which $Q^1$, X, W and $Q^2$ have the meaning described above and:

Embodiment 1

$A^1$ is $C(R^2, R^3)$, $A^2$ is $C(R^2, R^3)$, each B is $C(R^2, R^3)$, n is 0, 1, 2, 3

Embodiment 1.A $A^1$ is $C(R^2, R^3)$, $A^2$ is $C(R^2, R^3)$, n is 0; preferred embodiments describe compounds of the formulae 1.A.1 and 1.A.2.

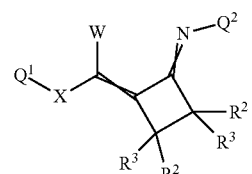

Formula 1.A.1

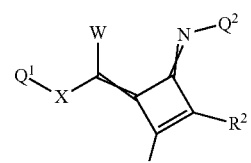

Formula 1.A.2

Embodiment 1.B $A^1$ is $C(R^2, R^3)$, $A^2$ is $C(R^2, R^3)$, each B is $C(R^2, R^3)$, n is 1; preferred embodiments describe compounds of the formulae 1.B.1, 1.B.2, 1.B.3, 1.B.4 and 1.B.5.

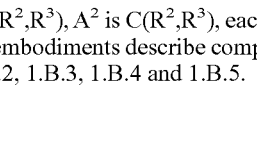

Formula 1.B.1

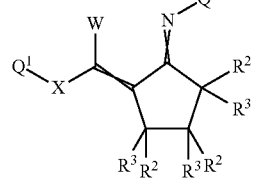

Formula 1.B.2
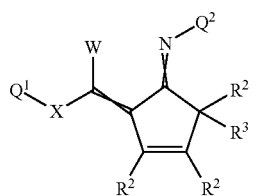

Formula 1.B.3
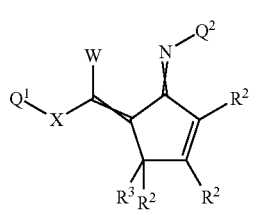

Formula 1.B.4
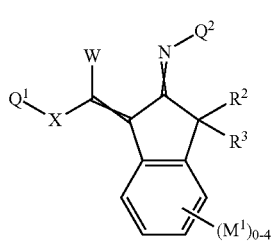

Formula 1.B.5
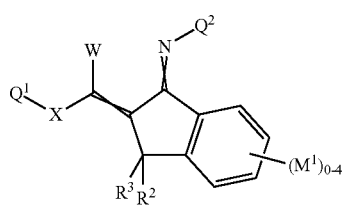

Embodiment 1.C $A^1$ is $C(R^2,R^3)$, $A^2$ is $C(R^2,R^3)$, each B is $C(R^2,R^3)$, n is 2; preferred embodiments describe compounds of the formulae 1.C.1, 1.C.2, 1.C.3, 1.C.4, 1.C.5, 1.C.6, 1.C.7 and 1.C.8.

Formula 1.C.1
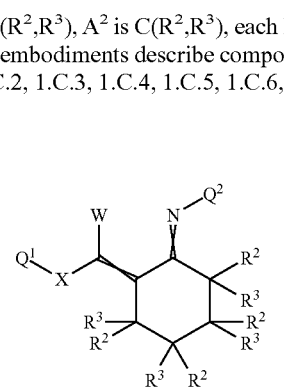

Formula 1.C.2
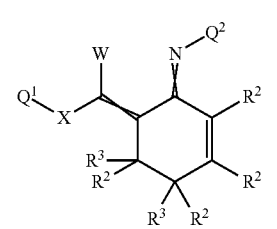

Formula 1.C.3
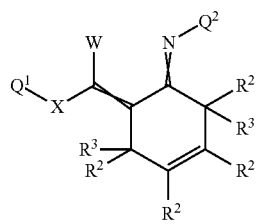

Formula 1.C.4
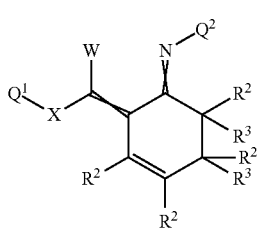

Formula 1.C.5
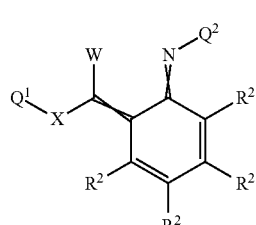

Formula 1.C.6
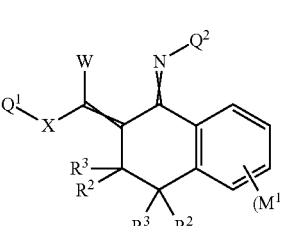

Formula 1.C.7
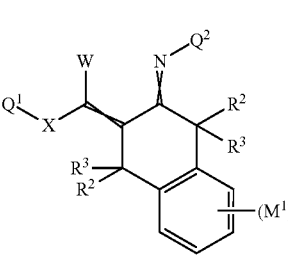

Formula 1.C.8
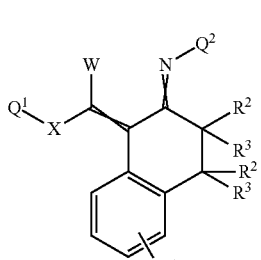

Embodiment 1.D $A^1$ is $C(R^2,R^3)$, $A^2$ is $C(R^2,R^3)$, each B is $C(R^2,R^3)$, n is 3; preferred embodiments describe compounds of the formulae 1.D.1, 1.D.2, 1.D.3, 1.D.4, 1.D.5, 1.D.6, 1.D.7, 1.D.8, 1.D.9, 1.D.10, 1.D.11 and 1.D.12.

Formula 1.D.1
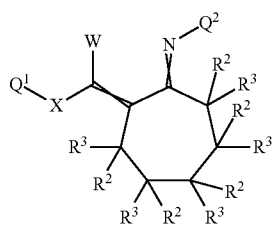

Formula 1.D.2
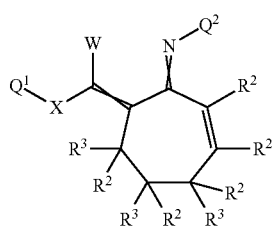

Formula 1.D.3
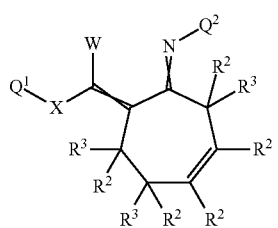

Formula 1.D.4
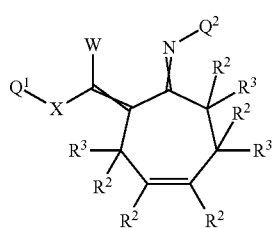

Formula 1.D.5
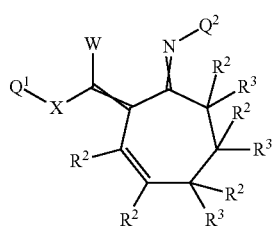

Formula 1.D.6
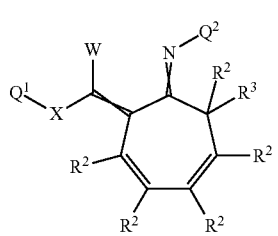

Formula 1.D.7
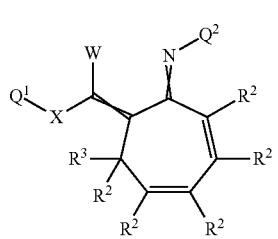

Formula 1.D.8
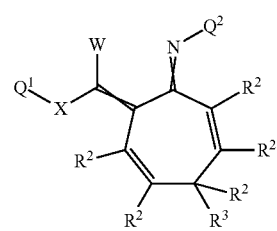

Formula 1.D.9
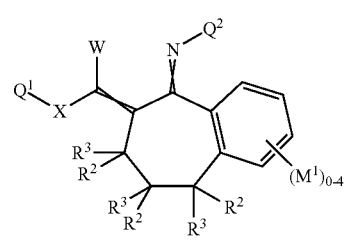

Formula 1.D.10
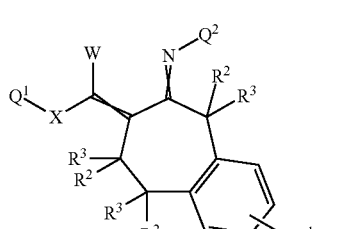

Formula 1.D.11
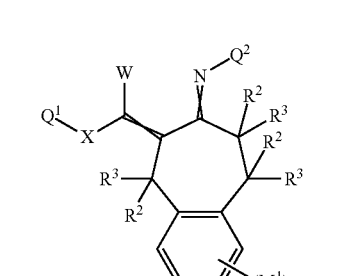

Formula 1.D.12
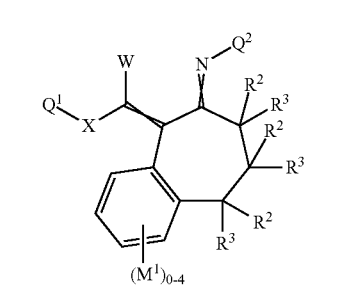

In a further embodiment, the $C(=C(W,X-Q^1)-C(=N-Q^2)-A^1-[B]_n-A^2$ ring of the basic structure of the formula (I) forms 4-membered heterocycles which are described in more detail below:

Embodiment 2

$A^1$ is Y, $A^2$ is $C(R^2, R^3)$, n is 0; preferred embodiments describe compounds of the formula 2.A.1.

Formula 2.A.1

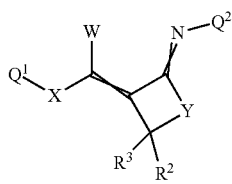

In a further embodiment, the C(=C(W,X-$Q^1$)—C(=N-$Q^2$)-$A^1$-[B]$_n$-$A^2$ ring of the basic structure of the formula (I) forms heterocycles which are described in more detail below:

Embodiment 3

$A^1$ is Y, $A^2$ is C($R^2$,$R^3$), each B is C($R^2$,$R^3$), n is 0, 1, 2, 3, where at least one of these ($R^2$,$R^3$) pairs represents V.

Embodiment 3.A $A^1$ is Y, $A^2$ is C($R^2$,$R^3$), each B is C($R^2$,$R^3$), n is 1, where at least one of these ($R^2$,$R^3$) pairs represents V; preferred embodiments describe compounds of the formulae 3.A.1 and 3.A.2.

Formula 3.A.1

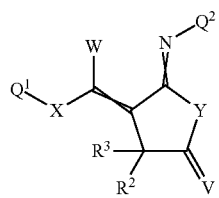

Formula 3.A.2

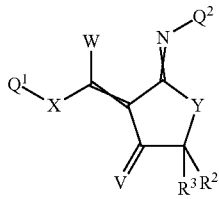

Embodiment 3.B $A^1$ is Y, $A^2$ is C($R^2$,$R^3$), each B is C($R^2$,$R^3$), n is 1, where at least one of these ($R^2$,$R^3$) pairs represents =O; preferred embodiments describe compounds of the formulae 3.B.1 and 3.B.2.

Formula 3.B.1

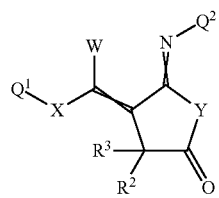

Formula 3.B.2

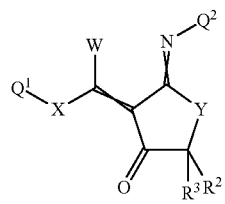

Embodiment 3.C $A^1$ is Y, $A^2$ is C($R^2$,$R^3$), each B is C($R^2$,$R^3$), n is 2, where at least one of these ($R^2$,$R^3$) pairs represents V; preferred embodiments describe compounds of the formulae 3.C.1, 3.C.2 and 3.C.3.

Formula 3.C.1

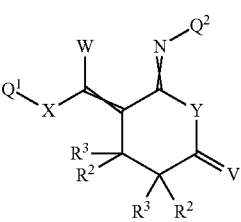

Formula 3.C.2

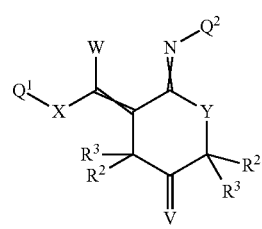

Formula 3.C.3

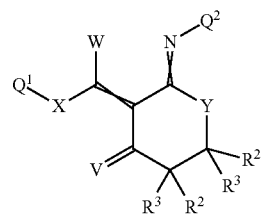

Embodiment 3.D $A^1$ is Y, $A^2$ is C($R^2$,$R^3$), each B is C($R^2$,$R^3$), n is 2, where at least one of these ($R^2$,$R^3$) pairs represents =O; preferred embodiments describe compounds of the formulae 3.D.1, 3.D.2 and 3.D.3.

Formula 3.D.1

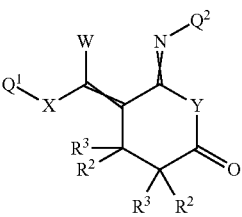

Formula 3.D.2

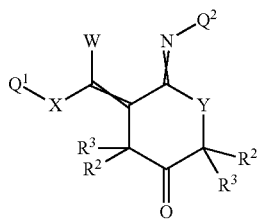

Formula 3.D.3

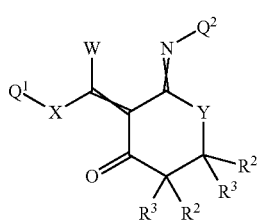

Embodiment 3.E

A$^1$ is Y, A$^2$ is C(R$^2$,R$^3$), each B is C(R$^2$,R$^3$), n is 3, where at least one of these (R$^2$,R$^3$) pairs represents V; preferred embodiments describe compounds of the formulae 3.E.1, 3.E.2, 3.E.3 and 3.E.4.

Formula 3.E.1

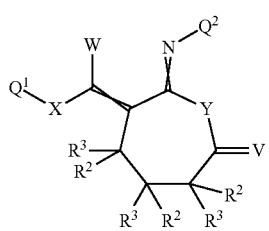

Formula 3.E.2

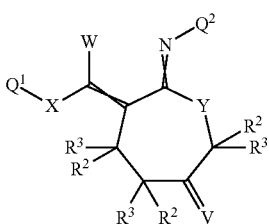

Formula 3.E.3

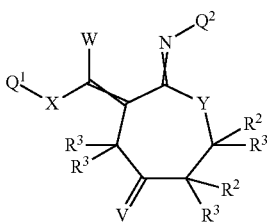

Formula 3.E.4

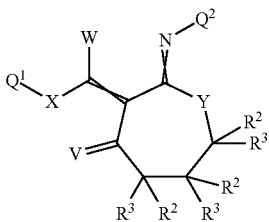

Embodiment 3.F

A$^1$ is Y, A$^2$ is C(R$^2$,R$^3$), each B is C(R$^2$,R$^3$), n is 3, where at least one of these (R$^2$,R$^3$) pairs represents =O; preferred embodiments describe compounds of the formulae 3.F.1, 3.F.2, 3.F.3 and 3.F.4.

Formula 3.F.1

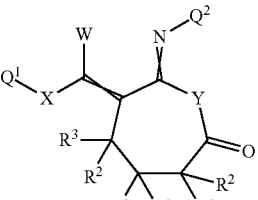

Formula 3.F.2

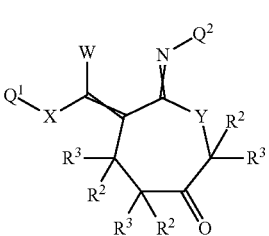

Formula 3.F.3

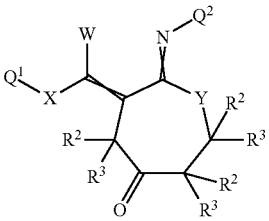

Formula 3.F.4

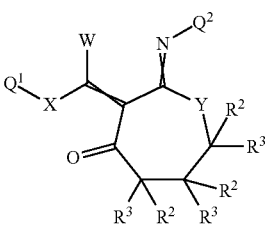

In a further embodiment, the C(=C(W,X-Q$^1$))—C(=N-Q$^2$)-A$^1$-[B]$_n$-A$^2$ ring of the basic structure of the formula (I) forms heterocycles having exactly one heteroatom Y which are described in more detail below:

Embodiment 4 of A$^1$, B and A$^2$, exactly one is Y, all others are C(R$^2$,R$^3$), n is 0, 1, 2, 3.

Embodiment 4.A

A$^1$ and A$^2$ are C(R$^2$,R$^3$), one B is Y, further B are C(R$^2$,R$^3$), n is 1, 2, 3.

Embodiment 4.B

A$^1$ and A$^2$ are C(R$^2$,R$^3$), B is Y, n is 1; preferred embodiments describe compounds of the formula 4.B.1.

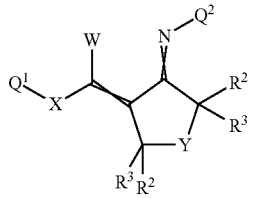

Formula 4.B.1

Embodiment 4.C $A^1$ and $A^2$ are $C(R^2,R^3)$, one B is Y and the second B is $C(R^2,R^3)$, n is 2.

Embodiment 4.D $A^1$ and $A^2$ are $C(R^2,R^3)$, one B is Y and the second B is $C(R^2,R^3)$, n is 2, where Y is adjacent to $A^1$; preferred embodiments describe compounds of the formulae 4.D.1 and 4.D.2.

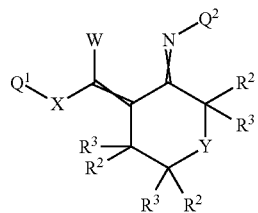

Formula 4.D.1

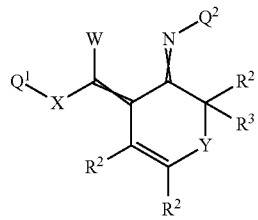

Formula 4.D.2

Embodiment 4.E $A^1$ and $A^2$ are $C(R^2,R^3)$, one B is Y and the second B is $C(R^2,R^3)$, n is 2, where Y is adjacent to $A^2$; preferred embodiments describe compounds of the formulae 4.E.1 and 4.E.2.

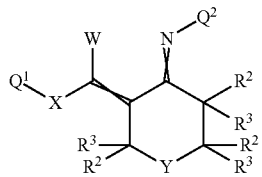

Formula 4.E.1

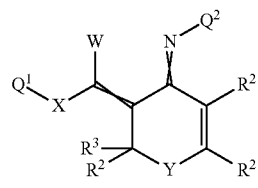

Formula 4.E.2

Embodiment 4.F $A^1$ and $A^2$ are $C(R^2,R^3)$, exactly one B is Y, all other B are $C(R^2,R^3)$, n is 3.

Embodiment 4.G $A^1$ and $A^2$ are $C(R^2,R^3)$, exactly one B is Y, all other B are $C(R^2,R^3)$, n is 3, where Y is adjacent to $A^1$; preferred embodiments describe compounds of the formulae 4.G.1, 4.G.2 and 4.G.3.

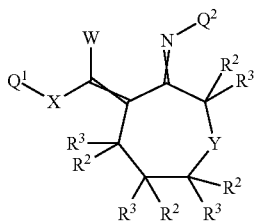

Formula 4.G.1

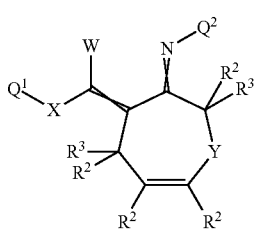

Formula 4.G.2

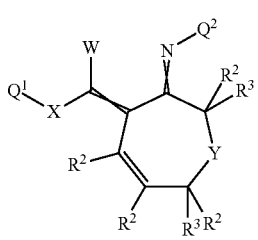

Formula 4.G.3

Embodiment 4.H $A^1$ and $A^2$ are $C(R^2,R^3)$, exactly one B is Y, all other B are $C(R^2,R^3)$, n is 3, where Y is non-adjacent to $A^1$ and non-adjacent to $A^2$; preferred embodiments describe compounds of the formulae 4.H.1, 4.H.2, 4.H.3 and 4.H.4.

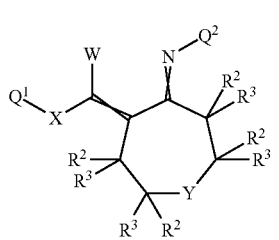

Formula 4.H.1

-continued

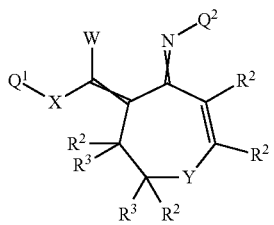
Formula 4.H.2

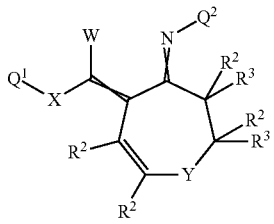
Formula 4.H.3

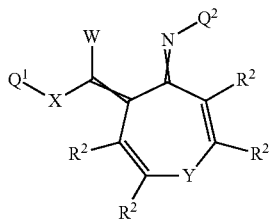
Formula 4.H.4

Embodiment 4.I $A^1$ and $A^2$ are $C(R^2,R^3)$, exactly one B is Y, all other B are $C(R^2,R^3)$, n is 3, where Y is adjacent to $A^2$; preferred embodiments describe compounds of the formulae 4.I.1, 4.I.2 and 4.I.3.

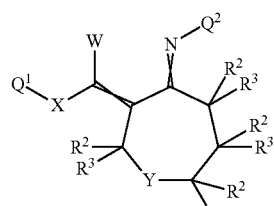
Formula 4.I.1

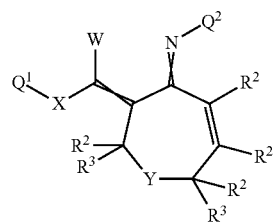
Formula 4.I.2

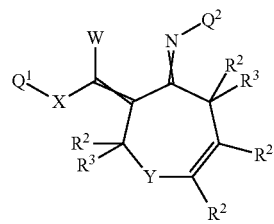
Formula 4.I.3

Embodiment 4.J $A^1$ is $C(R^2,R^3)$, $A^2$ is Y, each B is $C(R^2,R^3)$, n is 0, 1, 2, 3.

Embodiment 4.K $A^1$ is $C(R^2,R^3)$, $A^2$ is Y, n is 0; preferred embodiments describe compounds of the formula 4.K.1.

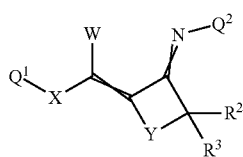
Formula 4.K.1

Embodiment 4.L $A^1$ is $C(R^2,R^3)$, $A^2$ is Y, B is $C(R^2,R^3)$, n is 1; preferred embodiments describe compounds of the formulae 4.L.1 and 4.L.2.

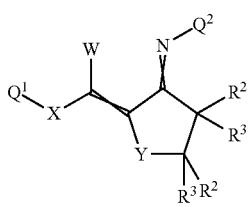
Formula 4.L.1

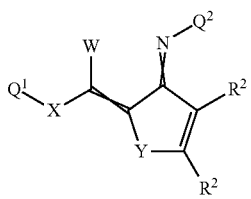
Formula 4.L.2

Embodiment 4.M $A^1$ is $C(R^2,R^3)$, $A^2$ is Y, each B is $C(R^2,R^3)$, n is 2; preferred embodiments describe compounds of the formulae 4.M.1, 4.M.2 and 4.M.3.

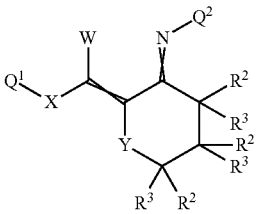
Formula 4.M.1

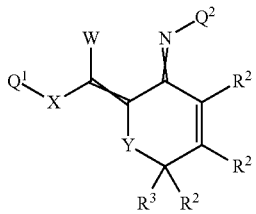
Formula 4.M.2

Formula 4.M.3

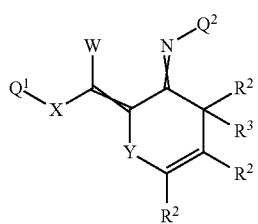

Embodiment 4.N $A^1$ is $C(R^2,R^3)$, $A^2$ is Y, each B is $C(R^2,R^3)$, n is 3; preferred embodiments describe compounds of the formulae 4.N.1, 4.N.2, 4.N.3, 4.N.4 and 4.N.5.

Formula 4.N.1

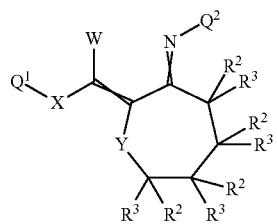

Formula 4.N.2

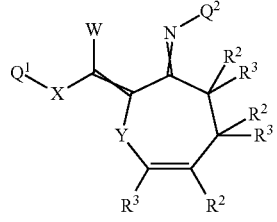

Formula 4.N.3

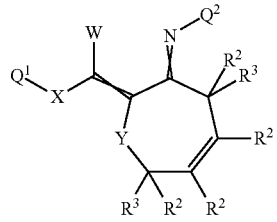

Formula 4.N.4

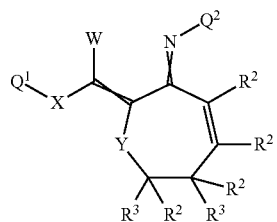

Formula 4.N.5

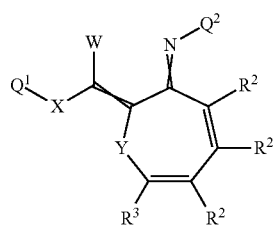

In a further embodiment, the $C(=C(W,X-Q^1)-C(=N-Q^2)-A^1-[B]_n-A^2$ ring of the basic structure of the formula (I) forms heterocycles having exactly one heteroatom N which are described in more detail below:

Embodiment 5 of $A^1$, B and $A^2$, exactly one is $—N(R^1)—$, all others are $C(R^2,R^3)$.

Embodiment 5.A $A^1$ and $A^2$ are $C(R^2,R^3)$, of B, exactly one is $—N(R^1)—$, all others are $C(R^2,R^3)$, n is 1, 2, 3.

Embodiment 5.B $A^1$ and $A^2$ are $C(R^2,R^3)$, B is $—N(R^1)—$, n is 1; preferred embodiments describe compounds of the formula 5.B.1.

Formula 5.B.1

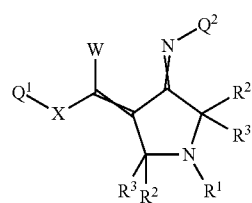

Embodiment 5.C $A^1$ and $A^2$ are $C(R^2,R^3)$, one B is $—N(R^1)—$ and the second B is $C(R^2,R^3)$, n is 2.

Embodiment 5.D $A^1$ and $A^2$ are $C(R^2,R^3)$, one B is $—N(R^1)—$ and the second B is $C(R^2,R^3)$, n is 2, where the group $—N(R^1)—$ is adjacent to $A^1$; preferred embodiments describe compounds of the formulae 5.D.1, 5.D.2, 5.D.3, 5.D.4 and 5.D.5.

Formula 5.D.1

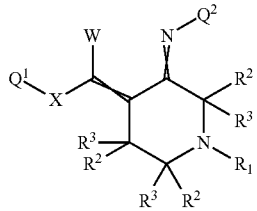

Formula 5.D.2

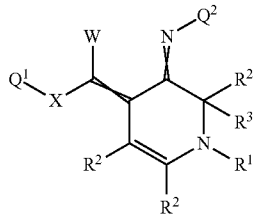

Formula 5.D.3

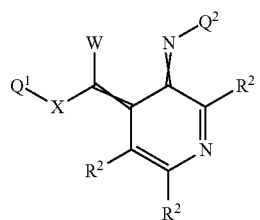

Formula 5.D.4

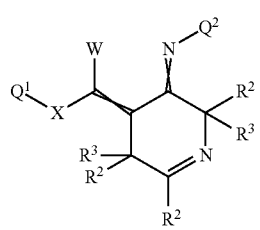

Formula 5.D.5

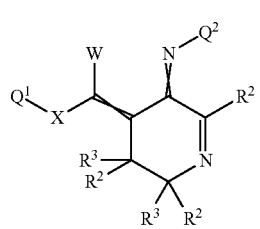

Embodiment 5.E $A^1$ and $A^2$ are $C(R^2,R^3)$, one B is —$N(R^1)$— and the second B is $C(R^2,R^3)$, n is 2, where the group —$N(R^1)$— is adjacent to $A^2$; preferred embodiments describe compounds of the formulae 5.E.1, 5.E.2, 5.E.3, 5.E.4 and 5.E.5.

Formula 5.E.1

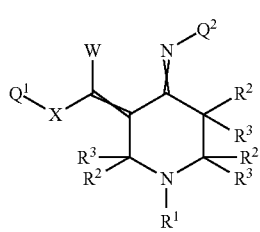

Formula 5.E.2

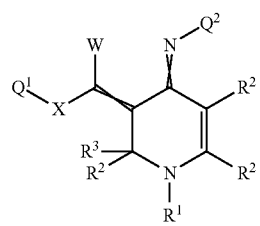

Formula 5.E.3

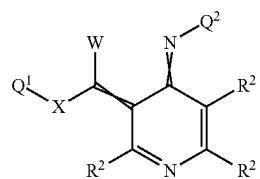

Formula 5.E.4

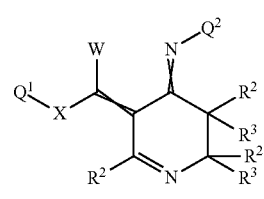

Formula 5.E.5

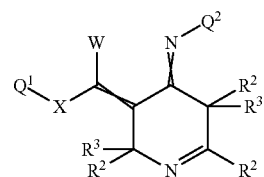

Embodiment 5.F $A^1$ and $A^2$ are $C(R^2,R^3)$, exactly one B is —$N(R^1)$—, all other B are $C(R^2,R^3)$, n is 3.

Embodiment 5.G $A^1$ and $A^2$ are $C(R^2,R^3)$, exactly one B is —$N(R^1)$—, all other B are $C(R^2,R^3)$, n is 3, where the group —$N(R^1)$— is adjacent to $A^1$; preferred embodiments describe compounds of the formulae 5.G.1, 5.G.2 and 5.G.3.

Formula 5.G.1

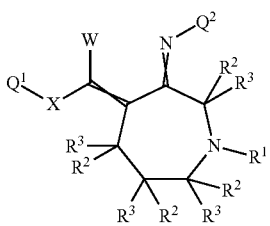

Formula 5.G.2

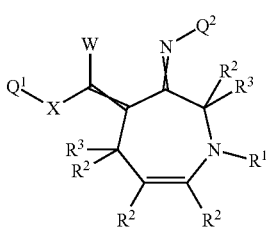

Formula 5.G.3

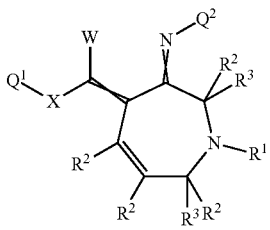

Embodiment 5.H $A^1$ and $A^2$ are $C(R^2,R^3)$, exactly one B is —$N(R^1)$—, all other B are $C(R^2,R^3)$, n is 3, where —$N(R^1)$— is not adjacent to $A^1$ and $A^2$; preferred embodiments describe compounds of the formulae 5.H.1, 5.H.2, 5.H.3 and 5.H.4.

Formula 5.H.1

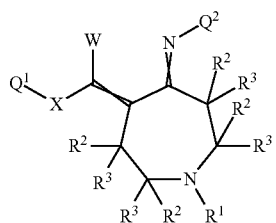

Formula 5.H.2

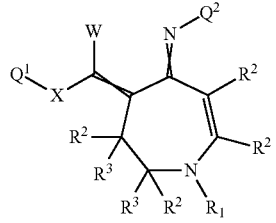

Formula 5.H.3

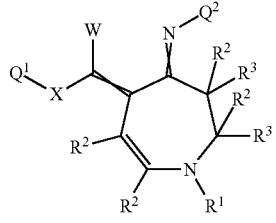

Formula 5.H.4

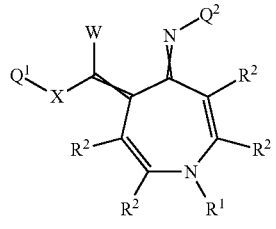

Embodiment 5.I $A^1$ and $A^2$ are $C(R^2,R^3)$, exactly one B is —N($R^1$)—, all other B are $C(R^2,R^3)$, n is 3, where —N($R^1$)— is adjacent to $A^2$; preferred embodiments describe compounds of the formulae 5.I.1, 5.I.2 and 5.I.3.

Formula 5.I.1

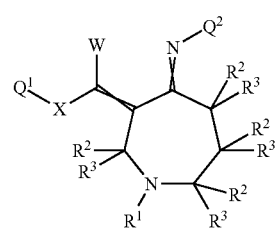

Formula 5.I.2

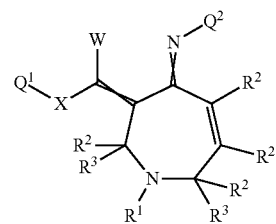

Formula 5.I.3

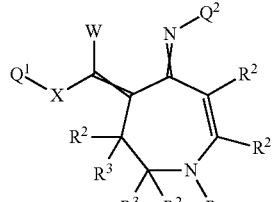

Embodiment 5.J $A^1$ is —N($R^1$)—, $A^2$ is $C(R^2,R^3)$, each B is $C(R^2,R^3)$, n is 0, 1, 2, 3.

Embodiment 5.K $A^1$ is —N($R^1$)—, $A^2$ is $C(R^2,R^3)$, n is 0; preferred embodiments describe compounds of the formula 5.K.1.

Formula 5.K.1

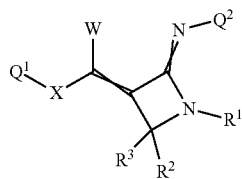

Embodiment 5.L $A^1$ is —N($R^1$)—, $A^2$ is $C(R^2,R^3)$, B is $C(R^2,R^3)$, n is 1; preferred embodiments describe compounds of the formulae 5.L.1, 5.L.2 and 5.L.3.

Formula 5.L.1

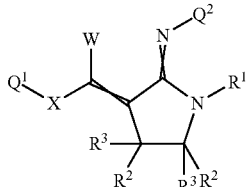

Formula 5.L.2

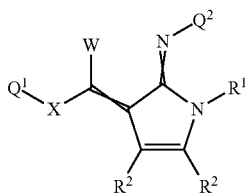

Formula 5.L.3

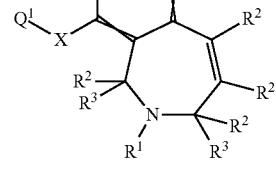

Embodiment 5.M $A^1$ is —$N(R^1)$—, $A^2$ is $C(R^2,R^3)$, each B is $C(R^2,R^3)$, n is 2; preferred embodiments describe compounds of the formulae 5.M.1, 5.M.2, 5.M.3 and 5.M.4.

Formula 5.M.1

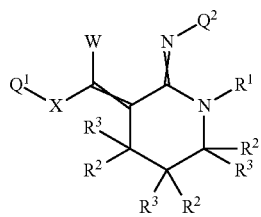

Formula 5.M.2

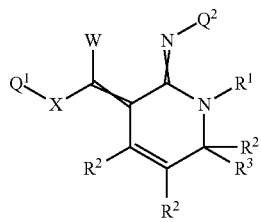

Formula 5.M.3

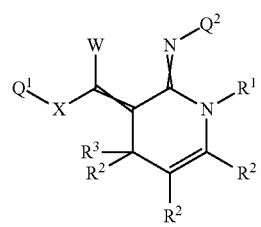

Formula 5.M.4

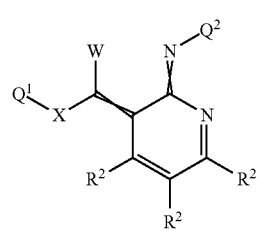

Embodiment 5.N $A^1$ is —$N(R^1)$—, $A^2$ is $C(R^2,R^3)$, each B is $C(R^2,R^3)$, n is 3; preferred embodiments describe compounds of the formulae 5.N.1, 5.N.2, 5.N.3, 5.N.4 and 5.N.5.

Formula 5.N.1

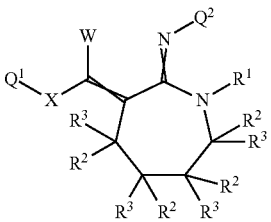

Formula 5.N.2

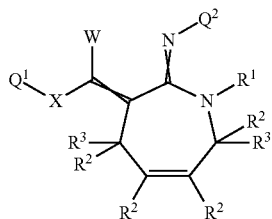

Formula 5.N.3

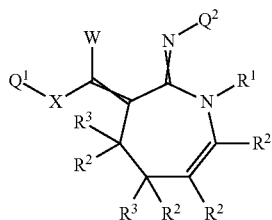

Formula 5.N.4

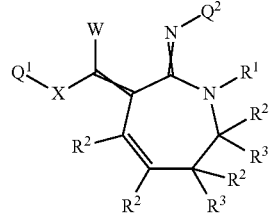

Formula 5.N.5

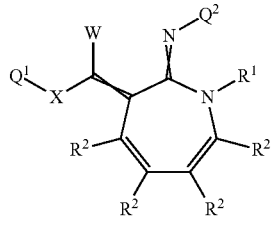

Embodiment 5.O $A^1$ is $C(R^2,R^3)$, $A^2$ is —$N(R^1)$—, each B is $C(R^2,R^3)$, n is 0, 1, 2, 3.

Embodiment 5.P $A^1$ is $C(R^2,R^3)$, $A^2$ is —$N(R^1)$—, n is 0; preferred embodiments describe compounds of the formula 5.P.1.

Formula 5.P.1

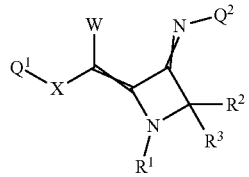

Embodiment 5.Q $A^1$ is $C(R^2,R^3)$, $A^2$ is —$N(R^1)$—, B is $C(R^2,R^3)$, n is 1; preferred embodiments describe compounds of the formulae 5.Q.1 and 5.Q.2.

Formula 5.Q.1

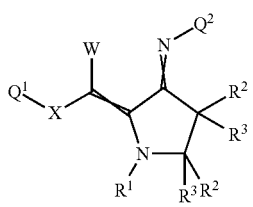

Formula 5.Q.2

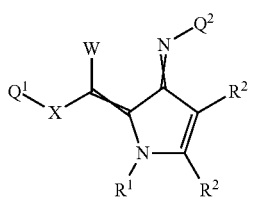

Embodiment 5.R $A^1$ is $C(R^2,R^3)$, $A^2$ is —$N(R^1)$—, each B is $C(R^2,R^3)$, n is 2; preferred embodiments describe compounds of the formulae 5.R.1, 5.R.2, 5.R.3, 5.R.4 and 5.R.5.

Formula 5.R.1

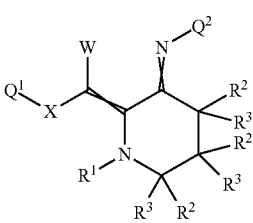

Formula 5.R.2

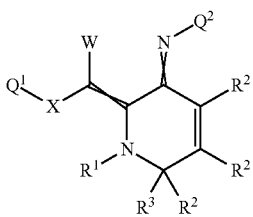

Formula 5.R.3

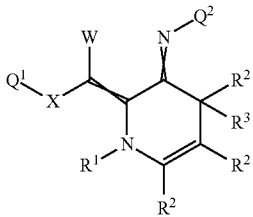

Formula 5.R.4

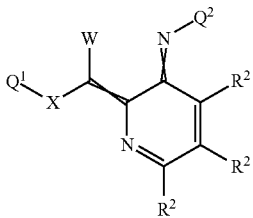

Formula 5.R.5

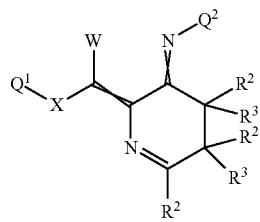

Embodiment 5.S $A^1$ is $C(R^2,R^3)$, $A^2$ is —$N(R^1)$—, each B is $C(R^2,R^3)$, n is 3; preferred embodiments describe compounds of the formulae 5.S.1, 5.S.2, 5.S.3, 5.S.4 and 5.S.5.

Formula 5.S.1

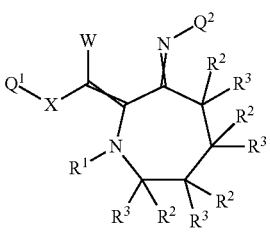

Formula 5.S.2

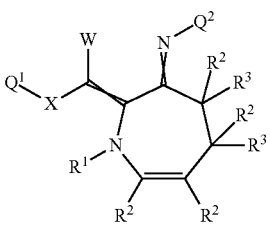

Formula 5.S.3

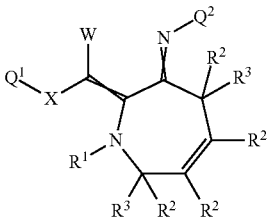

Formula 5.S.4

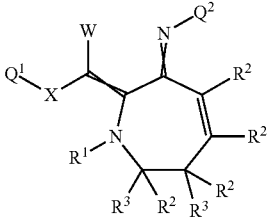

Formula 5.S.5

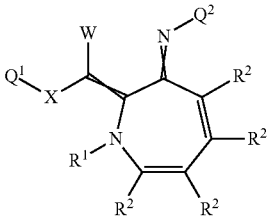

In a further embodiment, the C(=C(W,X-Q$^1$)-C(=N-Q$^2$)-A$^1$-[B]$_n$-A$^2$ ring of the basic structure of the formula (I) forms heterocycles having 2 or 3 heteroatoms (A$^1$ is C(R$^2$,R$^3$)) which are described in more detail below:

Embodiment 6.A

A$^1$ is C(R$^2$,R$^3$), of A$^2$ and B, at least two positions are Y or —N(R$^1$)—, n is 1, 2, 3.

Embodiment 6.B

A$^1$ and A$^2$ are C(R$^2$,R$^3$), two B are Y and/or —N(R$^1$)—, any third B present (if n equals 3) is C(R$^2$,R$^3$), n is 2, 3.

Embodiment 6.C

A$^1$ and A$^2$ are C(R$^2$,R$^3$), each B is Y or —N(R$^1$)—, n is 2; preferred embodiments describe compounds of the formulae 6.C.1, 6.C.2 and 6.C.3.

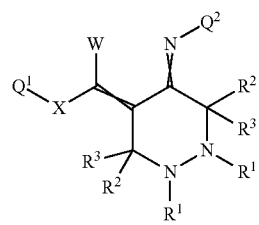

Formula 6.C.1

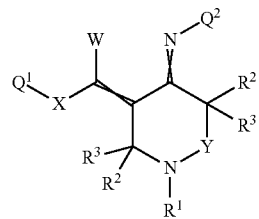

Formula 6.C.2

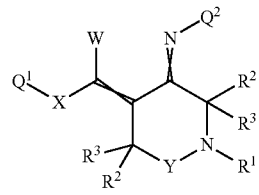

Formula 6.C.3

Embodiment 6.D

A$^1$ and A$^2$ are C(R$^2$,R$^3$), two B are Y and/or —N(R$^1$)—, any third B present is C(R$^2$,R$^3$), n is 3; preferred embodiments describe compounds of the formulae 6.D.1, 6.D.2, 6.D.3, 6.D.4, 6.D.5, 6.D.6, 6.D.7, 6.D.8, 6.D.9, 6.D.10, 6.D.11, 6.D.12 and 6.D.13.

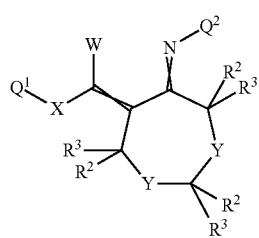

Formula 6.D.1

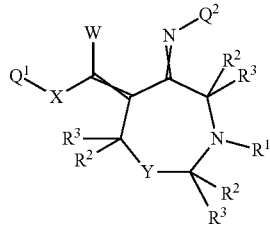

Formula 6.D.2

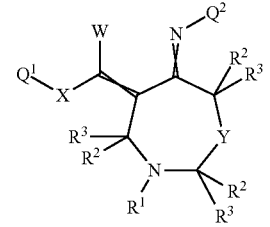

Formula 6.D.3

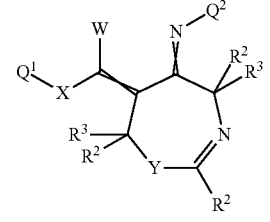

Formula 6.D.4

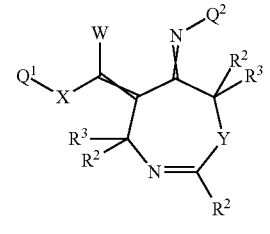

Formula 6.D.5

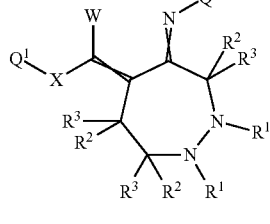

Formula 6.D.6

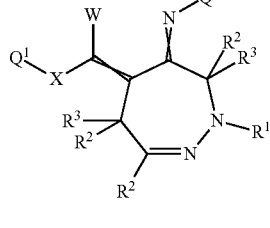

Formula 6.D.7

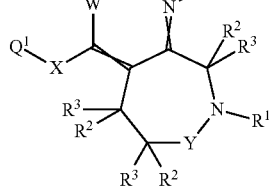

Formula 6.D.8

-continued

Formula 6.D.9

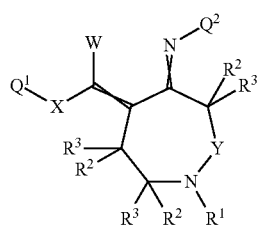

Formula 6.D.10

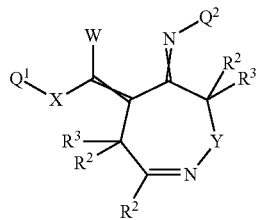

Formula 6.D.11

Formula 6.D.12

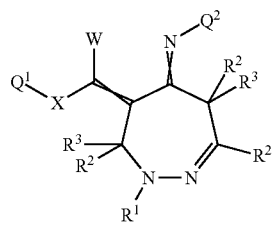

Formula 6.D.13

Embodiment 6.E $A^1$ is $C(R^2,R^3)$, $A^2$ is Y, at least one B is Y or —$N(R^1)$—, n is 1, 2, 3.

Embodiment 6.F $A^1$ is $C(R^2,R^3)$, $A^2$ is Y, B is —$N(R^1)$—, n is 1; preferred embodiments describe compounds of the formulae 6.F.1 and 6.F.2.

Formula 6.F.1

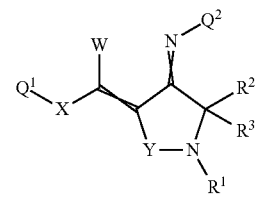

-continued

Formula 6.F.2

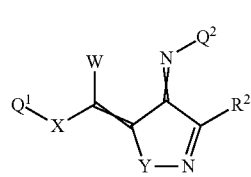

Embodiment 6.G $A^1$ is $C(R^2,R^3)$, $A^2$ is Y, at least one B is Y or —$N(R^1)$—, n is 2; preferred embodiments describe compounds of the formulae 6.G.1, 6.G.2 and 6.G.3.

Formula 6.G.1

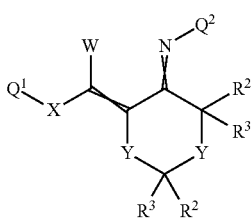

Formula 6.G.2

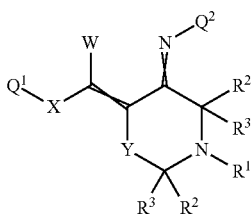

Formula 6.G.3

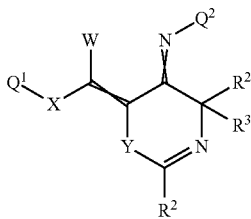

Embodiment 6.H $A^1$ is $C(R^2,R^3)$, $A^2$ is Y, at least one B is Y or —$N(R^1)$, n is 3; preferred embodiments describe compounds of the formulae 6.H.1, 6.H.2, 6.H.3, 6.H.4, 6.H.5, 6.H.6, 6.H.7 and 6.H.8.

Formula 6.H.1

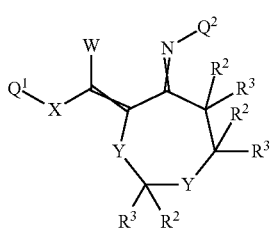

-continued

Formula 6.H.2
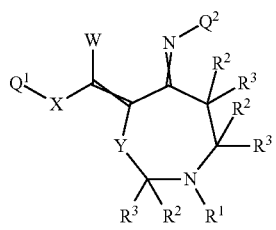

Formula 6.H.3
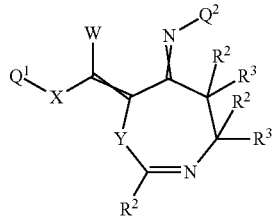

Formula 6.H.4
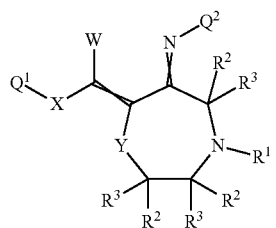

Formula 6.H.5
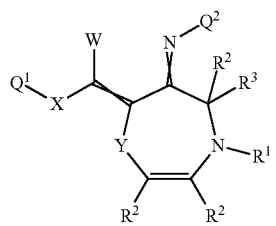

Formula 6.H.6
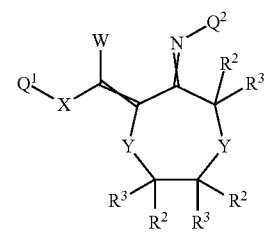

Formula 6.H.7
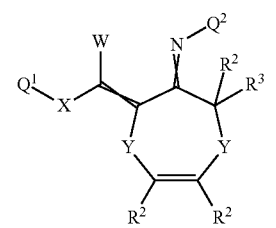

Formula 6.H.8
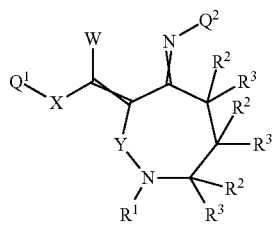

Embodiment 6.I $A^1$ is $C(R^2,R^3)$, $A^2$ is —$N(R^1)$—, at least one B is Y or —$N(R^1)$—, n is 1, 2, 3.

Embodiment 6.J $A^1$ is $C(R^2,R^3)$, $A^2$ is —$N(R^1)$—, B is Y or —$N(R^1)$—, n is 1; preferred embodiments describe compounds of the formulae 6.J.1, 6.J.2 and 6.J.3.

Formula 6.J.1
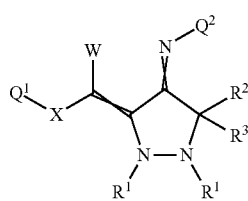

Formula 6.J.2
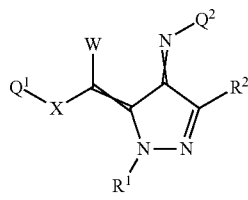

Formula 6.J.3
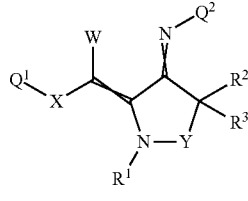

Embodiment 6.K $A^1$ is $C(R^2,R^3)$, $A^2$ is —$N(R^1)$—, at least one B is Y or —$N(R^1)$—, n is 2; preferred embodiments describe compounds of the formulae 6.K.1, 6.K.2, 6.K.3, 6.K.4, 6.K.5 and 6.K.6.

Formula 6.K.1
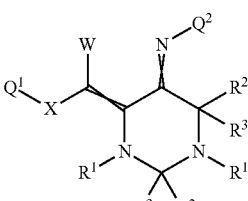

Formula 6.K.2
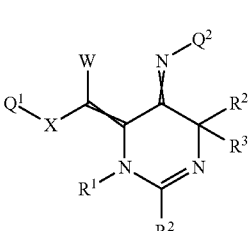

Formula 6.K.3

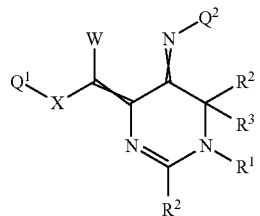

Formula 6.K.4

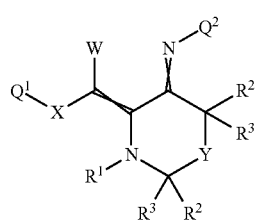

Formula 6.K.5

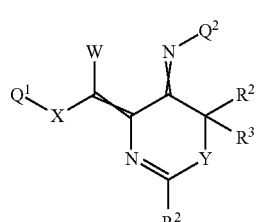

Formula 6.K.6

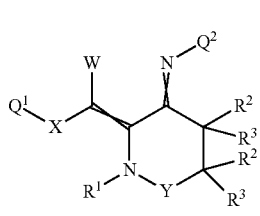

Embodiment 6.L $A^1$ is $C(R^2,R^3)$, $A^2$ is —$N(R^1)$—, at least one B is Y or —$N(R^1)$—, n is 3; preferred embodiments describe compounds of the formulae 6.L.1, 6.L.2, 6.L.3 and 6.L.4.

Formula 6.L.1

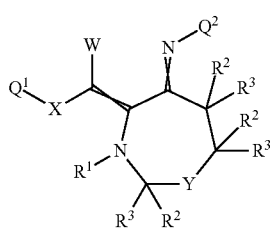

Formula 6.L.2

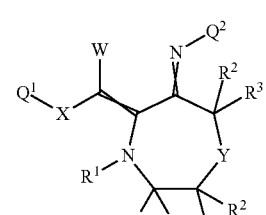

Formula 6.L.3

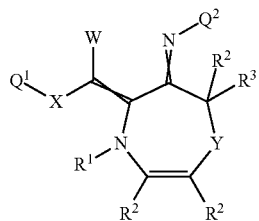

Formula 6.L.4

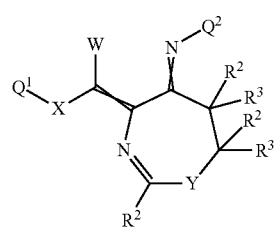

In a further embodiment, the $C(=C(W,X-Q^1))—C(=N-Q^2)-A^1-[B]_n-A^2$ ring of the basic structure of the formula (I) forms heterocycles having 2 or 3 heteroatoms ($A^1$ is Y) which are described in more detail below:

Embodiment 7.A $A^1$ is Y, of $A^2$ and B, at least one is Y or —$N(R^1)$—, n is 1, 2, 3.

Embodiment 7.B $A^1$ is Y, $A^2$ is $C(R^2,R^3)$ and at least one B is Y or —$N(R^1)$—, n is 1, 2, 3.

Embodiment 7.C $A^1$ is Y, $A^2$ is $C(R^2,R^3)$ and B is —$N(R^1)$—, n is 1; preferred embodiments describe compounds of the formulae 7.C.1 and 7.C.2.

Formula 7.C.1

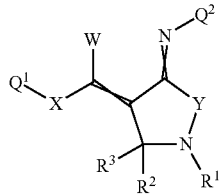

Formula 7.C.2

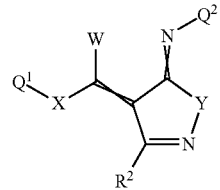

Embodiment 7.D $A^1$ is Y, $A^2$ is $C(R^2,R^3)$ and at least one B is Y or —$N(R^1)$—, n is 2; preferred embodiments describe compounds of the formulae 7.D.1, 7.D.2, 7.D.3, 7.D.4, 7.D.5 and 7.D.6.

Formula 7.D.1
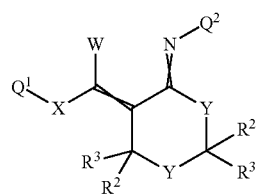
Formula 7.D.2
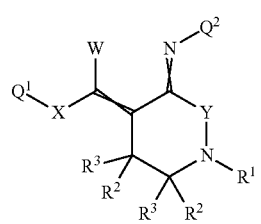
Formula 7.D.3
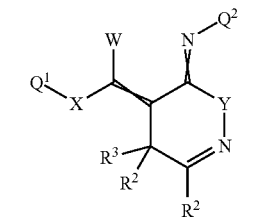
Formula 7.D.4
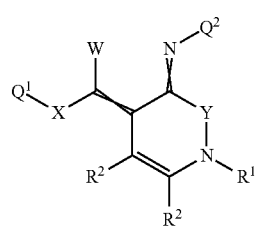
Formula 7.D.5
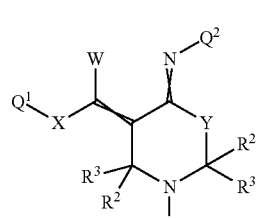
Formula 7.D.6
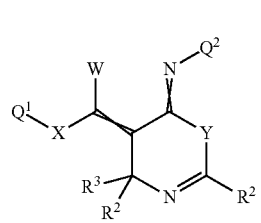
Embodiment 7.E
$A^1$ is Y, $A^2$ is $C(R^2,R^3)$ and at least one B is Y or —$N(R^1)$—, n is 3; preferred embodiments describe compounds of the formulae 7.E.1, 7.E.2, 7.E.3, 7.E.4, 7.E.5, 7.E.6, 7.E.7, 7.E.8, 7.E.9, 7.E.10, 7.E.11, 7.E.12 and 7.E.13.
Formula 7.E.1
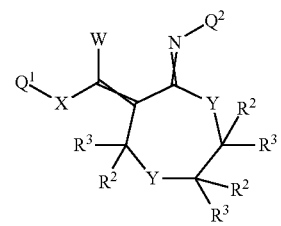
Formula 7.E.2
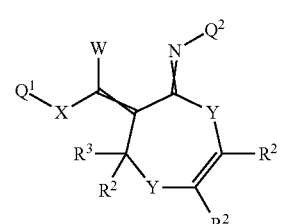
Formula 7.E.3
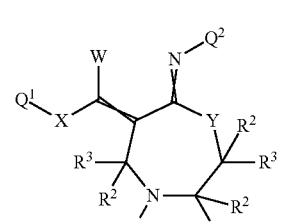
Formula 7.E.4
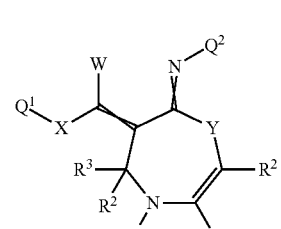
Formula 7.E.5
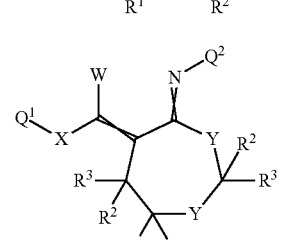
Formula 7.E.6
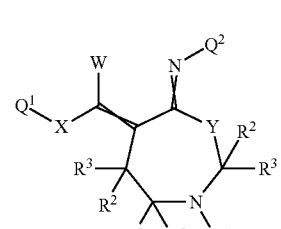
Formula 7.E.7
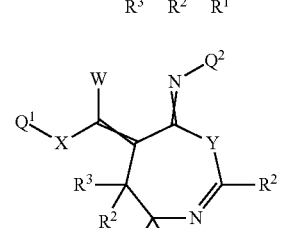

-continued

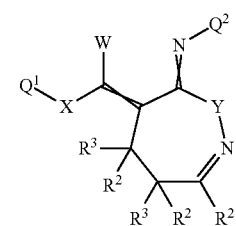
Formula 7.E.8

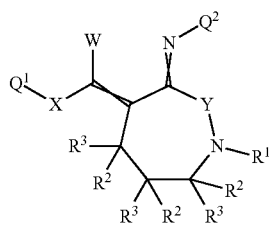
Formula 7.E.9

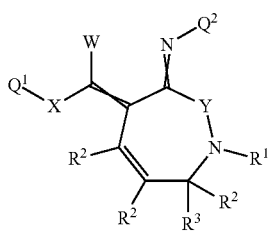
Formula 7.E.10

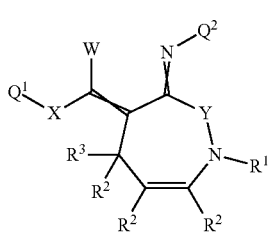
Formula 7.E.11

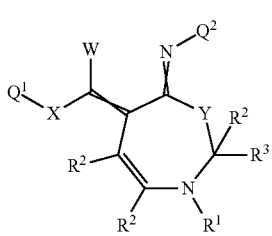
Formula 7.E.12

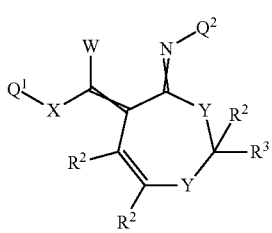
Formula 7.E.13

Embodiment 7.F $A^1$ and $A^2$ are Y, all B are in each case independently of one another $C(R^2,R^3)$, Y or —$N(R^1)$—, n is 1, 2, 3.

Embodiment 7.G $A^1$ and $A^2$ are Y, B is $C(R^2,R^3)$, n is 1; preferred embodiments describe compounds of the formulae 7.G.1.

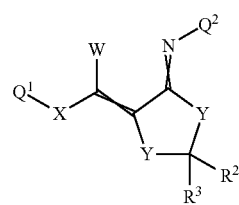
Formula 7.G.1

Embodiment 7.H $A^1$ and $A^2$ are Y, all B are in each case independently of one another $C(R^2,R^3)$ or —$N(R^1)$—, n is 2; preferred embodiments describe compounds of the formulae 7.H.1 and 7.H.2.

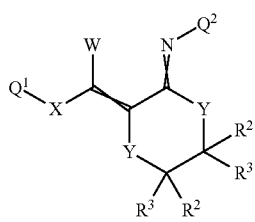
Formula 7.H.1

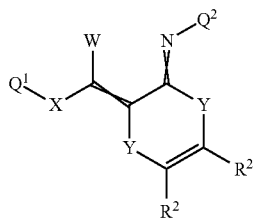
Formula 7.H.2

Embodiment 7.I $A^1$ and $A^2$ are Y, all B are in each case independently of one another $C(R^2,R^3)$, Y or —$N(R^1)$—, n is 3; preferred embodiments describe compounds of the formulae 7.I.1, 7.I.2 and 7.I.3.

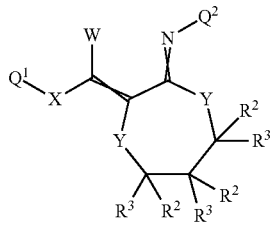
Formula 7.I.1

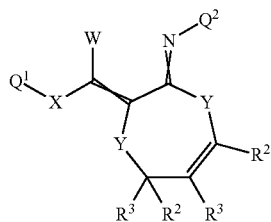
Formula 7.I.2

-continued

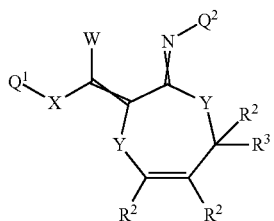

Formula 7.I.3

Embodiment 7.J $A^1$ is Y, $A^2$ is —N($R^1$)—, all B are in each case independently of one another C($R^2,R^3$), Y or —N($R^1$)—, n is 0, 1, 2, 3.

Embodiment 7.K $A^1$ is Y, $A^2$ is —N($R^1$)—, n is 0; preferred embodiments describe compounds of the formulae 7.K.1.

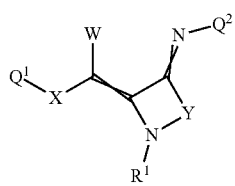

Formula 7.K.1

Embodiment 7.L $A^1$ is Y, $A^2$ is —N($R^1$)—, B is C($R^2,R^3$), n is 1; preferred embodiments describe compounds of the formulae 7.L.1 and 7.L.2.

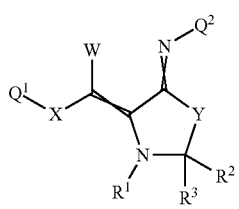

Formula 7.L.1

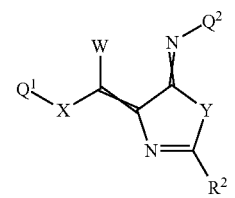

Formula 7.L.2

Embodiment 7.M $A^1$ is Y, $A^2$ is —N($R^1$)—, all B are in each case independently of one another C($R^2,R^3$), Y or —N($R^1$)—, n is 2; preferred embodiments describe compounds of the formulae 7.M.1 and 7.M.2.

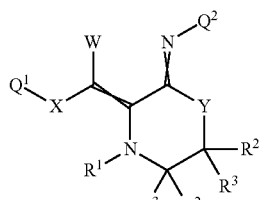

Formula 7.M.1

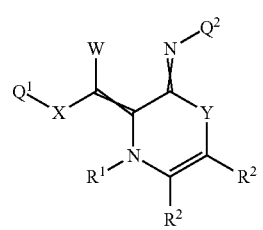

Formula 7.M.2

Embodiment 7.N $A^1$ is Y, $A^2$ is —N($R^1$)—, all B are in each case independently of one another C($R^2,R^3$), Y or —N($R^1$)—, n is 3; preferred embodiments describe compounds of the formulae 7.N.1, 7.N.2 and 7.N.3.

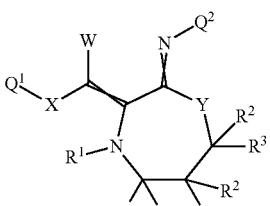

Formula 7.N.1

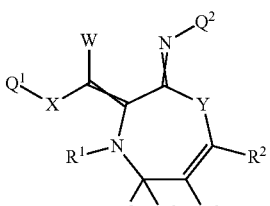

Formula 7.N.2

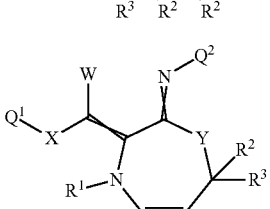

Formula 7.N.3

In a further embodiment, the C(=C(W,X-$Q^1$)-C(=N-$Q^2$)-$A^1$-[B]$_n$-$A^2$ ring of the basic structure of the formula (I) forms heterocycles having 2 or 3 heteroatoms ($A^1$ is N$R^1$) which are described in more detail below:

Embodiment 8.A $A^1$ is —N($R^1$)—, of $A^2$ and B, at least one is Y or —N($R^1$)—, n is 1, 2, 3.

Embodiment 8.B $A^1$ is —N($R^1$)—, $A^2$ is C($R^2$,$R^3$) and at least one B is Y or —N($R^1$)—, n is 1, 2, 3.

Embodiment 8.C $A^1$ is —N($R^1$)—, $A^2$ is C($R^2$,$R^3$) and B is Y or —N($R^1$)—, n is 1; preferred embodiments describe compounds of the formulae 8.C.1, 8.C.2 and 8.C.3.

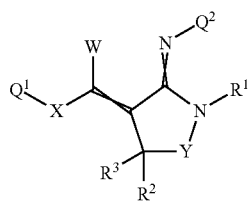

Formula 8.C.1

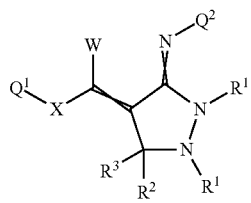

Formula 8.C.2

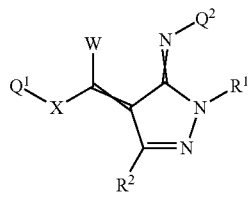

Formula 8.C.3

Embodiment 8.D $A^1$ is —N($R^1$)—, $A^2$ is C($R^2$,$R^3$) and at least one B is Y or —N($R^1$)—, n is 2; preferred embodiments describe compounds of the formulae 8.D.1, 8.D.2, 8.D.3, 8.D.4, 8.D.5, 8.D.6, 8.D.7, 8.D.8 and 8.D.9.

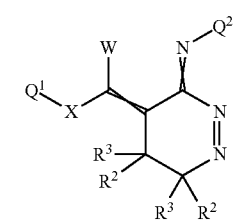

Formula 8.D.1

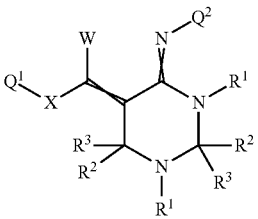

Formula 8.D.2

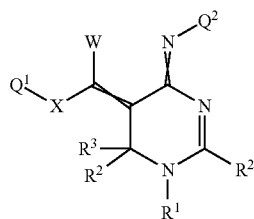

Formula 8.D.3

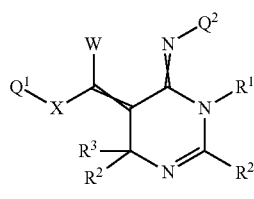

Formula 8.D.4

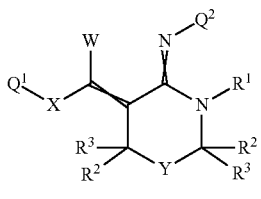

Formula 8.D.5

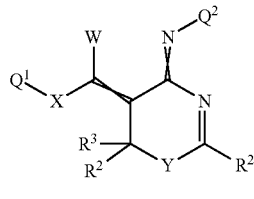

Formula 8.D.6

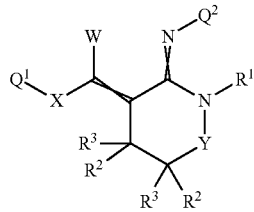

Formula 8.D.7

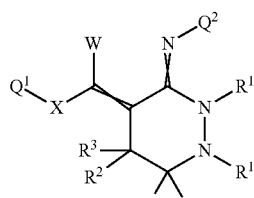

Formula 8.D.8

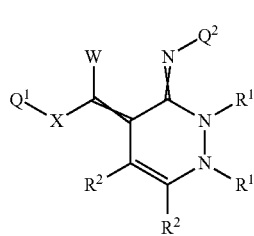

Formula 8.D.9

Embodiment 8.E $A^1$ is —N($R^1$)—, $A^2$ is C($R^2$,$R^3$) and at least one B is Y or —N($R^1$)—, n is 3; preferred embodiments describe compounds of the formulae 8.E.1, 8.E.2, 8.E.3, 8.E.4, 8.E.5, 8.E.6, 8.E.7, 8.E.8, 8.E.9, 8.E.10, 8.E.11, 8.E.12, 8.E.13 and 8.E.14.
Formula 8.E.1
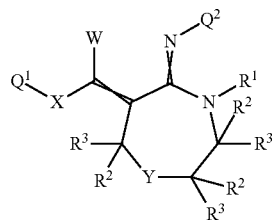
Formula 8.E.2
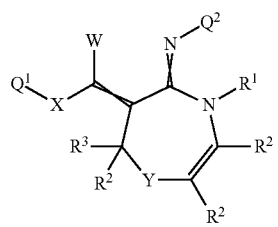
Formula 8.E.3
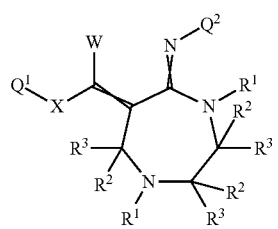
Formula 8.E.4
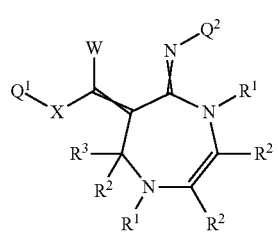
Formula 8.E.5
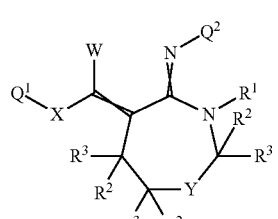
Formula 8.E.6
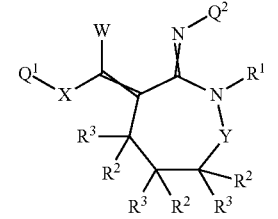
-continued
Formula 8.E.7
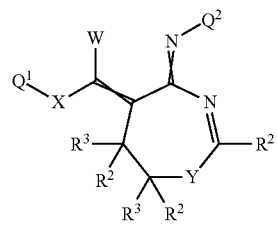
Formula 8.E.8
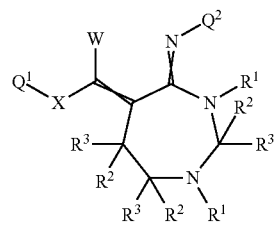
Formula 8.E.9
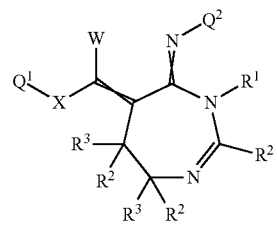
Formula 8.E.10
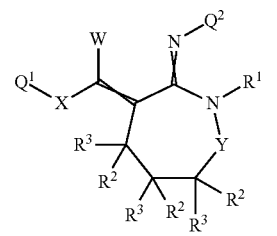
Formula 8.E.11
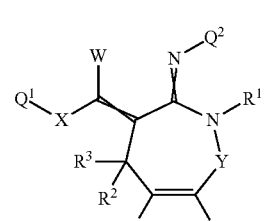
Formula 8.E.12
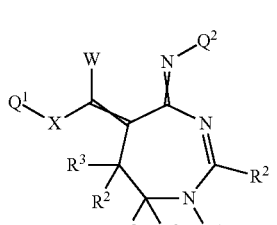
Formula 8.E.13
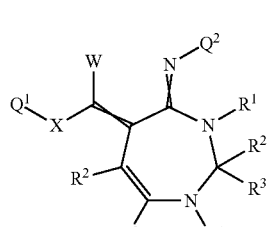

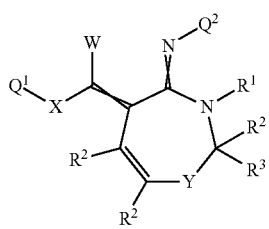

Formula 8.E.14

Embodiment 8.F $A^1$ is —$N(R^1)$—, $A^2$ is Y and B is $C(R^2,R^3)$, Y or —$N(R^1)$—, n is 0, 1, 2, 3.

Embodiment 8.G $A^1$ is —$N(R^1)$—, $A^2$ is Y, n is 0; preferred embodiments describe compounds of the formula 8.G.1.

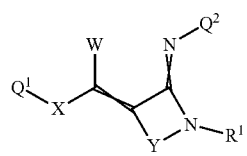

Formula 8.G.1

Embodiment 8.H $A^1$ is —$N(R^1)$—, $A^2$ is Y and B is $C(R^2,R^3)$, n is 1; preferred embodiments describe compounds of the formulae 8.H.1 and 8.H.2.

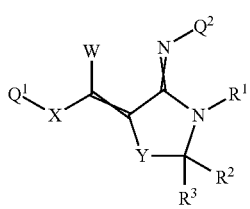

Formula 8.H.1

Formula 8.H.2

Embodiment 8.I

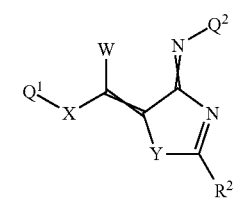

$A^1$ is $NR^1$, $A^2$ is Y and B is in each case independently of the others $C(R^2,R^3)$, Y or —$N(R^1)$—, n is 2; preferred embodiments describe compounds of the formulae 8.I.1 and 8.I.2.

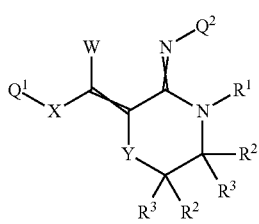

Formula 8.I.1

Formula 8.I.2

Embodiment 8.J $A^1$ is $NR^1$, $A^2$ is Y and B is in each case independently of the others $C(R^2,R^3)$, Y or —$N(R^1)$—, n is 3; preferred embodiments describe compounds of the formulae 8.J.1, 8.J.2 and 8.J.3.

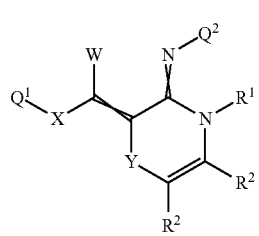

Formula 8.J.1

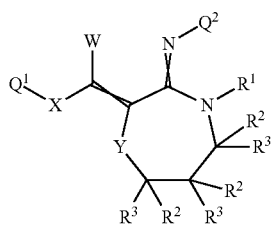

Formula 8.J.2

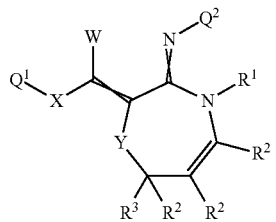

Formula 8.J.3

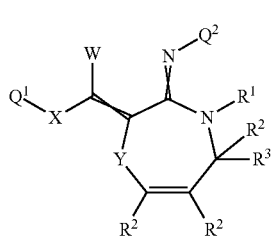

Embodiment 8.K $A^1$ and $A^2$ are —$N(R^1)$— and B is in each case independently of the others $C(R^2,R^3)$, Y or $NR^1$, n is 0, 1, 2, 3.

Embodiment 8.L $A^1$ and $A^2$ are —$N(R^1)$— and B is $C(R^2,R^3)$, n is 1; preferred embodiments describe compounds of the formulae 8.L.1, 8.L.2 and 8.L.3.

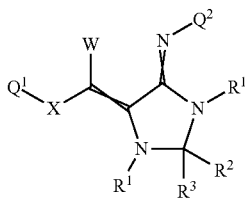

Formula 8.L.1

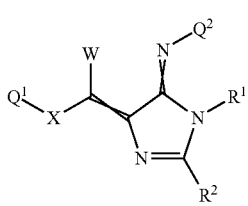

Formula 8.L.2

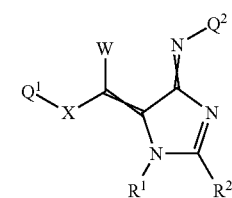

Formula 8.L.3

Embodiment 8.M $A^1$ and $A^2$ are —N($R^1$)— and B is in each case independently of the other C($R^2$,$R^3$), Y or —N($R^1$)—, n is 2; preferred embodiments describe compounds of the formulae 8.M.1 and 8.M.2.

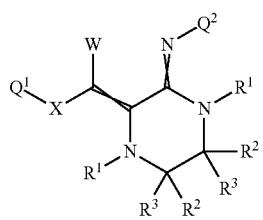

Formula 8.M.1

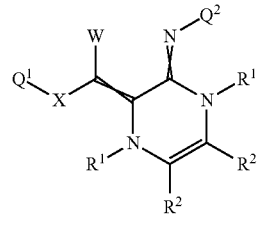

Formula 8.M.2

Embodiment 8.N $A^1$ and $A^2$ are —N($R^1$)— and B is in each case independently of the others C($R^2$,$R^3$), Y or —N($R^1$)—, n is 3; preferred embodiments describe compounds of the formulae 8.N.1, 8.N.2 and 8.N.3.

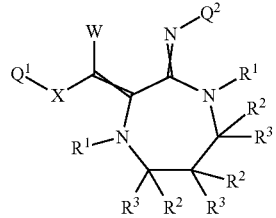

Formula 8.N.1

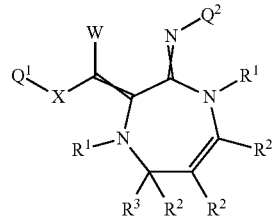

Formula 8.N.2

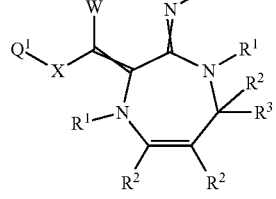

Formula 8.N.3

A further embodiment describes compounds of the formula I-a

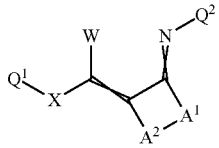

Formula I-a in which $Q^1$, $Q^2$, W, X, $A^1$ and $A^2$ are as described above (n is 0).

In one embodiment of compounds of the formula I-a, $A^1$ represents C($R^2$,$R^3$) and $A^2$ represents C($R^2$,$R^3$) and the two $R^3$ may optionally represent a joint double bond. Exemplary embodiments are compounds of the formulae 1.A.1 and 1.A.2 in which $R^2$,$R^3$, $Q^1$, $Q^2$, W and X are as described above.

A further embodiment describes compounds of the formula I-a in which $Q^1$, $Q^2$, W and X are as described above, $A^1$ represents Y or —N($R^1$) and $A^2$ represents C($R^2$,$R^3$), and n represents 0. Exemplary embodiments are compounds of the formulae 2.A.1 and 5.K.1 in which $R^1$, $R^2$, $R^3$, $Q^1$, $Q^2$, W, X and Y are as described above.

A further embodiment describes compounds of the formula I-a in which $Q^1$, $Q^2$, W and X are as described above, $A^1$ represents C($R^2$,$R^3$) and $A^2$ represents Y or —N($R^1$)$^1$, and n represents 0. Exemplary embodiments are compounds of the formulae 4.K.1 and 5.P.1 in which $R^1$, $R^2$,$R^3$, $Q^1$, $Q^2$, X and Y are as described above.

A further embodiment describes compounds of the formula I-a in which $Q^1$, $Q^2$, W and X are as described above, $A^1$ represents Y or —N($R^1$) and $A^2$ represents Y or —N($R^1$), and n represents 0. Exemplary embodiments are compounds of the formulae 7.K.1 and 8.G.1 in which $R^1$, $Q^1$, W, X and Y are as described above.

A further embodiment describes compounds of the formula I-b

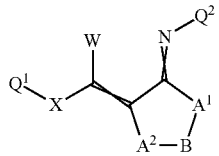

Formula I-b in which $Q^1, Q^2, W, X, A^1, A^2$ and B are as described above (n is 1).

In one embodiment of compounds of the formula I-b, $A^1$ represents $C(R^2,R^3)$, $A^2$ represents $C(R^2,R^3)$ and B represents $C(R^2,R^3)$, where two adjacent $R^3$ may optionally represent a joint double bond, and n represents 1. Exemplary embodiments are compounds of the formulae 1.B.1, 1.B.2 and 1.B.3, in which $R^2, R^3$, $Q^1$, $Q^2$, W and X are as described above. Further exemplary embodiments are compounds of the formulae 1.B.4 and 1.B.5 in which two adjacent $R^3$ represent a double bond and are part of a fused aromatic $C_6$-carbocyclic system which may optionally be substituted.

A further embodiment describes compounds of the formula I-b in which $Q^1, Q^2$, W and X are as described above, $A^1$ represents —$N(R^1)$, $A^2$ represents $C(R^2,R^3)$ and B represents $C(R^2,R^3)$, where two adjacent $R^3$ or adjacent $R^1$ and $R^3$ may optionally represent a joint double bond, and n represents 1. Further exemplary embodiments are compounds of the formulae 5.L.1, 5.L.2 and 5.L.3 in which $R^1$, $R^2$, $R^3$, $Q^1$, $Q^2$, W and X are as described above.

A further embodiment describes compounds of the formula I-b in which $Q^1, Q^2$, W and X are as described above, $A^1$ represents Y, $A^2$ represents $C(R^2,R^3)$ and B represents $C(R^2,R^3)$, where at least one of these $(R^2,R^3)$ pairs represents V, and n represents 1. Exemplary embodiments are compounds of the formulae 3.A.1 and 3.A.2 in which $R^2,R^3$, $Q^1$, $Q^2$, V, W, X and Y are as described above. Further exemplary embodiments are compounds of the formulae 3.B.1 and 3.B.2.

A further embodiment describes compounds of the formulae I-b in which $Q^1, Q^2$, W and X are as described above, $A^1$ represents $C(R^2,R^3)$, $A^2$ represents $C(R^2,R^3)$ and B represents Y or —$N(R^1)$—, and n represents 1. Exemplary embodiments are compounds of the formulae 4.B.1 and 5.B.1.

A further embodiment describes compounds of the formula I-b in which $Q^1, Q^2$, W and X are as described above, $A^1$ represents $C(R^2,R^3)$, $A^2$ represents Y or —$N(R^1)$— and B represents $C(R^2,R^3)$, where two adjacent $R^3$ or adjacent $R^1$ and $R^3$ may optionally represent a joint double bond, and n represents 1. Exemplary embodiments are compounds of the formulae 4.L.1, 4.L.2, 5.Q.1 and 5.Q.2.

A further embodiment describes compounds of the formula I-b in which $Q^1, Q^2$, W and X are as described above, $A^1$ represents Y or $NR^1$, $A^2$ represents $C(R^2,R^3)$ and B represents Y or —$N(R^1)$, where two adjacent $R^3$ or adjacent $R^1$ and $R^3$ may optionally represent a joint double bond, and n represents 1. Exemplary embodiments are compounds of the formulae 7.C.1, 7.C.2, 8.C.1, 8.C.2 and 8.C.3.

A further embodiment describes compounds of the formula I-b in which $Q^1, Q^2$, W and X are as described above, $A^1$ represents Y or —$N(R^1)$—, $A^2$ represents Y or —$N(R^1)$— and B represents $C(R^2,R^3)$, where adjacent $R^1$ and $R^3$ may optionally represent a joint double bond, and n represents 1. Exemplary embodiments are compounds of the formulae 7.G.1, 7.L.1, 7.L.2, 8.H.1, 8.H.2, 8.L.1 and 8.L.2.

A further embodiment describes compounds of the formula I-b in which $Q^1, Q^2$, W and X are as described above, $A^1$ represents $C(R^2,R^3)$, $A^2$ represents Y or —$N(R^1)$— and B represents Y or —$N(R^1)$—, where adjacent $R^1$ and $R^3$ may optionally represent a joint double bond, and n represents 1. Exemplary embodiments are compounds of the formulae 6.F.1, 6.F.2, 6.J.1 and 6.J.2.

A further embodiment describes compounds of the formula I-c,

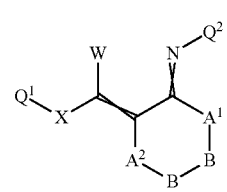

Formula I-c in which $Q^1, Q^2, W, X, A^1, A^2$ and B are as described above (n is 2).

In one embodiment of compounds of the formula I-c, $A^1$ represents $C(R^2,R^3)$ and $A^2$ represents $C(R^2,R^3)$ and each B represents $C(R^2,R^3)$, where two adjacent $R^3$ may optionally represent a joint double bond. Exemplary embodiments are compounds of the formulae 1.C.1, 1.C.2, 1.C.3, 1.C.4 and 1.C.5. Further exemplary embodiments are compounds of the formulae 1.C.6, 1.C.7 and 1.C.8.

A further embodiment describes compounds of the formula I-c in which $A^1$ represents —$N(R^1)$— and $A^2$ represents $C(R^2,R^3)$, each B represents $C(R^2,R^3)$, where two adjacent $R^3$ or adjacent $R^1$ and $R^3$ may optionally represent a joint double bond. Exemplary embodiments are compounds of the formulae 5.M.1, 5.M.2, 5.M.3 and 5.M.4.

A further embodiment describes compounds of the formula I-c in which $A^1$ represents Y and $A^2$ represents $C(R^2,R^3)$, optionally each B represents $C(R^2,R^3)$ where at least one of these $(R^2,R^3)$ pairs represents V, and n represents 2. Exemplary embodiments are compounds of the formulae 3.C.1, 3.C.2 and 3.C.3. Further exemplary embodiments are compounds of the formulae 3.D.1, 3.D.2 and 3.D.3.

A further embodiment describes compounds of the formula I-c in which $A^1$ represents $C(R^2,R^3)$ and $A^2$ represents $C(R^2,R^3)$, each B optionally represents Y or $C(R^2,R^3)$, but at least one B represents Y, and where two adjacent $R^3$ may optionally represent a joint double bond. Exemplary embodiments are compounds of the formulae 4.D.1, 4.D.2, 4.E.1 and 4.E.2.

A further embodiment describes compounds of the formula I-c in which $A^1$ represents $C(R^2,R^3)$ and $A^2$ represents $C(R^2,R^3)$, each B optionally represents —$N(R^1)$— or $C(R^2,R^3)$, but at least one B represents —$N(R^1)$—, and where two adjacent $R^3$ or adjacent $R^1$ and $R^3$ may optionally represent a joint double bond. Exemplary embodiments are compounds of the formulae 5.D.1, 5.D.2, 5.D.3, 5.D.4 and 5.D.5. Further exemplary embodiments are compounds of the formulae 5.E.1, 5.E.2, 5.E.3, 5.E.4 and 5.E.5.

A further embodiment describes compounds of the formula I-c in which $Q^1, Q^2$, W and X are as described above, $A^1$ represents $C(R^2,R^3)$ and $A^2$ represents Y, each B represents $C(R^2,R^3)$, where two adjacent $R^3$ may optionally represent a joint double bond. Exemplary embodiments are compounds of the formulae 4.M.1, 4.M.2 and 4.M.3.

A further embodiment describes compounds of the formula I-c in which $Q^1, Q^2$, W and X are as described above, $A^1$ represents $C(R^2,R^3)$ and $A^2$ represents —$N(R^1)$—, each B represents $C(R^2,R^3)$, where two adjacent $R^3$ or adjacent $R^1$ and $R^3$ may optionally represent a joint double bond, and n represents 2. Exemplary embodiments are compounds of the formulae 5.R.1, 5.R.2, 5.R.3, 5.R.4 and 5.R.5.

A further embodiment describes compounds of the formula I-c in which $A^1$ represents $C(R^2,R^3)$ and $A^2$ represents $C(R^2,R^3)$, each B independently of the others represents Y or —N($R^1$)—. Exemplary embodiments are compounds of the formulae 6.C.1, 6.C.2 and 6.C.3.

A further embodiment describes compounds of the formula I-c, $A^1$ represents $C(R^2,R^3)$ and $A^2$ represents Y or —N($R^1$)—, the B adjacent to the $A^1$ represents Y or —N($R^1$)—, the B adjacent to the $A^2$ represents $C(R^2,R^3)$, and where adjacent $R^1$ and $R^3$ may optionally represent a joint double bond. Exemplary embodiments are compounds of the formulae 6.G.1, 6.G.2, 6.G.3, 6.K.1, 6.K.2, 6.K.3, 6.K.4 and 6.K.5.

A further embodiment describes compounds of the formula I-c in which $A^1$ represents Y or —N($R^1$)— and $A^2$ represents $C(R^2,R^3)$, the B adjacent to the $A^1$ represents $C(R^2,R^3)$, the B adjacent to the $A^2$ represents Y or —N($R^1$)—, and where adjacent $R^1$ and $R^3$ may optionally represent a joint double bond. Exemplary embodiments are compounds of the formulae 7.D.1, 7.D.5, 7.D.6, 8.D.2, 8.D.3, 8.D.4, 8.D.5 and 8.D.6.

A further embodiment describes compounds of the formula I-c in which $A^1$ represents Y or $NR^1$ and $A^2$ represents $C(R^2,R^3)$, the B adjacent to the $A^1$ represents Y or $NR^1$, the B adjacent to the $A^2$ represents $C(R^2,R^3)$, where two adjacent $R^1$ or adjacent $R^1$ and $R^3$ may optionally represent a joint double bond. Exemplary embodiments are compounds of the formulae 7.D.2, 7.D.3, 7.D.4, 8.D.1, 8.D.7, 8.D.8 and 8.D.9.

A further embodiment describes compounds of the formula I-c in which $A^1$ represents Y or $NR^1$ and $A^2$ represents Y or $NR^1$, each B independently of the others represents $C(R^2,R^3)$, and where two adjacent $R^3$ may optionally represent a joint double bond. Exemplary embodiments are compounds of the formulae 7.H.1, 7.H.2, 7.M.1, 7.M.2, 8.1.1, 8.1.2, 8.M.1 and 8.M.2 in which $R^1$, $R^2$, $R^3$, $Q^1$, $Q^2$, W, X and Y are as described above.

A further embodiment describes compounds of the formula I-c in which $A^1$ represents $C(R^2,R^3)$ and $A^2$ represents Y or —N($R^1$)—, the B adjacent to the $A^1$ represents $C(R^2,R^3)$ and the B adjacent to the $A^2$ represents Y or —N($R^1$)—. Exemplary embodiments are compounds of the formula 6.K.6.

A further embodiment describes compounds of the formula I-d,

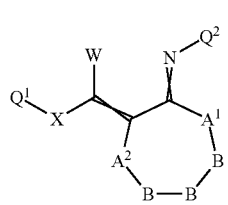

Formula I-d in which $Q^1$, $Q^2$, W, X, $A^1$, $A^2$ and B are as described above (n is 3).

In one embodiment of compounds of the formula I-d, $A^1$ represents $C(R^2,R^3)$ and $A^2$ represents $C(R^2,R^3)$, each B represents $C(R^2,R^3)$ and two adjacent $R^3$ may optionally represent a joint double bond, n is 3. Exemplary embodiments are compounds of the formulae 1.D.1, 1.D.2, 1.D.3, 1.D.4, 1.D.5, 1.D.6, 1.D.7 and 1.D.8. A further exemplary embodiment are compounds of the formulae 1.D.9, 1.D.10, 1.D.11 and 1.D.12 in which two adjacent $R^3$ represent a double bond, which are a component of a fused aromatic $C_6$-carbocyclic system which may optionally be substituted.

A further embodiment describes compounds of the formula I-d, in which $A^1$ represents —N($R^1$)— and $A^2$ represents $C(R^2,R^3)$, each B represents $C(R^2,R^3)$ and where two adjacent $R^3$ may optionally represent a joint double bond. Exemplary embodiments are compounds of the formulae 5.N.1, 5.N.2, 5.N.3, 5.N.4 and 5.N.5.

A further embodiment describes compounds of the formula I-d in which $A^1$ represents Y and $A^2$ represents $C(R^2,R^3)$, optionally each B represents $C(R^2,R^3)$, where at least one of these ($R^2,R^3$) pairs represents V, and n represents 3. Exemplary embodiments are compounds of the formulae 3.E.1, 3.E.2, 3.E.3 and 3.E.4.

A further embodiment describes compounds of the formula I-d in which at least one ($R^2,R^3$) pair represents =O. Exemplary embodiments are compounds of the formulae 3.F.1, 3.F.2, 3.F.3 and 3.F.4.

A further embodiment describes compounds of the formula I-d in which $A^1$ represents $C(R^2,R^3)$ and $A^2$ represents $C(R^2,R^3)$, the B adjacent to the $A^1$ represents Y or $NR^1$, and the remaining B each represent $C(R^2,R^3)$, and where two adjacent $R^3$ may optionally represent a joint double bond. Exemplary embodiments are compounds of the formulae 4.G.1, 4.G.2, 4.G.3, 5.G.1, 5.G.2 and 5.G.3.

A further embodiment describes compounds of the formula I-d in which $A^1$ represents $C(R^2,R^3)$ and $A^2$ represents $C(R^2,R^3)$, the B adjacent to the $A^1$ represents $C(R^2,R^3)$, the B adjacent to the $A^2$ represents $C(R^2,R^3)$, and the remaining B represents Y or —N($R^1$)—, and where two adjacent $R^3$ may optionally represent a joint double bond. Exemplary embodiments are compounds of the formulae 4.H.1, 4.H.2, 4.H.3, 4.H.4, 5.H.1, 5.H.2, 5.H.3 and 5.H.4.

A further embodiment describes compounds of the formula I-d in which $A^1$ represents $C(R^2,R^3)$ and $A^2$ represents $C(R^2,R^3)$, the B adjacent to the $A^1$ represents $C(R^2,R^3)$, the B adjacent to the $A^2$ represents Y or —N($R^1$)—, and the remaining B represents $C(R^2,R^3)$, and where two adjacent $R^3$ may optionally represent a joint double bond. Exemplary embodiments are compounds of the formulae 4.I.1, 4.I.2, 4.I.3, 5.I.1, 5.I.2 and 5.I.3.

A further embodiment describes compounds of the formula I-d in which $A^1$ represents $C(R^2,R^3)$ and $A^2$ represents Y or —N($R^1$)—, each B represents $C(R^2,R^3)$ and where two adjacent $R^3$ may optionally represent a joint double bond. Exemplary embodiments are compounds of the formulae 4.N.1, 4.N.2, 4.N.3, 4.N.4, 4.N.5, 5.S.1, 5.S.2, 5.S.3, 5.S.4 and 5.S.5.

A further embodiment describes compounds of the formula I-d in which $A^1$ represents Y or $NR^1$ and $A^2$ represents $C(R^2,R^3)$, the B adjacent to the $A^1$ represents Y or —N($R^1$)—, the remaining B represent $C(R^2,R^3)$, and where two adjacent $R^3$ may optionally represent a joint double bond. Exemplary embodiments are compounds of the formulae 7.E.8, 7.E.9, 7.E.10, 7.E.11, 8.E.6, 8.E.10 and 8.E.11.

A further embodiment describes compounds of the formula I-d in which $A^1$ represents Y or $NR^1$ and $A^2$ represents $C(R^2,R^3)$, the B adjacent to the $A^1$ represents $C(R^2,R^3)$ and the B adjacent to the $A^2$ represents $C(R^2,R^3)$, the remaining B represents Y or —N($R^1$)—, and where two adjacent $R^3$ or adjacent $R^1$ and $R^3$ may optionally represent a joint double bond. Exemplary embodiments are compounds of the formulae 7.E.5, 7.E.6, 7.E.7, 7.E.12, 7.E.13, 8.E.5, 8.E.7, 8.E.8, 8.E.9, 8.E.12, 8.E.13 and 8.E.14.

A further embodiment describes compounds of the formula I-d in which $A^1$ represents Y or $NR^1$ and $A^2$ represents $C(R^2,R^3)$, the B adjacent to the $A^1$ represents $C(R^2,R^3)$ and the B adjacent to the $A^2$ represents Y or —$N(R^1)$—, the remaining B represents $C(R^2,R^3)$, and where two adjacent $R^3$ may optionally represent a joint double bond. Exemplary embodiments are compounds of the formulae 7.E.1, 7.E.2, 7.E.3, 7.E.4, 8.E.1, 8.E.2, 8.E.3 and 8.E.4.

A further embodiment describes compounds of the formula I-d in which $A^1$ represents Y or $NR^1$ and $A^2$ represents Y or —$N(R^1)$—, each B represents $C(R^2,R^3)$, and where two adjacent $R^3$ may optionally represent a joint double bond. Exemplary embodiments are compounds of the formulae 7.I.1, 7.I.2, 7.I.3, 7.N.1, 7.N.2, 7.N.3, 8.J.1, 8.J.2, 8.J.3, 8.N.1, 8.N.2 and 8.N.3.

A further embodiment describes compounds of the formula I-d in which $A^1$ represents $C(R^2,R^3)$ and $A^2$ represents $C(R^2,R^3)$, the B adjacent to the $A^2$ represents $C(R^2,R^3)$ and the remaining B each represent Y or $NR^1$, and where adjacent $R^1$ and $R^3$ may optionally represent a joint double bond. Exemplary embodiments are compounds of the formulae 6.D.6, 6.D.7, 6.D.8, 6.D.9 and 6.D.10.

A further embodiment describes compounds of the formula I-d in which $A^1$ represents $C(R^2,R^3)$ and $A^2$ represents $C(R^2,R^3)$, the B adjacent to the $A^1$ represents Y or —$N(R^1)$—, the B adjacent to the $A^2$ represents Y or $NR^1$ and the remaining B represents $C(R^2,R^3)$, and where adjacent $R^1$ and $R^3$ may optionally represent a joint double bond. Exemplary embodiments are compounds of the formulae 6.D.1, 6.D.2, 6.D.3, 6.D.4 and 6.D.5.

A further embodiment describes compounds of the formula I-d in which $A^1$ represents $C(R^2,R^3)$ and $A^2$ represents Y or —$N(R^1)$—, the B adjacent to the $A^1$ represents Y or —$N(R^1)$—, the B adjacent to the $A^2$ represents $C(R^2,R^3)$ and the remaining B represents $C(R^2,R^3)$, and where two adjacent $R^3$ or adjacent $R^1$ and $R^3$ may optionally represent a joint double bond. Exemplary embodiments are compounds of the formulae 6.L.2, 6.L.3, 6.H.4, 6.H.5, 6.H.6 and 6.H.7.

A further embodiment describes compounds of the formula I-d in which $A^1$ represents $C(R^2,R^3)$ and $A^2$ represents $C(R^2,R^3)$, the B adjacent to the $A^1$ represents $C(R^2,R^3)$, the B adjacent to the $A^2$ represents Y or —$N(R^1)$— and the remaining B represents Y or —$N(R^1)$—, and where adjacent $R^1$ and $R^3$ may optionally represent a joint double bond. Exemplary embodiments are compounds of the formulae 6.D.11, 6.D.12 and 6.D.13.

A further embodiment describes compounds of the formula I-d in which $A^1$ represents $C(R^2,R^3)$ and $A^2$ represents Y or —$N(R^1)$—, the B adjacent to the $A^1$ represents $C(R^2,R^3)$, the B adjacent to the $A^2$ represents $C(R^2,R^3)$ and the remaining B represents Y or —$N(R^1)$—, and where two adjacent $R^3$ or adjacent $R^1$ and $R^3$ may optionally represent a joint double bond. Exemplary embodiments are compounds of the formulae 6.H.1, 6.H.2, 6.H.3, 6.L.1 and 6.L.4.

A further embodiment describes compounds of the formula I-d in which $A^1$ represents $C(R^2,R^3)$ and $A^2$ represents Y or —$N(R^1)$—, the B adjacent to the $A^1$ represents $C(R^2,R^3)$, the B adjacent to the $A^2$ represents Y or —$N(R^1)$— and the remaining B represents $C(R^2,R^3)$, and where two adjacent $R^3$ or adjacent $R^1$ and $R^3$ may optionally represent a joint double bond. Exemplary embodiments are compounds of the formula 6.H.8.

In a further embodiment, compounds of the formula (I) are compounds of the formula (I-e)

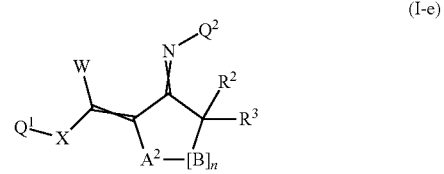

(I-e)

in which $A^2$, W, $R^2$, $R^3$, $Q^1$, $Q^2$, B and n have the meanings described above and X represents oxygen or sulphur. Embodiments which can be summarized under compounds of the formula (I-e) have already been disclosed in the present application.

In a further embodiment, compounds of the formula (I) are compounds of the formula (I-f)

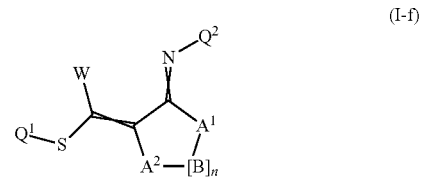

(I-f)

in which $Q^1$, $Q^2$, W, $A^1$, $A^2$, B and n have the meanings described above.

In a further embodiment, compounds of the formula (I) are compounds of the formula (I-g)

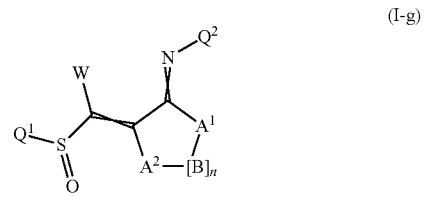

(I-g)

in which $Q^1$, $Q^2$, W, $A^1$, $A^2$, B, n have the meanings described above.

In a further embodiment, compounds of the formula (I) are compounds of the formula (I-h)

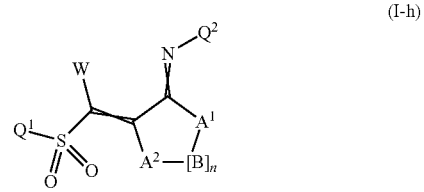

(I-h)

in which $Q^1$, $Q^2$, W, $A^1$, $A^2$, B, n have the meanings described above.

In a further embodiment, compounds of the formula (I) are compounds of the formula (I-i)

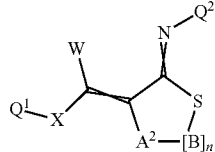
(I-i)

in which $Q^1$, $Q^2$, W, $A^2$, B and n have the meanings described above and X represents oxygen or sulphur.

In a further embodiment, compounds of the formula (I) are compounds of the formula (I-j)

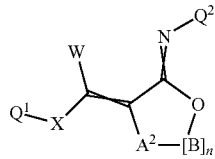
(I-j)

in which $Q^1$, $Q^2$, W, $A^2$, B and n have the meanings described above and X represents oxygen or sulphur. Embodiments which can be summarized under compounds of the formula (I-j) have already been disclosed in the present application.

In a further embodiment, compounds of the formula (I) are compounds of the formula (I-k)

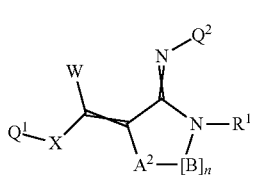
(I-k)

in which $R^1$, W, $A^2$, $Q^1$, $Q^2$, B and n have the meanings described above and X represents oxygen or sulphur. Embodiments which can be summarized under compounds of the formula (I-k) have already been disclosed in the present application.

A further aspect of the present invention is the provision of novel intermediates for the synthesis of the compounds according to the invention. Novel intermediates are, for example, compounds of the formula (II). In one embodiment, compounds of the formula (II) are compounds of the formula (II-a):

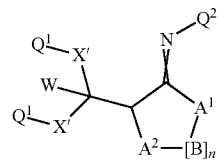
(II)

-continued

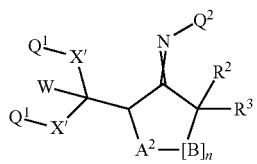
(II-a)

in which $A^1$, $A^2$, W, $R^2$, $R^3$, $Q^1$, $Q^2$, B and n have the meanings described above and X' represents oxygen or sulphur. Compounds of the formula (II) also have insecticidal action. Accordingly, one aspect of the invention also relates to an insecticidal composition, characterized in that it comprises an active compound of the formula (II) and extenders and/or surfactants. Furthermore, the invention also encompasses a method for protecting transgenic or conventional seed and the plant resulting therefrom against attack by pests, which method is characterized in that seed is treated with at least one compound of the formula (II). Accordingly, the invention also comprises the use of a compound of the formula (II) or an insecticidal composition comprising a compound of the formula (II) for controlling pests and in vector control. The present invention also encompasses seed to which a compound of the formula (II) is applied to the seed as component of a coating or as a further layer or further layers in addition to a coating.

Like compounds of the formula (I), compounds of the formula (II) have insecticidal action. Accordingly, the present invention can also be described as providing compounds of the formula (A) in which all parameters may be defined as for compounds of the formulae (I) and (II):

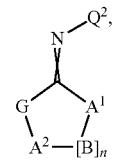
(0)

in which G represents

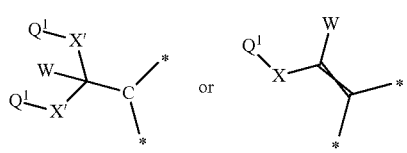

and $A^1$, $A^2$, W, $Q^1$, $Q^2$, B and n have the meanings described herein and X' represents oxygen or sulphur and X represents —O—, —S—, —S(O)— or —S(O)$_2$—.

Preferably, a compound of the formula (A) is a compound of the formula (I) or a compound of the formula (II) as described herein.

Syntheses

The compounds according to the invention can be prepared by customary methods known to the person skilled in the art.

Reaction scheme 1 shows the general preparation process A for the compounds (I) according to the invention.

Reaction scheme 1

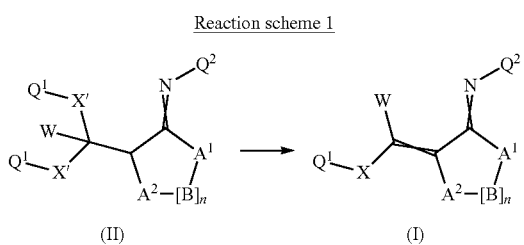

The radicals $A^1$, $A^2$, W, $Q^1$, $Q^2$, B and n have the meanings described above. In this case, X' and X represent oxygen or sulphur.

Compounds according to the invention of the general structure (I) can be formed from (thio)acetals (W corresponds to H) or (thio)ketals (W corresponds to alkyl) of the general structure (II) by formal elimination of $Q^1$-X—H. Suitable bases (for example, 1,8-diazabicyclo[5.4.0]undec-7-ene as in *J. Am. Chem. Soc.* 1989, 111, 7487-500), acids (for example titanium tetrachloride) or, in the case of X equals sulphur, even oxidizing agents (for example meta-chloroperbenzoic acid) may be used here.

A specific embodiment of the preparation process A is shown in reaction scheme 2 (preparation process B) for preparing the compounds (I-e) according to the invention.

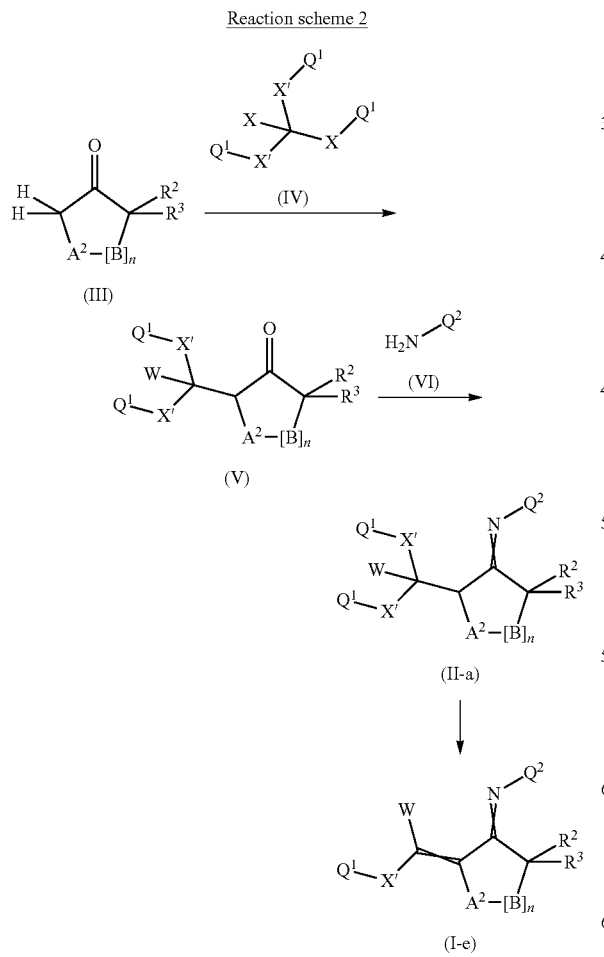

The radicals $A^2$, W, $R^2$, $R^3$, $Q^1$, $Q^2$, B and n have the meanings described above. In this case, X' and X represent oxygen or sulphur.

alpha-beta-Unsaturated imines of type (I-e) according to the invention can be formed from (thio)acetals (W corresponds to H) or (thio)ketals (W corresponds to alkyl) of the general structure (II-a) by formal elimination of $Q^1$-X—H. Here, it is possible to use, inter alia, the processes mentioned in paragraph [0300].

The imines (II-a) can be obtained by reacting amines $Q^2NH_2$ (VI) with cyclic carbonyl compounds of the general formula (V). In this step, too, it is possible to use a suitable acid.

For example, the reaction of 6-methoxy-3,4-dihydronaphthalen-1(2H)-one with 4-methoxyaniline in the presence of p-toluenesulphonic acid is described in *Aust. J. Chem.* 1994, 47, 649-662, or the reaction of 6-methoxy-3,4-dihydronaphthalen-1(2H)-one with 3-methylaniline in the presence of titanium tetrachloride is described in *Org. Lett.* 2000, 2, 713-716.

The (thio)acetals (W corresponds to H) or (thio)ketals (W corresponds to alkyl) of the general structure (V) can be obtained, for example, by reacting carbonyl compounds of the general formula (III) with thioorthoesters (IV, X corresponds to S) or orthoesters (IV, X corresponds to O). In this step, it is possible to use a suitable acid or base. Furthermore, the carbonyl compounds (III) can be used as their silylenol ethers.

Thus, for example, the reaction of the trimethylsilylenol ether of cyclopentanone with triphenyl trithioorthoformate to give the corresponding compound of type (V) is described in *J. Am. Chem. Soc.* 1989, 111, 7487-500. Specifically, the novel process B provides a very efficient synthetic route to type (I-e) compounds, in particular also in comparison with the processes disclosed in WO 2010/070910 and WO 2011/058963.

Reaction scheme 3 shows the general preparation process C for the compounds (1-g) and (1-h) according to the invention.

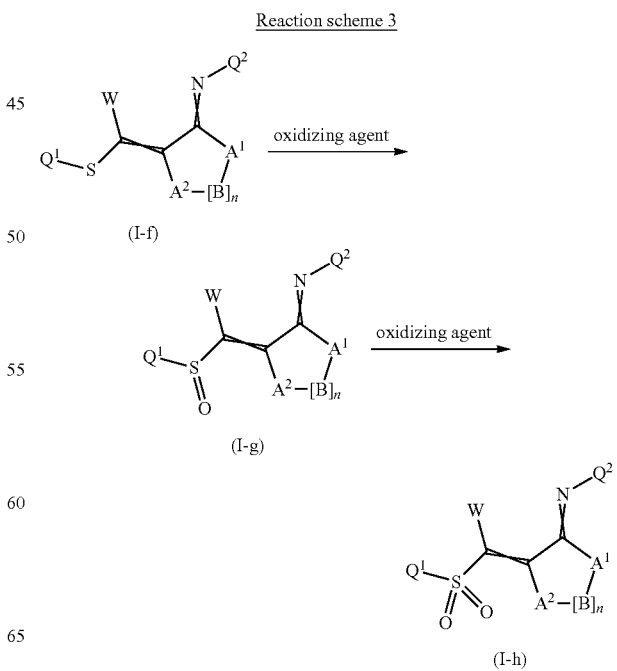

The radicals $A^1$, $A^2$, W, $Q^1$, $Q^2$, B and n have the meanings described above.

alpha-beta-Unsaturated imines according to the invention of type (I-g, sulphoxides) and type (I-h, sulphones) can be formed from the corresponding sulphides of the general structure (I-f) by oxidizing the sulphur. Both by choosing the suitable oxidizing agent and by using one or at least two equivalents of oxidizing agent, it is possible to prepare the sulphoxide or the sulphone.

Thus, for example, *Org. Lett.* 2008, 10, 721-724 describes the oxidation of the vinyl sulphide (E)-2-phenylthiomethyl-ene-6-methyl-3(2H)-benzofuranone with one equivalent of meta-chloroperbenzoic acid to give the corresponding vinyl sulphoxide. In WO2007/63702, using excess meta-chloroperbenzoic acid, the vinyl sulphide phenyl (2E)-N-phenyl-3-(phenylsulphanyl)prop-2-enimidoate is oxidized to the corresponding vinyl sulphone. In *J. Am. Chem. Soc.* 1989, 111, 7487-500 an analogous oxidation of vinyl sulphides to vinyl sulphones using the oxidizing agent Oxone is reported.

Reaction scheme 4 shows the general preparation process D for the compounds (I-i) and (I-j) according to the invention.

The radicals W, $A^2$, $Q^1$, $Q^2$, B and n have the meanings described above, where the B which is adjacent to position $A^1$ in formulae (I-i) and (I-j) represents $C(R^2,R^3)$. X represents oxygen or sulphur, R represents an optionally substituted alkyl or aryl radical, PG represents a suitable protective group, such as, for example, t-butyldiphenylsilyl and LG, finally, represents a suitable leaving group, such as, for example, chlorine.

An analogous preparation process has already been described in detail in WO2010/070910.

Reaction scheme 5 shows the general preparation process E for the compound (I-k) according to the invention.

Reaction scheme 5

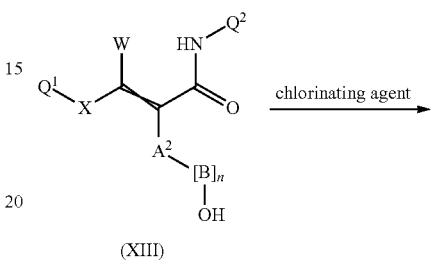

(XIII)

Reaction scheme 4

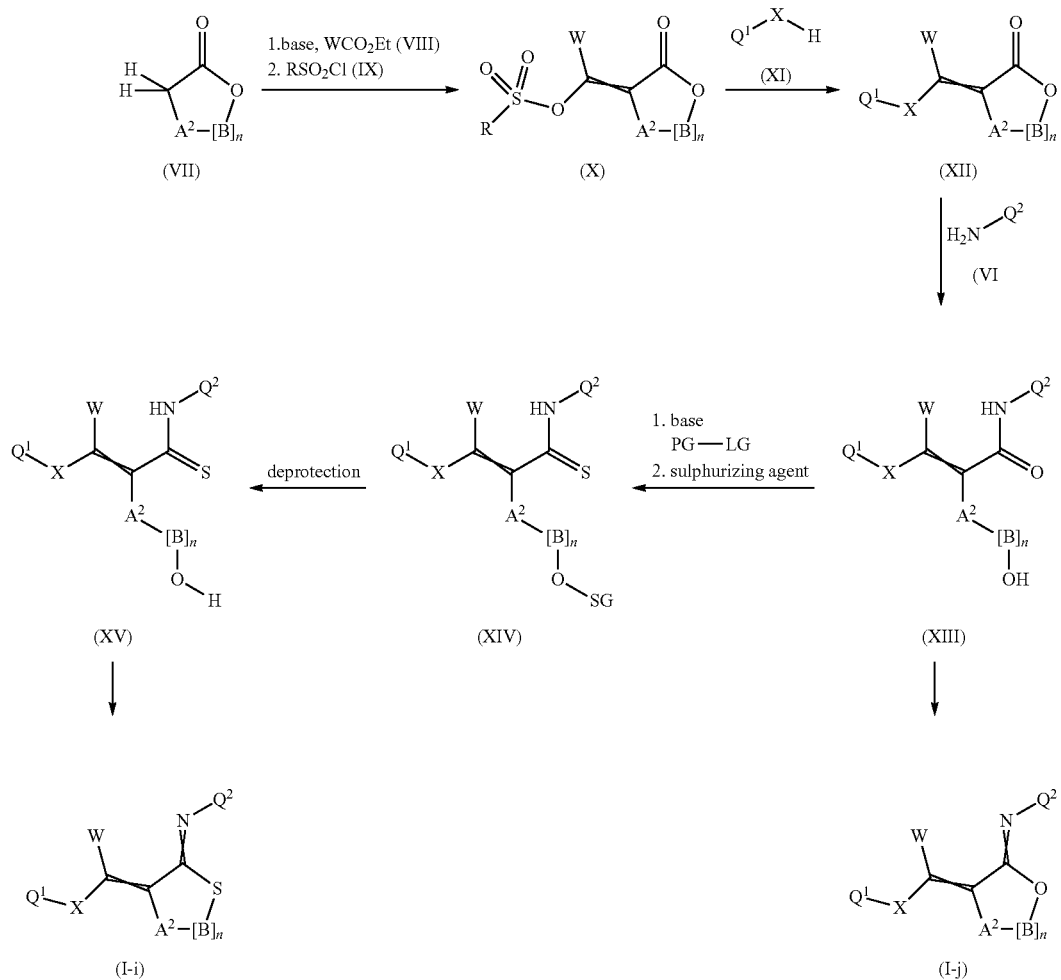

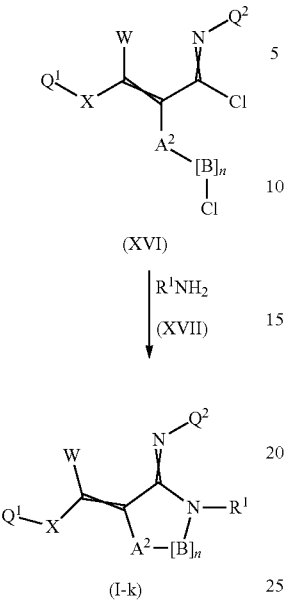

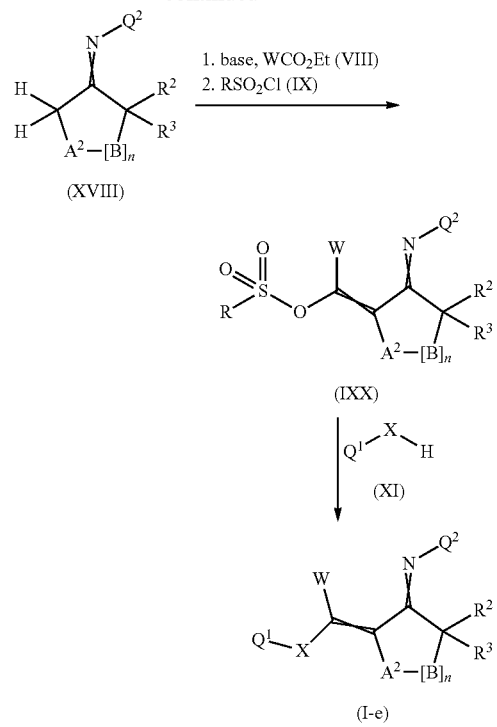

The radicals $R^1$, W, $A^2$, $Q^1$, $Q^2$, B and n have the meanings described above, where the B which is adjacent to position $A^1$ in formulae (I-i) and (I-j) represents $C(R^2,R^3)$. In this case, X represents oxygen and sulphur.

Compounds according to the invention of the general structures (I-k) can be prepared by a cyclization reaction from an acyclic precursor of the general structure (XVI) and an amine of the general structure (XVII).

Thus, for example, J. Med. Chem. 2000, 43, 3837-3851 describes the cyclization of 4-chloro-5-(2-chloroethyl)-6-methylpyrimidine-2-amine with benzylamine in the presence of triethylamine and n-butanol to give 7-benzyl-4-methyl-6,7-dihydro-5H-pyrrolo[2,3-d]pyrimidine-2-amine.

The compounds of the general structure (XVI) can be produced by reacting compounds of the general structure (XIII) with chlorinating agents.

Thus, for example, IN 2003-MU444 describes the reaction of N-cyclohexyl-5-hydroxypentanamide with phosphorus pentachloride to give 5-chloro-N-cyclohexylpentaneimidoyl chloride. WO 2007/063702 provides the reaction of N-phenyl-3-(phenylsulphanyl)acrylamide with thionyl chloride and catalytical amounts of N,N-dimethylformamide to give N-phenyl-3-(phenylsulphanyl)prop-2-enimidoyl chloride.

Reaction scheme 6 shows the general preparation process F for the compounds (I) according to the invention.

Reaction scheme 6

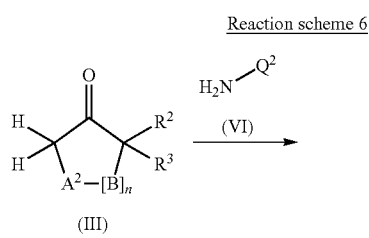

The radicals W, $A^2$, $Q^1$, $Q^2$, B, $R^1$, $R^2$ and n have the meanings described above, where X represents oxygen or sulphur. R represents an optionally substituted alkyl or aryl radical.

The imines (XVIII) can be obtained by reacting amines $Q^2NH_2$ (VI) with cyclic carbonyl compounds of the general formula (III). In this step, a suitable acid may be used.

The reaction of 6-methoxy-3,4-dihydronaphthalen-1(2H)-one with 4-methoxyaniline in the presence of p-toluenesulphonic acid, for example, is described in Aust. J. Chem. 1994, 47, 649-662, and the reaction of 6-methoxy-3,4-dihydronaphthalen-1(2H)-one with 3-methylaniline in the presence of titanium tetrachloride is described in Org. Lett. 2000, 2, 713-716.

An analogous preparation process for converting compounds of the structure (XVIII) into (IXX) into (I-e) has already been described in detail in WO2010/070910 and WO 2011/058963.

Further aspects of the present invention are the use of compounds of the formula (I) according to the invention and the compounds of the formulae

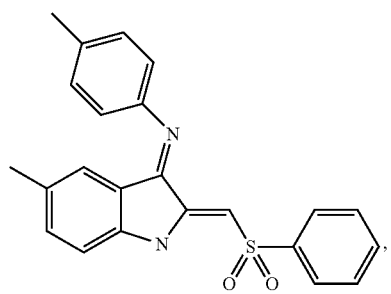

-continued

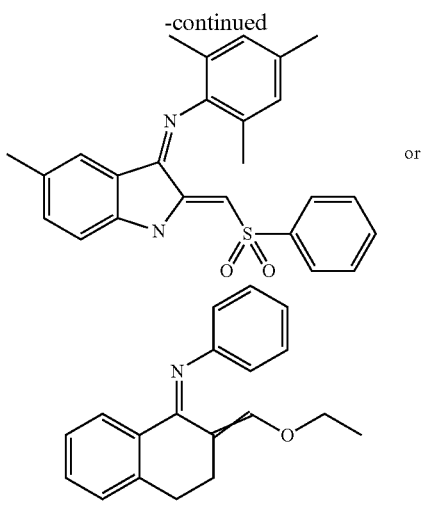

and their salts, N-oxides and tautomeric forms for controlling animals pests; for controlling unwanted microorganisms, for use in the treatment of seed; for use on transgenic plants; for controlling vectors (in other words, compounds of the formula (I) according to the invention can be used in the control of vectors, in particular in the control of mosquitoes, lice, fleas, flies, mites and ticks).

A further aspect of the present invention is a crop protection composition (insecticidal composition) comprising at least one active compound of the formula (I) or an active compound of the formula

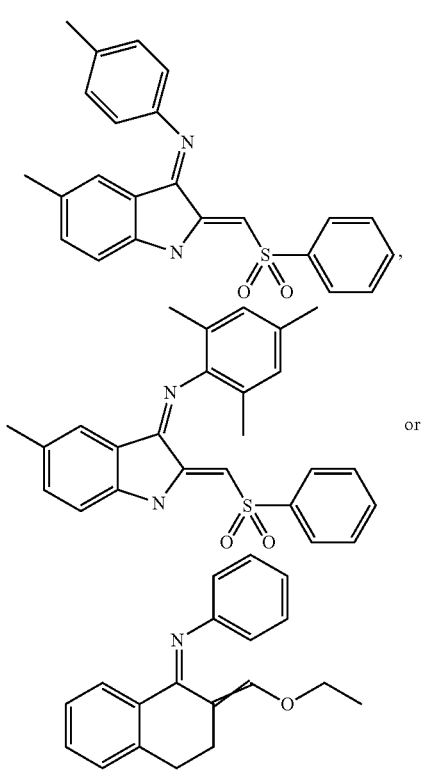

and salts, N-oxides and tautomeric forms thereof and an extender and/or a surfactant. The invention also encompasses a process for preparing an insecticidal composition of this kind, characterized in that an active compound according to the invention is mixed with extenders and/or surfactants.

A further aspect of the present invention is a method for controlling pests, characterized in that a compound of the formula (I) according to the invention or a compound of the formulae

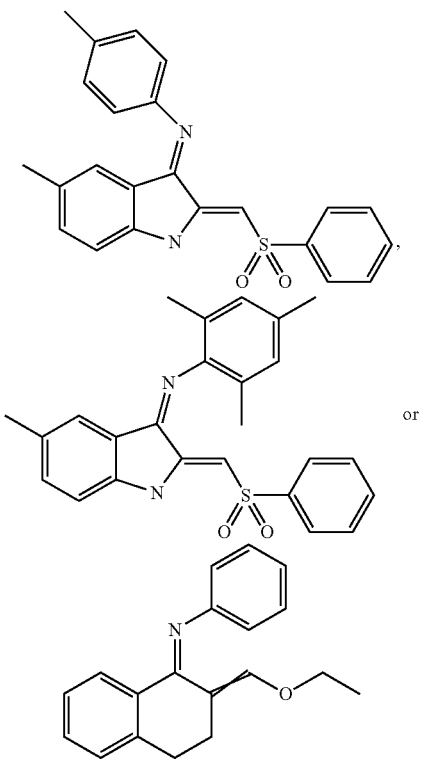

and salts, N-oxides and tautomeric forms thereof are allowed to act on the pests and/or the plant to be protected and/or their/its habitat.

The active compounds according to the invention, having good plant compatibility, favourable homeotherm toxicity and good environmental compatibility, are suitable for protecting plants and plant organs, for increasing harvest yields, improving the quality of the harvested material and for controlling animal pests, in particular insects, arachnids, helminths, nematodes and molluscs, encountered in agriculture, in horticulture, in animal breeding, in forests, in gardens and leisure facilities, in the protection of stored products and materials and in the hygiene sector. Unless explicitly mentioned otherwise, the term "agriculture" refers to the field of crop cultivation, in other words, animal husbandry and procedures on the animal or human body are in this case not comprised by the term. Correspondingly, plant pests are pests which damage plants and which are encountered in the field of crop cultivation or crop utilization. Such pests occur on and in plants and parts of plants, the area of soil surrounding a plant, for example in the catchment area of its root system, fields, meadows, plantations, horticulture, forests, gardens, leisure facilities, etc., and damage the plants or parts of plants. They can preferably be used as crop protection agents. They act against normally sensitive and resistant species and against all or individual development stages. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizullyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthulraphus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Dermaptera, for example, *Forficula auricularia.*

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control protozoa, such as Eimeria.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptullossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Mono-morium pharaonis, Vespa* spp.

From the order of the Isopoda, for example, *Armadillidium vulgare, Oniscus asellus, Porcellio scaber.*

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp.,

*Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Litho-colletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci, Globora* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In a preferred embodiment, the compounds according to the invention are suitable in particular for use in the control of plant pests in agriculture, in horticulture, in forests, in gardens and leisure facilities, and also in the protection of stored products and materials.

In a further preferred embodiment, the compounds according to the invention can be employed for use in the control of pests in animal breeding, animal husbandry and animal production and in the hygiene sector.

Seed Treatment

The present invention also relates to a method for protecting seed and germinating plants from attack by pests, by treating the seed with an active compound according to the invention.

The invention likewise relates to the use of an active compound according to the invention for treating seed for the purpose of protecting the seed and the resultant plant against animal pests.

The invention relates, furthermore, to seed which for protecting against animal pests has been treated with an active compound according to the invention. Accordingly, the invention also relates to seed where an active compound according to the invention has been applied to the seed as a component of a coating or as a further layer or further layers in addition to a coating.

Furthermore, the invention relates to seed which, following treatment with an active compound according to the invention, is subjected to a film-coating process in order to prevent dust abrasion on the seed.

One of the advantages of the present invention is that, owing to the particular systemic properties of the compositions according to the invention, the treatment of the seed with these compositions provides protection from animal pests not only to the seed itself but also to the plants originating from the seed, after they have emerged. In this way, it may not be necessary to treat the crop directly at the time of sowing or shortly thereafter.

A further advantage is to be seen in the fact that, through the treatment of the seed with the active compound according to the invention, germination and emergence of the treated seed may be promoted.

It is likewise considered to be advantageous that active compounds according to the invention may also be used, in particular, on transgenic seed.

It is also stated that active compounds according to the invention may be used in combination with agents of the signalling technology, as a result of which, for example, colonization with symbionts is improved, such as *rhizobia, mycorrhiza* and/or *endophytic* bacteria, for example, is enhanced, and/or nitrogen fixation is optimized.

The compositions according to the invention are suitable for protecting seed of any variety of plant which is used in agriculture, in greenhouses, in forests or in horticulture. More particularly, the seed in question is that of cereals (for example wheat, barley, rye, millet and oats), maize, cotton, soya beans, rice, potatoes, sunflower, coffee, tobacco, canola, oilseed rape, beets (for example sugarbeet and fodder beet), peanuts, vegetables (for example tomato, cucumber, bean, brassicas, onions and lettuce), fruit plants, lawns and ornamentals. Particularly important is the treatment of the seed of cereals (such as wheat, barley, rye and oats), maize, soya beans, cotton, canola, oilseed rape and rice.

As already mentioned above, the treatment of transgenic seed with an active compound according to the invention is particularly important, too. The seed in question here is that of plants which generally contain at least one heterologous gene that controls the expression of a polypeptide having, in particular, insecticidal and/or nematicidal properties. The heterologous genes in transgenic seed may come from microorganisms such as *Bacillus, Rhizobium, Pseudomonas, Serratia, Trichoderma, Clavibacter, Glomus* or *Gliocladium*. The present invention is particularly suitable for the treatment of transgenic seed which contains at least one heterologous gene which comes from *Bacillus* sp. With particular preference, the heterologous gene in question comes from *Bacillus thuringiensis*.

For the purposes of the present invention, a composition according to the invention is applied alone or in a suitable formulation to the seed. The seed is preferably treated in a condition in which its stability is such that no damage occurs in the course of the treatment. Generally speaking, the seed may be treated at any point in time between harvesting and sowing. Typically, seed is used which has been separated from the plant and has had cobs, hulls, stems, husks, hair or pulp removed. Thus, for example, seed may be used that has been harvested, cleaned and dried to a moisture content of less than 15% by weight. Alternatively, seed can also be used that after drying has been treated with water, for example, and then dried again.

When treating the seed it is necessary, generally speaking, to ensure that the amount of the composition of the invention, and/or of other additives, that is applied to the seed is selected such that the germination of the seed is not adversely affected, and/or the plant which emerges from the seed is not damaged. This is the case in particular with active compounds which may exhibit phytotoxic effects at certain application rates.

The compositions according to the invention can be applied directly, in other words without comprising further components and without having been diluted. As a general rule, it is preferable to apply the compositions in the form of a suitable formulation to the seed. Suitable formulations and methods for seed treatment are known to the person skilled in the art and are described in, for example, the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compounds which can be used according to the invention may be converted into the customary seed-dressing formulations, such as solutions, emulsions, suspensions, powders, foams, slurries or other coating compositions for seed, and also ULV formulations.

These formulations are prepared in a known manner, by mixing the active compounds with customary additives, such as, for example, customary extenders and also solvents or diluents, colorants, wetting agents, dispersants, emulsifiers, antifoams, preservatives, secondary thickeners, tackifiers, gibberellins, and also water.

Colorants which may be present in the seed-dressing formulations which can be used in accordance with the invention include all colorants which are customary for such purposes. In this context it is possible to use not only pigments, which are of low solubility in water, but also water-soluble dyes. Examples include the colorants known under the designations Rhodamin B, C.I. Pigment Red 112 and C.I. Solvent Red 1.

Wetting agents which may be present in the seed-dressing formulations which can be used in accordance with the invention include all of the substances which promote wetting and which are customary in the formulation of agrochemically active compounds. Use may be made preferably of alkylnaphthalenesulphonates, such as diisopropyl- or diisobutylnaphthalenesulphonates.

Dispersants and/or emulsifiers which may be present in the seed-dressing formulations which can be used in accordance with the invention include all of the nonionic, anionic and cationic dispersants that are customary in the formulation of agrochemically active compounds. Use may be made preferably of nonionic or anionic dispersants or of mixtures of nonionic or anionic dispersants. Suitable nonionic dispersants are, in particular, ethylene oxide/propylene oxide block polymers, alkylphenol polyglycol ethers and also tristyrylphenol polyglycol ethers, and the phosphated or sulphated derivatives of these. Suitable anionic dispersants are, in particular, lignosulphonates, salts of polyacrylic acid and arylsulphonate/formaldehyde condensates.

Antifoams which may be present in the seed-dressing formulations which can be used in accordance with the invention include all of the foam inhibitors that are customary in the formulation of agrochemically active compounds. Use may be made preferably of silicone antifoams and magnesium stearate.

Preservatives which may be present in the seed-dressing formulations which can be used in accordance with the invention include all of the substances which can be employed for such purposes in agrochemical compositions. Examples include dichlorophen and benzyl alcohol hemiformal.

Secondary thickeners which may be present in the seed-dressing formulations which can be used in accordance with the invention include all substances which can be used for such purposes in agrochemical compositions. Those contemplated with preference include cellulose derivatives, acrylic acid derivatives, xanthan, modified clays and finely divided silica.

Tackifiers which may be present in the seed-dressing formulations which can be used in accordance with the invention include all customary binders which can be used in seed-dressing products. Preferred mention may be made of polyvinylpyrrolidone, polyvinyl acetate, polyvinyl alcohol and tylose.

Gibberellins which may be present in the seed-dressing formulations which can be used in accordance with the invention include preferably the gibberellins A1, A3 (=gibberellic acid), A4 and A7, with gibberellic acid being used with particular preference. The gibberellins are known (cf. R. Wegler, "Chemie der Pflanzenschutz- and Scheädlingsbekämpfungsmittel" [Chemistry of plant protection and pest control agents], Volume 2, Springer Verlag, 1970, pp. 401-412).

The seed-dressing formulations which can be used in accordance with the invention may be used, either directly or after prior dilution with water, to treat seed of any of a wide variety of types. Accordingly, the concentrates or preparations obtainable therefrom by dilution with water may be employed to dress the seed of cereals, such as wheat, barley, rye, oats and triticale, and also the seed of maize, rice, oilseed rape, peas, beans, cotton, sunflowers and beets, or else the seed of any of a very wide variety of vegetables. The seed-dressing formulations which can be used in accordance with the invention, or their diluted preparations, may also be used to dress seed of transgenic plants. In this case, additional synergistic effects may also occur in interaction with the substances formed through expression.

For the treatment of seed with the seed-dressing formulations which can be used in accordance with the invention, or with the preparations produced therefrom by addition of water, suitable mixing apparatus includes all such equipment which can typically be employed for dressing. Specifically, the procedure when carrying out dressing is to place the seed in a mixer, to add the particular desired amount of seed-dressing formulations, either as such or following dilution with water beforehand, and to carry out mixing until the distribution of the formulation on the seed is uniform. This may be followed by a drying operation.

The application rate of the seed-dressing formulations which can be used in accordance with the invention may be varied within a relatively wide range. It depends on the particular amount of the active compound according to the invention in the formulations, and on the seed. The application rates in the case of active compounds according to the invention are generally between 0.001 and 50 g per kilogram of seed, preferably between 0.01 and 15 g per kilogram of seed.

A further embodiment relates to a coating for seed, the coating comprising a compound of the formula (I) or (II).

Animal Treatment

In addition, the active compounds according to the invention can be used for controlling a wide variety of pests, including, for example, harmful sucking insects, biting insects and other plant-parasitic pests, stored product pests, pests which destroy technical materials, and hygiene pests as well as pests, including parasites, in the animal health field and can be employed for their control, like, for example, eradication and extermination. Therefore, the present invention also encompasses a method for controlling pests.

In the animal health field, i.e. in the field of veterinary medicine, the active compounds according to the present invention are active against animal parasites, in particular ectoparasites or endoparasites. The term endoparasites includes in particular helminths, such as cestodes, nematodes or trematodes, and protozoae, such as kozzidia. Ectoparasites are typically and preferably arthropods, in particular insects such as flies (stinging and licking), parasitic fly larvae, lice, hair lice, bird lice, fleas and the like; or acarids, such as ticks, for example hard ticks or soft ticks, or mites, such as scab mites, harvest mites, bird mites and the like.

These parasites include:

From the order of the Anoplurida, for example, *Haematopinus* spp., *Linognathus* spp., *Pediculus* spp., *Phtirus* spp., *Solenopotes* spp.; specific examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;*

From the order of the Mallophagida and the suborders Amblycerina and also Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; specific examples are: *Bovicola bovis, Bovicola ovis, Bovicola limbata, Damalina bovis, Trichodectes canis, Felicola subrostratus, Bovicola caprae, Lepikentron ovis, Werneckiella equi;*

From the order of the Diptera and the suborders Nematocerina and also Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Ochlerotatus* spp., *Culiseta* spp., *Psorophora* spp., *Mansonia* spp., *Haemagoggus* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; specific examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorrhoidalis, Gasterophilus inermis, Gasterophilus nasalis, Gasterophilus nigricornis, Gasterophilus pecorum, Braula coeca;*

From the order of the Siphonapterida, for example, *Pulex* spp., *Ctenocephalides* spp., *Tunga* spp., *Xenopsylla* spp., *Ceratophyllus* spp.; specific examples are: *Ctenocephalides canis, Ctenocephalides felis, Pulex irritans, Tunga penetrans, Xenopsylla cheopis;*

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattella germanica, Supella* spp. (for example, *Supella longipalpa*).

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Rhipicephalus* (*Boophilus*) spp., *Dermacentor* spp., *Haemophysalis* spp., *Hyalomma* spp., *Dermanyssus* spp., *Rhipicephalus* spp. (from the original genus of multi-host ticks), *Ornithonyssus* spp., *Pneumonyssus* spp., *Raillietia* spp., *Pneumonyssus* spp., *Sternostoma* spp., *Varroa* spp., *Acarapis* spp.; specific examples are: *Argas persicus, Argas reflexus, Ornithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;*

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; specific examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschöngastia xerothermobia, Trombicula akamushi, Otodectes cynotis, Notoedres cati, Sarcoptis canis, Sarcoptes bovis, Sarcoptes ovis, Sarcoptes rupicaprae* (=*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

The active compounds according to the invention are also suitable for controlling arthropods, helminths and protozoa which infest animals. The animals include agricultural productive livestock, such as, for example, cattle, sheep, goats, horses, pigs, donkeys, camels, buffalo, rabbits, chickens, turkeys, ducks, geese, ornamental fish, bees. The animals also include pets—also referred to as domestic animals—such as, for example, dogs, cats, caged birds and aquarium fish, and also so-called test animals, such as, for example, hamsters, guinea pigs, rats and mice.

By controlling these arthropods, helminths and/or protozoa, cases of death should be diminished, and productivity (for meat, milk, wool, hides, eggs, honey etc.) and the health of the host animal should improve so that more economic and easier animal husbandry is possible by use of the active compounds according to the invention.

Accordingly it is desirable, for example, to prevent or interrupt the uptake of host blood by the parasites (if appropriate). Parasite control may also contribute to preventing transmission of infectious substances.

The term "control", as used herein with regard to the animal health field, means that the active compounds act by reducing the occurrence of the parasite in question in an animal infected by such parasites to harmless levels. More specifically, "control", as used herein, means that the active compound kills the parasite in question, inhibits its growth or inhibits its proliferation.

Generally, the active compounds according to the invention, when used for treating animals, can be applied directly. They are preferably applied as pharmaceutical compositions which may comprise pharmaceutically acceptable excipients and/or auxiliaries known in the prior art.

The active compounds are used (administered) in the veterinary sector and in animal husbandry in a known manner by enteral administration in the form of, for example, tablets, capsules, portions, drenches, granules, pastes, boluses, the feed-through process and suppositories, by parenteral administration, such as, for example, by injection (intramuscular, subcutaneous, intravenous, intraperitoneal and the like), implants by nasal administration, by dermal administration in the form, for example, of dipping or bathing, spraying, pouring on and spotting on, washing and powdering, and also with the aid of moulded articles containing the active compound, such as collars, ear marks, tail marks, limb bands, halters, marking devices and the like. The active compounds may be formulated as a shampoo or as a suitable formulation which may be used in aerosols or non-pressurized sprays, for example, pump sprays and atomizers.

When used for livestock, poultry, pets and the like, the active compounds according to the invention can be used as formulations (for example powders, wettable powders "WP", emulsions, emulsifiable concentrates "EC", free-flowing compositions, homogeneous solutions and suspension concentrates "SC"), which comprise the active compounds in an amount of 1 to 80% by weight, directly or after dilution (for example 100 to 10 000-fold dilution), or they can be used as a chemical bath.

When used in the animal health field, the active compounds according to the invention can be used in combination with suitable synergists or other active compounds such as, for example, acarids, insecticides, anthelmintics, compositions against protozoa.

Control of Vectors

The active compounds according to the invention can also be used in the control of vectors. In the sense of the present invention, a vector is an arthropod, in particular an insect or arachnid, capable of transferring pathogens such as, for example, viruses, worms, single-cell organisms and bacteria from a reservoir (plant, animal, human, etc.) to a host. The pathogens may either be transferred mechanically onto a host (for example trachoma by non-biting flies) or transferred by injection into a host (for example malaria parasites by mosquitoes).

Examples of vectors and the diseases or pathogens transferred by them are:
1) mosquitoes
    *Anopheles*: malaria, filariasis;
    *Culex*: Japanese encephalitis, filariasis, other viral diseases, transfer of worms;
    *Aedes*: yellow fever, Dengue fever, filariasis, other viral diseases;
    Simuliidae: transfer of worms, in particular *Onchocerca volvulus*
2) Lice: skin infections, epidemic typhus;
3) Fleas: plague, murine typhus;
4) Flies: sleeping sickness (trypanosomiasis); cholera, other bacterial diseases
5) Mites: Acariose, epidemic typhus, Rickettsialpox, Tularamia, Saint-Louis encephalitis, tick-borne encephalitis (TBE), Krim-Kongo haematologic fever, epidemic typhus, borreliosis;
6) Ticks: Borelliosis such as *Borrelia duttoni*, tick-borne encephalitis, Q fever (*Coxiella burnetii*), babesiosis (*Babesia canis canis*).

Examples of vectors in the sense of the present invention are insects such as aphids, flies, leaf hoppers or thrips capable of transferring plant viruses to plants. Further vectors capable of transferring plant viruses are spider mites, lice, beetles and nematodes.

Further examples of vectors vectors in the sense of the present invention are insects and arachnids such as mosquitoes, in particular of the genera *Aedes*, *Anopheles*, for example, *A. gambiae*, *A. arabiensis*, *A. funestus*, *A. dirus* (Malaria) and *Culex*, lice, fleas, flies, mites and ticks capable of transferring pathogens to animals and/or humans.

A control of vectors is also possible with resistance-breaking compounds.

Compounds of the present invention are suitable for use in the prevention of diseases or of pathogens transferred by vectors. A further aspect of the present invention is the use of compounds according to the invention for controlling vectors, for example in agriculture, in horticulture, in forests, in gardens and leisure facilities, and also in the protection of stored products and materials.

Material

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina*.

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

The compounds according to the invention can likewise be employed for protecting objects which come into contact with saltwater or brackish water, in particular hulls, screens, nets, buildings, moorings and signalling systems, against fouling.

Furthermore, the compounds according to the invention, alone or in combination with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Avicularidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

Further Use

At certain concentrations or application rates, the compounds according to the invention can also be used as herbicides, safeners, growth regulators or agents for improving plant properties, or as microbicides, for example as fungicides, antimycotics, bactericides, viricides (including agents against viroids) or as agents against MLO (mycoplasma-like organism) and RLO (rickettsia-like organism). They can also be used as intermediates or precursors for the synthesis of other active compounds.

Formulations

The active compounds can be converted into the customary formulations, such as solutions, emulsions, wettable powders, water- and oil-based suspensions, powders, dusts, pastes, soluble powders, soluble granules, granules for broadcasting, suspension-emulsion concentrates, natural compounds impregnated with active compound, synthetic substances impregnated with active compound, fertilizers and also microencapsulations in polymeric substances.

These formulations are produced in a known manner, for example by mixing the active compounds with extenders, i.e. liquid solvents and/or solid carriers, optionally with the use of surfactants, i.e. emulsifiers and/or dispersants and/or foam formers. The formulations are produced either in suitable plants or else before or during application.

Suitable for use as auxiliaries are substances which are suitable for imparting to the composition itself and/or to preparations derived therefrom (for example spray liquors, seed dressings) particular properties, such as certain technical properties and/or else particular biological properties.

Typical auxiliaries include: extenders, such as water or polar or nonpolar organic liquids, solvents, such as aromatics or aliphatic hydrocarbons, and carriers such as ammonium salts and ground natural minerals.

Tackifiers, such as carboxymethylcellulose, colorants, such as inorganic pigments or organic dyes, or further additives, such as perfumes, mineral or vegetable oils, which are optionally modified, waxes and nutrients (including trace nutrients) can be used in the formulations.

Stabilizers, such as low-temperature stabilizers, preservatives, antioxidants, light stabilizers or other agents which improve chemical and/or physical stability, may also be present.

The formulations generally comprise between 0.01 and 98% by weight of active compound, preferably between 0.5 and 90%.

The active compounds according to the invention may be used as such or in formulations thereof, including in a mixture with one or more suitable fungicides, bactericides, acaricides, nematicides, insecticides, microbicides, fertilizers, attractants, sterilants, synergists, safeners, semiochemicals and/or plant growth regulators, in order thus, for example, to broaden the spectrum of action, to prolong the duration of action, to increase the rate of action, to prevent repellence or to prevent evolution of resistance. Furthermore, active compound combinations of this kind can improve plant growth, increase tolerance to high or low temperatures, to drought or to levels of water and/or soil salinity, improve flowering performance, facilitate harvesting and increase yields, accelerate ripening, increase the quality and/or nutritional value of the harvested products, prolong storage life and/or improve the processability of the harvested products. By combining the active compounds according to the invention and mixing partners, synergist effects are obtained, i.e. the efficacy of the mixture in question is greater than was to be expected owing to the efficacies of the individual components. Generally, the combinations can be used either as seed treatments or in premixes, tank mixes or ready mixes.

Each additional active compound may be mixed with the active compounds according to the invention in a wide range, preferably in a ratio of from 100:1 to 1.100, particularly preferably from 5:1 to 1:5.

Particularly favourable mixing partners are, for example, insecticides, acaricides and/or nematicides as listed below:

(1) Ergosterol biosynthesis inhibitors, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulphate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifin (65472-88-0), (1.33) nuarimol (63284-71-9), (1.34) oxpoconazole (174212-12-5), (1.35) paclobutrazole (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizol (68694-11-1), (1.54) triforine (26644-46-2), (1.55) triticonazole (131983-72-7), (1.56) uniconazole (83657-22-1), (1.57) uniconazol-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl-1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]-1H-imidazole-1-carbothioate (111226-71-2).

(2) Respiration inhibitors (respiratory chain inhibitors), such as, for example, (2.1) bixafen (581809-46-3), (2.2) boscalid (188425-85-6), (2.3) carboxin (5234-68-4), (2.4) diflumetorim (130339-07-0), (2.5) fenfuram (24691-80-5), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam mixture of the syn-epimeric racemate 1RS,4SR,9RS and of the anti-epimeric racemate 1RS,4SR,9SR (881685-58-1), (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamid (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7), (2.28) 5,8-difluoro-N-[2-(2-fluoro-4-{[4-(trifluoromethyl)pyridin-2-yl]oxy}phenyl)ethyl]quinazoline-4-amine (1210070-84-0) (known from WO2010025451), (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) acting on complex III of the respiratory chain, for example (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.5) dimoxystrobin (141600-52-4), (3.6) enestroburin (238410-11-2) (known from WO 2004/058723), (3.9) famoxadon (131807-57-3) (known from WO 2004/058723), (3.10) fenamidone (161326-34-7) (known from WO 2004/058723), (3.11) fenoxystrobin (918162-02-4), (3.12) fluoxastrobin (361377-29-9) (known from WO 2004/058723), (3.13) kresoxim-methyl (143390-89-0) (known from WO 2004/058723), (3.14) metominostrobin (133408-50-1) (known from WO 2004/058723), (3.15) orysastrobin (189892-69-1) (known from WO 2004/058723), (3.16) picoxystrobin (117428-22-5) (known from WO 2004/058723), (3.17) pyraclostrobin (175013-18-0) (known from WO 2004/058723), (3.18) pyrametostrobin (915410-70-7) (known from WO 2004/058723), (3.19) pyraoxystrobin (862588-11-2) (known from WO 2004/058723), (3.20) pyribencarb (799247-52-2) (known from WO 2004/058723), (3.21) triclopyricarb (902760-40-1), (3.22) trifloxystrobin (141517-21-7) (known from WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (known from WO 2004/058723), (3.24) (2E)-2-(methoxyimino)-N-methyl-2-(2-{[({(1E)-1-[3-(trifluoromethyl)phenyl]ethylidene}amino)oxy]methyl}phenyl)ethanamide (known from WO 2004/058723), (3.25) (2E)-2-(methoxyimino)-N-methyl-2-{2-[(E)-({1-[3-(trifluoromethyl)phenyl]ethoxy}imino)methyl]phenyl}ethanamide (158169-73-4), (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl-(2E)-2-{2-[({cyclopropyl[(4-methoxyphenyl)imino]methyl}sulphanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Mitosis and cell division inhibitors, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds with multisite activity, for example (5.1) Bordeaux mixture (8011-63-0), (5.2) captafol (2425-06-1), (5.3) captan (133-06-2) (known from WO 02/12172), (5.4) chlorothalonil (1897-45-6), (5.5) copper preparations such as copper hydroxide (20427-59-2), (5.6) copper naphthenate (1338-02-9), (5.7) copper oxide (1317-39-1), (5.8) copper oxychloride (1332-40-7), (5.9) copper sulphate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) metriram zinc (9006-42-2), (5.27) oxine-copper (10380-28-6), (5.28) propamidine (104-32-5), (5.29) propineb (12071-83-9), (5.30) sulphur and sulphur preparations, for example calcium polysulphide (7704-34-9), (5.31) thiram (137-26-8), (5.32) tolylfluanid (731-27-1), (5.33) zineb (12122-67-7) and (5.34) ziram (137-30-4).

(6) Resistance inductors, for example (6.1) acibenzolar-5-methyl (135158-54-2), (6.2) isotianil (224049-04-1), (6.3) probenazole (27605-76-1) and (6.4) tiadinil (223580-51-6).

(7) Amino acid and protein biosynthesis inhibitors, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (known from WO2005070917).

(8) ATP production inhibitors, for example (8.1) fentin acetate (900-95-8), (8.2) fentin chloride (639-58-7), (8.3) fentin hydroxide (76-87-9) and (8.4) silthiofam (175217-20-6).

(9) Cell wall synthesis inhibitors, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Lipid and membrane synthesis inhibitors, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Melanin biosynthesis inhibitors, for example (11.1) carpropamid (104030-54-8), (11.2) diclocymet (139920-32-4), (11.3) fenoxanil (115852-48-7), (11.4) fthalide (27355-22-2), (11.5) pyroquilon (57369-32-1), (11.6) tricyclazole (41814-78-2) and (11.7) 2,2,2-trifluoroethyl {3-methyl-1-[(4-methylbenzoyl)amino]butan-2-yl}carbamate (851524-22-6) (known from WO2005042474).

(12) Nucleic acid synthesis inhibitors, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Signal transduction inhibitors, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Decouplers, for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds, for example (15.1) benthiazole (21564-17-0), (15.2) bethoxazin (163269-30-5), (15.3) capsimycin (70694-08-5), (15.4) carvone (99-49-0), (15.5) chinomethionate (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulphate (43222-48-6), (15.17) diphenylamine (122-39-4), (15.18) ecomat, (15.19) fenpyrazamine (473798-59-3), (15.20) flumetover (154025-04-4), (15.21) fluoromide (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methylisothiocyanate (556-61-6), (15.31) metrafenon (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and salts thereof (87-86-5), (15.40) phenothrin, (15.41) phosphoric acid and salts thereof (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl)prop-2-en-1-one (1231776-28-5), (15.45z) (2Z)-3-(4-tert-butylphenyl)-3-(2-chloropyridin-4-yl)-1-(morpholin-4-yl)prop-2-en-1-one (1231776-29-6), (15.46) pyrrolnitrin (1018-71-9) (known from EP-A 1 559 320), (15.47) tebufloquin (376645-78-2), (15.48) tecloftalam (76280-91-6), (15.49) tolnifanid (304911-98-6), (15.50) triazoxide (72459-58-6), (15.51) trichlamide (70193-21-4), (15.52) zarilamide (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate (517875-34-2) (known from WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9), (15.57) 1-(4-methoxyphenoxy)-3,3-dimethylbutan-2-yl]-1H-imidazol-1-carboxylate (111227-17-9), (15.58) 2,3,5,6-tetrachloro-4-(methylsulphonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c']dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7), (15.62) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl]pyridine, (15.66) 2-phenylphenol and salts thereof (90-43-7), (15.67) 3-(4,4,5-trifluoro-3,3-dimethyl-3,4-dihydroisoquinolin-1-yl)quinoline (861647-85-0) (known from WO2005070917), (15.68) 3,4,5-trichloropyridin-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulphonohydrazide (134-31-6), (15.74) 5-fluoro-2-[(4-fluorobenzyl)oxy]pyrimidine-4-amine (1174376-11-4) (known from WO2009094442), (15.75) 5-fluoro-2-[(4-methylbenzyl)oxy]pyrimidine-4-amine (1174376-25-0) (known from WO2009094442), (15.76) 5-methyl-6-octyl[1,2,4]triazolo[1,5-a]pyrimidine-7-amine, (15.77) ethyl (2Z)-3-amino-2-cyano-3-phenylprop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[1(5-bromo-3-chloropyridin-2-yl)methyl]-2,4-dichloropyridin-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N-{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6), (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5), (15.90) pentyl-{6-[({[(1-methyl-1H-tetrazol-5-yl)(phenyl)methylidene]amino}oxy)methyl]pyridin-2-yl}carbamate, (15.91) phenazine-1-carboxylic acid, (15.92) quinolin-8-ol (134-31-6), (15.93) quinolin-8-ol sulphate (2:1) (134-31-6) and (15.94) tert-butyl {6-[({[(1-methyl-1H-tetrazol-5-yl)(phenyl)methylene]amino}oxy)methyl]pyridin-2-yl}carbamate.

(16) Further compounds, for example (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl)biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide, (16.7) 5-fluoro-1,3-dimethyl-N-[4'-(prop-1-yn-1-yl)biphenyl-2-yl]-1H-pyrazole-4-carboxamide, (16.8) 2-chloro-N-[4'-(prop-1-yn-1-yl)biphenyl-2-yl]pyridine-3-carboxamide, (16.9) 3-(difluoromethyl)-N-[4'-(3,3-dimethylbut-1-yn-1-yl)biphenyl-2-yl]-1-methyl-1H-pyrazole-4-carboxamide, (16.10) N-[4'-(3,3-dimethylbut-1-yn-1-yl)biphenyl-2-yl]-5-fluoro-1,3-dimethyl-1H-pyrazole-4-carboxamide, (16.11) 3-(difluoromethyl)-N-(4'-ethynylbiphenyl-2-yl)-1-methyl-1H-pyrazole-4-carboxamide, (16.12) N-(4'-ethynylbiphenyl-2-yl)-5-fluoro-1,3-dimethyl-1H-pyrazole-4-carboxamide, (16.13) 2-chloro-N-(4'-ethynylbiphenyl-2-yl)pyridine-3-carboxamide, (16.14) 2-chloro-N-[4'-(3,3-dimethylbut-1-yn-1-yl)biphenyl-2-yl]pyridine-3-carboxamide (known from EP-A 1 559 320), (16.15) 4-(difluoromethyl)-2-methyl-N-[4'-(trifluoromethyl)biphenyl-2-yl]-1,3-thiazole-5-carboxamide, (16.16) 5-fluoro-N-[4'-(3-hydroxy-3-methylbut-1-yn-1-yl)

biphenyl-2-yl]-1,3-dimethyl-1H-pyrazole-4-carboxamide, (16.17) 2-chloro-N-[4'-(3-hydroxy-3-methylbut-1-yn-1-yl)biphenyl-2-yl]pyridine-3-carboxamide, (16.18) 3-(difluoromethyl)-N-[4'-(3-methoxy-3-methylbut-1-yn-1-yl)biphenyl-2-yl]-1-methyl-1H-pyrazole-4-carboxamide, (16.19) 5-fluoro-N-[4'-(3-methoxy-3-methylbut-1-yn-1-yl)biphenyl-2-yl]-1,3-dimethyl-1H-pyrazole-4-carboxamide, (16.20) 2-chloro-N-[4'-(3-methoxy-3-methylbut-1-yn-1-yl)biphenyl-2-yl]pyridine-3-carboxamide, (16.21) (5-bromo-2-methoxy-4-methylpyridin-3-yl)(2,3,4-trimethoxy-6-methylphenyl)methanone, (16.22) N-[2-(4-{[3-(4-chlorophenyl)prop-2-yn-1-yl]oxy}-3-methoxyphenyl)ethyl]-N2-(methylsulphonyl)valinamide (220706-93-4), (16.23) 4-oxo-4-[(2-phenylethyl)amino]butanoic acid and (16.24) but-3-yn-1-yl{6-[({[(Z)-(1-methyl-1H-tetrazol-5-yl)(phenyl)methylene]amino}oxy)methyl]pyridin-2-yl}carbamate.

All mixing partners mentioned of classes (1) to (16) can, if they are capable thereof by virtue of their functional groups, optionally form salts with suitable bases or acids.

Herbicides

Combination partners which can be used for the compounds according to the invention in mixture formulations or in the tank mix are, for example, known active compounds which are based on an inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase. The active compounds referred to herein by their common name are known to the person skilled in the art and described in relevant textbooks or the world wide web (for example http://www.alanwood.net/pesticides). Known herbicides or plant growth regulators which can be combined with the compounds according to the invention are, for example, the following active compounds (the compounds are referred to either by the common name according to the International Organization for Standardization (ISO) or by the chemical name or by the code number); in each case, they comprise all application forms, such as acids, salts, esters and isomers, such as stereoisomers and optical isomers. Here, one and in some cases more application forms are mentioned by way of example: acetochlor, acibenzolar, acibenzolar-s-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminocyclopyrachlor-potassium, aminocyclopyrachlor-methyl, aminopyralid, amitrole, ammonium sulphamate, ancymidol, anilofos, asulam, atrazine, azafenidin, azimsulfuron, aziprotryn, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]-phenyl]ethanesulphonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)-ethyl-(2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indole acetic acid (IAA), 4-indol-3-ylbutyric acid (IBA), iodosulfuron, iodosulfuron-methyl-sodium, iofensulfuron, iofensulfuron-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulphonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulphate, monolinuron, monosulfuron, monosulfuron-ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolat-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SW-065, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioximidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryn, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and also the compounds below:

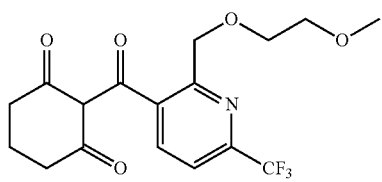

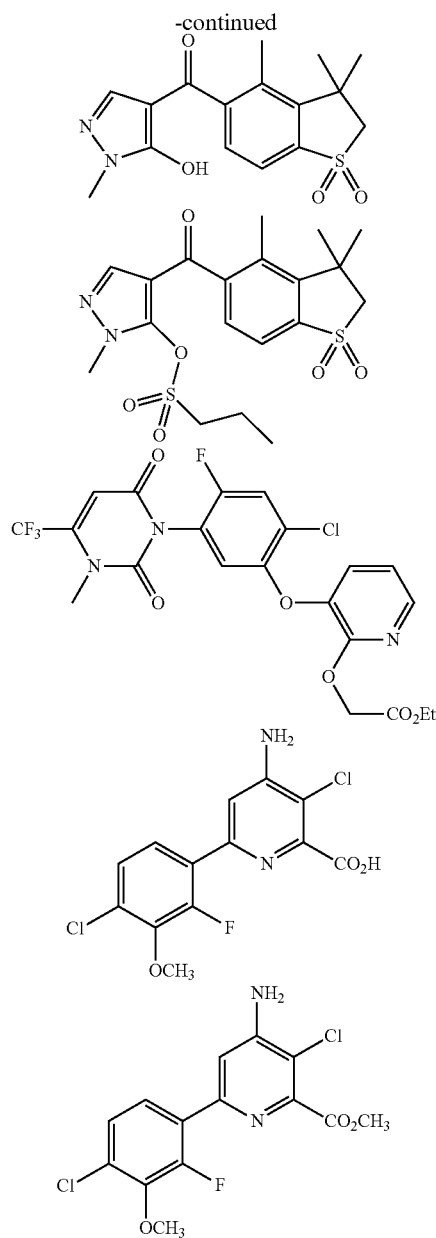

The active compounds referred to herein by their common name are known and are described, for example, in the pesticide handbook ("The Pesticide Manual" 14th Ed., British Crop Protection Council 2006) or can be found on the Internet (for example http://www.alanwood.net/pesticides).

(1) Acetylcholinesterase (AChE) inhibitors, for example carbamates, for example alanycarb (II-1-1), aldicarb (II-1-2), bendiocarb (II-1-3), benfuracarb (II-1-4), butocarboxim (II-1-5), butoxycarboxim (II-1-6), carbaryl (II-1-7), carbofuran (II-1-8), carbosulfan (II-1-9), ethiofencarb (II-1-10), fenobucarb (II-1-11), formetanate (II-1-12), furathiocarb (II-1-13), isoprocarb (II-1-14), methiocarb (II-1-15), methomyl (II-1-16), metolcarb (II-1-17), oxamyl (II-1-18), pirimicarb (II-1-19), propoxur (II-1-20), thiodicarb (II-1-21), thiofanox (II-1-22), triazamate (II-1-23), trimethacarb (II-1-24), XMC (II-1-25) and xylylcarb (II-1-26); or organophosphates, for example acephate (II-1-27), azamethiphos (II-1-28), azinphos-ethyl (II-1-29), azinphos-methyl (II-1-30), cadusafos (II-1-31), chlorethoxyfos (II-1-32), chlorfenvinphos (II-1-33), chlormephos (II-1-34), chlorpyrifos (II-1-35), chlorpyrifos-methyl (II-1-36), coumaphos (II-1-37), cyanophos (II-1-38), demeton-S-methyl (II-1-39), diazinon (II-1-40), dichlorvos/DDVP (II-1-41), dicrotophos (II-1-42), dimethoate (II-1-43), dimethylvinphos (II-1-44), disulfoton (II-1-45), EPN (II-1-46), ethion (II-1-47), ethoprophos (II-1-48), famphur (II-1-49), fenamiphos (II-1-50), fenitrothion (II-1-51), fenthion (II-1-52), fosthiazate (II-1-53), heptenophos (II-1-54), imicyafos (II-1-55), isofenphos (II-1-56), isopropyl O-(methoxyaminothiophosphoryl) salicylate (II-1-57), isoxathion (II-1-58), malathion (II-1-59), mecarbam (II-1-60), methamidophos (II-1-61), methidathion (II-1-62), mevinphos (II-1-63), monocrotophos (II-1-64), naled (II-1-65), omethoate (II-1-66), oxydemeton-methyl (II-1-67), parathion (II-1-68), parathion-methyl (II-1-69), phenthoate (II-1-70), phorate (II-1-71), phosalone (II-1-72), phosmet (II-1-73), phosphamidon (II-1-74), phoxim (II-1-75), pirimiphos-methyl (II-1-76), profenofos (II-1-77), propetamphos (II-1-78), prothiofos (II-1-79), pyraclofos (II-1-80), pyridaphenthion (II-1-81), quinalphos (II-1-82), sulfotep (II-1-83), tebupirimfos (II-1-84), temephos (II-1-85), terbufos (II-1-86), tetrachlorvinphos (II-1-87), thiometon (II-1-88), triazophos (II-1-89), triclorfon (II-1-90) and vamidothion (II-1-91).

(2) GABA-gated chloride channel antagonists, for example cyclodiene organochlorines, for example chlordane (II-2-1) and endosulfan (II-2-2); or phenylpyrazoles (fiproles), for example ethiprole (II-2-3) and fipronil (II-2-4).

(3) Sodium channel modulators/voltage-dependent sodium channel blockers, for example pyrethroids, for example acrinathrin (II-3-1), allethrin (II-3-2), d-cis-trans allethrin (II-3-3), d-trans allethrin (II-3-4), bifenthrin (II-3-5), bioallethrin (II-3-6), bioallethrin S-cyclopentenyl isomer (II-3-7), bioresmethrin (II-3-8), cycloprothrin (II-3-9), cyfluthrin (II-3-10), beta-cyfluthrin (II-3-11), cyhalothrin (II-3-12), lambda-cyhalothrin (II-3-13), gamma-cyhalothrin (II-3-14), cypermethrin (II-3-15), alpha-cypermethrin (II-3-16), beta-cypermethrin (II-3-17), theta-cypermethrin (II-3-18), zeta-cypermethrin (II-3-19), cyphenothrin [(1R)-trans isomers] (II-3-20), deltamethrin (II-3-21), empenthrin [(EZ)-(1R) isomers] (II-3-22), esfenvalerate (II-3-23), etofenprox (II-3-24), fenpropathrin (II-3-25), fenvalerate (II-3-26), flucythrinate (II-3-27), flumethrin (II-3-28), tau-fluvalinate (II-3-29), halfenprox (II-3-30), imiprothrin (II-3-31), kadethrin (II-3-32), permethrin (II-3-33), phenothrin [(1R)-trans isomer) (II-3-34), prallethrin (II-3-35), pyrethrins (pyrethrum) (II-3-36), resmethrin (II-3-37), silafluofen (II-3-38), tefluthrin (II-3-39), tetramethrin (II-3-40), tetramethrin [(1R) isomers)] (II-3-41), tralomethrin (II-3-42) and transfluthrin (II-3-43); or DDT (II-3-44); or methoxychlor (II-3-45).

(4) Nicotinergic acetylcholine receptor (nAChR) agonists, for example neonicotinoids, for example acetamiprid (II-4-1), clothianidin (II-4-2), dinotefuran (II-4-3), imidacloprid (II-4-4), nitenpyram (II-4-5), thiacloprid (II-4-6) and thiamethoxam (II-4-7); or nicotine (II-4-8).

(5) Allosteric nicotinergic acetylcholine receptor (nAChR) activators, for example spinosyns, for example spinetoram (II-5-1) and spinosad (II-5-2).

(6) Chloride channel activators, for example avermectins/milbemycins, for example abamectin (II-6-1), emamectin benzoate (II-6-2), lepimectin (II-6-3) and milbemectin (II-6-4).

(7) Juvenile hormone imitators, for example juvenile hormone analogues, for example hydroprene (II-7-1), kinoprene (II-7-2) and methoprene (II-7-3); or fenoxycarb (II-7-4); or pyriproxyfen (II-7-5).

(8) Active compounds with unknown or non-specific mechanisms of action, for example alkyl halides, for example methyl bromide (II-8-1) and other alkyl halides; or chloropicrin (II-8-2); or sulphuryl fluoride (II-8-3); or borax (II-8-4); or tartar emetic (II-8-5).

(9) Selective anti-feedants, for example pymetrozine (II-9-1); or flonicamid (II-9-2).

(10) Mite growth inhibitors, for example clofentezine (II-10-1), hexythiazox (II-10-2) and diflovidazin (II-10-3); or etoxazole (II-10-4).

(11) Microbial disruptors of the insect gut membrane, for example *Bacillus thuringiensis* subspecies *israelensis* (II-11-1), *Bacillus sphaericus* (II-11-2), *Bacillus thuringiensis* subspecies *aizawai* (II-11-3), *Bacillus thuringiensis* subspecies *kurstaki* (II-11-4), *Bacillus thuringiensis* subspecies *tenebrionis* (II-11-5) and BT plant proteins: Cry1Ab, Cry1Ac, Cry1Fa, Cry2Ab, mCry3A, Cry3Ab, Cry3Bb, Cry34/35Ab1 (II-11-6).

(12) Oxidative phosphorylation inhibitors, ATP disruptors, for example diafenthiuron (II-12-1); or organotin compounds, for example azocyclotin (II-12-2), cyhexatin (II-12-3) and fenbutatin oxide (II-12-4); or propargite (II-12-5); or tetradifon (II-12-6).

(13) Oxidative phosphorylation decouplers acting by interrupting the H proton gradient, for example chlorfenapyr (II-13-1), DNOC (II-13-2) and sulfluramid (II-13-3).

(14) Nicotinergic acetylcholine receptor antagonists, for example bensultap (II-14-1), cartap hydrochloride (II-14-2), thiocyclam (II-14-3) and thiosultap-sodium (II-14-4).

(15) Chitinbiosynthesis inhibitors, type 0, for example bistrifluoron (II-15-1), chlorfluazuron (II-15-2), diflubenzuron (II-15-3), flucycloxuron (II-15-4), flufenoxuron (II-15-5), hexaflumuron (II-15-6), lufenuron (II-15-7), novaluron (II-15-8), noviflumuron (II-15-9), teflubenzuron (II-15-10) and triflumuron (II-15-11).

(16) Chitinbiosynthesis inhibitors, type 1, for example buprofezin (II-16-1).

(17) Molting disruptors, dipteran, for example cyromazine (II-17-1).

(18) Ecdysone receptor agonists, for example chromafenozide (II-18-1), halofenozide (II-18-2), methoxyfenozide (II-18-3) and tebufenozide (II-18-4).

(19) Octopaminergic agonists, for example amitraz (II-19-1).

(20) Complex III electron transport inhibitors, for example hydramethylnon (II-20-1); or acequinocyl (II-20-2); or fluacrypyrim (II-20-3).

(21) Complex I electron transport inhibitors, for example METI acaricides, for example fenazaquin (II-21-1), fenpyroximate (II-21-2), pyrimidifen (II-21-3), pyridaben (II-21-4), tebufenpyrad (II-21-5) and tolfenpyrad (II-21-6); or rotenone (derris) (II-21-7).

(22) Voltage-dependent sodium channel blockers, for example indoxacarb (II-22-1); or metaflumizone (II-22-2).

(23) Inhibitors of acetyl-CoA carboxylase, for example tetronic and tetramic acid derivatives, for example spirodiclofen (II-23-1), spiromesifen (II-23-2) and spirotetramat (II-23-3).

(24) Complex IV electron transport inhibitors, for example phosphines, for example aluminium phosphide (II-24-1), calcium phosphide (II-24-2), phosphine (II-24-3) and zinc phosphide (II-24-4); or
cyanide (II-24-5).
(25) Complex II electron transport inhibitors, for example cyenopyrafen (II-25-1).
(28) Ryanodine receptor effectors, for example diamides, for example chlorantraniliprole (II-28-1) and flubendiamide (II-28-2).

Further active compounds with unknown mechanism of action, for example amidoflumet (II-29-1), azadirachtin (II-29-2), benclothiaz (II-29-3), benzoximate (II-29-4), bifenazate (II-29-5), bromopropylate (II-29-6), chinomethionat (II-29-7), cryolite (II-29-8), cyantraniliprole (cyazypyr) (II-29-9), cyflumetofen (II-29-10), dicofol (II-29-11), diflovidazin (II-29-12), fluensulfone (II-29-13), flufenerim (II-29-14), flufiprole (II-29-15), fluopyram (II-29-16), fufenozide (II-29-17), imidaclothiz (II-29-18), iprodione (II-29-19), meperfluthrin (II-29-20), pyridalyl (II-29-21), pyrifluquinazon (II-29-22), tetramethylfluthrin (II-29-23) and iodomethane (II-29-24); furthermore preparations based on *Bacillus firmus* (in particular strain CNCM 1-1582, for example VOTiVO™, BioNem) (II-29-25), and the following known active compounds:
3-Bromo-N-{2-bromo-4-chloro-6-[(1-cyclopropylethyl)carbamoyl]phenyl}-1-(3-chloropyridin-2-yl)-1H-pyrazole-5-carboxamide (II-29-26) (known from WO2005/077934), 4-{[(6-bromopyrid-3-yl)methyl](2-fluoroethyl)amino}furan-2(5H)-one (II-29-27) (known from WO2007/115644), 4-{[(6-fluoropyrid-3-yl)methyl](2,2-difluoroethyl)amino}furan-2(5H)-one (II-29-28) (known from WO2007/115644), 4-{[(2-chloro-1,3-thiazol-5-yl)methyl](2-fluoroethyl)amino}furan-2(5H)-one (II-29-29) (known from WO2007/115644), 4-{[(6-chloropyrid-3-yl)methyl](2-fluoroethyl)amino}furan-2(5H)-one (II-29-30) (known from WO2007/115644), flupyradifurone (II-29-31), 4-{[(6-chloro-5-fluoropyrid-3-yl)methyl](methyl)amino}furan-2(5H)-one (II-29-32) (known from WO2007/115643), 4-{[(5,6-dichloropyrid-3-yl)methyl](2-fluoroethyl)amino}furan-2(5H)-one (II-29-33) (known from WO2007/115646), 4-{[(6-chloro-5-fluoropyrid-3-yl)methyl](cyclopropyl)amino}furan-2(5H)-one (II-29-34) (known from WO2007/115643), 4-{[(6-chloropyrid-3-yl)methyl](cyclopropyl)amino}furan-2(5H)-one (II-29-35) (known from EP-A-0 539 588), 4-{[(6-chloropyrid-3-yl)methyl](methyl)amino}furan-2(5H)-one (II-29-36) (known from EP-A-0 539 588), {[1-(6-chloropyridin-3-yl)ethyl](methyl)oxido-$\lambda^4$-sulphanylidene}cyanamide (II-29-37) (known from WO2007/149134) and its diastereomers {[(1R)-1-(6-chloropyridin-3-yl)ethyl](methyl)oxido-$\lambda^4$-sulphanylidene}cyanamide (A) (II-29-38) and {[(1S)-1-(6-chloropyridin-3-yl)ethyl](methyl)oxido-$\lambda^4$-sulphanylidene}cyanamide (B) (II-29-39) (also known from WO2007/149134) and also sulphoxaflor (II-29-40) and its diastereomers [(R)-methyl(oxido){(1R)-1-[6-(trifluoromethyl)pyridin-3-yl]ethyl}-$\lambda^4$-sulphanylidene]cyanamide (A1) (II-29-41) and [(S)-methyl(oxido){(1S)-1-[6-(trifluoromethyl)pyridin-3-yl]ethyl}-$\lambda^4$-sulphanylidene]cyanamide (A2) (II-29-42), referred to diastereomer group A (known from WO 2010/074747, WO 2010/074751), [(R)-methyl (oxido) {(1S)-1-[6-(trifluoromethyl)pyridin-3-yl]ethyl}-$\lambda^4$-sulphanylidene]cyanamide (B1) (II-29-43) and [(S)-methyl (oxido){(1R)-1-[6-(trifluoromethyl)pyridin-3-yl]ethyl}-$\lambda^4$-sulphanylidene]cyanamide (B2) (II-29-44), referred to as diastereomer group B (also known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (II-29-45) (known from WO2006/089633), 3-(4'-fluoro-2,4-dimethylbiphenyl-3-yl)-4-hydroxy-8-oxa-1-azaspiro[4.5]dec-3-en-2-one (II-29-46) (known from WO2008/067911), 1-{2-fluoro-4-methyl-5-[(2,2,2-trifluoroethyl)sulphinyl]phenyl}-3-(trifluoromethyl)-1H-1,2,4-triazole-5-amine (II-29-47) (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (II-29-48) (known from WO2008/066153), 2-cyano-3-(difluoromethoxy)-N,N-dimethylbenzenesulphonamide (II-29-49) (known from WO2006/056433), 2-cyano-3-(difluoromethoxy)-N-methylbenzenesulphonamide (II-29-50) (known from WO2006/100288), 2-cyano-3-(difluoromethoxy)-N-ethylbenzenesulphonamide (II-29-51) (known from WO2005/035486), 4-(difluoromethoxy)-N-ethyl-N-methyl-1,2-benzothiazole-3-amine 1,1-dioxide (II-29-52) (known from WO2007/057407), N-[1-(2,3-dimethylphenyl)-2-(3,5-dimethylphenyl)ethyl]-4,5-dihydro-1,3-thiazole-2-amine (II-29-53) (known from WO2008/104503), {1'-[(2E)-3-(4-chlorophenyl)prop-2-en-1-yl]-5-fluorospiro[indol-3,4'-piperidin]-1(2H)-yl}(2-chloropyridin-4-yl)methanone (II-29-54) (known from WO2003/106457), 3-(2,5-dimethylphenyl)-4-hydroxy-8-methoxy-1,8-diazaspiro[4.5]dec-3-en-2-one (II-29-55) (known from WO2009/049851), 3-(2,5-dimethylphenyl)-8-methoxy-2-oxo-1,8-diazaspiro[4.5]dec-3-en-4-yl ethyl carbonate (II-29-56) (known from WO2009/049851), 4-(but-2-yn-1-yloxy)-6-(3,5-dimethylpiperidin-1-yl)-5-fluoropyrimidine (II-29-57) (known from WO2004/099160), (2,2,3,3,4,4,5,5-octafluoropentyl)(3,3,3-trifluoropropyl)malononitrile (II-29-58) (known from WO2005/063094), (2,2,3,3,4,4,5,5-octafluoropentyl)(3,3,4,4,4-pentafluorobutyl)malononitrile (II-29-59) (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (II-29-60) (known from WO2007/040280), flometoquin (II-29-61), PF1364 (CAS-Reg. No. 1204776-60-2) (II-29-62) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (II-29-63) (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (II-29-64) (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (II-29-65) (known from WO2005/085216), 4-{[(6-chloropyridin-3-yl)methyl](cyclopropyl)amino}-1,3-oxazol-2(5H)-one (II-29-66), 4-{[(6-chloropyridin-3-yl)methyl](2,2-difluoroethyl)amino}-1,3-oxazol-2(5H)-one (II-29-67), 4-{[(6-chloropyridin-3-yl)methyl](ethyl)amino}-1,3-oxazol-2(5H)-one (II-29-68), 4-{[(6-chloropyridin-3-yl)methyl](methyl)amino}-1,3-oxazol-2(5H)-one (II-29-69) (all known from WO2010/005692), NNI-0711 (II-29-70) (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (II-29-71) (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (II-29-72) (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (II-29-73) (known from WO2005/085216), methyl 2-[2-({[3-bromo-1-(3-chloropyridin-2-yl)-1H-pyrazol-5-yl]

carbonyl}amino)-5-cyano-3-methylbenzoyl]-2-methylhydrazinecarboxylate (II-29-74) (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (II-29-75) (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (II-29-76) (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (II-29-77) (known from WO2007/101369), 2-{6-[2-(5-fluoropyridin-3-yl)-1,3-thiazol-5-yl]pyridin-2-yl}pyrimidine (II-29-78) (known from WO2010/006713), 2-{6-[2-(pyridin-3-yl)-1,3-thiazol-5-yl]pyridin-2-yl}pyrimidine (II-29-79) (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (II-29-80) (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (II-29-81) (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (II-29-82) (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (II-29-83) (known from WO2010/069502), (1E)-N-[(6-chloropyridin-3-yl)methyl]N'-cyano-N-(2,2-difluoroethyl)ethanimidamide (II-29-84) (known from WO2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (II-29-85) (known from CN102057925) and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (II-29-86) (known from WO2011/049233).

In a preferred embodiment of the invention, a penetrant is additionally added to the crop protection compositions to enhance the action. Suitable penetrants also include, for example, substances which promote the availability of the compounds of the formula (I) in the spray coating. These include, for example, mineral and vegetable oils. Suitable oils are all mineral or vegetable oils—modified or otherwise—which can usually be used in agrochemical compositions. By way of example, mention may be made of sunflower oil, rapeseed oil, olive oil, castor oil, colza oil, corn seed oil, cottonseed oil and soybean oil of the esters of said oils. Preference is given to rapeseed oil, sunflower oil and their methyl or ethyl esters, especially rapeseed oil methyl ester.

The concentration of penetrant in the compositions of the invention can be varied within a wide range. In the case of a formulated crop protection composition, it is generally from 1 to 95% by weight, preferably from 1 to 55% by weight, particularly preferably 15-40% by weight. In the ready-to-use compositions (spray liquors), the concentration is generally between 0.1 and 10 g/l, preferably between 0.5 and 5 g/l.

When used as insecticides, the active compounds according to the invention may furthermore be present in their commercially available formulations and in the use forms, prepared from these formulations, as a mixture with synergists. Synergists are compounds which enhance the action of the active compounds, without any need for the synergist added to be active itself.

When used as insecticides, the active compounds according to the invention may furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations may vary within wide limits. The active compound concentration of the application forms may be from 0.00000001 to 95% by weight of active compound, preferably between 0.00001 and 1% by weight.

The compounds are employed in a customary manner appropriate for the use forms.

All plants and plant parts can be treated in accordance with the invention. Plants are understood here to mean all plants and plant populations, such as desired and undesired wild plants or crop plants (including naturally occurring crop plants). Crop plants can thus be plants which can be obtained by conventional breeding and optimization methods or by biotechnological and genetic engineering methods or combinations of these methods, including the transgenic plants and including the plant varieties which can or cannot be protected by varietal property rights. Examples which may be mentioned are the important crop plants, such as cereals (wheat, rice), maize, soybeans, potatoes, sugar beet, tomatoes, peas and other vegetable species, cotton, tobacco, oilseed rape, and also fruit plants (with the fruits apples, pears, citrus fruits and grapes). Parts of plants are to be understood as meaning all above- and below-ground parts and organs of plants, such as shoot, leaf, flower and root, examples which may be mentioned being leaves, needles, stems, trunks, flowers, fruitbodies, fruits and seeds and also roots, tubers and rhizomes. The plant parts also include harvested material and vegetative and generative propagation material, for example cuttings, tubers, rhizomes, slips and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on, injection and, in the case of propagation material, and in particular in the case of seed, also by applying one or more coats.

As already mentioned above, it is possible to treat all plants and their parts in accordance with the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

More preferably, plants of the plant cultivars which are each commercially available or in use are treated in accordance with the invention. Plant cultivars are to be understood as meaning plants having new properties ("Traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the treatment according to the invention may also result in superadditive ("synergist") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, increased flowering performance, easier harvesting, accelerated ripening, higher yields, higher quality and/or higher nutrient value of the harvested products, increased storage life and/or processability of the harvested products, which exceed the effects normally to be expected.

The preferred transgenic plants or plant cultivars (i.e. those obtained by genetic engineering) which are to be treated according to the invention include all plants which, in the genetic modification, receive genetic material which imparts particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soybeans, potatoes, sugar beet, tomatoes, peas and other vegetable species, cotton, tobacco, oilseed rape, and also fruit plants (with the fruits apples, pears, citrus fruits and grapes), and particular emphasis is given to maize, soybeans, potatoes, cotton, tobacco and oilseed rape. Traits that are emphasized are in particular increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and also resistance genes and corresponding expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combinations with one another in the transgenic plants. Examples of "Bt plants" which may be mentioned are maize varieties, cotton varieties, soybean varieties and potato varieties which are sold under the trade names YIELD GARD® (for example maize, cotton, soybeans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soybean varieties which are sold under the trade name Roundup Ready® (tolerance to glyphosate, for example maize, cotton, soybeans), Liberty Link® (tolerance to phosphinotricin, for example, oilseed rape), IMF) (tolerance to imidazolinones) and STS® (tolerance to sulphonylureas, for example maize). Herbicide-resistant plants (plants breed in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated in a particularly advantageous manner according to the invention with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

GMO

Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US2002120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control-herbicide tolerance, deposited as PTA-6233, described in WO2005/103266 or US2005216969); Event 3006-210-23 (cotton, insect control-herbicide tolerance, deposited as PTA-6233, described in US2007143876 or WO2005/103266); Event 3272 (corn, quality trait, deposited as PTA-9972, described in WO2006098952 or US2006230473); Event 40416 (corn, insect control-herbicide tolerance, deposited as ATCC PTA-11508, described in WO2011/075593); Event 43A47 (corn, insect control-herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US2006162007 or WO2004053062); Event B16 (corn, herbicide tolerance, not deposited, described in US2003126634); Event BPS-CV127-9 (soybean, herbicide tolerance, deposited as NCIMB No. 41603, described in WO2010/080829); Event CE43-67B (cotton, insect control, deposited as DSM ACC2724, described in US2009217423 or WO2006/128573); Event CE44-69D (cotton, insect control, not deposited, described in US20100024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US2006130175 or WO2004039986); Event COT202 (cotton, insect control, not deposited, described in US2007067868 or WO2005054479); Event COT203 (cotton, insect control, not deposited, described in WO2005/054480); Event DAS40278 (corn, herbicide tolerance, deposited as ATCC PTA-10244, described in WO2011/022469); Event DAS-59122-7 (corn, insect control-herbicide tolerance, deposited as ATCC PTA 11384, described in US2006070139); Event DAS-59132 (corn, insect control-herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US2009137395 or WO2008/112019); Event DP-305423-1 (soybean, quality trait, not deposited, described in US2008312082 or WO2008/054747); Event DP-32138-1 (corn, hybridization system, deposited as ATCC PTA-9158, described in US20090210970 or WO2009/103049); Event DP-356043-5 (soybean, herbicide tolerance, deposited as ATCC PTA-8287, described in US20100184079 or WO2008/002872); Event EE-1 (brinjal, insect control, not deposited, described in WO2007/091277); Event FI117 (corn, herbicide tolerance, deposited as ATCC 209031, described in US2006059581 or WO1998/044140); Event GA21 (corn, herbicide tolerance, deposited as ATCC 209033, described in US2005086719 or WO1998/044140); Event GG25 (corn, herbicide tolerance, deposited as ATCC 209032, described in US2005188434 or WO1998/044140); Event GHB119 (cotton, insect control-herbicide tolerance, deposited as ATCC PTA-8398, described in WO2008/151780); Event GHB614 (cotton, herbicide tolerance, deposited as ATCC PTA-6878, described in US2010050282 or WO2007/017186); Event GJ11 (corn, herbicide tolerance, deposited as ATCC 209030, described in US2005188434 or WO1998/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US2004172669 or WO2004/074492); Event JOPLIN1 (wheat, disease tolerance, not deposited, described in US2008064032); Event LL27 (soybean, herbicide tolerance, deposited as NCIMB41658, described in WO2006/108674 or US2008320616); Event LL55 (soybean, herbicide tolerance, deposited as NCIMB 41660, described in WO2006/108675 or US2008196127); Event LLcotton25 (cotton, herbicide tolerance, deposited as ATCC PTA-3343, described in WO2003013224 or US2003097687); Event LLRICE06 (rice, herbicide tolerance, deposited as ATCC-23352, described in U.S. Pat. No. 6,468,747 or WO2000/026345); Event LLRICE601 (rice, herbicide tolerance, deposited as ATCC PTA-2600, described in US20082289060 or WO2000/026356); Event LY038 (corn, quality trait, deposited as ATCC PTA-5623, described in US2007028322 or WO2005061720); Event MIR162 (corn, insect control, deposited as PTA-8166, described in US2009300784 or WO2007/142840); Event MIR604 (corn, insect control, not deposited, described in US2008167456 or WO2005103301); Event MON15985 (cotton, insect control, deposited as ATCC PTA-2516, described in US2004-250317 or WO2002/100163); Event MON810 (corn, insect control, not deposited, described in US2002102582); Event MON863 (corn, insect control, deposited as ATCC PTA-2605, described in WO2004/011601 or US2006095986); Event MON87427 (corn, pollination control, deposited as ATCC PTA-7899, described in WO2011/062904); Event MON87460 (corn, stress tolerance, deposited as ATCC PTA-8910, described in WO2009/111263 or US20110138504); Event MON87701 (soybean, insect control, deposited as ATCC PTA-8194, described in US2009130071 or WO2009/064652); Event MON87705 (soybean, quality trait-herbicide tolerance, deposited as ATCC PTA-9241, described in US20100080887 or WO2010/037016); Event MON87708 (soybean, herbicide tolerance, deposited as ATCC PTA9670, described in WO2011/034704); Event MON87754 (soybean, quality trait, deposited as ATCC PTA-9385, described in WO2010/024976); Event MON87769 (soybean, quality trait, deposited as ATCC PTA-8911, described in US20110067141 or WO2009/102873); Event MON88017 (corn, insect control-herbicide tolerance, deposited as ATCC PTA-5582, described in US2008028482 or WO2005/059103); Event MON88913 (cotton, herbicide tolerance, deposited as ATCC PTA-4854, described in WO2004/072235 or US2006059590); Event MON89034 (corn, insect control, deposited as ATCC PTA-7455, described in WO2007/140256 or US2008260932); Event MON89788 (soybean, herbicide tolerance, deposited as ATCC PTA-6708, described in US2006282915 or WO2006/130436); Event MS11 (oilseed rape, pollination control-herbicide tolerance, deposited as ATCC PTA-850 or PTA-2485, described in WO2001/031042); Event MS8 (oilseed rape, pollination control-herbicide tolerance, deposited as ATCC PTA-730, described in WO2001/041558 or US2003188347); Event NK603 (corn, herbicide tolerance, deposited as ATCC PTA-2478, described in US2007-292854); Event PE-7 (rice, insect control, not deposited, described in WO2008/114282); Event RF3 (oilseed rape, pollination control-herbicide tolerance, deposited as ATCC PTA-730, described in WO2001/041558 or US2003188347); Event RT73 (oilseed rape, herbicide tolerance, not deposited, described in WO2002/036831 or US2008070260); Event T227-1 (sugar beet, herbicide tolerance, not deposited, described in WO2002/44407 or US2009265817); Event T25 (corn, herbicide tolerance, not deposited, described in US2001029014 or WO2001/051654); Event T304-40 (cotton, insect control-herbicide tolerance, deposited as ATCC PTA-8171, described in US2010077501 or WO2008/122406); Event T342-142 (cotton, insect control, not deposited, described in WO2006/128568); Event TC1507 (corn, insect control-herbicide tolerance, not deposited, described in US2005039226 or WO2004/099447); Event VIP1034 (corn, insect control-herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621).

FURTHER EMBODIMENTS OF THE INVENTION

Compounds of the formula (I) where $A^1$ represents —$C(R^2,R^3)$—.

Compounds of the formula (I) where $A^1$ represents a —$C(R^2,R^3)$— group and where
  this —$C(R^2,R^3)$— group forms a double bond with the adjacent B position, or
  this —$C(R^2,R^3)$— group is a bridging group which, together with a further bridging group and any B groups, located between these bridging groups, of the C(=C(W, X-Q$^1$)—C(=N-Q$^2$)-A$^1$-[B]$_n$-A$^2$ ring and a corresponding bridge U forms an unsubstituted or substituted cyclic system, or
  this —$C(R^2,R^3)$— group carries a substituent V.

Compounds of the formula (I) where $A^1$ is part of a cyclic system.

Compounds of the formula (I) where $A^1$ is part of a carbocyclic system having 6 ring atoms or part of a 5- or 6-membered heterocyclic system.

Compound of the formula (I) where $A^1$ is part of an aromatic system having 6 ring atoms or part of a 5- or 6-membered heteroaromatic system.

Compounds of the formula (I) where n is 2.

Compounds of the formula (I) where the compounds are compounds of the formula (I-5)

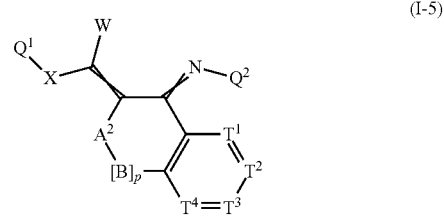

(I-5)

in which $Q^1$, $Q^2$, W, X, $A^2$, B and $M^1$ have the meaning described above, p represents 0, 1 or 2 and $T^1$, $T^2$, $T^3$ and $T^4$ independently of one another represent CH or $CM^1$ or N, where at most 2 T selected from $T^1$, $T^2$, $T^3$ and $T^4$ represent N.

Compounds of the formula (I) where the compounds are compounds of the formula (I-6)

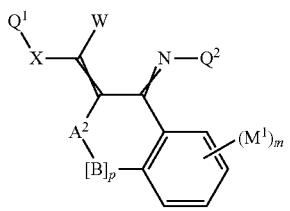
(I-6)

in which $Q^1$, $Q^2$, W, X, $A^2$, B, and $M^1$ are defined as described herein, p represents 0, 1 or 2, preferably 1, and m represents 0, 1, 2, 3 or 4.

Compounds of the formula (II)

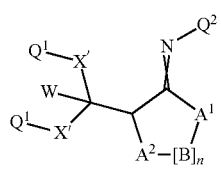
(II)

in which $A^1$, $A^2$, W, $Q^1$, $Q^2$, B and n have the meanings described herein and X' represents oxygen or sulphur.

Compounds of the formula (A)

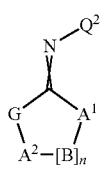
(A)

in which G represents

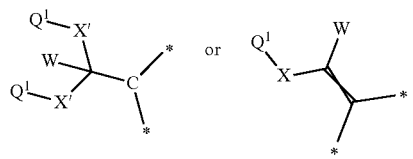

and $A^1$, $A^2$, W, $Q^1$, $Q^2$, B and n have the meanings described herein and X' represents oxygen or sulphur and X represents —O—, —S—, —S(O)— or —S(O)$_2$—. * Denotes the bond of G in the central G-$A^2$-[B]$_n$-$A^1$-C(=N-Q) ring.

Insecticidal composition, characterized in that it comprises at least one compound of the formula (I) or a compound of the formula

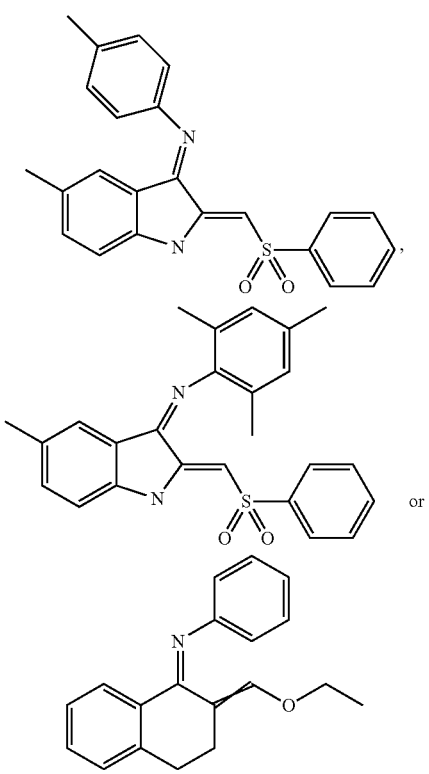

and customary extenders and/or surfactants.

Process for controlling pests, characterized in that a compound of the formula (I) or a compound of the formula

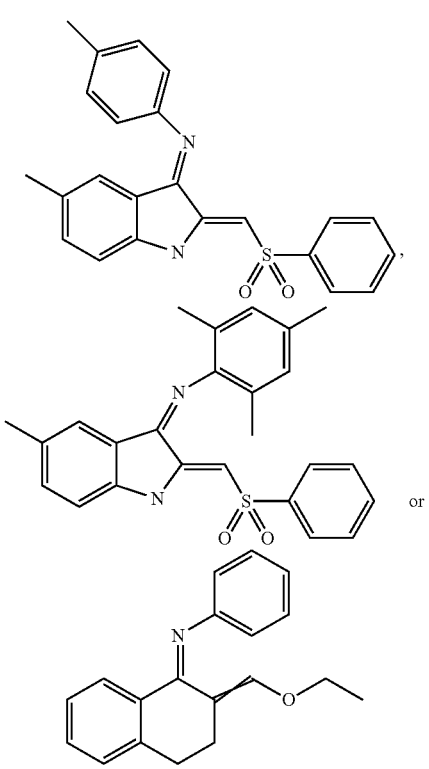

or a compound of the formula (II) or a composition comprising one of these compounds is allowed to act on the pests and/or the plant to be protected and/or its habitat.

Method for protecting transgenic or conventional seed and the plant resulting therefrom against attack by pests, characterized in that the seed is treated with at least one compound of the formula (I) or a compound of the formula

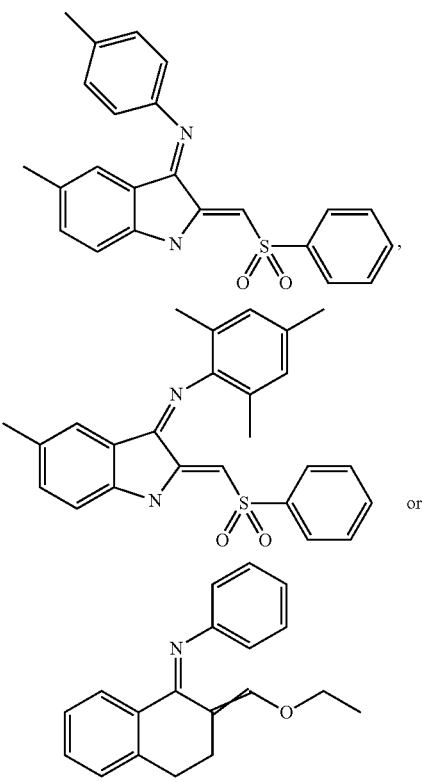

or a compound of the formula (II).

Use of compounds of the formula (I) or of compositions as described herein or of a compound of the formula

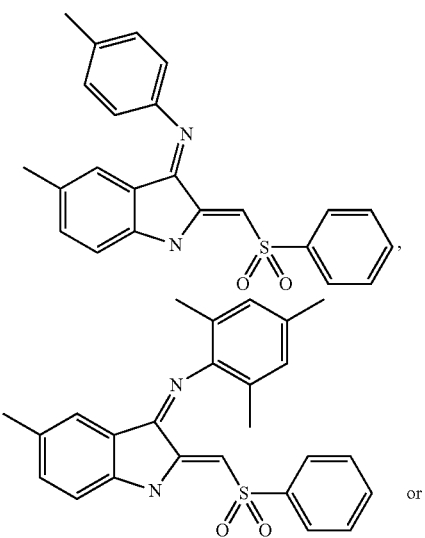

or a compound of the formula (II) or of compositions as described herein for controlling pests.

Use of the compounds of the formula (I) or a compound of the formula

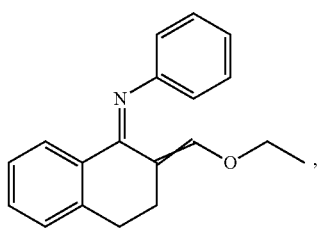

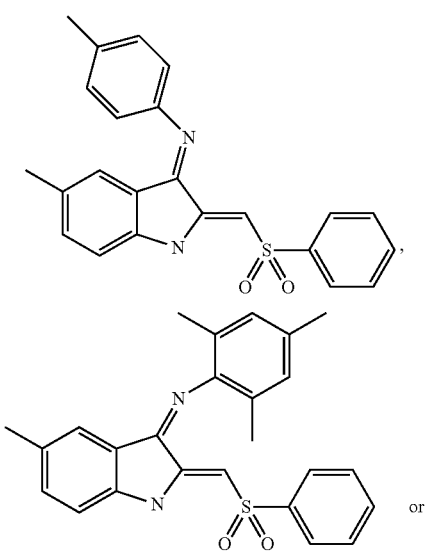

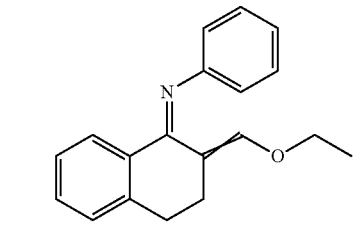

or a compound of the formula (II) for controlling vectors.

Seed to which a compound of the formula (I) or a compound of the formula

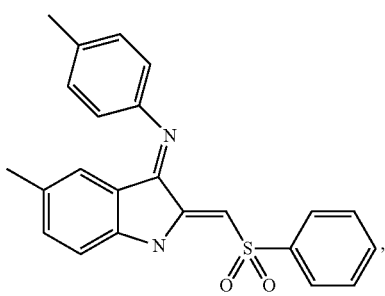

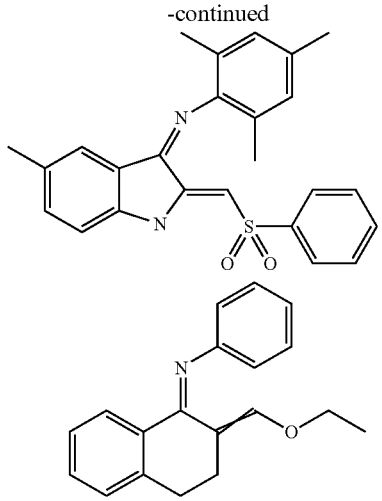

or

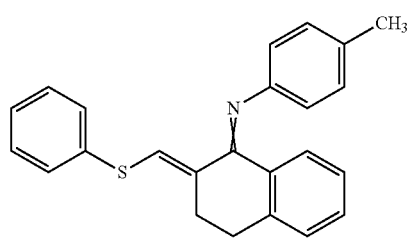 [SMILES: Cc1ccc(N=C2/C(=C/Sc3ccccc3)CCc3ccccc32)cc1]

or a compound of the formula (II) is applied as component of a coating or as a further layer or further layers in addition to a coating onto the seed.

PREPARATION EXAMPLES

N-[(2E)-2-[(Phenylsulphanyl)methylene]-3,4-dihydronaphthalen-1(2H)-ylidene]aniline Example 1-1

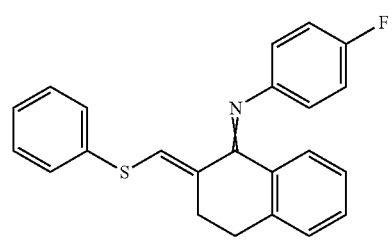 [SMILES: Fc1ccc(N=C2/C(=C/Sc3ccccc3)CCc3ccccc32)cc1]

270 mg (0.58 mmol) of N-{2-[bis(phenylsulphanyl)methyl]-3,4-dihydronaphthalen-1(2H)-ylidene}aniline are dissolved in 25 ml of dichloromethane, 157 mg (0.64 mmol) of 70 percent strength meta-chloroperbenzoic acid are added at 0° C. and the mixture is stirred at 0° C. for 1 h. The mixture is then diluted with dichloromethane and washed with saturated aqueous sodium bicarbonate solution, and the organic phase is dried over sodium sulphate and concentrated under reduced pressure. Purification of the residue by preparative HPLC (RP$_{18}$, mobile phase: acetonitrile/water) gives 45 mg of N-[(2E)-2-[(phenylsulphanyl)methylene]-3,4-dihydronaphthalen-1(2H)-ylidene]aniline.

$^1$H-NMR (CD$_3$CN): δ=2.38 (s, 3H), 2.78 (t, 2H), 3.03 (t, 2H), 6.32 (s, 1H), 6.76 (m, 4H), 7.20 (m, 5H), 7.27 (d, 1H), 7.31 (t, 1H), 7.40 (t, 1H), 8.19 (d, 1H).

4-Fluoro-N-[(2E)-2-[(phenylsulphanyl)methylene]-3,4-dihydronaphthalen-1(2H)-ylidene]aniline Example 1-3

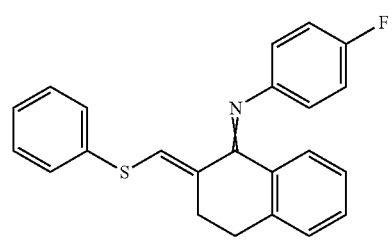 [SMILES: Fc1ccc(N=C2/C(=C/Sc3ccccc3)CCc3ccccc32)cc1]

266 mg (0.56 mmol) of N-{2-[bis(phenylsulphanyl)methyl]-3,4-dihydronaphthalen-1(2H)-ylidene}-4-fluoroaniline are dissolved in 50 ml of toluene, 0.26 ml (0.26 mmol of a titanium(IV) tetrachloride solution (1 M in dichloromethane) is added a little at a time at 25° C. and the mixture is stirred for 1 h. 431 mg (2.83 mmol) of 1,8-diazabicyclo[5.4.0]undec-7-ene and 5 ml of dichloromethane are added, and this mixture is poured into water and extracted with ethyl acetate. After washing with saturated aqueous sodium chloride solution, the organic phase is dried over sodium sulphate and concentrated under reduced pressure. Purification of the residue by column chromatography on RP$_{18}$ (mobile phase: acetonitrile/water) gives 84 mg of 4-fluoro-N-[(2E)-2-[(phenylsulphanyl)methylene]-3,4-dihydronaphthalen-1(2H)-ylidene]aniline.

$^1$H-NMR (CD$_3$CN): δ=2.83 (t, 2H), 3.08 (t, 2H), 6.31 (s, 1H), 6.88 (m, 4H), 7.15 (t, 2H), 7.23-7-39 (m, 5H), 7.45 (t, 1H), 8.23 (d, 1H).

Examples 1-1 to 1-94 were prepared by the same process.

N-{2,6-Bis[(phenylsulphanyl)methylene]cyclohexylidene}-4-methylaniline

Example 1-60

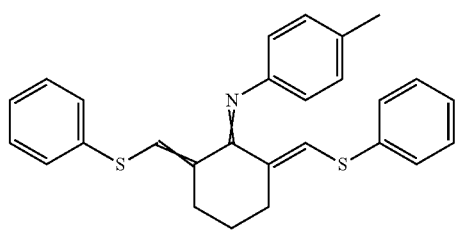 [SMILES: Cc1ccc(N=C2C(=CSc3ccccc3)CCC/C2=C\Sc2ccccc2)cc1]

N-{2,6-Bis[(phenylsulphanyl)methylene]cyclohexylidene}-4-methylaniline is prepared analogously to Example I-3 from N-{2,6-bis[bis(phenylsulphanyl)methylcyclohexylidene}-4-methylaniline.

$^1$H-NMR, CD3CN, δ=1.88 (m, 2H), 2.34 (s, 3H), 2.52 (t, 2H), 2.59 (t, 2H), 6.16 (s, 1H), 6.66 (d, 2H), 6.76 (m, 2H), 7.16 (d, 2H), 7.18 (m, 2H), 7.32 (m, 2H), 7.40 (t, 2H), 7.48 (d, 2H).

N-(6-{[(2,4-Difluorophenyl)sulphanyl]methylene}-3-ethoxycyclohex-2-en-1-ylidene)-4-methylaniline Example 1-98

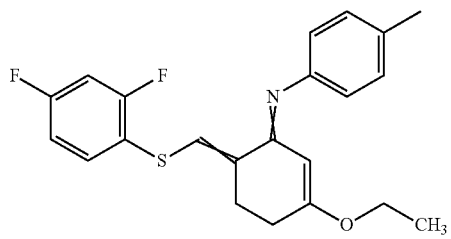 [SMILES: CCOC1=CC(=Nc2ccc(C)cc2)C(=CSc2ccc(F)cc2F)CC1]

100 mg (0.39 mmol) of (Z)-4-ethoxy-2-[(4-methylphenyl)imino]cyclohex-3-en-1-ylidene methanol are dissolved in 10 ml of anhydrous tetrahydrofuran, and 325 μl (2.3 mmol) of triethylamine and 60 μl (0.78 mmol) of methanesulphonyl chloride are added at 0° C. After 30 min of stirring at 25° C., the mixture is once more cooled to 0° C., 40 μl (0.35 mmol) of 2,4-difluorobenzenethiol are added and the mixture is stirred at 25° C. for a further 30 min. The reaction mixture is diluted with water and extracted with ethyl acetate, and the organic phase is washed with saturated aqueous sodium chloride solution and dried over sodium sulphate. Purification of the residue by column chromatography on silica gel (mobile phase: cyclohexane/ethyl acetate) gives 41 mg of N-(6-{[(2,4-difluorophenyl)sulphanyl]methylene}-3-ethoxycyclohex-2-en-1-ylidene)-4-methylaniline as an isomer mixture (ratio about 1:1).

$^1$H-NMR, DMSO-$d_6$, selected signals: δ=1.18+1.19 (2t, 3H), 2.26+2.29 (2s, 3H), 2.40+2.47 (2t, 2H), 2.69+2.73 (2t, 2H), 3.64+3.67 (2q, 2H), 5.33+5.39 (2s, 1H), 6.58 (s, 0.5H), 6.62+6.72 (2d, 2H), 7.08+7.13 (2d, 2H), 7.35+7.45 (2td, 1H), 7.65 (m, 1H).

Examples 1-95 to 1-100 were prepared by the same process.

N-(3-{[(4-Fluorophenyl)sulphanyl]methylene}-1-methylpiperidin-2-ylidene)-4-methylaniline Example 1-101

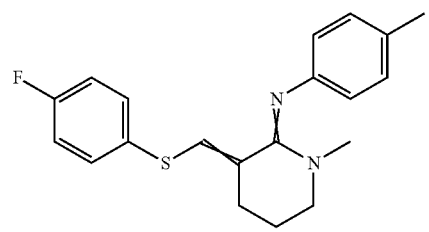 [SMILES: Cc1ccc(N=C2C(=CSc3ccc(F)cc3)CCCN2C)cc1]

687 mg (1.99 mmol) of 2-{[(4-fluorophenyl)sulphanyl]methylene}-5-hydroxy-N-(4-methylphenyl)-pentanamide (prepared by the method described in WO 2010/070910) are dissolved in 25 ml of dichloromethane, and 828 mg (3.98 mmol) of phosphorus pentachloride are added. After 12 h of stirring at room temperature, all volatile components are removed under reduced pressure and the residue is suspended in 9 ml of triethylamine. 36.4 mg (0.297 mmol) of DMAP and 4.97 ml of 2M methanamine in THF are added to the reaction mixture. The mixture is stirred in a CEM microwave at 80° C. for 60 min (divided into three microwave vessels). The reaction mixture is diluted with water and extracted with ethyl acetate, and the organic phase is washed with saturated aqueous sodium chloride solution and dried over sodium sulphate. Purification of the residue by column chromatography on silica gel (mobile phase: cyclohexane/ethyl acetate) gives 7.6 mg of N-(3-{[(4-fluorophenyl)sulphanyl]methylene}-1-methylpiperidin-2-ylidene)-4-methylaniline.

TABLE 1

Compounds of the formula (I)

| Ex. No. | Q$^1$ | X | W | Q$^2$ | 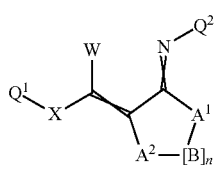 | Physical data: $^1$H-NMR, δ [ppm] |
|---|---|---|---|---|---|---|
| 1-1 | 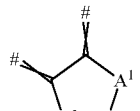 | S | H | H$_3$C–⟨phenyl⟩–# | # ⟨tetralin⟩ # | CD$_3$CN, δ = 2.38 (s, 3H), 2.78 (t, 2H), 3.03 (t, 2H), 6.32 (s, 1H), 6.76 (m, 4H), 7.20 (m, 5H), 7.27 (d, 1H), 7.31 (t, 1H), 7.40 (t, 1H), 8.19 (d, 1H). |

US 9,055,743 B2
TABLE 1-continued
Compounds of the formula
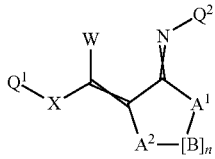
(I)
| Ex. No. | Q¹ | X | W | Q² | 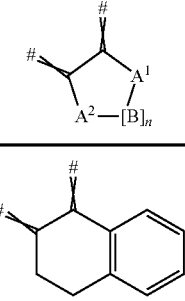 | Physical data: ¹H-NMR, δ [ppm] |
|---|---|---|---|---|---|---|
| 1-2 | 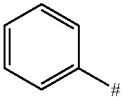 | SO₂ | H | 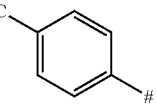 | 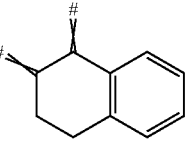 | CD₃CN, δ = 2.23 (s, 3H), 3.12 (t, 2H), 3.30 (t, 2H), 5.95 (s, 1H), 6.54 (d, 2H), 6.90 (d, 2H), 7.28 (d, 1H), 7.33 (t, 1H), 7.44 (t, 1H), 7.57 (m, 5H), 8.13 (d, 1H). |
| 1-3 | 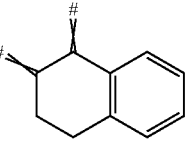 | S | H | 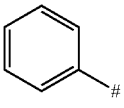 | 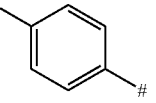 | CD₃CN, δ = 2.83 (t, 2H), 3.08 (t, 2H), 6.31 (s, 1H), 6.88 (m, 4H), 7.15 (t, 2H), 7.23-7.39 (m, 5H), 7.45(t, 1H), 8.23 (d, 1H). |
| 1-4 | 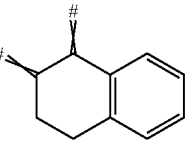 | S | H | 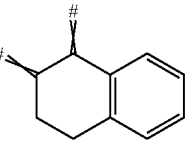 | 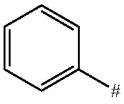 | CD₃CN, δ = 2.40 (s, 3H), 3.93 (s, 2H), 6.25 (s, 1H), 6.73 (d, 2H), 6.77 (d, 2H), 7.18-7.25 (m, 6H), 7.29 (d, 1H), 7.35 (t, 1H), 8.37 (d, 1H). |
| 1-5 | 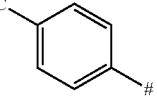 | S | H | 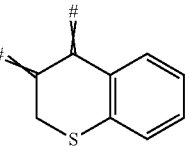 | 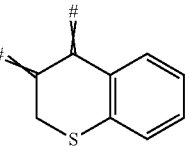 | Isomer mixture (about 1:1), CD₃CN, δ = 1.47 (d, 1.5H), 1.54 (d, 1.5H), 2.26 (s, 1.5 H), 2.36 (s, 1.5H), 3.90 (q, 0.5H), 4.00 (q, 0.5H), 6.53 (s, 0.5H), 6.62 (d, 0.5H), 6.76 (d, 1H), 6.79 (d, 1H), 6.98-7.58 (m, 10.5H), 7.81 (d, 0.5H). |
| 1-6 | 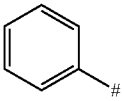 | S | H | 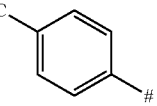 | 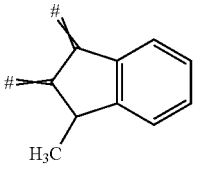 | Isomer mixture (about 1:1), CD₃CN, δ = 1.48 (d, 1.5H), 1.54 (d, 1.5H), 3.92 (q, 0.5H), 4.00 (q, 0.5H), 6.53 (s, 0.5H), 6.62 (d, 0.5H), 6.84-7.58 (m, 12.5H), 7.81 (d, 0.5H). |
| 1-7 | 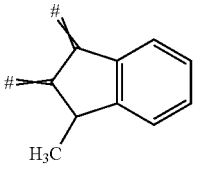 | S | H | 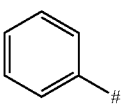 | 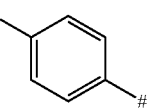 | CD₃CN, δ = 2.34 (s, 3H), 4.92 (s, 2H), 6.49-7.57 (m, 13H), 8.13 (d, 1H). |

TABLE 1-continued
Compounds of the formula
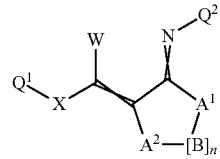
(I)
| Ex. No. | Q¹ | X | W | Q² | A²—[B]ₙ / A¹ structure | Physical data: ¹H-NMR, δ [ppm] |
|---|---|---|---|---|---|---|
| 1-8 | 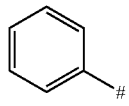 | S | H | 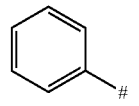 | 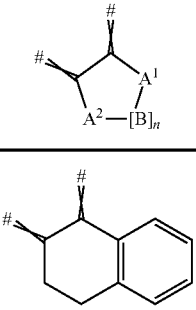 | CD₃CN, δ = 2.80 (t, 2H), 3.05 (t, 2H), 6.34 (s, 1H), 6.73 (d, 2H), 6.87 (d, 2H), 7.10-7.43 (m, 9H), 8.21 (d, 1H). |
| 1-9 | 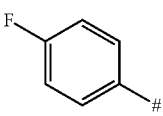 | S | H | 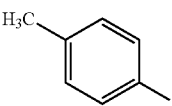 | 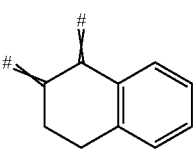 | CD₃CN, δ = 2.37 (s, 3H), 2.77 (t, 2H), 3.04 (t, 2H), 6.22 (s, 1H), 6.76 (d, 2H), 6.81 (dd, 2H), 6.96 (t, 2H), 7.20 (d, 2H), 7.28 (d, 1H), 7.32 (t, 1H), 7.41 (t, 1H), 8.19 (d, 1H). |
| 1-10 | 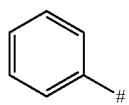 | S | H | 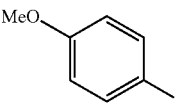 | 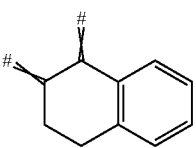 | CD₃CN, δ = 2.79 (t, 2H), 3.05 (t, 2H), 3.81 (s, 3H), 6.30 (s, 1H), 6.80 (m, 4H), 6.96 (d, 2H), 7.19 (m, 3H), 7.27 (d, 1H), 7.31 (t, 1H), 7.40 (t, 1H), 8.20 (d, 1H). |
| 1-11 | 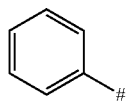 | S | H | 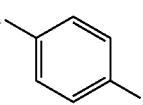 | 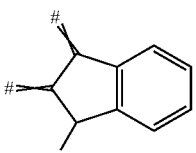 | LC-MS (neutral)*: logP = 6.38, (M + H)⁺ = 376 |
| 1-12 | 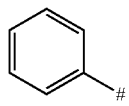 | S | H | 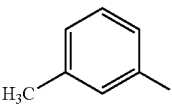 | 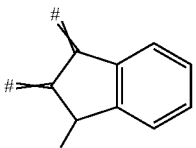 | Isomer mixture, CD₃CN, δ = [1.45 (d), 1.48 (d), 1.51 (d), together 3H], [2.29 (s), 2.30 (s), 2.32 (s), together 3H], [3.88 (q), 3.95 (q), 3.98 (q), together 1H], 6.52-7.80 (m, 14H). |
| 1-13 | 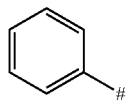 | S | H | 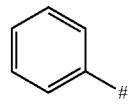 | 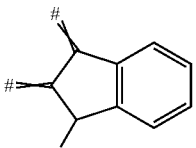 | Isomer mixture (about 1:1), CD₃CN, δ = 1.49 (d, 1.5H), 1.55 (d, 1.5H), 3.95 (m, 0.5H), 4.01 (m, 0.5H), 6.54 (d, 0.5H), 6.55 (d, 0.5H), 6.56-7.82 (m, 14H) |

TABLE 1-continued

Compounds of the formula (I)

| Ex. No. | Q¹ | X | W | Q² | A¹/A²/[B]n group | Physical data: ¹H-NMR, δ [ppm] |
|---|---|---|---|---|---|---|
| 1-14 | 4-F-C₆H₄ | S | H | 4-CH₃-C₆H₄ | 4-methyl-1,2,3,4-tetrahydronaphthalen-1,2-diyl | CD₃CN, δ = 1.29 (d, 3H), 2.37 (s, 3H), 2.67 (dd, 2H), 2.84 (dd, 1H), 3.29 (m, 1H), 6.32 (s, 1H), 6.75 (d, 2H), 6.79 (dd, 2H), 6.96 (t, 2H), 7.20 (d, 2H), 7.33 (m, 2H), 7.44 (t, 1H), 8.20 (d, 1H). |
| 1-15 | 4-F-C₆H₄ | S | H | 4-CH₃-C₆H₄ | 7-fluoro-1,2,3,4-tetrahydronaphthalen-1,2-diyl | CD₃CN, δ = 2.36 (s, 3H), 2.76 (t, 2H), 3.01 (t, 2H), 6.26 (s, 1H), 6.76 (d, 2H), 6.83 (dd, 2H), 6.96 (t, 2H), 7.16 (dd, 1H), 7.20 (d, 2H), 7.30 (m, 1H), 7.89 (dd, 1H). |
| 1-16 | 4-F-C₆H₄ | S | H | 4-CH₃-C₆H₄ | 6-fluoro-1,2,3,4-tetrahydronaphthalen-1,2-diyl | CD₃CN, δ = 2.36 (s, 3H), 2.77 (t, 2H), 3.03 (t, 2H), 6.23 (s, 1H), 6.74 (d, 2H), 6.81 (dd, 2H), 6.96 (t, 2H), 7.05 (m, 2H), 7.19 (d, 2H), 8.24 (dd, 1H). |
| 1-17 | 4-F-C₆H₄ | S | H | 4-CH₃-C₆H₄ | 6-methoxy-1,2,3,4-tetrahydronaphthalen-1,2-diyl | CD₃CN, δ = 2.36 (s, 3H), 2.76 (t, 2H), 3.00 (t, 2H), 3.83 (s, 3H), 6.19 (s, 1H), 6.72 (d, 2H), 6.79 (m, 3H), 6.95 (t, 2H), 7.18 (d, 2H), 8.14 (d, 1H). |
| 1-18 | C₆H₅ | S | H | 4-CH₃-C₆H₄ | 3,3-dimethylcyclohexane-1,2-diyl | CD₃CN, δ = 1.18 (s, 6H), 1.75 (m, 2H), 1.79 (m, 2H), 2.35 (s, 3H), 2.50 (m, 2H), 5.69 (s, 1H), 6.58 (d, 2H), 6.66 (m, 2H), 7.12-7.16 (m, 5H) |
| 1-19 | C₆H₅ | S | H | C₆H₅ | 3-phenyl-2,3-dihydro-1H-indene-1,2-diyl | Isomer mixture (about 1:1), CD₃CN, δ = 5.02 (br s, 0.5H), 5.13 (br s, 0.5H), 6.62 (d, 0.5H), 6.65 (d, 0.5H), 6.86 (m, 1H), 6.95-7.50 (m, 17H), 7.66 (d, 0.5H), 7.88 (d, 0.5H) |

TABLE 1-continued

Compounds of the formula (I)

| Ex. No. | Q¹ | X | W | Q² | A¹/A²/[B]ₙ group | Physical data: ¹H-NMR, δ [ppm] |
|---|---|---|---|---|---|---|
| 1-20 | phenyl | S | H | 4-methylphenyl | 1-phenyl-indane | Isomer mixture (about 1:1), CD$_3$CN, δ = 2.24 (s, 1.5H), 2.41 (s, 1.5H), 5.02 (br s, 0.5H), 5.14 (br s, 0.5H), 6.64 (d, 0.5H), 6.72 0.5H), 6.78-7.50 (m, 17H), 7.68 (d, 0.5H), 7.91 (d, 0.5H) |
| 1-21 | 4-fluorophenyl | S | H | 4-methylphenyl | 1,1-dimethyl-indane | Isomer mixture (about 2:1), DMSO-d6, Main component: δ = 1.61 (s, 6H), 2.33 (s, 3H), 6.56 (s, 1H), 6.74 (d, 2H), 7.03-7.70 (m, 10H), selected signals minor component: δ 1.48 (s, 6H), 2.18 (s, 3H) |
| 1-22 | phenyl | S | H | 4-methoxyphenyl | 1-methyl-indane | Isomer mixture (about 1:1), DMSO-d6, δ = 1.44 (d, 1.5H), 1.51 (d, 1.5H), 3.70 (s, 1.5H), 3.79 (s, 1.5H), 3.87 (m, 0.5H), 3.97 (m, 0.5H), 6.54 (d, 0.5H), 6.61 (d, 0.5H), 6.80 (d, 1H), 6.83 (d, 1H), 6.95-7.61 (m, 10.5), 7.79 (d, 0.5H) |
| 1-23 | 4-fluorophenyl | S | H | 4-methylphenyl | 6-fluorochroman | CD$_3$CN, δ = 2.32 (s, 3H), 4.88 (s, 2H), 6.45 (s, 1H), 6.75 (d, 2H), 6.98 (m, 3H), 7.02 (t, 2H), 7.18 (m, 3H), 7.80 (dd, 1H). |
| 1-24 | 4-fluorophenyl | S | H | 4-methylphenyl | 7-phenylchroman | CD$_3$CN, δ = 2.32 (s, 3H), 6.39 (s, 1H), 6.53 (d, 2H), 6.65 (s, 1H), 7.00-7.48 (m, 14H), 8.01 (d, 1H). |

TABLE 1-continued

Compounds of the formula (I)

| Ex. No. | Q¹ | X | W | Q² | A²—[B]ₙ part (ring) | Physical data: ¹H-NMR, δ [ppm] |
|---|---|---|---|---|---|---|
| 1-25 | 4-F-phenyl | S | H | 4-methylphenyl | 6-fluoro-2-methyl-chroman-4-ylidene | DMSO-d₆, selected signals: δ = 1.45 (d, 3H), 2.31 (s, 3H), 5.36 (q, 1H), 6.31 (s, 1H), 6.71 (d, 2H), 6.95 (dd, 2H), 7.13 (t, 2H), 7.19 (d, 3H), 7.74 (dd, 1H). |
| 1-26 | 4-F-phenyl | S | H | 4-methylphenyl | 4,5,6,7-tetrahydrobenzo[b]thiophen-4-ylidene | Isomer mixture (about 2:1), CD₃CN, selected signals main component: δ = 2.36 (s, 3H), 2.88 (t, 2H), 3.08 (t, 2H), 6.21 (s, 1H), 6.75 (d, 1H), 6.81(dd, 1H), 6.95 (t, 2H), 7.18 (d, 2H), 7.14 (d, 2H), 7.23 (d, 1H), 7.45 (d, 1H), selected signals minor component: δ = 2.32 (s, 3H), 6.06 (d, 1H), 6.61 (d, 2H), 6.87 (d, 1H), 7.47 (s, 1H), 7.53 (dd, 2H). |
| 1-27 | 4-F-phenyl | S | H | 4-methylphenyl | 4-fluoro-1-methyl-indan-3-ylidene | Isomer mixture (about 1:1), CD₃CN, δ = 1.45 (d, 1.5H), 1.53 (d, 1.5H), 2.24 (s, 1.5H), 2.36 (s, 1.5H), 3.88 (m, 0.5H), 4.00 (m, 0.5H), 6.35 (d, 0.5H), 6.61 (dd, 0.5H), 6.72-7.25 (m, 8H), 7.35 (dd, 1H), 7.43 (d, 0.5H), 7.56 (dd, 1H), 7.82 (dd, 0.5H) |
| 1-28 | 4-methylphenyl | S | H | 4-methylphenyl | 3,4-dihydronaphthalen-1(2H)-ylidene | CD₃CN, δ = 2.28 (s, 3H), 2.39 (s, 3H), 2.76 (t, 2H), 3.03 (t, 2H), 6.29 (s, 1H), 6.68 (d, 2H), 6.74 (d, 2H), 7.02 (d, 2H), 7.20 (d, 2H), 7.28 (d, 1H), 7.32 (t, 1H), 7.41 (t, 1H), 8.19 (d, 1H). |

TABLE 1-continued

Compounds of the formula (I)

| Ex. No. | Q¹ | X | W | Q² | A²—[B]ₙ / A¹ | Physical data: ¹H-NMR, δ [ppm] |
|---|---|---|---|---|---|---|
| 1-29 | 4-F-C₆H₄ | S | H | 4-CH₃-C₆H₄ | 4,5,6,7-tetrahydrobenzofuran-4,5-diyl | DMSO-d₆, δ = 2.30 (s, 3H), 2.87 (t, 2H), 2.96 (t, 2H), 5.02 (s, 1H), 6.22 (s, 1H), 6.62 (d, 2H), 7.14 (d, 2H), 7.30 (t, 2H), 7.36 (s, 1H), 7.39 (s, 1H), 7.58 (dd, 2H). |
| 1-30 | 4-F-C₆H₄ | S | H | 4-CH₃-C₆H₄ | 5,7-dimethyl-tetralin-1,2-diyl | DMSO-d₆, δ = 2.25 (s, 3H), 2.30 (s, 3H), 2.35 (s, 3H), 2.75 (t, 2H), 2.87 (t, 2H), 6.06 (s, 1H), 6.73 (d, 2H), 6.78 (dd, 2H), 7.03 (t, 2H), 7.14 (s, 1H), 7.19 (d, 2H), 7.86 (s, 1H). |
| 1-31 | 4-F-C₆H₄ | S | H | 4-CH₃-C₆H₄ | 5-methoxy-tetralin-1,2-diyl | DMSO-d₆, δ = 2.35 (s, 3H), 2.73 (t, 2H), 2.89 (t 2H), 3.84 (s, 3H), 6.10 (s, 1H), 6.74 (d, 2H), 6.78 (dd, 2H), 7.04 (t, 2H), 7.10 (d, 1H), 7.19 (d, 2H), 7.30 (t, 1H), 7.78 (d, 1H). |
| 1-32 | 4-F-C₆H₄ | S | H | 4-CH₃-C₆H₄ | 7-methoxy-tetralin-1,2-diyl | DMSO-d₆, δ = 2.35 (s, 3H), 2.72 (t, 2H), 2.94 (t, 2H), 3.78 (s, 3H), 6.16 (s, 1H), 6.75 (d, 2H), 6.78 (dd, 2H), 7.03 (m, 2H), 7.21 (m, 3H), 7.67 (d, 1H). |
| 1-33 | 4-F-C₆H₄ | S | H | 4-CH₃-C₆H₄ | 5,7-difluoro-tetralin-1,2-diyl | Isomer mixture (about 2:1), CD₃CN, selected signals main component: δ = 2.25 (s, 3H), 2.64 (m, 2H), 2.94 (t, 2 H), 6.55 (d, 2H), 7.00 (d, 2H), 7.18 (t, 2H), 7.44 (s, 1H), 7.54 (d, 2H), selected signals minor component: δ = 2.36 (s, 3H), 2.64 (m, 2H), 2.99 (t, 2H), 6.30 (s, 1H), 6.73 (d, 2H), 6.82 (dd, 2H), 6.97 (t, 2H), 7.20 (d, 2H). |

TABLE 1-continued

Compounds of the formula (I)

| Ex. No. | Q¹ | X | W | Q² | A²—[B]ₙ (ring) | Physical data: $^1$H-NMR, δ [ppm] |
|---|---|---|---|---|---|---|
| 1-34 | 4-F-C₆H₄- | S | H | 4-H₃C-C₆H₄- | 5-fluoro-tetrahydronaphthalene-1,2-diylidene | Isomer mixture (about 2:1), CD₃CN, selected signals main component: δ = 2.37 (s, 3H), 2.79 (t, 2H), 3.01 (t, 2H), 6.21 (s, 1H), 6.74 (d, 2H), 6.81 (dd, 2H), 6.96 (t, 2H), 7.20 (d, 2H), 8.05 (d, 1H), selected signals minor component: δ = 2.29 (s, 3H), 2.68 (t, 2H), 2.89 (m, 2H). |
| 1-35 | 4-F-C₆H₄- | S | H | 4-H₃C-C₆H₄- | thiochroman-3,4-diylidene | CD₃CN, δ = 2.39 (s, 3H), 3.91 (s, 2H), 6.15 (s, 1H), 6.77 (m, 4H), 7.20-7.48 (m, 5H), 8.36 (d, 1H). |
| 1-36 | 4-F-C₆H₄- | S | H | 4-H₃C-C₆H₄- | chroman-3,4-diylidene | CD₃CN, selected signals, δ = 2.32 (s, 3H), 4.90 (s, 2H), 6.42 (s, 1H), 6.75 (d, 2H), 6.98 (t, 2H), 7.16 (d, 2H), 7.41 (m, 1H), 8.13 (d, 1H). |
| 1-37 | 4-F-C₆H₄- | S | H | 4-H₃C-C₆H₄- | 1-ethyl-indan-2,3-diylidene | Isomer mixture (about 2:1), CD₃CN, selected signals main component: δ = 0.66 (t, 3H), 2.23 (s, 3H), 3.96 (m, 1H), 6.39 (d, 1H), 6.58-7.60 (m, 11H), 7.81 (d, 1H), selected signals minor component: δ = 0.73 (t, 3H), 4.08 (m, 1H) |
| 1-38 | C₆H₅- | S | H | 4-H₃C-C₆H₄- | cycloheptane-1,2-diylidene | LC-MS (neutral)*: logP = 6.20, (M + H)⁺ = 322 |

TABLE 1-continued

Compounds of the formula (I)

| Ex. No. | Q¹ | X | W | Q² | A¹/A²/[B]ₙ group | Physical data: ¹H-NMR, δ [ppm] |
|---|---|---|---|---|---|---|
| 1-39 | 4-F-C₆H₄ | S | H | 4-Et-C₆H₄ | 1,2,3,4-tetrahydronaphthalene-1,2-diyl | CD₃CN, δ = 1.25 (t, 3H), 2.69 (q, 2H), 2.79 (t, 2H), 3.06 (t, 2H), 6.25 (s, 1H), 6.78 (d, 2H), 6.85 (dd, 2H), 6.97 (t, 2H), 7.24 (d, 2H), 7.28-7.37 (m, 2H), 7.44 (t, 1H), 8.22 (d, 1H). |
| 1-40 | 4-F-C₆H₄ | S | H | 4-Me-C₆H₄ | bicyclic | CD₃CN, δ = 1.50-1.60 (m, 4H), 1.80-1.95 (m, 2H), 3H probably under water signal, 3.01 (s, 1H), 3.28 (s, 1H), 6.75 (d, 2H), 6.98 (s, 1H), 7.16-7.21 (m, 4H), 7.52 (dd, 2H) |
| 1-41 | 4-F-C₆H₄ | S | H | 3,4-diMe-C₆H₃ | 1,2,3,4-tetrahydronaphthalene-1,2-diyl | CD₃CN, δ = 2.23 (s, 3H), 2.29 (s, 3H), 2.76 (t, 2H), 3.03 (t, 2H), 6.27 (s, 1H), 6.56 (dd, 1H), 6.65 (d, 1H), 6.79 (dd, 2H), 6.95 (t, 2H), 7.12 (d, 1H), 7.28 (d, 1H), 7.31 (t, 1H), 7.41 (t, 1H), 8.18 (d, 1H). |
| 1-42 | 4-F-C₆H₄ | S | H | 4-iPr-C₆H₄ | 1,2,3,4-tetrahydronaphthalene-1,2-diyl | CD₃CN, δ = 1.23 (d, 6H), 2.77 (t, 2H), 2.93 (m, 1H), 3.04 (t, 2H), 6.24 (s, 1H), 6.77 (d, 2H), 6.87 (dd, 2H), 6.96 (t, 2H), 7.24 (d, 2H), 7.28 (d, 1H), 7.32 (t, 1H), 7.41 (t, 1H), 8.19 (d, 1H). |
| 1-43 | 4-F-C₆H₄ | S | H | 2,4-diMe-C₆H₃ | 1,2,3,4-tetrahydronaphthalene-1,2-diyl | CD₃CN, δ = 2.05 (s, 3H), 2.33 (s, 3H), 2.78 (t, 2H), 3.03 (t, 2H), 6.20 (s, 1H), 6.58 (d, 1H), 6.79 (dd, 2H), 6.97 (t, 2H), 7.03 (d, 1H), 7.07 (s, 1H), 7.28 (d, 1H), 7.32 (t, 1H), 7.41 (t, 1H), 8.24 (d, 1H). |

TABLE 1-continued

Compounds of the formula (I)

[Structure of formula (I): Q¹–X–C(=C(A²–[B]ₙ–A¹))–C(W)=N–O–Q²]

| Ex. No. | Q¹ | X | W | Q² | [Structure with A¹, A², [B]ₙ] | Physical data: ¹H-NMR, δ [ppm] |
|---|---|---|---|---|---|---|
| 1-44 | 4-F-phenyl | S | H | 4-CH₃-phenyl | 4,4-dimethylcyclohex-2-enylidene | Isomer mixture (about 2:1), DMSO-d₆, main component: δ = 1.12 (s, 6H), 2.26 (s, 3H), 5.93 (d, 1H), 6.36 (d, 1H), 6.61 (d, 2H), 7.10 (d, 2H), 7.25-7.30 (m, 3H), 7.53-7.57 (m, 2H) selected signals main component: δ = 1.05 (s, 6H), 2.29 (s, 3H), 5.97 (d, 1H), 6.30 (d, 1H), 6.68 (d, 2H) |
| 1-45 | 4-F-phenyl | S | H | 4-CH₃-phenyl | 4,4-dimethyl-3,4-dihydronaphthalen-1(2H)-ylidene | CD₃CN: δ = 1.38 (s, 6H), 2.37 (s, 3H), 2.66 (s, 2H), 6.29 (s, 1H), 6.75 (d, 2H), 6.80 (dd, 2H), 6.95 (dd, 2H), 7.19 (d, 2H), 7.31 (ddd, 1H), 7.44-7.50 (m, 2H), 8.21 (d, 1H) |
| 1-46 | 4-F-phenyl | S | H | 4-CH₃-phenyl | 6-methyl-3,4-dihydronaphthalen-1(2H)-ylidene | CD₃CN, δ = 2.35 (s, 3H), 2.36 (s, 3H), 2.75 (t, 2H), 2.99 (t, 2H), 6.20 (s, 1H), 6.73 (d, 2H), 6.81 (dd, 2H), 6.96 (t, 2H), 7.09 (s, 1H), 7.15 (d, 1H), 7.18 (d, 2H), 8.08 (dd, 1H). |
| 1-47 | 4-F-phenyl | S | H | 4-CH₃-phenyl | 6-chloro-3,4-dihydronaphthalen-1(2H)-ylidene | DMSO-d₆, δ = 2.34 (s, 3H), 2.72 (t, 2H), 3.01 (t, 2H), 6.20 (s, 1H), 6.75 (d, 2H), 6.82 (dd, 2H), 7.05 (t, 2H), 7.20 (d, 2H), 7.38 (dd, 1H), 7.42 (d, 1H), 8.16 (d, 1H). |
| 1-48 | 4-F-phenyl | S | H | 4-CH₃-phenyl | 6-acetamido-3,4-dihydronaphthalen-1(2H)-ylidene | LC-MS (neutral)*: logP = 4.64, (M + H)⁺ = 431. |

TABLE 1-continued

Compounds of the formula (I)

| Ex. No. | Q¹ | X | W | Q² | A²—[B]ₙ / A¹ | Physical data: ¹H-NMR, δ [ppm] |
|---|---|---|---|---|---|---|
| 1-49 | 4-F-C₆H₄ | S | H | 4-CH₃-C₆H₄ | 2-Br-5,5-dimethyl-cyclohexenyl | CD₃CN: δ = 1.17 (s, 6H), 2.37 (s, 3H), 2.55 (s, 2H), 6.14 (s, 1H), 6.68 (d, 2H), 6.78 (dd, 2H), 6.90 (s, 1H), 6.94 (dd, 2H), 7.17 (d, 2H) |
| 1-50 | 4-F-C₆H₄ | S | H | 4-CH₃-C₆H₄ | 6-Cl-3-methyl-indanyl | Isomer mixture (about 1:1), CD₃CN: δ = 1.45 (d, 1.5H), 1.54 (d, 1.5H), 2.22 (s, 1.5H), 2.35 (s, 1.5H), 3.87 (q, 0.5H), 3.98 (q, 0.5H), 6.38 (d, 0.5H), 6.53-6.58 (m), 6.72 (t), 6.95-7.25 (m), 7.40 (dd, 0.5H), 7.44 (d, 0.5H), 7.52-7.58 (m), 7.88 (d, 0.5H) |
| 1-51 | 4-F-C₆H₄ | S | H | 4-CH₃-C₆H₄ | 5-CH₃-3-methyl-indanyl | Isomer mixture (about 1:1), CD₃CN: selected signals δ = 1.45 (d, 1.5H), 1.52 (d, 1.5H), 3.87 (q, 0.5H), 3.95 (q, 0.5H), 6.34 (s, 0.5H), 6.50-7.70 (m) |
| 1-52 | 4-F-C₆H₄ | S | H | 4-CH₃-C₆H₄ | 7-OMe-8-methyl-chromanyl | CD₃CN, selected signals, δ = 3.87 (s, 3H), 4.89 (s, 2H), 6.39 (s, 1H), 7.98 (d, 1H). |
| 1-53 | 4-F-C₆H₄ | S | H | 4-CH₃-C₆H₄ | 7-OMe-chromanyl | CD₃CN, selected signals, δ = 2.31 (s, 3H), 3.82 (s, 3H), 4.96 (s, 2H), 6.39 (s, 1H), 8.03 (d, 1H). |

TABLE 1-continued

Compounds of the formula (I)

| Ex. No. | Q¹ | X | W | Q² | A²—[B]ₙ / A¹ | Physical data: ¹H-NMR, δ [ppm] |
|---|---|---|---|---|---|---|
| 1-54 | 4-F-C₆H₄- | S | H | 4-CH₃-C₆H₄- | 2-chloro-5,6,7,8-tetrahydroquinolin-6,5-diyl | CD₃CN, δ = 2.37 (s, 3H), 2.82 (t, 2H), 3.12 (t, 2H), 6.29 (s, 1H), 6.75 (d, 2H), 6.85 (dd, 2H), 6.97 (t, 2H), 7.20 (d, 2H), 7.35 (d, 1H), 7.42 (dd, 1H), 8.47 (d, 1H). |
| 1-55 | 4-F-C₆H₄- | S | H | 4-CH₃-C₆H₄- | 3-methyl-4,5,6,7-tetrahydrobenzo[d]isoxazol-4,5-diyl | CD₃CN, δ = 2.35 (s, 3H), 2.46 (s, 3H), 2.88 (t, 2H), 3.00 (t, 2H), 6.23 (s, 1H), 6.73 (d, 2H), 6.83 (dd, 2H), 6.96 (t, 2H), 7.17 (d, 2H). |
| 1-56 | 4-F-C₆H₄- | S | H | 4-CH₃-C₆H₄- | 2-benzylidenecyclohexyl | LC-MS (neutral)*: logP = 7.01, (M + H)⁺ = 414. |
| 1-57 | 4-F-C₆H₄- | S | H | 4-CH₃-C₆H₄- | 1-methylindan-2,3-diyl | Isomer mixture (about 1:1), CD₃CN: δ = 1.46 (d, 1.5H), 1.53 (d, 1.5H), 2.24 (s, 1.5H), 2.36 (s, 1.5H), 3.89 (q, 0.5H), 4.00 (q, 0.5H), 6.37 (d, 0.5H), 6.62 (d, 0.5H), 6.75 (dd, 2H), 6.97-7.60 (m, 9.5H), 7.80 (d, 0.5H) |
| 1-58 | 4-F-C₆H₄- | S | H | 4-CH₃-C₆H₄- | 7-fluorochroman-3,4-diyl | CD₃CN, selected signals, δ = 2.34 (s, 3H), 4.96 (s, 2H), 6.46 (s, 1H), 6.77 (d, 2H), 7.20 (d, 1H), 8.19 (dd, 1H). |
| 1-59 | 4-Cl-C₆H₄- | S | H | 4-CH₃-C₆H₄- | 1,2,3,4-tetrahydronaphthalen-1,2-diyl | CD₃CN: δ = 2.40 (s, 3H), 2.81 (t, 2H), 3.07 (t, 2H), 6.28 (s, 1H), 6.77 (d, 2H), 6.79 (d, 2H), 7.22 (d, 2H), 7.24 (d, 2H), 7.30-7.57 (m, 3H), 8.22 (d, 1H) |

TABLE 1-continued

Compounds of the formula (I)

| Ex. No. | Q¹ | X | W | Q² | A¹/A²/[B]ₙ group | Physical data: ¹H-NMR, δ [ppm] |
|---|---|---|---|---|---|---|
| 1-60 | phenyl | S | H | 4-methylphenyl | cyclohexane with =CH-S-phenyl substituent | CD₃CN, δ = 1.88 (m, 2H), 2.34 (s, 3H), 2.52 (t, 2H), 2.59 (t, 2H), 6.16 (s, 1H), 6.66 (d, 2H), 6.76 (m, 2H), 7.16 (d, 2H), 7.18 (m, 2H), 7.32 (m, 2H), 7.40 (t, 2H), 7.48 (d, 2H). |
| 1-61 | 4-fluorophenyl | S | H | 4-methylphenyl | 7-chloro-1-methylindane | CD₃CN: δ = 1.45 (d, 3H), 2.23 (s, 3H), 3.86 (q, 1H), 6.35 (d, 1H), 6.73 (d, 2H), 7.02-7.08 (m, 4H), 7.15 (d, 2H), 7.38-7.50 (m, 3H) |
| 1-62 | 3-chlorophenyl | S | H | 4-methylphenyl | 1,2,3,4-tetrahydronaphthalene | CD₃CN: δ = 2.35 (s, 3H), 2.79 (t, 2H), 3.04 (t, 2H), 6.28 (s, 1H), 6.63 (dd, 1H), 6.77 (d, 2H), 6.91 (dd, 1H), 7.13-7.33 (m, 6H), 7.40 (ddd, 1H), 8.20 (d, 1H) |
| 1-63 | 4-fluorophenyl | S | H | 3,4-dimethylphenyl | 5-fluoro-1-methylindane | Isomer mixture (about 1:1), DMSO-d6, δ = 1.43 (d, 1.5H), 1.50 (d, 1.5H), 2.11 (s, 1.5H), 2.16 (s, 1.5H), 2.20 (s, 1.5H), 2.23 (s, 1.5H), 3.85 (q, 0.5H), 3.96 (q, 0.5H), 6.33 (d, 0.5H), 6.56-6.62 (m, 1.5H), 6.65-6.68 (m, 1H), 6.95 (td, 0.5H), 7.05-7.50 (m, 6H), 7.60-7.67 (m, 1H), 7.82 (dd, 0.5H) |
| 1-64 | 4-fluorophenyl | S | H | 3,4-dimethylphenyl | 4,4-dimethylcyclohex-2-enyl | DMSO-d6: δ = 1.09 (s, 6H), 2.15 (s, 6H), 2.50 (s, 2H), 5.91 (d, 1H), 6.32 (d, 1H), 6.41 (dd, 1H), 6.49 (d, 1H), 7.02 (d, 1H), 7.24 (s, 1H), 7.26 (dd, 2H), 7.52 (dd, 2H) |

TABLE 1-continued

Compounds of the formula (I)

| Ex. No. | Q¹ | X | W | Q² | A²—[B]ₙ / A¹ | Physical data: ¹H-NMR, δ [ppm] |
|---|---|---|---|---|---|---|
| 1-65 | 4-F-phenyl | S | H | 4-methylphenyl | 1-methyl-6-methoxy-indane (2,3-positions) | Isomer mixture (about 1:1), CD₃CN, δ = 1.46 (d, 1.5H), 1.52 (d, 1.5H), 2.23 (s, 1.5H), 2.35 (s, 1.5H), 3.79 (s, 1.5H), 3.83 (q, 0.5H), 3.87 (s, 1.5H), 3.94 (q, 0.5H), 6.40 (s, 0.5H), 6.50-6.58 (m), 6.70-6.80 (m), 6.94-7.23 (m), 7.38-7.42 (m), 7.53-7.61 (m), 7.72 (d, 0.5H) |
| 1-66 | 4-F-phenyl | S | H | 4-methylphenyl | 2-chloro-4,5,6,7-tetrahydrobenzothiophene (4,5-positions) | CD₃CN: δ = 2.38 (s, 3H), 2.89 (t, 2H), 3.02 (t, 2H), 6.23 (s, 1H), 6.74 (d, 2H), 6.73 (dd, 2H), 6.98 (dd, 2H), 7.20 (d, 2H), 7.36 (s, 1H) |
| 1-67 | 4-F-phenyl | S | H | 3,5-dimethylphenyl | 1,2,3,4-tetrahydronaphthalene (1,2-positions) | CD₃CN, δ = 2.25 (s, 6H), 2.77 (t, 2H), 3.03 (t, 2H), 6.35 (s, 1H), 6.46 (s, 2H), 6.77 (dd, 2H), 6.97 (t, 2H), 7.28 (d, 1H), 7.32 (t, 1H), 7.41 (t, 1H), 8.17 (d, 1H). |
| 1-68 | 4-F-phenyl | S | H | 2-methyl-5-cyanophenyl | 1,2,3,4-tetrahydronaphthalene (1,2-positions) | CD₃CN, δ = 2.50 (s, 3H), 2.79 (t, 2H), 3.05 (t, 2H), 6.14 (s, 1H), 6.90 (dd, 2H), 7.00 (m, 3H), 7.13 (s, 1H), 7.31 (m, 3H), 7.43 (t, 1H), 8.18 (d, 1H). |
| 1-69 | 2-Cl-phenyl | S | H | 4-methylphenyl | 1,2,3,4-tetrahydronaphthalene (1,2-positions) | CD₃CN: δ = 2.41 (s, 3H), 2.91 (t, 2H), 3.11 (t, 2H), 6.21 (dd, 1H), 6.30 (s, 1H), 6.71 (d, 2H), 7.07 (ddd, 1H), 7.19 (ddd, 1H), 7.23 (d, 2H), 7.30-7.45 (m, 4H), 8.24 (d, 1H) |

TABLE 1-continued

Compounds of the formula (I)

| Ex. No. | Q¹ | X | W | Q² | A¹/A²/[B]ₙ group | Physical data: $^1$H-NMR, δ [ppm] |
|---|---|---|---|---|---|---|
| 1-70 | 4-F-phenyl | S | H | 4-methylphenyl | 5,8-dimethyl-tetrahydronaphthalenylidene | CD$_3$CN, δ = 2.32 (s, 3H), 2.38 (s, 3H), 2.57 (s, 3H), 2.57 (m, 2H), 2.89 (t, 2H), 6.19 (s, 1H), 6.77 (d, 2H), 6.80 (dd, 2H), 6.96 (t, 2H), 7.05 (d, 1H), 7.12 (d, 1H), 7.20 (d, 2H). |
| 1-71 | 4-F-phenyl | S | H | 3,4-dimethylphenyl | 1-methyl-6-methyl-indanylidene | Isomer mixture (about 1:1), DMSO-d6, δ = 1.40 (d, 1.5H), 1.48 (d, 1.5H), 2.11 (s, 1.5H), 2.16 (s, 1.5H), 2.29 (s, 1.5H), 2.23 (s, 1.5H), 2.30 (s, 1.5H), 2.41 (s, 1.5H), 3.80 (q, 0.5H), 3.90 (q, 0.5H), 6.32 (d, 0.5H), 6.45-6.68 (m), 6.83-6.88 (m), 7.05-7.40 (m), 7.60-7.68 (m) |
| 1-72 | 4-F-phenyl | S | H | 3,5-dimethylphenyl | 1-methyl-6-methyl-indanylidene | Isomer mixture (about 1:1), DMSO-d6, δ = 1.41 (d, 1.5H), 1.49 (d, 1.5H), 2.20 (s, 1.5H), 2.24 (s, 3H), 2.27 (s, 1.5H), 2.31 (s, 1.5H), 2.41 (s, 1.5H), 3.82 (q, 0.5H), 3.40 (q, 0.5H), 6.43-6.52 (m), 6.65-6.88 (m), 7.04-7.12 (m), 7.18-7.40 (m), 7.60-7.67 (m) |
| 1-73 | 4-MeO-phenyl | S | H | 4-methylphenyl | tetrahydronaphthalenylidene | CD$_3$CN, δ = 2.37 (s, 3H), 2.74 (t, 2H), 3.02 (t, 2H), 3.76 (s, 3H), 6.21 (s, 1H), 6.72 (d, 2H), 6.76 (s, 4H), 7.18 (d, 2H), 7.26-7.43 (m, 3H), 8.18 (d, 1H) |

US 9,055,743 B2

159 160

TABLE 1-continued

Compounds of the formula (I)

| Ex. No. | Q¹ | X | W | Q² | A²—[B]ₙ structure | Physical data: $^1$H-NMR, δ [ppm] |
|---|---|---|---|---|---|---|
| 1-74 | 3,4-difluorophenyl (F, F substituted) | S | H | 4-methylphenyl (H₃C-) | tetrahydronaphthalene | CD₃CN, δ = 2.37 (s, 3H), 2.80 (t, 2H), 3.07 (t, 2H), 6.23 (s, 1H), 6.62-6.71 (m, 2H), 6.78 (d, 2H), 7.06-7.16 (m, 1H), 7.22 (d, 2H), 7.28-7.35 (m, 2H), 7.43 (t, 1H), 8.22 (d, 1H) |
| 1-75 | 4-fluorophenyl | S | H | 4-methylphenyl | 7-tert-butyl-chroman | CD₃CN, selected signals, δ = 1.31 (s, 9H), 2.31 (s, 3H), 4.88 (s, 2H), 6.40 (s, 1H), 8.03 (d, 1H). |
| 1-76 | 4-fluorophenyl | S | H | 4-methylphenyl | 7-methyl-thiochroman | CD₃CN, selected signals, δ = 2.32 (s, 3H), 2.38 (s, 3H), 3.89 (s, 2H), 6.13 (s, 1H), 6.75 (m, 4H), 6.96 (t, 2H), 7.05 (d, 1H), 7.10 (s, 1H), 7.19 (d, 2H), 8.24 (d, 1H). |
| 1-77 | 4-fluorophenyl | S | H | 4-methylphenyl | 5,7-dimethyl-tetrahydronaphthalene | CD₃CN, δ = 2.28 (s, 6H), 2.36 (s, 3H), 2.74 (t, 2H), 2.96 (t, 2H), 6.17 (s, 1H), 6.72 (d, 2H), 6.79 (dd, 2H), 6.96 (t, 2H), 7.03 (s, 1H), 7.18 (d, 2H), 7.95 (s, 1H). |
| 1-78 | 3-fluorophenyl | S | H | 4-methylphenyl | tetrahydronaphthalene | CD₃CN, δ = 2.35 (s, 3H), 2.79 (t, 2H), 3.05 (t, 2H), 6.30 (s, 1H), 6.50-7.32 (m, 6H), 6.78 (d, 2H), 7.20 (d, 2H), 7.40 (t, 1H), 8.20 (d, 1H) |
| 1-79 | 2,4-difluorophenyl | S | H | 4-methylphenyl | tetrahydronaphthalene | CD₃CN, δ = 2.32 (s, 3H), 2.81 (t, 2H), 3.05 (t, 2H), 6.08 (s, 1H), 6.52-6.59 (m, 1H), 6.71 (d, 2H), 6.76-7.05 (m, 2H), 7.15 (d, 2H), 7.25-7.37 (m, 2H), 7.42 (t, 1H), 8.19 (d, 1H) |

TABLE 1-continued

Compounds of the formula (I)

| Ex. No. | Q¹ | X | W | Q² | A²—[B]ₙ / A¹ | Physical data: ¹H-NMR, δ [ppm] |
|---|---|---|---|---|---|---|
| 1-80 | 2-F-phenyl | S | H | 4-methylphenyl | 1,2,3,4-tetrahydronaphthalen-1,2-diyl | CD₃CN, δ = 2.35 (s, 3H), 2.83 (t, 2H), 3.07 (t, 2H), 6.20 (s, 1H), 6.40 (t, 1H), 6.74 (d, 2H), 6.98 (t, 1H), 7.03-7.08 (m, 1H), 7.18 (d, 2H), 7.22-7.35 (m, 3H), 7.40 (t, 1H), 8.19 (d, 1H) |
| 1-81 | 3,5-diF-phenyl | S | H | 4-methylphenyl | 1,2,3,4-tetrahydronaphthalen-1,2-diyl | CD₃CN, δ = 2.35 (s, 3H), 2.84 (t, 2H), 3.08 (t, 2H), 6.29 (s, 1H), 6.38-6.42 (m, 2H), 6.78-6.83 (m, 3H), 7.23 (d, 2H), 7.30-7.38 (m, 2H), 7.45 (t, 1H), 8.22 (d, 1H) |
| 1-82 | 4-CF₃-phenyl | S | H | 4-methylphenyl | 1,2,3,4-tetrahydronaphthalen-1,2-diyl | CD₃CN, δ = 2.38 (s, 3H), 2.84 (t, 2H), 3.06 (t, 2H), 6.32 (s, 1H), 6.78 (d, 2H), 6.87 (d, 2H), 7.23 (d, 2H), 7.28-7.35 (m, 2H), 7.43 (t, 1H), 7.45 (d, 2H), 8.20 (d, 1H) |
| 1-83 | 4-F-phenyl | S | H | 4-methylphenyl | 6-phenyl-1,2,3,4-tetrahydronaphthalen-1,2-diyl | CD₃CN, selected signals, δ = 2.40 (s, 3H), 2.84 (t, 2H), 3.04 (t, 2H), 6.28 (s, 1H), 6.78 (d, 2H), 6.86 (dd, 2H), 6.99 (t, 2H), 7.23 (d, 2H), 7.74 (d, 2H), 8.08 (dd, 1H). |
| 1-84 | 4-F-phenyl | S | H | 4-methylphenyl | 6-ethyl-1,2,3,4-tetrahydronaphthalen-1,2-diyl | CD₃CN, δ = 6.22 (s, 1H), 6.75 (d, 2H), 6.82 (dd, 2H), 6.97 (t, 2H), 7.20 (d, 2H), 8.12 (d, 1H). |

TABLE 1-continued

Compounds of the formula (I)

| Ex. No. | Q¹ | X | W | Q² | A¹/A²-[B]ₙ | Physical data: $^1$H-NMR, δ [ppm] |
|---|---|---|---|---|---|---|
| 1-85 | 4-F-phenyl | S | H | 2,4-dimethylphenyl (H₃C, CH₃) | methyl-indane | Isomer mixture (about 1:1), DMSO-d6, δ = 1.40 (d, 1.5H), 1.49 (d, 1.5H), 1.93-2.42 (m, 9H), 3.80 (q, 0.5H), 3.92 (q, 0.5H), 6.30 (s, 0.5H), 6.38 (d, 0.5H), 6.45 (d, 0.5H), 6.59-6.66 (m, 1H), 6.86 (d, 0.5H), 6.95-7.65 (m, 7.5H), 7.72 (d, 0.5H) |
| 1-86 | 4-F-phenyl | S | H | 4-methylphenyl | 5-methyl-chromane | CD₃CN, selected signals, δ = 2.70 (s, 3H), 4.86 (s, 2H), 6.34 (s, 1H), 6.77 (d, 2H), 7.20 (d, 2H), 7.28 (t, 1H). |
| 1-87 | cyclopentyl | S | H | 4-methylphenyl | tetrahydronaphthalene | CD₃CN, δ = 1.10-1.18 (m, 2H), 1.45-1.52 (m, 2H), 1.55-1.63 (m, 2H), 1.70-1.78 (m, 2H), 2.30-2.40 (m, 4H), 2.62 (t, 2H), 2.95 (t, 2H), 6.26 (s, 1H), 6.73 (d, 2H), 7.18 (d, 2H), 7.25-7.33 (m, 2H), 7.40 (t, 1H), 8.19 (d, 2H) |
| 1-88 | 4-F-phenyl | S | H | 3-methylphenyl | tetrahydronaphthalene | CD₃CN, δ = 2.30 (s, 3H), 2.77 (t, 2H), 3.04 (t, 2H), 6.29 (s, 1H), 6.61 (d, 1H), 6.69 (s, 1H), 6.76 (dd, 2H), 6.96 (t, 2H), 7.22-7.35 (m, 3H), 7.41 (t, 1H), 8.18 (d, 1H). |
| 1-89 | 4-F-phenyl | S | H | 3-fluoro-4-methylphenyl | tetrahydronaphthalene | CD₃CN, δ = 2.26 (s, 3H), 2.78 (t, 2H), 3.034 (t, 2H), 6.27 (s, 1H), 6.57 (m, 2H), 6.89 (dd, 2H), 6.98 (t, 2H), 7.20 (t, 1H), 7.28 (d, 1H), 7.31 (t, 1H), 7.41 (t, 1H), 8.18 (d, 1H). |

TABLE 1-continued

Compounds of the formula (I)

| Ex. No. | Q¹ | X | W | Q² | A¹/A²/B structure | Physical data: ¹H-NMR, δ [ppm] |
|---|---|---|---|---|---|---|
| 1-90 | 4-F-C₆H₄ | S | H | 4-CH₃-C₆H₄ | 1,7-dimethylindane | CD₃CN, δ = 1.43 (d, 3H), 2.24 (s, 3H), 2.68 (s, 3H), 3.81 (q, 1H), 6.31 (d, 1H), 6.50-7.40 (m, 11H) |
| 1-91 | 4-F-C₆H₄ | S | H | 4-CH₃-C₆H₄ | 2-chloro-4,5,6,7-tetrahydrobenzothiophene | Isomer mixture CD₃CN: main component δ = 2.38 (s, 3H), 2.83 (s, 4H), 6.70 (d, 2H), 6.79 (s, 1H), 6.82 (s, 1H), 7.14 (dd, 2H), 7.23 (d, 2H), 7.52 (dd, 2H); selected signals minor component δ = 7.40 (d, 1H) |
| 1-92 | 4-F-C₆H₄ | S | H | 3-F-4-CH₃-C₆H₃ | 3,4-dihydrophenanthrene | CD₃CN, δ = 2.39 (s, 3H), 2.96 (t, 2H), 3.49 (t, 2H), 6.19 (s, 1H), 6.78 (d, 2H), 6.81 (dd, 2H), 6.96 (t, 2H), 7.21 (d, 2H), 7.62 (m, 2H), 7.82 (d, 1H), 7.92 (m, 1H), 8.17 (m, 1H), 8.38 (d, 1H). |
| 1-93 | 4-F-C₆H₄ | S | H | 4-CH₃-C₆H₄ | 4,4,6,6-tetramethyl-cyclohexenyl with CH₃ | CD₃CN: δ = 1.11 (s, 6H), 1.89 (s, 3H), 2.36 (s, 3H), 2.50 (s, 2H), 6.03 (s, 1H), 6.17 (s, 1H), 6.64 (d, 2H), 6.74 (dd, 2H), 6.90 (dd, 2H), 7.15 (d, 2H) |
| 1-94 | 4-F-C₆H₄ | S | H | 4-CH₃-C₆H₄ | 2-chloro-4,4-dimethylcyclohexenyl | CD₃CN: δ = 1.17 (s, 6H), 2.36 (s, 3H), 2.54 (s, 2H), 6.16 (s, 1H), 6.65 (s, 1H), 6.68 (d, 2H), 6.78 (dd, 2H), 6.94 (dd, 2H), 7.18 (d, 2H) |

TABLE 1-continued

Compounds of the formula (I)

| Ex. No. | Q¹ | X | W | Q² | A²—[B]ₙ / A¹ | Physical data: ¹H-NMR, δ [ppm] |
|---|---|---|---|---|---|---|
| 1-95 | phenyl | S | H | 4-methylphenyl | cyclohexenyl-S-CH₂CH₃ | Isomer mixture (about 2:1), DMSO-d₆, selected signals main component: δ = 2.29 (s, 3H), 5.93 (s, 1H), 6.72 (d, 2H), 7.28 (s, 1H), selected signals minor component: δ = 2.27 (s, 3H), 5.88 (s, 1H), 6.66 (d, 2H), 6.77 (s, 1H). |
| 1-96 | 4-fluorophenyl | S | H | 4-methylphenyl | cyclohexenyl-O-CH₂CH₃ | Isomer mixture (about 3:2), CD₃CN, main component: δ = 1.21 (t, 3H), 2.28 (s, 3H), 2.45 (t, 2H), 2.76 (t, 2H), 3.65 (q, 2H), 5.37 (s, 1H), 6.64 (d, 2H), 7.13 (m, 4H), 7.29 (s, 1H), 7.49 (m, 2H), minor component: δ = 1.21 (t, 3H), 2.32 (s, 3H), 2.43 (t, 2H), 2.72 (t, 2H), 3.67 (q, 2H), 5.39 (s, 1H), 6.60 (s, 1H), 6.71(d, 2H), 7.13 (m, 4H), 7.49 (m, 2H). |
| 1-97 | phenyl | S | H | 4-methylphenyl | cyclohexenyl-O-CH₂CH₃ | Isomer mixture (about 3:1), DMSO-d₆, selected signals main component: δ = 1.18 (t, 3H), 2.26 (s, 3H), 2.47 (t, 2H), 2.71 (t, 2H), 3.65 (q, 2H), 5.35 (s, 1H), 6.64 (d, 2H), 7.09 (d, 2H), selected signals minor component: δ = 1.18 (t, 3H), 2.29 (s, 3H), 5.37 (s, 1H), 6.69 (d, 2H), 6.77 (s, 1H), 7.13(d, 2H). |
| 1-98 | 2,4-difluorophenyl | S | H | 4-methylphenyl | cyclohexenyl-O-CH₂CH₃ | Isomer mixture (about 1:1), DMSO-d₆, selected signals: δ = 1.18 + 1.19 (2t, 3H), 2.26 + 2.29 (2s, 3H), 2.40 + 2.47 (2t, 2H), 2.69 + 2.73 (2t, 2H), 3.64 + 3.67 (2q, 2H), 5.33 + 5.39 (2s, 1H), 6.58 (s, 0.5H), 6.62 + 6.72 (2d, 2H), 7.08 + 7.13 (2d, 2H), 7.35 + 7.45 (2td, 1H), 7.65 (m, 1H). |

TABLE 1-continued

Compounds of the formula (I)

| Ex. No. | Q¹ | X | W | Q² | A²—[B]ₙ | Physical data: $^1$H-NMR, δ [ppm] |
|---|---|---|---|---|---|---|
| 1-99 | 4-F-C₆H₄ | S | H | 4-CH₃-C₆H₄ | 4-isopropoxy-cyclohex-3-enyl | Isomer mixture (about 3:2), DMSO-d₆, main component: δ = 1.01 (d, 6H), 2.26 (s, 3H), 2.42 (t, 2H), 2.69 (t, 2H), 4.12 (m, 1H), 5.29 (s, 1H), 6.62 (d, 2H), 7.10 (d, 2H), 7.25 (s, 1H), 7.27 (m, 2H), 7.53 (m, 2H), minor component: δ = 1.02 (d, 6H), 2.28(s, 3H), 2.38 (t, 2H), 2.70 (t, 2H), 4.12 (m, 1H), 5.33 (s, 1H), 6.68 (s, 1H), 6.68 (d, 2H), 7.13 (d, 2H), 7.23 (m, 2H), 7.53 (m, 2H). |
| 1-100 | C₆H₅ | S | H | 4-CH₃-C₆H₄ | bicyclo[2.2.1]heptyl | CD₃CN δ = 1.50-1.60 (m, 4H), 1.80-1.90 (m, 2H), 2.30 (s, 3H), 2.99 (m, 1H), 3.28 (m, 1H), 6.72 (d, 2H), 7.01 (s, 1H), 7.14 (d, 2H), 7.30-7.47 (m, 5H) |
| 1-101 | 4-F-C₆H₄ | S | H | 4-CH₃-C₆H₄ | 1-methylpiperidin-2-ylidene | DMSO-d₆ δ = 1.86 (m, 2H), 2.44 (t, 2H), 2.95 (s, 3H), 3.28 (t, 2H), 6.09 (s, 1H), 6.51 (d, 2H), 6.76 (dd, 2H), 6.99-7.04 (m, 4H) |
| 1-102 | 3-F-C₆H₄ | S | H | 4-CH₃-C₆H₄ | bicyclo[2.2.1]heptyl | CD₃CN δ = 1.50-1.60 (m, 4H), 1.80-1.90 (m, 2H), 2.31 (s, 3H), 2.99 (m, 1H), 3.31 (m, 1H), 6.72 (d, 2H), 6.91 (s, 1H), 7.14 (d, 2H), 7.15-7.25 (m, 2H), 7.38 (m, 1H), 7.51 (td, 1h) |
| 1-103 | 2-F-C₆H₄ | S | H | 4-CH₃-C₆H₄ | bicyclo[2.2.1]heptyl | CD₃CN δ = 1.50-1.60 (m, 4H), 1.80-1.90 (m, 2H), 2.31 (s, 3H), 3.00 (m, 1H), 3.28 (m, 1H), 6.73 (d, 2H), 7.01 (s, 1H), 7.05 (td, 1H), 7.14 (d, 2H), 7.15-7.42 (m, 3H) |

TABLE 1-continued

Compounds of the formula

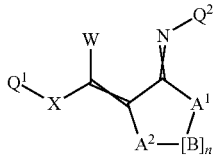

(I)

| Ex. No. | Q¹ | X | W | Q² | 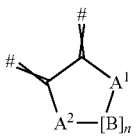 | Physical data: ¹H-NMR, δ [ppm] |
|---|---|---|---|---|---|---|

*The determination of the logP values was carried out in accordance with EU Guideline 79/831 Annex V.A8 by HPLC (High Performance Liquid Chromatography) on reversed-phase columns (C18) using the method below: the determination by LC-MS in the neutral range was carried out at pH 7.8 using the mobile phases 0.001-molar aqueous formic acid and acetonitrile and a linear gradient from 10% acetonitrile to 95% acetonitrile. Calibration was carried out using unbranched alkan-2-ones (having 3 to 16 carbon atoms) with known logP values (determination of the logP values by the retention times using linear interpolation between two successive alkanones).

Preparation of the Starting Materials

N-{2-[Bis(phenylsulphanyl)methyl]-3,4-dihydronaphthalen-1(2H)-ylidene}aniline

Example 2-1

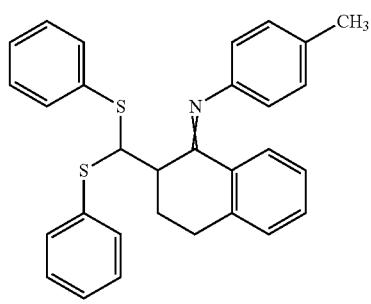 [SMILES: Cc1ccc(N=C2c3ccccc3CCC2C(Sc2ccccc2)Sc2ccccc2)cc1]

Under argon, 341 mg (3.19 mmol) of p-toluidine are added to 400 mg (1.06 mmol) of 2-[bis(phenylsulphanyl)methyl]-3,4-dihydronaphthalen-1(2H)-one in 20 ml of toluene. After cooling to 0° C., 0.53 ml (0.53 mmol) of a titanium(IV) tetrachloride solution (1 M in dichloromethane) is added slowly. After 1 h of stirring at 0° C. and a further 1 h at 25° C., 809 mg (5.31 mmol) of 1,8-diazabicyclo[5.4.0]undec-7-ene and 5 ml of dichloromethane are added. This mixture is poured into water and extracted with ethyl acetate. After washing with saturated aqueous sodium chloride solution, the organic phase is dried over sodium sulphate and concentrated under reduced pressure. Purification of the residue by column chromatography on silica gel (mobile phase: cyclohexane/ethyl acetate) gives 298 mg of N-{2-[bis(phenylsulphanyl)methyl]-3,4-dihydronaphthalen-1(2H)-ylidene}aniline.

¹H-NMR (DMSO-d6): δ=2.18 (m, 1H), 2.32 (m, 1H), 2.33 (s, 3H), 2.85 (m, 1H), 2.99 (m, 1H), 3.52 (m, 1H), 4.59 (d, 1H), 6.50 (d, 2H), 6.77 (d, 2H), 7.06 (d, 2H), 7.12-7.60 (m, 11H), 7.95 (m, 1H).

2-[Bis(phenylsulphanyl)methyl]-3,4-dihydronaphthalen-1(2H)-one

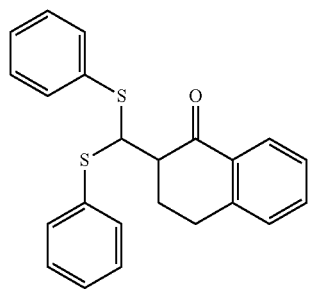 [SMILES: O=C1c2ccccc2CCC1C(Sc1ccccc1)Sc1ccccc1]

Under argon, 6.22 g (23.8 mmol) of triphenyl trithioorthoformate (1,1',1''-(methanetriyltrisulphanediyl)dibenzene) are dissolved in anhydrous dichloromethane and cooled to −70° C. 23.8 ml (23.8 mmol) of tin(IV) tetrachloride solution (1 M in dichloromethane) and 5.73 g (26.3 mmol) of (3,4-dihydronaphthalen-1-yloxy)trimethylsilane are added in succession, and the mixture is stirred at −70° C. for 40 min. The reaction mixture is poured into ice-water and extracted with dichloromethane. After washing with water, the organic phase is dried over sodium sulphate and concentrated under reduced pressure. Purification of the residue by column chromatography on silica gel (mobile phase: cyclohexane/ethyl acetate) gives 5.80 g of 2-[bis(phenylsulphanyl)methyl]-3,4-dihydronaphthalen-1(2H)-one.

¹H-NMR (DMSO-d6): δ=2.05 (m, 1H), 2.59 (m, 1H), 3.04 (m, 2H), 3.13 (ddd, 1H), 5.42 (d, 1H), 7.28-7.40 (m, 10H), 7.50 (d, 2H), 7.58 (td, 1H), 7.90 (dd, 1H).

1,1',1''-(Methanetriyltrisulphanediyl)tris(4-fluorobenzene)

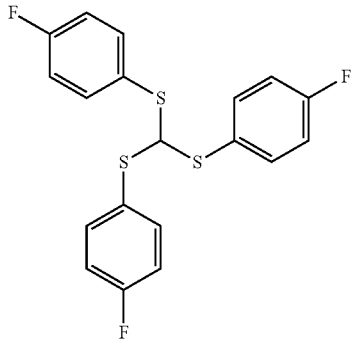 [SMILES: Fc1ccc(SC(Sc2ccc(F)cc2)Sc2ccc(F)cc2)cc1]

2.00 g (15.6 mmol) of 4-fluorothiophenol, 20 ml (250 mmol) of chloroform and 3.56 g (23.4 mmol) of 1,8-diazabicyclo[5.4.0]undec-7-ene are heated under reflux for 10 h. The reaction mixture is diluted with dichloromethane and washed with water, and the aqueous phase is re-extracted with dichloromethane. The combined organic phases are washed with saturated aqueous sodium chloride solution, dried over sodium sulphate and concentrated under reduced pressure. Purification of the residue by column chromatography on silica gel (mobile phase: cyclohexane/ethyl acetate) gives 1.69 g of 1,1',1''-(methanetriyltrisulphanediyl)tris(4-fluorobenzene).

$^1$H-NMR (DMSO-d6): δ=6.21 (s, 1H), 7.26 (t, 6H), 7.56 (dd, 6H).

Further Tristhioorthoesters were Prepared by the Same Process:

1,1',1''-(methanetriyltrisulphanediyl)tris(4-methylbenzene)
$^1$H-NMR (DMSO-d6): δ=6.01 (s, 1H), 7.20 (d, 6H), 7.38 (d, 6H)

1,1',1''-(methanetriyltrisulphanediyl)tris(3,4-difluorobenzene)
$^1$H-NMR (DMSO-d6): δ=6.57 (s, 1H), 7.36 (m, 3H), 7.49 (ddd, 3H), 7.68 (ddd, 3H)

1,1',1''-(methanetriyltrisulphanediyl)tris(3-chlorobenzene)
$^1$H-NMR (DMSO-d6): δ=6.70 (s, 1H), 7.41-7.44 (m, 6H), 7.48 (m, 3H), 7.63 (s, 3H)

1,1',1''-(methanetriyltrisulphanediyl)tris(2-chlorobenzene)
$^1$H-NMR (DMSO-d6): δ=6.44 (s, 1H), 7.35-7.43 (m, 6H), 7.52 (dd, 3H), 7.79 (dd, 3H)

1,1',1''-(methanetriyltrisulphanediyl)tris(4-chlorobenzene)
$^1$H-NMR (DMSO-d6): δ=6.47 (s, 1H), 7.47 (d, 6H), 7.53 (d, 6H)

1,1',1''-(methanetriyltrisulphanediyl)tris(4-methoxybenzene)
$^1$H-NMR (DMSO-d6): δ=3.77 (s, 9H), 5.64 (s, 1H), 6.95 (d, 6H), 7.40 (d, 6H)

1,1',1''-(methanetriyltrisulphanediyl)tris(2-fluorobenzene)
$^1$H-NMR (DMSO-d6): δ=6.13 (s, 1H), 7.24-7.32 (m, 6H), 7.46 (m, 3H), 7.43 (td, 3H)

1,1',1''-(methanetriyltrisulphanediyl)tris(2,4-difluorobenzene)
$^1$H-NMR (DMSO-d6): δ=5.92 (s, 1H), 7.18 (td, 3H), 7.39 (td, 3H), 7.69 (ddd, 3H)

1,1',1''-(methanetriyltrisulphanediyl)tris(3,5-difluorobenzene)
$^1$H-NMR (DMSO-d6): δ=6.97 (s, 1H), 7.26 (m, 3H), 7.30-7.40 (m, 6H)

1,1',1''-(methanetriyltrisulphanediyl)tris[4-(trifluoromethyl)benzene]
$^1$H-NMR (DMSO-d6): δ=7.03 (s, 1H), 7.76 (s, 12H)

1,1',1''-(methanetriyltrisulphanediyl)tris(3-fluorobenzene)
$^1$H-NMR (DMSO-d6): δ=6.74 (s, 1H), 7.19 (td, 3H), 7.34 (dd, 3H), 7.40-7.48 (m, 6H)

1,1',1''-(methanetriyltrisulphanediyl)tricyclopentane
$^1$H-NMR (DMSO-d6): δ=1.40-1.70 (m, 18H), 1.95.2.05 (m, 6H), 3H probably under water signal, 4.98 (s, 1H)

(Z)-{4-Ethoxy-2-[(4-methylphenyl)imino]cyclohex-3-en-1-ylidene}methanol

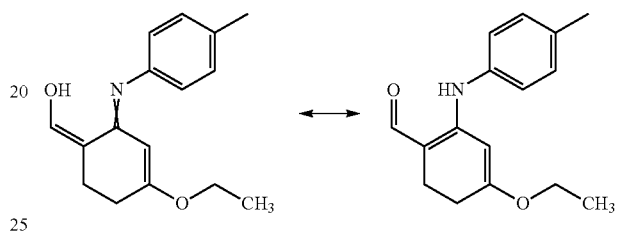

2.80 g (12.2 mmol) of N-(3-ethoxycyclohex-2-en-1-ylidene)-4-methylaniline (prepared from 3-[(4-methylphenyl)amino]cyclohex-2-en-1-one and ethyl iodide analogously to *J. Org. Chem.* 1984, 49, 3314) are dissolved in 40 ml of anhydrous tetrahydrofuran and, at −78° C., 7.94 ml of lithium diisopropylamide solution (2 M in tetrahydrofuran, heptane, ethylbenzene, 15.9 mmol) are added and the mixture is stirred for 30 min. At −78° C., 932 mg (12.2 mmol) of ethyl formate, dissolved in 10 ml of tetrahydrofuran, are added. After 1 h of stirring at −78° C., saturated aqueous ammonium chloride solution is added, the mixture is extracted with ethyl acetate and the organic phase is washed with saturated aqueous sodium chloride solution and dried over sodium sulphate. Purification of the residue by recrystallization (cyclohexane/ethyl acetate) gives 455 mg of (Z)-{4-ethoxy-2-[(4-methylphenyl)imino]cyclohex-3-en-1-ylidene}methanol.

$^1$H-NMR, DMSO-d$_6$: δ=1.24 (t, 3H), 2.30 (s, 3H), 2.34 (t, 2H), 2.48 (t, 2H), 3.84 (q, 2H), 5.37 (br. s, 1H), 7.08 (d, 2H), 7.20 (d, 2H), 8.91 (br. s, 1H), 12.60 (br. S, 1H).

N-[3-(Ethylsulphanyl)cyclohex-2-en-1-ylidene]-4-methylaniline

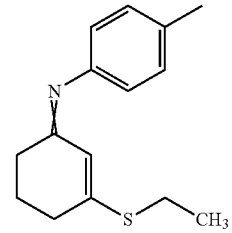 [SMILES: CCSC1=CC(=Nc2ccc(C)cc2)CCC1]

N-[3-(Ethylsulphanyl)cyclohex-2-en-1-ylidene]-4-methylaniline is prepared from 3-[(4-methyl-phenyl)amino]cyclohex-2-en-1-one by reaction with Lawesson reagent and subsequent alkylation with ethyl iodide analogously to *J. Org. Chem.* 1984, 49, 3314.

¹H-NMR, isomer mixture (about 3:2), DMSO-d₆: δ=1.09+1.27 (2t, 3H), 1.72+1.90 (2m, 2H), 2.25+2.26 (2s, 3H), 2.30+2.38 (2t, 2H), 2.56+2.90 (2q, 2H), 5.76+6.00 (2s, 1H), 6.60 (d, 2H), 7.09 (d, 2H).

N-{2,6-Bis[bis(phenylsulphanyl)methyl]cyclohexylidene}-4-methylaniline

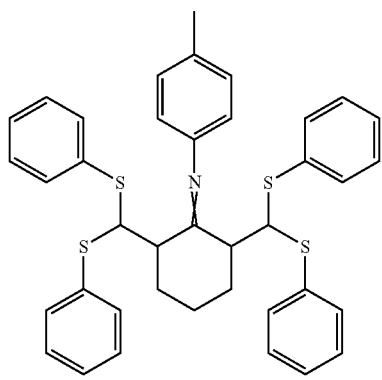 [SMILES: Cc1ccc(N=C2C(C(Sc3ccccc3)Sc3ccccc3)CCCC2C(Sc2ccccc2)Sc2ccccc2)cc1]

N-{2,6-Bis[bis(phenylsulphanyl)methyl]cyclohexylidene}-4-methylaniline is prepared analogously to Example 2-1 from 2,6-bis[bis(phenylsulphanyl)methyl]cyclohexanone.

2,6-Bis[bis(phenylsulphanyl)methyl]cyclohexanone

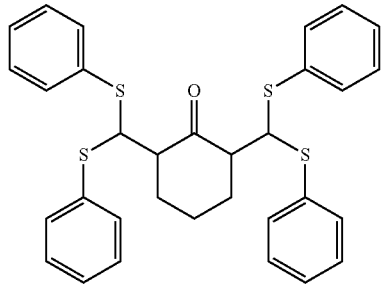 [SMILES: O=C1C(C(Sc2ccccc2)Sc2ccccc2)CCCC1C(Sc1ccccc1)Sc1ccccc1]

500 mg (1.52 mmol) of 2-[bis(phenylsulphanyl)methyl]cyclohexanone are dissolved in 30 ml of dichloromethane, 255 µl (1.83 mmol) of triethylamine and 385 µl (1.67 mmol) of tert-butyl(dimethyl)silyl trifluoromethanesulphonate are added successively at 0° C. and the mixture is stirred at 25° C. for 20 min. The reaction mixture is concentrated under reduced pressure, the residue is stirred with cyclohexane and the solution is once more concentrated under reduced pressure. The silylenol ether ((({6-[bis(phenylsulphanyl)methyl]cyclohex-1-en-1-yl}oxy)(tert-butyl)dimethylsilane) obtained in this manner is used further as a crude product.

400 mg (1.18 mmol) of 1,1',1''-(methanetriyltrisulphanediyl)tribenzene are dissolved in 25 ml of dichloromethane, and the mixture is cooled to –78° C. 1.41 ml (1.41 mmol) of tin(IV) tetrachloride solution (1 M in dichloromethane) and 520 mg (1.18 mmol) of (({6-[bis(phenylsulphanyl)methyl]-cyclohex-1-en-1-yl}oxy)(tert-butyl)dimethylsilane) are added in succession, and the mixture is stirred at –78° C. for 1 h. The reaction mixture is poured into ice-water and extracted with dichloromethane. After washing with water, the organic phase is dried over sodium sulphate and concentrated under reduced pressure. Purification of the residue by column chromatography on silica gel (mobile phase: cyclohexane/ethyl acetate) gives 341 mg of 2,6-bis[bis(phenylsulphanyl)methyl]cyclohexanone.

2-Chloro-6,7-dihydro-1-benzothiophen-4(5H)-one

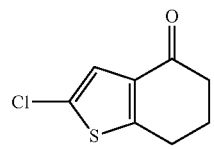 [SMILES: O=C1CCCc2sc(Cl)cc21]

First 0.096 ml (1.41 mmol) of orthophosphoric acid and then 4.12 g (20.14 mmol) of 4-(5-chloro-2-thienyl)butanoic acid are added to 5 ml of acetic acid, and the mixture is stirred at 120° C. for 2.5 h. The cooled reaction mixture is added to water and extracted with dichloromethane, and the extract is washed with 2 M NaOH. After washing with water, the organic phase is dried over sodium sulphate and concentrated under reduced pressure. The residue is extracted with diethyl ether. Undissolved crystals are filtered off with suction and discarded. The ether phase is concentrated under reduced pressure and the residue is purified by column chromatography on silica gel (mobile phase: cyclohexane/ethyl acetate). This gives 1.07 g of 2-chloro-6,7-dihydro-1-benzothiophen-4(5H)-one.

¹H-NMR (CD₃CN): δ=2.17 (m, 2H), 2.48 (dd, 2H), 2.95 (dd, 2H), 7.17 (s, 1H)

2-Chloro-5,6-dihydro-1-benzothiophen-7(4H)-one

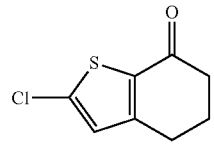 [SMILES: O=C1CCCc2cc(Cl)sc21]

10.0 g (57.9 mmol) of 2-chloro-4,5,6,7-tetrahydro-1-benzothiophene are dissolved in acetic acid/water (247 ml/82 ml), 127 g (231 mmol) of ammonium cerium (IV) nitrate in water (50 ml) are added and the mixture is stirred at room temperature for 5 h. The reaction mixture is added to ice-water and extracted with dichloromethane. After washing with water, the organic phase is dried over sodium sulphate and concentrated under reduced pressure. This gives 5.60 g of 2-chloro-5,6-dihydro-1-benzothiophen-7(4H)-one.

¹H-NMR (CD₃CN): δ=2.12 (m, 2H), 2.52 (dd, 2H), 2.80 (dd, 2H), 6.98 (s, 1H)

2-Chloro-4,5,6,7-tetrahydro-1-benzothiophene

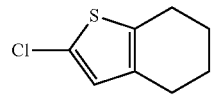

111 g (594 mmol) of 2-chloro-6,7-dihydro-1-benzothiophen-4(5H)-one together with 414 g (3.57 mol) of triethylsilane are initially charged in 1.25 ml of dichloromethane, and 506 g (3.57 mol) of boron trifluoride/ether complex are added at room temperature. The reaction mixture is stirred at room temperature for 84 h and then added to water. The organic phase is dried over sodium sulphate and concentrated under reduced pressure. This gives 90.0 g of 2-chloro-4,5,6,7-tetrahydro-1-benzothiophene.

All other starting materials are commercially available or known from the literature.

TABLE 2

Compounds of the formula

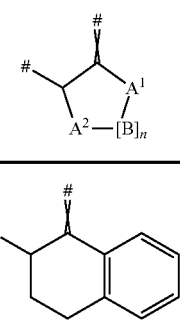

(II)

| Ex. No. | $Q^1$ | X | W | $Q^2$ | 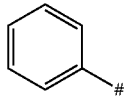 | Physical data: $^1$H-NMR, δ [ppm] or LC-MS (neutral)* |
|---|---|---|---|---|---|---|
| 2-1 | 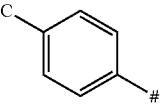 | S | H | 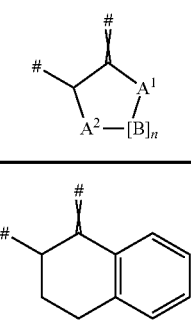 | 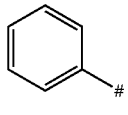 | DMSO-d6, δ = 2.18 (m, 1H), 2.32 (m, 1H), 2.33 (s, 3H), 2.85 (m, 1H), 2.99 (m, 1H), 3.52 (m, 1H), 4.59 (d, 1H), 6.50 (d, 2H), 6.77 (d, 2H), 7.06 (d, 2H), 7.12-7.60 (m, 11H), 7.95 (m, 1H). |
| 2-2 | 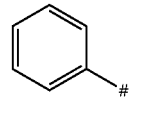 | S | H | 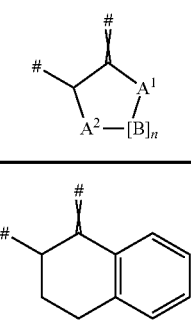 | 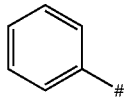 | DMSO-d6, δ = 2.19 (m, 1H), 2.32 (m, 1H), 2.89 (m, 1H), 2.99 (m, 1H), 3.50 (m, 1H), 4.60 (d, 1H), 6.51 (d, 2H), 6.77 (d, 2H), 7.10-7.60 (m, 14H), 7.92 (m, 1H). |
| 2-3 | 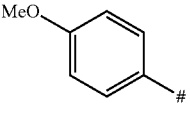 | S | H | 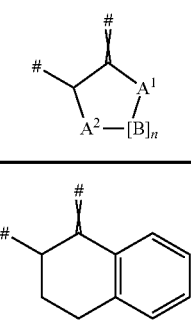 | 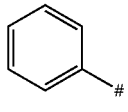 | DMSO-d6, δ = 2.19 (m, 1H), 2.34 (m, 1H), 2.85 (m, 1H), 3.00 (m, 1H), 3.54 (m, 1H), 3.79 (s, 3H), 4.58 (d, 1H), 6.55-7.60 (m, 17H), 7.95 (m, 1H). |
| 2-4 | 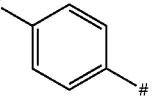 | S | H | 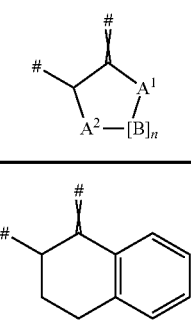 | 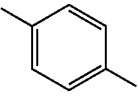 | Isomer mixture, DMSO-d6, selected signals: δ = 1.47 (d), 1.55 (d), 3.76 (m), 3.95 (m), 5.75 (s), 6.08 (s), 6.50-7.83 (m), 7.86 (s) |
| 2-5 | 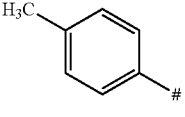 | S | H | 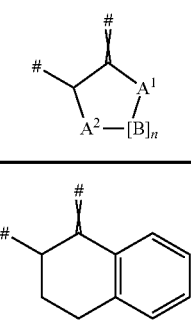 | 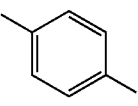 | DMSO-d6, δ = 2.18 (m, 1H), 2.30 (s, 3H), 2.37 (m, 1H), 2.88 (m, 1H), 3.07 (m, 1H), 3.37 (m under H$_2$O signal, 1H), 4.42 (d, 1H), 6.52 (d, 2H), 6.90 (m, 2H), 7.00-7.67 (m, 11H), 7.91 (m, 1H). |
| 2-6 | 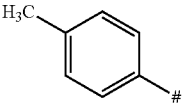 | S | H | 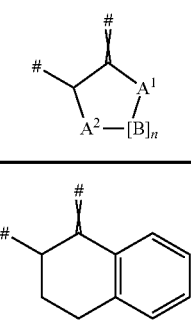 | | DMSO-d6, δ = 2.17 (m, 1H), 2.30 (s, 3H), 2.38 (m, 1H), 2.89 (m, 1H), 3.09 (m, 1H), 3.37 (m under H$_2$O signal, 1H), 4.43 (d, 1H), 6.52 (d, 2H), 6.93 (m, 2H), 7.03 (m, 4H), 7.12 (m, 4H), 7.31 (dd, 2H), 7.95 (dd, 1H). |

TABLE 2-continued

Compounds of the formula (II)

| Ex. No. | Q¹ | X | W | Q² | A²—[B]ₙ | Physical data: ¹H-NMR, δ [ppm] or LC-MS (neutral)* |
|---|---|---|---|---|---|---|
| 2-7 | 4-F-C₆H₄ | S | H | 4-CH₃-C₆H₄ | 4-methyl-1,2,3,4-tetrahydronaphthalen-1-ylidene | DMSO-d6, δ = 1.29 (d, 3H), 1.91 (m, 1H), 2.30 (s, 3H), 2.47 (m, 1H), 3.21 (m, 1H), 3.37 (m under H₂O signal, 1H), 4.37 (d, 1H), 6.50 (d, 2H), 6.88 (dd, 2H), 7.02 (m, 4H), 7.13 (t, 2H), 7.31 (m, 3H), 7.42 (d, 1H), 7.48 (t, 1H), 7.88 (d, 1H). |
| 2-8 | 4-F-C₆H₄ | S | H | 4-CH₃-C₆H₄ | 7-fluoro-1,2,3,4-tetrahydronaphthalen-1-ylidene | DMSO-d6, δ = 2.17 (m, 1H), 2.30 (s, 3H), 2.38 (m, 1H), 2.89 (m, 1H), 3.09 (m, 1H), 3.37 (m under H₂O signal, 1H), 4.43 (d, 1H), 6.52 (d, 2H), 6.93 (m, 2H), 7.03 (m, 4H), 7.12 (m, 4H), 7.31 (dd, 2H), 7.95 (dd, 1H). |
| 2-9 | C₆H₅ | S | H | 4-CH₃-C₆H₄ | 3-phenyl-2,3-dihydro-1H-inden-1-ylidene | Isomer mixture (about 5:1), CD₃CN, main component: δ = 2.35 (s, 3H), 3.80 (m, 1H), 4.60 (d, 1H), 4.83 (br s, 1H), 6.43-7.53 (m, 22H), 7.84 (d, 1H), selected signals minor component: δ = 3.46 (m, 1H), 4.75 (d, 1H), 5.29 (d, 1H) |
| 2-10 | C₆H₅ | S | H | C₆H₅ | 3-phenyl-2,3-dihydro-1H-inden-1-ylidene | Isomer mixture (about 3:1), CD₃CN, main component: δ = 3.76 (m, 1H), 4.62 (d, 1H), 4.84 (d, 1H), 6.41 (d, 2H), 6.57 (d, 2H), 6.98-7.53 (m, 19H), 7.84 (d, 1H), selected signals minor component: δ = 3.49 (m, 1H), 4.77 (d, 1H), 5.30 (d, 1H) |
| 2-11 | 4-F-C₆H₄ | S | H | 4-CH₃-C₆H₄ | chroman-4-ylidene | DMSO-d6, δ = 2.29 (s, 3H), 3.35 (m under H₂O-Signal, 1H), 4.31 (d, 1H), 4.43 (dd, 1H), 5.00 (d, 1H), 6.55 (d, 2H), 6.85 (dd, 2H), 6.95-7.08 (m, 6H), 7.19 (t, 2H), 7.35 (dd, 2H), 7.45 (t, 1H), 8.00 (d, 1H). |

*The determination of the logP values was carried out in accordance with EU Guideline 79/831 Annex V.A8 by HPLC (High Performance Liquid Chromatography) on reversed-phase columns (C18) using the method below: the determination by LC-MS in the neutral range was carried out at pH 7.8 using the mobile phases 0.001-molar aqueous formic acid and acetonitrile and a linear gradient from 10% acetonitrile to 95% acetonitrile. Calibration was carried out using unbranched alkan-2-ones (having 3 to 16 carbon atoms) with known logP values (determination of the logP values by the retention times using linear interpolation between two successive alkanones).

181
Biological Comparative Examples
1) Five-Membered Rings
Example 1a-32
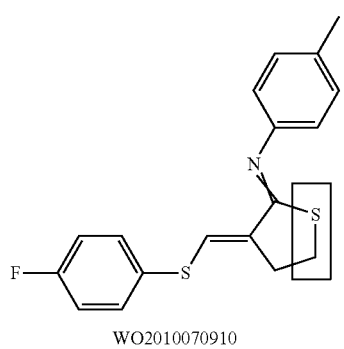
WO2010070910
Example 1-57
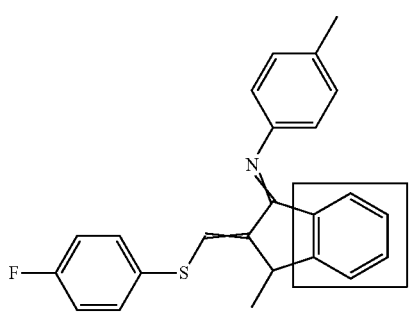
2) Five-Membered Rings with Dimethyl Substitution
Example A
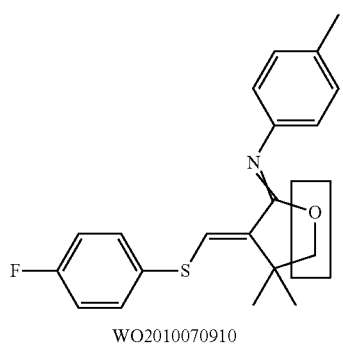
WO2010070910
Example 1-21
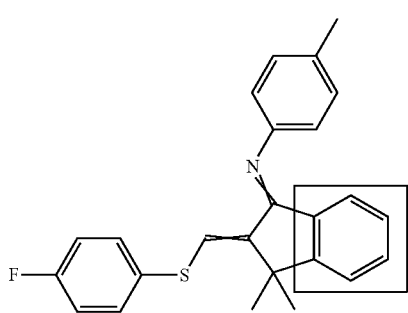
182
3) Six-Membered Rings
Example B
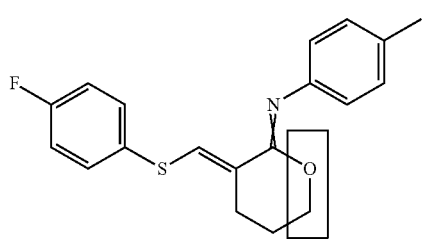
WO2010070910
Example 2a-78
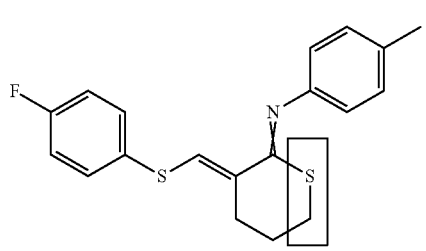
WO2010070910
Example 2-6
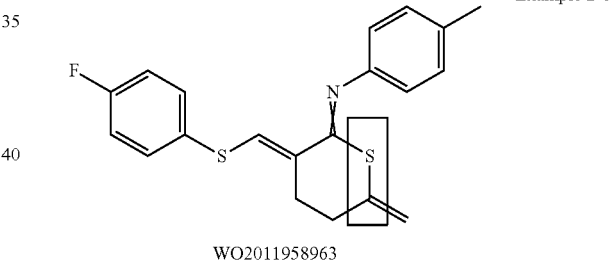
WO2011958963
Example 1-9
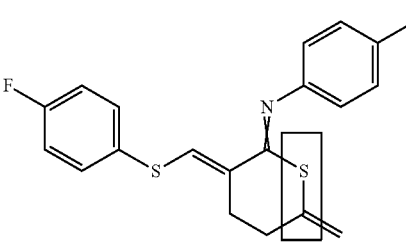
Example 1-16
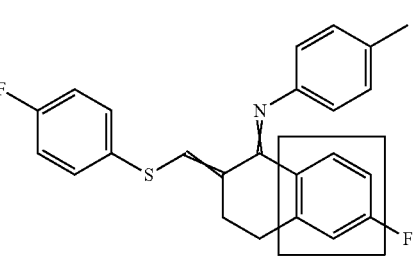

-continued

Example 1-35

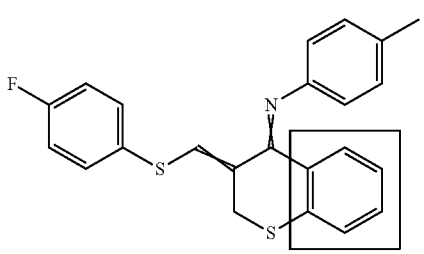

Biological Experiments

*Boophilus microplus* Test (BOOPMI Injection)

Solvent: Dimethyl Sulphoxide

To produce a suitable preparation of active compound, 10 mg of active compound are mixed with 0.5 ml of solvent and the concentrate is diluted with solvent to the desired concentration. The solution of active compound is injected into the abdomen (*Boophilus microplus*), and the animals are transferred into dishes and kept in a climatized room. The activity is assessed by position of fertile eggs.

After 7 days, the effect in % is determined 100% means that none of the ticks has laid any fertile eggs.

In this test, for example, the following compounds of the preparation examples shows an activity of 100% at an application rate of 20 µg/animal: 1-1, 1-3, 1-4, 1-5, 1-6, 1-9, 1-10, 1-16, 1-20, 1-26, 1-27, 1-28, 1-33, 1-34, 1-35, 1-36, 1-37, 1-57, 1-59, 1-62, 1-63, 1-69, 1-74, 1-79, 1-80, 1-81, 1-82, 1-85.

| Example | Active compound concentration in µg/animal | Kill rate in % after 7 days |
|---|---|---|
| WO2010070910 Example 2a-78 | 0.16 | 30 |
| Example 1-16 | 0.16 | 90 |

*Boophilus microplus* Test (DIP)
Test Animals: Adult Fat Females of the *Boophilus microplus* Strain Parkhurst—SP-Resistant)
Solvent: Dimethyl Sulphoxide 10 mg of active compound are dissolved in 0.5 ml of dimethyl sulphoxide. To produce a suitable formulation, the active compound solution is diluted with water to the particular desired concentration.

This active compound preparation is pipetted into tubes. 8-10 ticks are transferred into a further tube provided with holes. The tube is dipped into the active compound preparation, with all the ticks being wetted completely. After the liquid has run off, the ticks are transferred to filter discs in plastic dishes and kept in a climatized room. After 7 days, the activity is checked for deposition of fertile eggs. Eggs whose fertility is not visible from the outside are kept in glass tubes in a climatized cupboard until the larvae have hatched. An activity of 100% means that no tick has laid fertile eggs.

In this test, for example, the following compounds of the preparation examples show an activity of 80% at an application rate of 100 ppm: 1-34

In this test, for example, the following compounds of the preparation examples show an activity of 100% at an application rate of 100 ppm: 1-1, 1-4, 1-5, 1-16, 1-26, 1-27, 1-28, 1-29, 1-33, 1-59, 1-62

*Ctenocephalides Felis* Oral Test (CTECFE)
Solvent: 1 Part by Weight of Dimethyl Sulphoxide To produce a suitable preparation of active compound, 10 mg of active compound are mixed with 0.5 ml of dimethyl sulphoxide. Part of the concentrate is diluted with citrated cattle blood, and the desired concentration is prepared.

About 20 unfed adult fleas (*Ctenocephalides felis*) are placed into a chamber which is closed at the top and bottom with gauze. A metal cylinder whose bottom end is closed with parafilm is placed onto the chamber. The cylinder contains the blood/active compound preparation, which can be taken up by the fleas through the parafilm membrane. After two days, the kill in % is determined 100% means that all fleas have been killed; 0% means that none of the fleas have been killed.

In this test, for example, the following compounds of the preparation examples show an activity of 80% at an application rate of 100 ppm: 1-1, 1-10, 1-29, 1-74

In this test, for example, the following compounds of the preparation examples show an activity of 90% at an application rate of 100 ppm: 1-3, 1-36, 1-63, 1-80, 1-85

In this test, for example, the following compounds of the preparation examples show an activity of 95% at an application rate of 100 ppm: 1-26, 1-33

In this test, for example, the following compounds of the preparation examples show an activity of 100% at an application rate of 100 ppm: 1-4, 1-5, 1-6, 1-9, 1-16, 1-27, 1-28, 1-34, 1-35, 1-37, 1-57, 1-59, 1-62, 1-69, 1-79, 1-81, 1-82

*Lucilia cuprina* Test (LUCICU)
Solvent: Dimethyl Sulphoxide

To produce a suitable preparation of active compound, 10 mg of active compound are mixed with 0.5 ml of dimethyl sulphoxide and the concentrate is diluted with water to the desired concentration. Vessels containing horsemeat treated with the active compound preparation of the desired concentration are populated with about 20 *Lucilia cuprina* larvae.

After 2 days, the kill in % is determined. 100% means that all larvae have been killed; 0% means that none of the larvae have been killed.

In this test, for example, the following compounds of the preparation examples show an activity of 80% at an application rate of 100 ppm: 1-62

In this test, for example, the following compounds of the preparation examples show an activity of 90% at an application rate of 100 ppm: 1-10, 1-59

In this test, for example, the following compounds of the preparation examples show an activity of 100% at an application rate of 100 ppm: 1-1, 1-3, 1-4, 1-5, 1-6, 1-9, 1-16, 1-26, 1-27, 1-28, 1-29, 1-33, 1-34, 1-35, 1-36, 1-37, 1-57, 1-69, 1-74, 1-79, 1-80, 1-81, 1-82, 1-85

*Musca domestica* Test (MUSCDO)
Solvent: Dimethyl Sulphoxide

To produce a suitable preparation of active compound, 10 mg of active compound are mixed with 0.5 ml of dimethyl sulphoxide and the concentrate is diluted with water to the desired concentration. Vessels containing a sponge treated with the active compound preparation of the desired concentration are populated with adult *Musca domestica*.

After 2 days, the kill in % is determined 100% means that all flies have been killed; 0% means that none of the flies have been killed.

In this test, for example, the following compounds of the preparation examples show an activity of 80% at an application rate of 100 ppm: 1-16, 1-28, 1-33

In this test, for example, the following compounds of the preparation examples show an activity of 85% at an application rate of 100 ppm: 1-57

In this test, for example, the following compounds of the preparation examples show an activity of 90% at an application rate of 100 ppm: 1-9, 1-37

In this test, for example, the following compounds of the preparation examples show an activity of 100% at an application rate of 100 ppm: 1-5, 1-10, 1-26, 1-27, 1-29

Contact Test Against Fleas In-Vitro (CTECFE Contact)

An amount of 0.9 mg of active compound is weighed out, and 1 ml of acetone is added.

Of this acetone solution, either 250 μA are transferred directly into roll-necked test tubes or an aliquot is diluted with 4 parts of acetone 1:5. For its part, 250 μl of this dilution are pipetted into roll-necked test tubes, or the dilution is diluted further, etc., until the desired number of dilution steps is reached.

The roll-necked test tubes containing the solution of the active compound in acetone are immediately coated in a fume cupboard by 2 h of swing rotation at 30 rpm. After evaporation of the solvent, the active compound contained in the acetone gives, at the highest concentration tested, an active compound content of 500 g/ha (or 500 μg/dm$^2$) on the surface of the test tube.

10-20 Adult cat fleas (*Ctenocephalides felis*, fully sensitive laboratory strain) anesthetized with CO2 are transferred into the test tubes prepared in this manner, and the test tubes are closed with a plastic roll-necked lid provided with fine holes.

The test tubes are stored vertically at room temperature and humidity for 24 or 48 h. After 24 and 48 h, the activity of the active compound applied is determined by comparison with an acetone-treated control. Here, an observed normal activity for all fleas corresponds to 0% activity, a strongly restricted or uncoordinated (knock-down) movement or death of all fleas corresponds to 100% activity.

In this test, for example, active compound preparations of the following preparation examples had, at an application rate of 500 g/ha, excellent 100% activity against cat fleas after 48 h: 1-1, 1-3, 1-4, 1-5, 1-6, 1-7, 1-8, 1-9, 1-10, 1-14, 1-15, 1-16, 1-17, 1-18, 1-20, 1-21, 1-22, 1-23, 1-26, 1-27, 1-28, 1-29, 1-31, 1-32, 1-33, 1-34, 1-35, 1-36, 1-37, 1-38, 1-39, 1-46, 1-47, 1-54, 1-57, 1-58, 1-59, 1-62, 1-63, 1-69, 1-74, 1-79, 1-80, 1-81, 1-82, 1-84, 1-85, 2-11

| Example | Active compound concentration in g/ha | Kill rate in % after 2 days |
|---|---|---|
| WO2010070910 Example 1a-32 | 0.16 | 0 |
| Example 1-21 | 0.16 | 100 |
| Example 1-21 | 0.032 | 100 |
| WO2010070910 Example B | 0.032 | 0 |
| WO2010070910 Example 2a-78 | 0.032 | 0 |
| Example 1-9 | 0.032 | 100 |

Contact Test Against Ticks In Vitro (RHIPSA Contact)

An amount of 0.9 mg of active compound is weighed out, and 1 ml of acetone is added.

Of this acetone solution, either 250 μl are transferred directly into roll-necked test tubes or an aliquot is diluted with 4 parts of acetone 1:5. For its part, 250 μl of this dilution are pipetted into roll-necked test tubes, or the dilution is diluted further, etc., until the desired number of dilution steps is reached.

The roll-necked test tubes containing the solution of the active compound in acetone are immediately coated in a fume cupboard by 2 h of swing rotation at 30 rpm. After evaporation of the solvent, the active compound contained in the acetone gives, at the highest concentration tested, an active compound content of 500 g/ha (or 500 ng/dm$^2$) on the surface of the test tube.

5-10 Adult brown dog ticks (*Rhipicephalus sanguineus*, fully sensitive laboratory strain) are transferred into the test tubes prepared in this manner, and the test tubes are closed with a plastic roll-necked lid provided with fine holes.

The test tubes are stored vertically at room temperature and humidity for 24 or 48 h in the dark. After 24 and 48 h, the activity of the active compound applied is determined by comparison with an acetone-treated control. To this end, the ticks are shaken down to the bottom of the test tube, and the test tubes are heated on a hotplate to at most 50° C. for at most 10 minutes. Here, an observed normal activity (speedy recovery from a resting position and climbing of the test tube wall (heat avoidance)) for all ticks corresponds to 0% activity, a strongly restricted or uncoordinated (knock-down) movement or death of all ticks corresponds to 100% activity.

In this test, for example, active compound preparations of the following preparation examples had, at an application rate of 500 g/ha, an activity of at least 80% against the brown dog tick after 48 h: 1-1, 1-3, 1-4, 1-5, 1-6, 1-7, 1-8, 1-9, 1-10, 1-15, 1-16, 1-17, 1-21, 1-26, 1-27, 1-28, 1-29, 1-34, 1-35, 1-36, 1-37, 1-39, 1-46, 1-47, 1-58, 1-79, 1-80, 1-81, 1-82, 2-11.

| Example | Active compound concentration in g/ha | Kill rate in % after 2 days |
|---|---|---|
| WO2010070910 Example 2a-78 | 4 | 40 |
| Example 1-35 | 4 | 100 |

Phaedon Test (PHAECO Spray Treatment)

Solvents: 78.0 parts by weight of acetone
  1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifiers, and the concentrate is diluted with emulsifier-containing water to the desired concentration.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the activity in % is determined. 100% means that all beetle larvae have been killed; 0% means that none of the beetle larvae have been killed.

In this test, for example, the following compounds of the preparation examples show an activity of 100% at an application rate of 500 g/ha: 1-1, 1-3, 1-4, 1-5, 1-6, 1-7, 1-8, 1-9, 1-10, 1-12, 1-13, 1-14, 1-15, 1-16, 1-17, 1-19, 1-20, 1-21, 1-23, 1-26, 1-27, 1-28, 1-29, 1-33, 1-34, 1-35, 1-36, 1-37, 1-39, 1-40, 1-41, 1-43, 1-46, 1-47, 1-51, 1-54, 1-57, 1-58, 1-59, 1-60, 1-62, 1-63, 1-65, 1-66, 1-67, 1-68, 1-69, 1-71, 1-74, 1-78, 1-79, 1-80, 1-81, 1-82, 1-84, 1-85, 1-87, 1-88, 1-89, 1-91, 1-92, 1-100, 2-1, 2-9, 2-11

| Example | Active compound concentration in g/ha | Kill rate in % after 7 days |
|---|---|---|
| WO2010070910 Example A | 500 | 0 |
| Example 1-21 | 500 | 100 |

*Spodoptera frugiperda* Test (SPODFR Spray Treatment)

Solvents: 78.0 parts by weight of acetone
  1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of maize leaves (*Zea mays*) are sprayed with an active compound preparation of the desired concentration and, after drying, populated with caterpillars of the army worm (*Spodoptera frugiperda*) besetzt.

After 7 days, the activity in % is determined. 100% means that all caterpillars have been killed; 0% means that none of the caterpillars have been killed.

In this test, for example, the following compounds of the preparation examples show an activity of 83% at an application rate of 500 g/ha: 1-44, 1-98

In this test, for example, the following compounds of the preparation examples show an activity of 100% at an application rate of 500 g/ha: 1-1, 1-3, 1-4, 1-5, 1-6, 1-7, 1-8, 1-9, 1-10, 1-12, 1-13, 1-14, 1-15, 1-16, 1-17, 1-19, 1-20, 1-21, 1-22, 1-23, 1-25, 1-26, 1-27, 1-28, 1-29, 1-30, 1-31, 1-32, 1-33, 1-34, 1-35, 1-36, 1-37, 1-39, 1-41, 1-43, 1-46, 1-47, 1-49, 1-51, 1-54, 1-57, 1-58, 1-59, 1-60, 1-62, 1-63, 1-64, 1-65, 1-66, 1-67, 1-68, 1-69, 1-71, 1-72, 1-74, 1-75, 1-78, 1-79, 1-80, 1-81, 1-82, 1-84, 1-85, 1-88, 1-89, 1-91, 1-92, 1-100, 2-1, 2-8, 2-9, 2-10, 2-11.

| Example | Active compound concentration in g/ha | Kill rate in % after 7 days |
| --- | --- | --- |
| WO2010070910 Example A | 100 | 0 |
| Example 1-21 | 100 | 83 |

Myzus Test (MYZUPE Spray Treatment)
Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage leaves (*Brassica pekinensis*) which are infested by all stages of the green peach aphid (*Myzus persicae*) are sprayed with an active compound preparation of the desired concentration.

After 6 days, the activity in % is determined. 100% means that all aphids have been killed; 0% means that none of the aphids have been killed.

In this test, for example, the following compounds of the preparation examples show an activity of 80% at an application rate of 500 g/ha: 1-33, 1-54, 1-64, 1-67

In this test, for example, the following compounds of the preparation examples show an activity of 90% at an application rate of 500 g/ha: 1-24, 1-28, 1-41, 1-43, 1-49, 1-69, 1-71, 1-91, 1-96, 2-1

In this test, for example, the following compounds of the preparation examples show an activity of 100% at an application rate of 500 g/ha: 1-1, 1-3, 1-4, 1-5, 1-6, 1-7, 1-9, 1-13, 1-14, 1-15, 1-16, 1-17, 1-19, 1-20, 1-21, 1-26, 1-27, 1-29, 1-35, 1-36, 1-37, 1-39, 1-46, 1-47, 1-51, 1-57, 1-58, 1-59, 1-62, 1-63, 1-65, 1-74, 1-78, 1-79, 1-80, 1-81, 1-82, 1-84, 1-85, 1-87, 1-88, 1-100, 2-9, 2-10, 2-11

| Example | Active compound concentration in g/ha | Kill rate in % after 6 days |
| --- | --- | --- |
| WO2010070910 Example A | 500 | 0 |
| Example 1-21 | 500 | 100 |
| Example 1-21 | 100 | 100 |

*Tetranychus* Test; OP-Resistant (TETRUR Spray Treatment)
Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of bean leaves (*Phaseolus vulgaris*) infested by all stages of the greenhouse red spider mite (*Tetranychus urticae*) are sprayed with an active compound preparation of the desired concentration.

After 6 days, the activity in % is determined. 100% means that all spider mites have been killed; 0% means that none of the spider mites have been killed.

In this test, for example, the following compounds of the preparation examples show an activity of 80% at an application rate of 500 g/ha: 1-30, 1-39, 1-41, 1-42, 1-43, 1-54, 1-64, 1-73, 2-1

In this test, for example, the following compounds of the preparation examples show an activity of 90% at an application rate of 500 g/ha: 1-22, 1-44, 1-93, 1-96, 2-8

In this test, for example, the following compounds of the preparation examples show an activity of 100% at an application rate of 500 g/ha: 1-1, 1-3, 1-4, 1-5, 1-6, 1-7, 1-8, 1-9, 1-10, 1-12, 1-13, 1-14, 1-16, 1-15, 1-17, 1-19, 1-20, 1-21, 1-26, 1-27, 1-28, 1-29, 1-31, 1-32, 1-35, 1-36, 1-37, 1-40, 1-46, 1-47, 1-57, 1-58, 1-59, 1-62, 1-63, 1-65, 1-68, 1-69, 1-71, 1-74, 1-78, 1-79, 1-80, 1-81, 1-82, 1-84, 1-85, 1-87, 1-88, 1-89, 1-91, 1-92, 1-97, 1-98, 1-99, 2-9, 2-10, 2-11

| Example | Active compound concentration in g/ha | Kill rate in % after 6 days |
| --- | --- | --- |
| WO2010070910 Example A | 500 | 0 |
| Example 1-21 | 500 | 100 |
| Example 1-21 | 100 | 100 |

*Anopheles* Test (ANPHGB Surface Treatment)
Solvent: Acetone

To produce a suitable preparation of active compound, the active compound is dissolved in acetone (2 mg/ml). The active compound preparation is pipetted onto a glazed tile and, after drying, adult mosquitoes of the species *Anopheles gambiae* (homocygus kdr) are placed onto the treated tile. The exposition time is 30 minutes.

Two hours after contact to the treated surface, the knock-down proportion of the test animals in % is determined.

In this test, for example, the following compounds of the preparation examples show a knock-down activity of 100% at an application rate of 100 mg/m$^2$: 1-1, 1-4, 1-5, 1-7, 1-9, 1-16, 1-27, 1-28, 1-34, 1-35, 1-36, 1-38, 1-39, 1-40, 1-41, 1-43, 1-44, 1-46, 1-51, 1-58, 1-62, 1-64, 1-65, 1-71, 1-74, 1-76, 1-79, 1-80, 1-81, 1-82, 1-84, 1-85, 1-86, 1-88, 1-89, 1-100, 1-102, 1-103, 2-1, 2-2

In this test, for example, the following compounds of the preparation examples show a knock-down activity of 95% at an application rate of 100 mg/m$^2$: 1-10, 1-14, 1-17

In this test, for example, the following compounds of the preparation examples show a knock-down activity of 90% at an application rate of 100 mg/m$^2$: 1-69

In this test, for example, the following compounds of the preparation examples show a knock-down activity of 85% at an application rate of 100 mg/m$^2$: 1-8, 1-47, 1-50

In this test, for example, the following compounds of the preparation examples show a knock-down activity of 80% at an application rate of 100 mg/m$^2$: 1-3, 1-57, 1-87

24 hours after contact to the treated surface, the mortality in % is determined. Here, 100% means that all mosquitoes have been killed; 0% means that none of the mosquitoes has been killed.

In this test, for example, the following compounds of the preparation examples show an activity of 100% at an application rate of 100 mg/m²: 1-1, 1-3, 1-4, 1-5, 1-6, 1-7, 1-8, 1-9, 1-10, 1-11, 1-12, 1-13, 1-14, 1-15, 1-16, 1-17, 1-21, 1-23, 1-26, 1-27, 1-28, 1-29, 1-31, 1-33, 1-34, 1-35, 1-36, 1-38, 1-39, 1-40, 1-41, 1-43, 1-44, 1-46, 1-47, 1-50, 1-51, 1-53, 1-54, 1-57, 1-58, 1-59, 1-62, 1-64, 1-65, 1-69, 1-71, 1-73, 1-74, 1-75, 1-76, 1-78, 1-79, 1-80, 1-81, 1-82, 1-84, 1-85, 1-86, 1-87, 1-88, 1-89, 1-91, 1-100, 1-102, 1-103, 2-1, 2-2, 2-5

In this test, for example, the following compounds of the preparation examples show an activity of 95% at an application rate of 100 mg/m²: 1-63, 2-3, 2-6

In this test, for example, the following compounds of the preparation examples show an activity of 90% at an application rate of 100 mg/m²: 1-18, 1-19, 1-22, 1-67, 1-92

In this test, for example, the following compounds of the preparation examples show an activity of 85% at an application rate of 100 mg/m²: 1-37, 1-52, 1-96

In this test, for example, the following compounds of the preparation examples show an activity of 80% at an application rate of 100 mg/m²: 1-77

| Example | Active compound concentration in g/ha | Kill rate in % after 24 hours |
|---|---|---|
| WO2010070910 Example 1a-32 | 1.6 | 60 |
| Example 1-57 | 1.6 | 100 |
| WO2010070910 Example A | 8 | 30 |
| Example 1-21 | 8 | 100 |
| WO2010070910 Example 2a-78 | 1.6 | 60 |
| WO2011958963 Example 2-6 | 1.6 | 10 |
| Example 1-9 | 1.6 | 100 |
| Example 1-16 | 1.6 | 80 |
| Example 1-35 | 1.6 | 100 |

*Anopheles* Test (ANPHFU Surface Treatment)
Solvent: Acetone

To produce a suitable preparation of active compound, the active compound is dissolved in acetone (2 mg/ml). The active compound preparation is pipetted onto a glazed tile and, after drying, adult mosquitoes of the species *Anopheles funestus* strain FUMOZ-R (Hunt et al., Med Vet Entomol. 2005 September; 19(3):271-5) are placed onto the treated tile. The exposition time is 30 minutes.

Two hours after contact to the treated surface, the knock-down proportion of the test animals in % is determined.

In this test, for example, the following compounds of the preparation examples show a knock-down activity of 100% at an application rate of 100 mg/m²: 1-40, 1-100

24 hours after contact to the treated surface, the mortality in % is determined. Here, 100% means that all mosquitoes have been killed; 0% means that none of the mosquitoes has been killed.

In this test, for example, the following compounds of the preparation examples show an activity of 100% at an application rate of 100 mg/m²: 1-40, 1-58, 1-100

*Aedes* Test (AEDSAE Surface Treatment)
Solvent: Acetone

To produce a suitable preparation of active compound, the active compound is dissolved in acetone (2 mg/ml). The active compound preparation is pipetted onto a glazed tile and, after drying, adult mosquitoes of the species *Aedes aegypti* are placed onto the treated tile. The exposition time is 30 minutes.

Two hours after contact to the treated surface, the knock-down proportion of the test animals in % is determined.

In this test, for example, the following compounds of the preparation examples show a knock-down activity of 100% at an application rate of 100 mg/m²: 1-1, 1-9, 1-16, 1-17, 1-27, 1-34, 1-36, 1-38, 1-39, 1-40, 1-43, 1-46, 1-57, 1-58, 1-79, 1-84, 1-100, 1-102, 1-103, 2-1, 2-2

In this test, for example, the following compounds of the preparation examples show a knock-down activity of 95% at an application rate of 100 mg/m²: 1-41, 1-86, 1-74

In this test, for example, the following compounds of the preparation examples show a knock-down activity of 90% at an application rate of 100 mg/m²: 1-29, 1-35, 1-44

In this test, for example, the following compounds of the preparation examples show a knock-down activity of 85% at an application rate of 100 mg/m²: 1-7, 1-51, 1-65, 1-88

In this test, for example, the following compounds of the preparation examples show a knock-down activity of 80% at an application rate of 100 mg/m²: 1-28, 1-76, 1-80, 1-96

24 hours after contact to the treated surface, the mortality in % is determined Here, 100% means that all mosquitoes have been killed; 0% means that none of the mosquitoes has been killed.

In this test, for example, the following compounds of the preparation examples show an activity of 100% at an application rate of 100 mg/m²: 1-1, 1-4, 1-5, 1-7, 1-9, 1-10, 1-14, 1-15, 1-16, 1-17, 1-21, 1-27, 1-28, 1-29, 1-33, 1-34, 1-35, 1-36, 1-38, 1-39, 1-40, 1-41, 1-43, 1-44, 1-46, 1-47, 1-50, 1-51, 1-53, 1-57, 1-58, 1-59, 1-62, 1-63, 1-65, 1-71, 1-74, 1-76, 1-79, 1-80, 1-81, 1-82, 1-84, 1-85, 1-86, 1-87, 1-88, 1-89, 1-100, 1-102, 1-103, 2-1, 2-2

In this test, for example, the following compounds of the preparation examples show an activity of 95% at an application rate of 100 mg/m²: 1-37, 1-91, 1-96

In this test, for example, the following compounds of the preparation examples show an activity of 90% at an application rate of 100 mg/m²: 1-23, 1-26, 1-54

In this test, for example, the following compounds of the preparation examples show an activity of 85% at an application rate of 100 mg/m²: 1-64, 1-69, 1-97

In this test, for example, the following compounds of the preparation examples show an activity of 80% at an application rate of 100 mg/m²: 1-98

| Example | Active compound concentration in g/ha | Kill rate in % after 24 h |
|---|---|---|
| WO2010070910 Example 2a-78 | 1.6 | 5 |
| WO2011958963 Example 2-6 | 1.6 | 10 |
| Example 1-9 | 1.6 | 75 |
| Example 1-16 | 1.6 | 90 |
| Example 1-35 | 1.6 | 100 |

*Culex* Test (CULXFA Surface Treatment)
Solvent: Acetone

To produce a suitable preparation of active compound, the active compound is dissolved in acetone (2 mg/ml). The active compound preparation is pipetted onto a glazed tile and, after drying, adult mosquitoes of the species *Culex quinquefasciatus* are placed onto the treated tile. The exposition time is 30 minutes.

Two hours after contact to the treated surface, the knock-down proportion of the test animals in % is determined.

In this test, for example, the following compounds of the preparation examples show a knock-down activity of 100% at an application rate of 100 mg/m²: 1-9, 1-36, 1-46, 1-58

In this test, for example, the following compounds of the preparation examples show a knock-down activity of 95% at an application rate of 100 mg/m²: 1-16, 1-28

24 hours after contact to the treated surface, the mortality in % is determined. Here, 100% means that all mosquitoes have been killed; 0% means that none of the mosquitoes has been killed.

In this test, for example, the following compounds of the preparation examples show an activity of 100% at an application rate of 100 mg/m$^2$: 1-7, 1-9, 1-16, 1-27, 1-28, 1-35, 1-36, 1-41, 1-46, 1-47, 1-57, 1-58

In this test, for example, the following compounds of the preparation examples show an activity of 95% at an application rate of 100 mg/m$^2$: 1-5

In this test, for example, the following compounds of the preparation examples show an activity of 90% at an application rate of 100 mg/m$^2$: 1-26

Cimex Test (CIMXLE Surface Treatment)
Solvent: Acetone

To produce a suitable preparation of the active compound, the active compound is dissolved in acetone (2 mg/ml). The active compound preparation is pipetted onto a glazed tile and, after drying, adult bed bugs of the species *Cimex lectularius* are placed onto the treated tile. The exposition time is 30 minutes.

Two hours after contact to the treated surface, the knock-down proportion of the test animals in % is determined In this test, for example, the following compounds of the preparation examples show a knock-down activity of 80% at an application rate of 100 mg/m$^2$: 1-9

24 hours after contact to the treated surface, the mortality in % is determined. Here, 100% means that all bed bugs have been killed; 0% means that none of the bed bugs have been killed.

In this test, for example, the following compounds of the preparation examples show an activity of 100% at an application rate of 100 mg/m$^2$: 1-9, 1-47

In this test, for example, the following compounds of the preparation examples show an activity of 90% at an application rate of 100 mg/m$^2$: 1-16, 1-27, 1-46

In this test, for example, the following compounds of the preparation examples show an activity of 80% at an application rate of 100 mg/m$^2$: 1-28, 1-36

The invention claimed is:

1. A compound of formula (I)

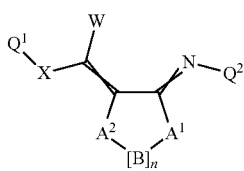
(I)

or a salt, N-oxide, metal complex, and/or tautomeric form of a compound of formula (I),
in which
Q$^1$ represents phenyl that is optionally substituted with one or more substituents selected from the group consisting of halogen, (C$_1$-C$_4$)-alkoxy, (C$_1$-C$_4$)-alkyl, and (C$_1$-C$_4$)-haloalkyl;
X represents —S—, or —S(O)$_2$—;
W represents H;
Q$^2$ represents phenyl that is optionally substituted with one or more substituents selected from the group consisting of halogen, cyano, (C$_1$-C$_4$)-alkyl, (C$_1$-C$_4$)-alkoxy, and (C$_1$-C$_4$)-haloalkyl;
A$^1$-[B]$_n$A$^2$ together with the carbon atoms to which A$^1$ and A$^2$ are attached represent a cyclic system selected from the group consisting of

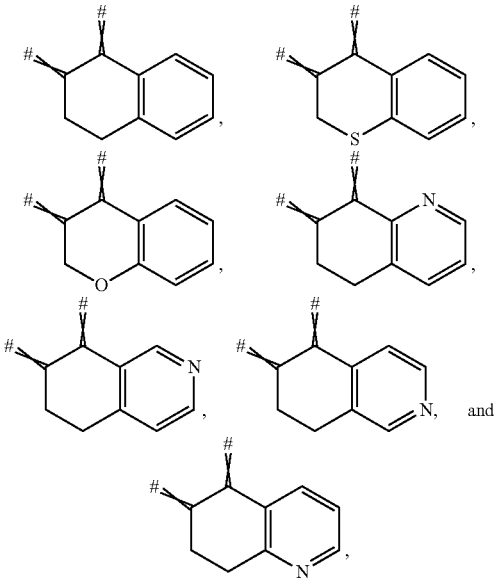

that is optionally substituted with Br, Cl, F, (C$_1$-C$_4$)-alkyl, phenyl, (C$_1$-C$_4$)-alkoxy, —NH—C(=)—(C$_1$-C$_4$)-alkyl, =CH—C$_6$H$_5$, or =CH—S—C$_6$H$_5$.

2. An insecticidal composition, wherein said insecticidal composition comprises at least one compound according to claim 1, and an extender and/or surfactant.

3. A method for protecting transgenic and/or conventional seed and a plant generated therefrom against attack by pests, comprising treating the seed with at least one compound according to claim 1.

4. A compound according to claim 1, capable of being used for controlling pests.

5. A compound according to claim 1, capable of being used for controlling vectors.

6. A seed in which a compound according to claim 1, has been applied to said seed as a constituent of a casing and/or as a further layer and/or further layers in addition to a casing.

7. An insecticidal composition according to claim 2 capable of being used for controlling pests.

* * * * *